(12) United States Patent
Liverton et al.

(10) Patent No.: US 7,259,157 B2
(45) Date of Patent: Aug. 21, 2007

(54) N-SUBSTITUTED NONARYL-HETEROCYCLO AMIDYL NMDA/NR2B ANTAGONISTS

(75) Inventors: Nigel J. Liverton, Harleysville, PA (US); John W. Butcher, Telford, PA (US); Charles McIntyre, Lansdale, PA (US); Christopher F. Claiborne, Cambridge, MA (US); David A. Claremon, Maple Glen, PA (US); John A. McCauley, Maple Glen, PA (US); Joseph J. Romano, Berwyn, PA (US); Wayne Thompson, Landsdale, PA (US); Peter M. Munson, Harleysville, PA (US)

(73) Assignee: Merck & Co., Inc., Rahway, NJ (US)

( * ) Notice: Subject to any disclaimer, the term of this patent is extended or adjusted under 35 U.S.C. 154(b) by 683 days.

(21) Appl. No.: 10/114,685

(22) Filed: Apr. 2, 2002

(65) Prior Publication Data

US 2003/0119811 A1 Jun. 26, 2003

Related U.S. Application Data

(60) Provisional application No. 60/281,166, filed on Apr. 3, 2001.

(51) Int. Cl.
*A61K 31/554* (2006.01)
*A61K 31/4965* (2006.01)
*A61K 31/44* (2006.01)
*A61K 31/425* (2006.01)
*A61K 31/52* (2006.01)

(52) U.S. Cl. .............. 514/211.01; 514/222.2; 514/228.8; 514/250; 514/262.1; 514/263.22; 514/252.03; 514/255.05; 514/256; 514/314; 514/315; 514/330; 514/336; 514/351; 514/354; 514/357; 514/365; 546/169; 546/180; 546/193; 546/194; 546/198; 546/199; 546/201; 546/207; 546/208; 546/209; 546/210; 546/211; 546/212; 546/213; 546/224; 546/226; 546/229; 546/231; 546/236; 546/237; 544/238; 544/262; 544/277; 544/335; 544/406; 548/146; 548/189; 548/200; 548/202; 548/203; 548/204; 548/205

(58) Field of Classification Search ................ 514/183, 514/211.01, 222.2, 228.8, 250, 315, 330, 514/336, 351, 354, 357, 365, 262.1, 263.22, 514/252.03, 255.05, 256, 314, 318, 320, 514/322, 323, 326; 546/186, 209, 229, 236, 546/237, 167, 193, 194, 198, 199, 201, 207, 546/208, 210, 211, 212, 213, 224, 226, 231; 544/238, 262, 277, 335, 406; 548/146, 189, 548/200, 202, 203, 204, 205

See application file for complete search history.

(56) References Cited

U.S. PATENT DOCUMENTS

| | | | | |
|---|---|---|---|---|
| 5,306,723 A | * | 4/1994 | Chenard et al. | ............ 514/304 |
| 5,436,255 A | * | 7/1995 | Butler et al. | ............... 514/320 |
| 5,648,368 A | | 7/1997 | Egertson et al. | |
| 6,197,769 B1 | * | 3/2001 | Alisi et al. | ............. 514/234.5 |
| 6,303,637 B1 | | 10/2001 | Bao et al. | |
| 6,706,740 B2 | * | 3/2004 | Ricks et al. | ............... 514/357 |

FOREIGN PATENT DOCUMENTS

| | | |
|---|---|---|
| DE | 3702755 | 8/1988 |
| EP | 441506 | 8/1991 |
| EP | 532456 | 3/1993 |
| EP | 787493 | 8/1997 |
| EP | 846683 | 6/1998 |
| WO | WO91/17156 | 11/1991 |
| WO | WO91/19709 | 12/1991 |
| WO | 9203415 * | 3/1992 |
| WO | WO92/18502 | 10/1992 |
| WO | WO93/02052 | 2/1993 |
| WO | WO94/20062 | 2/1994 |
| WO | WO94/14776 | 7/1994 |
| WO | WO94/21615 | 9/1994 |
| WO | WO96/02250 | 2/1996 |
| WO | WO96/10035 | 4/1996 |
| WO | WO96/34856 | 11/1996 |
| WO | WO96/37226 | 11/1996 |
| WO | WO97/28139 | 8/1997 |

(Continued)

OTHER PUBLICATIONS

Richter et al,PubMed Abstract 12498913, also cited as Eur.J. Pharmacol. 458/1-2,107-10(2003).*

(Continued)

*Primary Examiner*—Peter O'Sullivan
(74) *Attorney, Agent, or Firm*—Mollie M. Yang; David L. Rose

(57) ABSTRACT

Compounds represented by Formula (I):

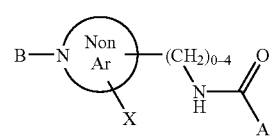

or pharmaceutically acceptable salts thereof, are effective as NMDA NR2B antagonists useful for relieving pain.

16 Claims, No Drawings

FOREIGN PATENT DOCUMENTS

| WO | WO97/28141 | 8/1997 |
| WO | WO97/45119 | 12/1997 |
| WO | WO98/04913 | 2/1998 |
| WO | WO98/05336 | 2/1998 |
| WO | WO98/31669 | 7/1998 |
| WO | WO98/31677 | 7/1998 |
| WO | WO98/46589 | 10/1998 |
| WO | WO 00/00197 | 1/2000 |
| WO | WO 00/08015 | 2/2000 |
| WO | WO 00/11002 | 3/2000 |
| WO | WO 00/25786 | 5/2000 |
| WO | WO 00 71518 | 11/2000 |
| WO | 100207 | * 1/2001 |

OTHER PUBLICATIONS

Kuraishi et al,PubMed Abstract 113338373,also cited as Nippon Yakurigaku Zasshi,117/4,248-54(2001).*
Wright et al,PubMed Abstract 10522697, also cited as Bioorg. Med. Chem. Lett.,9/19,2815-8(1999).*
Chabrier et al, PubMed Abstract 10442086, also cited as Cell Mol. Life Sci.,55/8-9,1029-35(1999).*
Laurie et al,PubMed Abstract 7528680, also cited as Eur. J. Pharmacol. 268/3,335-45(1994).*
Alisi et al. Chemical Abstracts, vol. 129:316219, 1998.*
Ricks et al., Chemical Abstracts, vol. 134:131431, 2001.*
T. Ishii, et al., J.Biol. Chem., 268:2836-2843(1993).
M.B. Max, et al., Clin. Neuropharmacology, 18:360-368(1995).
D.J. Knox, et al., Anaesth. Intens. Care, 23:620-622(1995).
P.K. Eide, et al., Pain, 61:221-228(1995).
J.D. Kristensen, et al., Pain, 51:249-253(1992).
K. Taniguchi, et al., Brit. J. Pharmacology, 122:809-812(1997).
R. Jain, et al., Tetrahedron, 54:3235-3242(1998).
W. Danysz, et al., Pharmacological Rev., 50:597-664(1998).
R.D. Clark, et al., J. Med. Chem., 26:855-861(1983).
A. Dickenson, TIPS, 11:307-309(1990).
A. Wenzel, et al., Neurochemistry, 7:45-48(1995).
J.N.C. Kew, et al., Brit. J. Pharmacology, 123:463-472(1998).
Electronic Database Printout, CAPLUS 1999:617466,218th ACS Nat. Mtg., N. Orleans, Aug. 22-26, 1999.
Z.-L. Zhou, et al., J. Med. Chem., 42:2993-3000(1999).
S. Boyce, et al., Neuropharmacology, 38:611-623(1999).
D.J. Laurie, et al., Mol. Brain Res., 51:23-32(1997).
Electronic Database Printout CAPLUS STN No. 98:191287 (1983).
Electronic Database Printout CAPLUS STN No. 135:298146 (2001).

* cited by examiner

N-SUBSTITUTED NONARYL-HETEROCYCLO AMIDYL NMDA/NR2B ANTAGONISTS

RELATED APPLICATION DATA

This application claims the benefit of U.S. provisional application 60/281,166, which was filed Apr. 3, 2001.

BACKGROUND OF THE INVENTION

Field of the Invention

This invention relates to N-substituted nonarylheterocyclo amidyl compounds. In particular, this invention relates to N-substituted nonarylheterocyclo amidyl compounds that are effective as NMDA NR2B antagonists useful for relieving pain.

Ions such as glutamate play a key role in processes related to chronic pain and pain-associated neurotoxicity—primarily by acting through N-methyl-D-aspartate ("NMDA") receptors. Thus, inhibition of such action—by employing ion channel antagonists, particularly NMDA antagonists—can be beneficial in the treatment and control of pain.

Known NMDA antagonists include ketamine, dextromophan, and 3-(2-carboxypiperazin4-yl)-propyl-1-phosphonic acid ("CPP"). Although these compounds have been reported (J. D. Kristensen, et al., *Pain,* 51:249–253 (1992); P. K. Eide, et al., *Pain,* 61:221–228 (1995); D. J. Knox, et al., *Anaesth. Intensive Care* 23:620–622 (1995); and M. B. Max, et al., *Clin. Neuropharmacol.* 18:360–368 (1995)) to produce symptomatic relief in a number of neuropathies including postherpetic neuralgia, central pain from spinal cord injury, and phantom limb pain, widespread use of these compounds is precluded by their undesirable side effects. Such side effects at analgesic doses include psychotomimetic effects such as dizziness, headache, hallucinations, dysphoria, and disturbances of cognitive and motor function. Additionally, more severe hallucinations, sedation, and ataxia are produced at doses only marginally higher than analgesic doses. Thus, it would be desirable to provide novel NMDA antagonists that are absent of undesirable side effects or that produce fewer and/or milder side effects.

NMDA receptors are heteromeric assemblies of subunits, of which two major subunit families designated NR1 and NR2 have been cloned. Without being bound by theory, it is generally believed that the various functional NMDA receptors in the mammalian central nervous system ("CNS") are only formed by combinations of NR1 and NR2 subunits, which respectively express glycine and glutamate recognition sites. The NR2 subunit family is in turn divided into four individual subunit types: NR2A, NR2B, NR2C, and NR2D. T. Ishii, et al., *J. Biol. Chem.,* 268:2836–2843 (1993), and D. J. Laurie et al., *Mol. Brain Res.,* 51:23–32 (1997) describe how the various resulting combinations produce a variety of NMDA receptors differing in physiological and pharmacological properties such as ion gating properties, magnesium sensitivity, pharmacological profile, as well as in anatomical distribution.

For example, while NR1 is found throughout the brain, NR2 subunits are differentially distributed. In particular, it is believed that the distribution map for NR2B lowers the probability of side effects while producing pain relief. For example, S. Boyce, et al., *Neuropharmacology,* 38:611–623 (1999) describes the effect of selective NMDA NR2B antagonists on pain with reduced side effects. Thus, it would be desirable to provide novel NMDA antagonists that target the NR2B receptor. Such antagonists would be useful in the treatment of pain, migraine, depression, anxiety, schizophrenia, Parkinson's disease, stroke, glaucoma, or tinitus—maladies that are amenable to amelioration through inhibition of NMDA NR2B receptors.

U.S. Pat. No. 6,020,347 and International Patent Publication WO99/25685 describes 4-substituted-4-piperidine carboxamide derivatives that are antagonists of VLA-4 ("Very Late Antigen-4"). International Patent Publication WO 01/00207 describes substituted pyrimidine compounds that are inhibitors of tyrosine kinases. International Patent Publication WO 00/61551 describes oxopyrimidinealkanoate compounds that are integrin-receptor ligands. International Patent Publication EP 604800 describes carboxyalkyl-phenyl aminocarbonyl-phenyl-piperidine compounds that are blood platelet aggregation inhibitors. International Patent Publication EP 611660 describes benzimidazoles, xanthines, and analogs as tissue aggregation inhibitors. International Patent Publication EP 771799 and U.S. Pat. No. 5,861,396 describe purin-6-one derivatives for the treatment of cardiovascular and urogenital diseases. International Patent Publication WO94/21615 describes benzimidazole-piperidine compounds utilized as dopamine D4 antagonists. German Patent No. DE4241632 describes substituted phenyl or cyclohexyl-carboxylic acid derivatives that inhibit cell aggregation.

International Patent Publication WO 00/25786 describes heterocyclic potassium channel inhibitors. International Patent Publication WO 00/08015 describes non-peptidic amino derivatives that are follicle stimulating hormone agonists for the treatment of infertility. International Patent Publication WO 98/46589 describes indazole amide compounds as serotoninergic agents. International Patent Publication WO 98/05336 describes compounds that are inhibitors of cysteine protease. International Patent Publication WO 98/04913 describes pharmacophore models of integrin VLA-4 inhibitors. International Patent Publication WO 97/45119 describes the use of substance P antagonists for treating social phobia. International Patent Publication WO 97/28141 describes aromatic piperazines derived from substituted cycloazanes. International Patent Publication WO 97/28139 describes naphthylpiperazines derived from substituted cycloazanes. International Patent Publication WO 96/34856 describes 2-ureido-benzamide derivatives. International Patent Publication WO 96/10035 describes inhibitors of farnesyl-protein transferase. International Patent Publication WO 94/20062 describes balanoids. International Patent Publication WO 94/14776 describes bicyclic fibrinogen antagonists. International Patent Publication EP 532456 describes 1-acylpiperidine derivatives used as substance-P antagonists. International Patent Publication WO/19709 describes imidazolylbenzoyl substituted heterocycles. Japanese Patent Publication JP 10120644 describes 2-ureido-benzamide derivatives for treating ACAT-related diseases. International Patent Publication WO 00/11002 describes 9-dialkylamino purinone derivatives. International Patent Publication WO 98/31669 describes arylpiperazine antidepressants derived from piperidine. International Patent Publication WO 98/31677 describes aromatic amines derived from cyclic amines. R. D. Clark et al., *J. Med. Chem.,* 26:855–861(1983) describes antihypertensive 9-subtituted 1-oxa-4,9-diazaspiro[5.5]undecan-3-ones.

Phenol compounds described as NMDA antagonists are described in U.S. Pat. Nos. 5,306,723 and 5,436,255, and in International Patent Publications WO91/17156, WO92/19502, WO93/02052, WO96/37226, and EP 441506. Benzyl piperidine substituted with phenols or imidazoles are described in Z. L. Zhou, et al., *J. Medicinal Chemistry*, 42:2993–3000(1999); T. F. Gregory, et al., Poster #94, 218th National Meeting American Chemical Society, New Orleans, La., Aug. 22–26, 1999. Other NMDA NR2B selective compounds are described in European Patent Publication EP 787493 and J. N. C. Kew et al., *British J. Pharmacol.*, 123:463(1998). However, there continues to be a need for novel NMDA antagonists that target the NR2B receptor.

SUMMARY OF THE INVENTION

The present invention relates to N-substituted nonarylheterocyclic compounds represented by Formula (I):

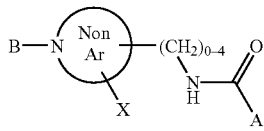

(I)

or pharmaceutically acceptable salts thereof. The present invention also forms pharmaceutical compositions utilizing the compounds. Further, this invention includes novel methods to treat pain by utilizing the compounds.

DETAILED DESCRIPTION OF THE INVENTION

The compounds of this invention are represented by Formula (I):

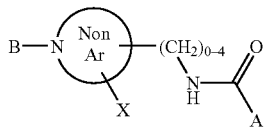

(I)

or pharmaceutically acceptable salts thereof, wherein

NonAr is a nonaromatic 5–7 membered ring containing a) 1 nitrogen ring atom, b) 2 nitrogen ring atoms, c) 1 nitrogen and 1 oxygen ring atom, or d) 1 nitrogen and 1 sulfur ring atom, wherein the remaining ring atoms are carbon;

A is a phenyl optionally substituted with 1–5 substituents, each substituent independently is $C_{1-4}$alkyl, $C_{3-7}$cycloalkyl, —$CF_3$, halogen, —OH, —CN, imidazolyl, —$C_{0-4}$alkyl-N($C_{0-5}$alkyl)($C_{0-5}$alkyl), —O—$C_{1-4}$alkyl, —C(O)—$C_{0-4}$alkyl, —C(O)—O—$C_{0-4}$alkyl, —O—C(O)—$C_{0-4}$alkyl, —O—C(O)—$C_{0-4}$alkylphenyl, —$C_{0-4}$alkyl-N($C_{0-5}$alkyl)—C(O)—$C_{0-4}$alkyl, —$C_{0-4}$alkyl-N($C_{0-5}$alkyl)—C(O)—O—$C_{0-4}$alkyl, —$C_{0-4}$alkyl-N($C_{0-5}$alkyl)—C(O)—O—$C_{1-4}$alkyl, or —NHSO$_2$—$C_{1-4}$alkyl, —O—$C_{1-4}$alkylphenyl, or hydroxyiminoethyl; any alkyl optionally substituted with 1–6 —OH or halogen; or A is pyrrolyl, imidazolyl, pyrazolyl, triazolyl, thiophenyl, thiazolyl, thiadiazolyl, oxazolyl, or isoxazolyl, each optionally substituted with 1–3 substituents, each substituent independently is —$C_{1-4}$alkyl, —$C_{3-7}$cycloalkyl, —$CF_3$, halogen, —OH, —CN, —$C_{1-4}$alkoxyl, phenyl, —$C_{0-4}$alkyl-N($C_{0-5}$alkyl)($C_{0-5}$alkyl), —$C_{1-4}$hydroxyalkyl; or A is pyridyl, pyradazinyl, pyrimidinyl, or pyrazinyl, each optionally substituted with 1–5 substituents; each substituent independently is —$C_{1-4}$alkyl, —$C_{3-7}$cycloalkyl, —$CF_3$, halogen, —OH, —CN, phenyl, pyrrolidinyl, azepanyl, —$C_{1-4}$hydroxyalkyl, —$C_{1-4}$alkoxy, $(CH_3)_2N$—$(CH_2)_2$—NH—, —$SO_2$—$C_{1-4}$alkyl, —$C_{0-4}$alkyl-N($C_{0-5}$alkyl)($C_{0-5}$alkyl), —$C_{0-4}$alkyl-N($C_{3-6}$cycloalkyl)($C_{0-5}$alkyl), —$C_{0-4}$alkyl-N($C_{0-5}$alkyl)($C_{1-4}$alkyloxy$C_{1-4}$alkyl), —N($C_{0-5}$alkyl)-$C_{0-4}$alkyl-phenyl(C1–4alkoxyl)$_{0-3}$, —N($C_{0-5}$alkyl)—$C_{0-4}$alkylthiaphenyl, dimethoxyphenyl-$CH_2$—NH—; any phenyl optionally substituted with 1–5 —OH, halogen, or $C_{1-4}$alkyl; any alkyl optionally substituted with 1–5 —OH or halogen; or the substituent taken with a neighboring bond is =O; or A is pyrrolophenyl, imidazolophenyl, pyrazolophenyl, triazolophenyl, pyridinoimidazolyl, naphthyridinyl, tetrahydrocyclopentopyrazolyl, quinolinyl, pyrimidinopyrazololyl, benzothiazolyl, benzoimidazolyl, benzoxazolonyl, oxodihydrobenzoxazolyl, indolinonyl, oxadihydroquinolinyl, oxatetrahydroquinolinyl, or purinyl, each optionally substituted with 1–5 substituents, each substituent independently is —$C_{1-4}$alkyl, —$C_{3-7}$cycloalkyl, —$CF_3$, halogen, —OH, or —CN;

B is aryl$(CH_2)_{0-3}$—O—$(CH_2)_{0-2}$—C(O)—, heteroaryl$(CH_2)_{1-3}$—O—$(CH_2)_{0-2}$—(O)—, indanyl$(CH_2)_{0-3}$—O—$(CH_2)_{0-2}$—C(O)—, aryl$(CH_2)_{1-3}$—C(O)—$(CH_2)_{0-2}$—, arylcyclopropyl-C(O)—$(CH_2)_{0-2}$—, heteroaryl$(CH_2)_{1-3}$—C(O)—, aryl$(CH_2)_{1-3}$—, heteroaryl$(CH_2)_{1-3}$—, aryl$(CH_2)_{1-3}$—NH—C(O)—, aryl$(CH_2)_{1-3}$—NH—C(NCN)—, aryl$(CH_2)_{1-3}$—$SO_2$—, aryl$(CH_2)_{0-3}$—S—$(CH_2)_{0-2}$—C(O)—, or heteroaryl$(CH_2)_{1-3}$—$SO_2$— wherein any of the aryl or heteroaryl is optionally substituted by 1–5 substituents, each substituent independently is $C_{1-4}$alkyl, $C_{3-6}$cycloalkyl, $C_{1-4}$alkoxy, trifluoromethyl, phenyl, —O—$C_{1-4}$alkylphenyl, —S(O)—$C_{1-4}$alkyl, bromo, fluoro, chloro, or 2 substituents together form methylene dioxy; any $(CH_2)$ optionally is substituted with $C_{1-2}$alkyl; or B is

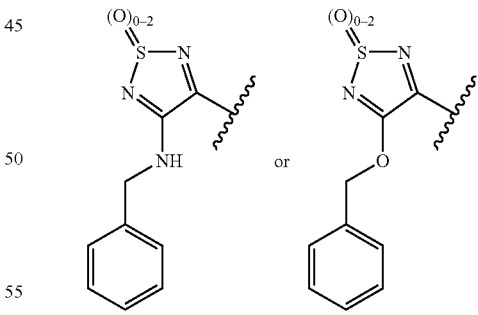

wherein the phenyl is optionally substituted by 1–3 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, —N($C_{0-5}$alkyl)($C_{0-5}$alkyl), phenyl, or =O.

In one aspect, the compounds of this invention are represented by Formula (I) or pharmaceutically acceptable salts thereof, wherein NonAr is a nonaromatic 6 membered ring containing 1 nitrogen ring atom, wherein the remaining ring atoms are carbon;

A is a phenyl optionally substituted with 1–5 substituents, each substituent independently is $C_{1-4}$alkyl, $C_{3-7}$cycloalkyl, —$CF_3$, halogen, —OH, —CN, imidazolyl, —$C_{0-4}$alkyl-N($C_{0-5}$alkyl)($C_{0-5}$alkyl), —O—$C_{1-4}$alkyl, —C(O)—$C_{0-4}$alkyl, —C(O)—O—$C_{0-4}$alkyl, —O—C(O)—$C_{0-4}$alkyl, —O—C(O)—$C_{0-4}$alkylphenyl, —$C_{0-4}$alkyl-N($C_{0-5}$alkyl)-C(O)—$C_{0-4}$alkyl, —$CO_4$alkyl-N($C_{0-5}$alkyl)-C(O)—O—$C_{0-4}$alkyl, —$C_{0-4}$alkyl-N($C_{0-5}$alkyl)-C(O)—O—$C_{1-4}$alkyl, or —$NHSO_2$-$C_{1-4}$alkyl, —O—$C_{1-4}$alkylphenyl, or hydroxyiminoethyl; any alkyl optionally substituted with 1–6 —OH or halogen; or A is pyrrolyl, imidazolyl, pyrazolyl, triazolyl, thiophenyl, thiazolyl, thiadiazolyl, oxazolyl, or isoxazolyl, each optionally substituted with 1–3 substituents, each substituent independently is —$C_{1-4}$alkyl, —$C_{3-7}$cycloalkyl, —$CF_3$, halogen, —OH, —CN, —$C_{1-4}$alkoxyl, phenyl, —$C_{0-4}$alkyl-N($C_{0-5}$alkyl)($C_{0-5}$alkyl), —$C_{1-4}$hydroxyalkyl; or A is pyridyl, pyradazinyl, pyrimidinyl, or pyrazinyl, each optionally substituted with 1–5 substituents; each substituent independently is —$C_{1-4}$alkyl, —$C_{3-7}$cycloalkyl, —$CF_3$, halogen, —OH, —CN, phenyl, pyrrolidinyl, azepanyl, —$C_{1-4}$hydroxyalkyl, —$C_{1-4}$alkoxy, $(CH_3)_2N$—$(CH_2)_2$—NH—, —$SO_2$—$C_{1-4}$alkyl, —$C_{0-4}$alkyl-N($C_{0-5}$alkyl)($C_{0-5}$alkyl), —$C_{0-4}$alkyl-N($C_{3-6}$cycloalkyl)($C_{0-5}$alkyl), —$C_{0-4}$alkyl-N($C_{0-5}$alkyl)($C_{1-4}$alkyloxy$C_{1-4}$alkyl), —N($C_{0-5}$alkyl)-$C_{0-4}$alkyl-phenyl($C1-4$alkoxyl)$_{0-3}$, —N($C_{0-5}$alkyl)-$C_{0-4}$alkylthiaphenyl, dimethoxyphenyl-$CH_2$—NH—; any phenyl optionally substituted with 1–5 —OH, halogen, or $C_{1-4}$alkyl; any alkyl optionally substituted with 1–5 —OH or halogen; or the substituent taken with a neighboring bond is =O; or A is pyrrolophenyl, imidazolophenyl, pyrazolophenyl, triazolophenyl, pyridinoimidazolyl, naphthyridinyl, tetrahydrocyclopentopyrazolyl, quinolinyl, pyrimidinopyrazololyl, benzothiazolyl, benzoimidazolyl, benzoxazolonyl, oxodihydrobenzoxazolyl, indolinonyl, oxadihydroquinolinyl, oxatetrahydroquinolinyl, or purinyl, each optionally substituted with 1–5 substituents, each substituent independently is —$C_{1-4}$alkyl, —$C_{3-7}$cycloalkyl, —$CF_3$, halogen, —OH, or —CN;

B is aryl$(CH_2)_{0-3}$—O—$(CH_2)_{0-2}$—C(O)—, heteroaryl$(CH_2)_{1-3}$—O—$(CH_2)_{0-2}$—C(O)—, indanyl$(CH_2)_{0-3}$—O—$(CH_2)_{0-2}$—C(O)—, aryl$(CH_2)_{1-3}$—C(O)—$(CH_2)_{0-2}$—, arylcyclopropyl-C(O)—$(CH_2)_{0-2}$—, heteroaryl$(CH_2)_{1-3}$—C(O)—, aryl$(CH_2)_{1-3}$—, heteroaryl$(CH_2)_{1-3}$—, aryl$(CH_2)_{1-3}$—NH—C(O)—, aryl$(CH_2)_{1-3}$—NH—C(NCN)—, aryl$(CH_2)_{1-3}$—$SO_2$—, aryl$(CH_2)_{0-3}$—S—$(CH_2)_{0-2}$—C(O)—, or heteroaryl$(CH_2)_3$—$SO_2$— wherein any of the aryl or heteroaryl is optionally substituted by 1–5 substituents, each substituent independently is $C_{1-4}$alkyl, $C_{3-6}$cycloalkyl, $C_{1-4}$alkoxy, trifluoromethyl, phenyl, —O—$C_{1-4}$alkylphenyl, —S(O)—$C_{1-4}$alkyl, bromo, fluoro, chloro, or 2 substituents together form methylene dioxy; any ($CH_2$) optionally is substituted with $C_{1-2}$alkyl; or B is

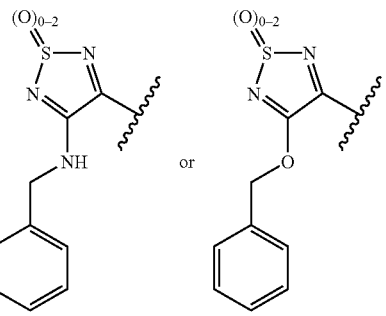

wherein the phenyl is optionally substituted by 1–3 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, —N($C_{0-5}$alkyl)($C_{0-5}$alkyl), phenyl, or =O.

In an embodiment of the first aspect, the compounds of this invention are represented by Formula (I) or pharmaceutically acceptable salts thereof, wherein NonAr is a nonaromatic 6 membered ring containing 1 nitrogen ring atom, wherein the remaining ring atoms are carbon;

A is a phenyl optionally substituted with 1–5 substituents, each substituent independently is $C_{1-4}$alkyl, $C_{3-7}$cycloalkyl, —$CF_3$, halogen, —OH, —CN, imidazolyl, —$C_{0-4}$alkyl-N($C_{0-5}$alkyl)($C_{0-5}$alkyl), —O—$C_{1-4}$alkyl, —C(O)—$C_{0-4}$alkyl, —C(O)—O—$C_{0-4}$alkyl, —O—C(O)—$C_{0-4}$alkyl, —O—C(O)—$C_{0-4}$alkylphenyl, —$C_{0-4}$alkyl-N($C_{0-5}$alkyl)-C(O)—$C_{0-4}$alkyl, —$C_{0-4}$alkyl-N($C_{0-5}$alkyl)-C(O)—O—$C_{0-4}$alkyl, —$C_{0-4}$alkyl-N($C_{0-5}$alkyl)-C(O)—O—$C_{1-4}$alkyl, or —$NHSO_2$—$C_{1-4}$alkyl, —O—$C_{1-4}$alkylphenyl, or hydroxyiminoethyl; any alkyl optionally substituted with 1–6 —OH or halogen;

B is aryl$(CH_2)_{0-3}$—O—$(CH_2)_{0-2}$—C(O)—, heteroaryl$(CH_2)_{1-3}$—O—$(CH_2)_{0-2}$—C(O)—, indanyl$(CH_2)_{0-3}$—O—$(CH_2)_{0-2}$—C(O)—, aryl$(CH_2)_{1-3}$—C(O)—$(CH_2)_{0-2}$—, arylcyclopropyl-C(O)—$(CH_2)_{0-2}$—, heteroaryl$(CH_2)_{1-3}$—C(O)—, aryl$(CH_2)_{1-3}$—, heteroaryl$(CH_2)_{1-3}$—, aryl$(CH_2)_{1-3}$—NH—C(O)—, aryl$(CH_2)_{1-3}$—NH—C(NCN)—, aryl$(CH_2)_{1-3}$—$SO_2$—, aryl$(CH_2)_{0-3}$—S—$(CH_2)_{0-2}$—C(O)—, or heteroaryl$(CH_2)_{1-3}$—$SO_2$— wherein any of the aryl or heteroaryl is optionally substituted by 1–5 substituents, each substituent independently is $C_{1-4}$alkyl, $C_{3-6}$cycloalkyl, $C_{1-4}$alkoxy, trifluoromethyl, phenyl, —O—$C_{1-4}$alkylphenyl, —S(O)—$C_{1-4}$alkyl, bromo, fluoro, chloro, or 2 substituents together form methylene dioxy; any ($CH_2$) optionally is substituted with $C_{1-2}$alkyl; or B is

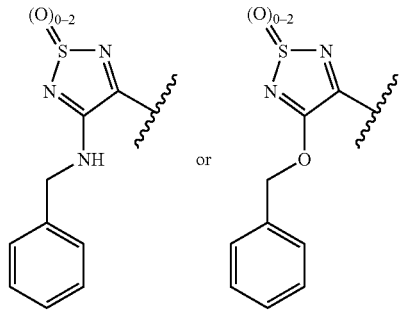

wherein the phenyl is optionally substituted by 1–3 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, —N($C_{0-5}$alkyl)($C_{0-5}$alkyl), phenyl, or =O.

In another aspect of the first aspect, the compounds of this invention are represented by Formula (I) or pharmaceutically acceptable salts thereof, wherein NonAr is a nonaromatic 6 membered ring containing 1 nitrogen ring atom, wherein the remaining ring atoms are carbon;

A is pyrrolyl, imidazolyl, pyrazolyl, triazolyl, thiophenyl, thiazolyl, thiadiazolyl, oxazolyl, or isoxazolyl, each optionally substituted with 1–3 substituents, each substituent independently is —$C_{1-4}$alkyl, —$C_{3-7}$cycloalkyl, —$CF_3$, halogen, —OH, —CN, —$C_{1-4}$alkoxyl, phenyl, —$C_{0-4}$alkyl-N($C_{0-5}$alkyl)($C_{0-5}$alkyl), —$C_{1-4}$hydroxyalkyl;

B is aryl$(CH_2)_{0-3}$—O—$(CH_2)_{0-2}$—C(O)—, heteroaryl$(CH_2)_{1-3}$—O—$(CH_2)_{0-2}$—C(O)—, indanyl$(CH_2)_{0-3}$—O—$(CH_2)_{0-2}$—C(O)—, aryl$(CH_2)_{1-3}$—C(O)—$(CH_2)_{0-2}$—, arylcyclopropyl-C(O)—$(CH_2)_{0-2}$—, heteroaryl$(CH_2)_{1-3}$—C(O)—, aryl$(CH_2)_{1-3}$—, heteroaryl$(CH_2)_{1-3}$—, aryl$(CH_2)_{1-3}$—NH—C(O)—, aryl$(CH_2)_{1-3}$—NH—C(NCN)—, aryl$(CH_2)_{1-3}$—$SO_2$—, aryl$(CH_2)_{0-3}$—S—$(CH_2)_{0-2}$—C(O)—, or heteroaryl$(CH_2)_{1-3}$—$SO_2$— wherein any of the aryl or heteroaryl is optionally substituted by 1–5 substituents, each substituent independently is $C_{1-4}$alkyl, $C_{3-6}$cycloalkyl, $C_{1-4}$alkoxy, trifluoromethyl, phenyl, —O—$C_{1-4}$alkylphenyl, —S(O)—$C_{1-4}$alkyl, bromo, fluoro, chloro, or 2 substituents together form methylene dioxy; any $(CH_2)$ optionally is substituted with $C_{1-2}$alkyl; or B is

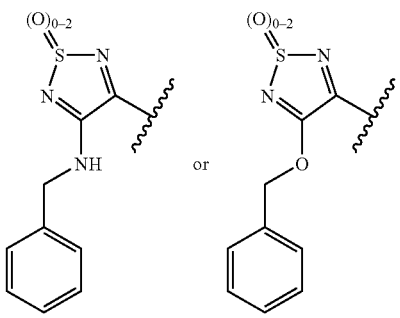

wherein the phenyl is optionally substituted by 1–3 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, —N($C_{0-5}$alkyl)($C_{0-5}$alkyl), phenyl, or =O.

In still another embodiment of the first aspect, the compounds of this invention are represented by Formula (I) or pharmaceutically acceptable salts thereof, wherein NonAr is a nonaromatic 6 membered ring containing 1 nitrogen ring atom, wherein the remaining ring atoms are carbon;

A is pyridyl, pyradazinyl, pyrimidinyl, or pyrazinyl, each optionally substituted with 1–5 substituents; each substituent independently is —$C_{1-4}$alkyl, —$C_{3-7}$cycloalkyl, —$CF_3$, halogen, —OH, —CN, phenyl, pyrrolidinyl, azepanyl, —$C_{1-4}$hydroxyalkyl, —$C_4$alkoxy, $(CH_3)_2N$—$(CH_2)_2$—NH—, —$SO_2$—$C_{1-4}$alkyl, —$C_{0-4}$alkyl-N($C_{0-5}$alkyl)($C_{0-5}$alkyl), —$CO_4$alkyl-N($C_{3-6}$cycloalkyl)($C_{0-5}$alkyl), —$C_{0-4}$alkyl-N($C_{0-5}$alkyl)($C_{1-4}$alkyloxy$C_{1-4}$alkyl), —N($C_{0-5}$alkyl)-$C_{0-4}$alkyl-phenyl($C1$-4alkoxyl)$_{0-3}$, —N($C_{0-5}$alkyl)-$C_{0-4}$alkylthiaphenyl, dimethoxyphenyl-$CH_2$—NH—; any phenyl optionally substituted with 1–5 —OH, halogen, or $C_{1-4}$alkyl; any alkyl optionally substituted with 1–5 —OH or halogen; or the substituent taken with a neighboring bond is =O;

B is aryl$(CH_2)_{0-3}$—O—$(CH_2)_{0-2}$—C(O)—, heteroaryl$(CH_2)_{1-3}$—O—$(CH_2)_{0-2}$—C(O)—, indanyl$(CH_2)_{0-3}$—O—$(CH_2)_{0-2}$—C(O)—, aryl$(CH_2)_{1-3}$—C(O)—$(CH_2)_{0-2}$—, arylcyclopropyl-C(O)—$(CH_2)_{0-2}$—, heteroaryl$(CH_2)_{1-3}$—C(O)—, aryl$(CH_2)_{1-3}$—, heteroaryl$(CH_2)_{1-3}$—, aryl$(CH_2)_{1-3}$—NH—C(O)—, aryl$(CH_2)_{1-3}$—NH—C(NCN)—, aryl$(CH_2)_{1-3}$—$SO_2$—, aryl$(CH_2)_{0-3}$—S—$(CH_2)_{0-2}$—C(O)—, or heteroaryl$(CH_2)_{1-3}$—$SO_2$— wherein any of the aryl or heteroaryl is optionally substituted by 1–5 substituents, each substituent independently is $C_{1-4}$alkyl, $C_{3-6}$cycloalkyl, $C_{1-4}$alkoxy, trifluoromethyl, phenyl, —O—$C_{1-4}$alkylphenyl, —S(O)—$C_{1-4}$alkyl, bromo, fluoro, chloro, or 2 substituents together form methylene dioxy; any $(CH_2)$ optionally is substituted with $C_{1-2}$alkyl; or B is

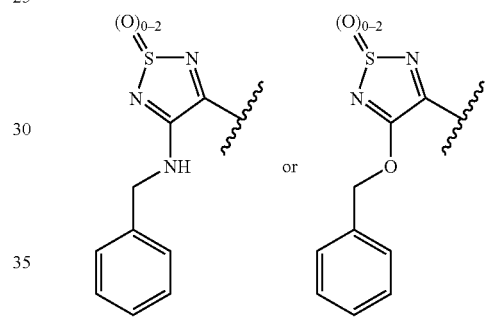

wherein the phenyl is optionally substituted by 1–3 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, —N($C_{0-5}$alkyl)($C_{0-5}$alkyl), phenyl, or =O.

In another embodiment of the first aspect, the compounds of this invention are represented by Formula (I) or pharmaceutically acceptable salts thereof, wherein NonAr is a nonaromatic 6 membered ring containing 1 nitrogen ring atom, wherein the remaining ring atoms are carbon;

A is pyrrolophenyl, imidazolophenyl, pyrazolophenyl, triazolophenyl, pyridinoimidazolyl, naphthyridinyl, tetrahydrocyclopentopyrazolyl, quinolinyl, pyrimidinopyrazololyl, benzothiazolyl, benzoimidazolyl, benzoxazolonyl, oxodihydrobenzoxazolyl, indolinonyl, oxadihydroquinolinyl, oxatetrahydroquinolinyl, or purinyl, each optionally substituted with 1–5 substituents, each substituent independently is —$C_{1-4}$alkyl, —$C_{3-7}$cycloalkyl, —$CF_3$, halogen, —OH, or —CN;

B is aryl$(CH_2)_{0-3}$—O—$(CH_2)_{0-2}$—C(O)—, heteroaryl$(CH_2)_{1-3}$—O—$(CH_2)_{0-2}$—C(O)—, indanyl$(CH_2)_{0-3}$—O—$(CH_2)_{0-2}$—C(O)—, aryl$(CH_2)_{1-3}$—C(O)—$(CH_2)_{0-2}$—, arylcyclopropyl-C(O)—$(CH_2)_{0-2}$—, heteroaryl$(CH_2)_{1-3}$—C(O)—, aryl$(CH_2)_{1-3}$—, heteroaryl$(CH_2)_{1-3}$—, aryl$(CH_2)_{1-3}$—NH—C(O)—, aryl$(CH_2)_{1-3}$—NH—C(NCN)—, aryl$(CH_2)_{1-3}$—$SO_2$—, aryl$(CH_2)_{0-3}$—S—$(CH_2)_{0-2}$—C(O)—, or heteroaryl(CH$_2$)$_{1-3}$—SO$_2$— wherein any of the aryl or heteroaryl is optionally substituted by 1–5 substituents, each substituent independently is C$_{1-4}$alkyl, C$_{3-6}$cycloalkyl, C$_{1-4}$alkoxy, trifluoromethyl, phenyl, —O—C$_{1-4}$alkylphenyl, —S(O)—C$_{1-4}$alkyl, bromo, fluoro, chloro, or 2 substituents together form methylene dioxy; any (CH$_2$) optionally is substituted with C$_{1-2}$alkyl; or B is

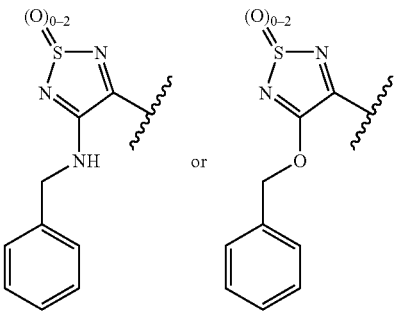

wherein the phenyl is optionally substituted by 1–3 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, —N(C$_{0-5}$alkyl)(C$_{0-5}$alkyl), phenyl, or =O.

In a second aspect, the compounds of this invention are represented by Formula (I) or pharmaceutically acceptable salts thereof, wherein NonAr is a nonaromatic 5 membered ring containing 1 nitrogen ring atom, wherein the remaining ring atoms are carbon;

A is a phenyl optionally substituted with 1–5 substituents, each substituent independently is C$_{1-4}$alkyl, C$_{3-7}$cycloalkyl, —CF$_3$, halogen, —OH, —CN, imidazolyl, —C$_{0-4}$alkyl-N(C$_{0-5}$alkyl)(C$_{0-5}$alkyl), —O—C$_{1-4}$alkyl, —C(O)—C$_{0-4}$alkyl, —C(O)—O—C$_{0-4}$alkyl, —O—C(O)—C$_{0-4}$alkyl, —O—C(O)—C$_{0-4}$alkylphenyl, —C$_{0-4}$alkyl-N(C$_{0-5}$alkyl)-C(O)—C$_{0-4}$alkyl, —C$_{0-4}$alkyl-N(C$_{0-5}$alkyl)-C(O)—O—C$_{0-4}$alkyl, —C$_{0-4}$alkyl-N(C$_{0-5}$alkyl)-C(O)—O—C$_{1-4}$alkyl, or —NHSO$_2$—C$_{1-4}$alkyl, —O—C$_{1-4}$alkylphenyl, or hydroxyiminoethyl; any alkyl optionally substituted with 1–6 —OH or halogen; or A is pyrrolyl, imidazolyl, pyrazolyl, triazolyl, thiophenyl, thiazolyl, thiadiazolyl, oxazolyl, or isoxazolyl, each optionally substituted with 1–3 substituents, each substituent independently is —C$_{1-4}$alkyl, —C$_{3-7}$cycloalkyl, —CF$_3$, halogen, —OH, —CN, —C$_{1-4}$alkoxyl, phenyl, —C$_{0-4}$alkyl-N(C$_{0-5}$alkyl)(C$_{0-5}$alkyl), —C$_{1-4}$hydroxyalkyl; or A is pyridyl, pyradazinyl, pyrimidinyl, or pyrazinyl, each optionally substituted with 1–5 substituents; each substituent independently is —C$_{1-4}$alkyl, —C$_{3-7}$cycloalkyl, —CF$_3$, halogen, —OH, —CN, phenyl, pyrrolidinyl, azepanyl, —C$_{1-4}$hydroxyalkyl, —C$_{1-4}$alkoxy, (CH$_3$)$_2$N—(CH$_2$)$_2$—NH—, —SO$_2$—C$_{1-4}$alkyl, —C$_{0-4}$alkyl-N(C$_{0-5}$alkyl)(C$_{0-5}$alkyl), —C$_{0-4}$alkyl-N(C$_{3-6}$cycloalkyl)(C$_{0-5}$alkyl), —C$_{0-4}$alkyl-N(C$_{0-5}$alkyl)(C$_{1-4}$alkyloxyC$_{1-4}$alkyl), —N(C$_{0-5}$alkyl)-C$_{0-4}$alkyl-phenyl(C1–4alkoxyl)$_{0-3}$, —N(C$_{0-5}$alkyl)-C$_{0-4}$alkylthiaphenyl, dimethoxyphenyl-CH$_2$—NH—; any phenyl optionally substituted with 1–5 —OH, halogen, or C$_{1-4}$alkyl; any alkyl optionally substituted with 1–5 —OH or halogen; or the substituent taken with a neighboring bond is =O; or A is pyrrolophenyl, imidazolophenyl, pyrazolophenyl, triazolophenyl, pyridinoimidazolyl, naphthyridinyl, tetrahydrocyclopentopyrazolyl, quinolinyl, pyrimidinopyrazololyl, benzothiazolyl, benzoimidazolyl, benzoxazolonyl, oxodihydrobenzoxazolyl, indolinonyl, oxadihydroquinolinyl, oxatetrahydroquinolinyl, or purinyl, each optionally substituted with 1–5 substituents, each substituent independently is —C$_{1-4}$alkyl, —C$_{3-7}$cycloalkyl, —CF$_3$, halogen, —OH, or —CN;

B is aryl(CH$_2$)$_{0-3}$—O—(CH$_2$)$_{0-2}$—C(O)—, heteroaryl(CH$_2$)$_{1-3}$—O—(CH$_2$)$_{0-2}$—C(O)—, indanyl(CH$_2$)$_{0-3}$—O—(CH$_2$)$_{0-2}$—C(O)—, aryl(CH$_2$)$_{1-3}$—C(O)—(CH$_2$)$_{0-2}$—, arylcyclopropyl-C(O)—(CH$_2$)$_{0-2}$—, heteroaryl(CH$_2$)$_{1-3}$—C(O)—, aryl(CH$_2$)$_{1-3}$—, heteroaryl(CH$_2$)$_{1-3}$—, aryl(CH$_2$)$_{1-3}$—NH—C(O)—, aryl(CH$_2$)$_{1-3}$—NH—C(NCN)—, aryl(CH$_2$)$_{1-3}$—SO$_2$—, aryl(CH$_2$)$_{0-3}$—S—(CH$_2$)$_{0-2}$—C(O)—, or heteroaryl(CH$_2$)$_{1-3}$—SO$_2$— wherein any of the aryl or heteroaryl is optionally substituted by 1–5 substituents, each substituent independently is C$_{1-4}$alkyl, C$_{3-6}$cycloalkyl, C$_{1-4}$alkoxy, trifluoromethyl, phenyl, —O—C$_{1-4}$alkylphenyl, —S(O)—C$_{1-4}$alkyl, bromo, fluoro, chloro, or 2 substituents together form methylene dioxy; any (CH$_2$) optionally is substituted with C$_{1-2}$alkyl; or B is

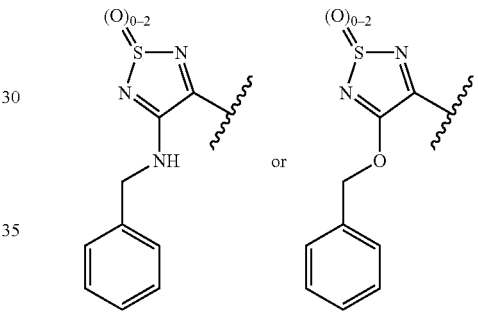

wherein the phenyl is optionally substituted by 1–3 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, —N(C$_{0-5}$alkyl)(C$_{0-5}$alkyl), phenyl, or =O.

In an embodiment of the second aspect, the compounds of this invention are represented by Formula (I) or pharmaceutically acceptable salts thereof, wherein NonAr is a nonaromatic 5 membered ring containing 1 nitrogen ring atom, wherein the remaining ring atoms are carbon;

A is a phenyl optionally substituted with 1–5 substituents, each substituent independently is C$_{1-4}$alkyl, C$_{3-7}$cycloalkyl, —CF$_3$, halogen, —OH, —CN, imidazolyl, —C$_{0-4}$alkyl-N(C$_{0-5}$alkyl)(C$_{0-5}$alkyl), —O—C$_{1-4}$alkyl, —C(O)—C$_{0-4}$alkyl, —C(O)—O—C$_{0-4}$alkyl, —O—C(O)—C$_{0-4}$alkyl, —O—C(O)—C$_{0-4}$alkylphenyl, —C$_{0-4}$alkyl-N(C$_{0-5}$alkyl)-C(O)—C$_{0-4}$alkyl, —C$_{0-4}$alkyl-N(C$_{0-5}$alkyl)-C(O)—O—C$_{0-4}$alkyl, —C$_{0-4}$alkyl-N(C$_{0-5}$alkyl)-C(O)—O—C$_{1-4}$alkyl, or —NHSO$_2$—C$_{1-4}$alkyl, —O—C$_{1-4}$alkylphenyl, or hydroxyiminoethyl; any alkyl optionally substituted with 1–6 —OH or halogen;

B is aryl(CH$_2$)$_{0-3}$—O—(CH$_2$)$_{0-2}$—C(O)—, heteroaryl(CH$_2$)$_{1-3}$—O—(CH$_2$)$_{0-2}$—C(O)—, indanyl(CH$_2$)$_{0-3}$—O—(CH$_2$)$_{0-2}$—C(O)—, aryl(CH$_2$)$_{1-3}$—C(O)—(CH$_2$)$_{0-2}$—, arylcyclopropyl-C(O)—(CH$_2$)$_{0-2}$—, heteroaryl(CH$_2$)$_{1-3}$—C (O)—, aryl(CH$_2$)$_{1-3}$—, heteroaryl(CH$_2$)$_{1-3}$—, aryl(CH$_2$)$_{1-3}$—NH—C(O)—, aryl(CH$_2$)$_{1-3}$—NH—C(NCN)—, aryl(CH$_2$)$_{1-3}$—SO$_2$—, aryl(CH$_2$)$_{0-3}$—S—(CH$_2$)$_{0-2}$—C(O)—, or heteroaryl(CH$_2$)$_{1-3}$—SO$_2$— wherein any of the aryl or heteroaryl is optionally substituted by 1–5 substituents, each substituent independently is C$_{1-4}$alkyl, C$_{3-6}$cycloalkyl, C$_{1-4}$alkoxy, trifluoromethyl, phenyl, —O—C$_{1-4}$alkylphenyl, —S(O)—C$_{1-4}$alkyl, bromo, fluoro, chloro, or 2 substituents together form methylene dioxy; any (CH$_2$) optionally is substituted with C$_{1-2}$alkyl; or B is

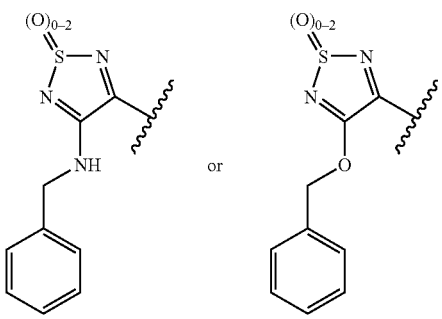

wherein the phenyl is optionally substituted by 1–3 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, —N(C$_{0-5}$alkyl)(C$_{0-5}$alkyl), phenyl, or =O.

In a third aspect, the compounds of this invention are represented by Formula (I) or pharmaceutically acceptable salts thereof, wherein NonAr is a nonaromatic 6 membered ring containing 2 nitrogen ring atoms, wherein the remaining ring atoms are carbon;

A is a phenyl optionally substituted with 1–5 substituents, each substituent independently is C$_{1-4}$alkyl, C$_{3-7}$cycloalkyl, —CF$_3$, halogen, —OH, —CN, imidazolyl, —C$_{0-4}$alkyl-N(C$_{0-5}$alkyl)(C$_{0-5}$alkyl), —O—C$_{1-4}$alkyl, —C(O)—C$_{0-4}$alkyl, —C(O)—O—C$_{0-4}$alkyl, —O—C(O)—C$_{0-4}$alkyl, —O—C(O)—C$_{0-4}$alkylphenyl, —C$_{0-4}$alkyl-N(C$_{0-5}$alkyl)—C(O)—C$_{0-4}$alkyl, —C$_{0-4}$alkyl-N(C$_{0-5}$alkyl)-C(O)—O—C$_{0-4}$alkyl, —C$_{0-4}$alkyl-N(C$_{0-5}$alkyl)-C(O)—O—C$_{1-4}$alkyl, or —NHSO$_2$—C$_{1-4}$alkyl, —O—C$_{1-4}$alkylphenyl, or hydroxyiminoethyl; any alkyl optionally substituted with 1-6 —OH or halogen; or A is pyrrolyl, imidazolyl, pyrazolyl, triazolyl, thiophenyl, thiazolyl, thiadiazolyl, oxazolyl, or isoxazolyl, each optionally substituted with 1–3 substituents, each substituent independently is —C$_{1-4}$alkyl, —C$_{3-7}$cycloalkyl, —CF$_3$, halogen, —OH, —CN, —C$_{1-4}$alkoxyl, phenyl, —C$_{0-4}$alkyl-N(C$_{0-5}$alkyl)(C$_{0-5}$alkyl), —C$_{1-4}$hydroxyalkyl; or A is pyridyl, pyradazinyl, pyrimidinyl, or pyrazinyl, each optionally substituted with 1–5 substituents; each substituent independently is —C$_{1-4}$alkyl, —C$_{3-7}$cycloalkyl, —CF$_3$, halogen, —OH, —CN, phenyl, pyrrolidinyl, azepanyl, —C$_{1-4}$hydroxyalkyl, —C$_{1-4}$alkoxy, (CH$_3$)$_2$N—(CH$_2$)$_2$—NH—, —SO$_2$—C$_{1-4}$alkyl, —C$_{0-4}$alkyl-N(C$_{0-5}$alkyl)(C$_{0-5}$alkyl), —C$_{0-4}$alkyl-N(C$_{3-6}$cycloalkyl)(C$_{0-5}$alkyl), —C$_{0-4}$alkyl-N(C$_{0-5}$alkyl)(C$_{1-4}$alkyloxyC$_{1-4}$alkyl), —N(C$_{0-5}$alkyl)-C$_{0-4}$alkyl-phenyl(C1–4alkoxyl)$_{0-3}$, —N(C$_{0-5}$alkyl)-C$_{0-4}$alkylthiaphenyl, dimethoxyphenyl-CH$_2$—NH—; any phenyl optionally substituted with 1–5 —OH, halogen, or C$_{1-4}$alkyl; any alkyl optionally substituted with 1–5 —OH or halogen; or the substituent taken with a neighboring bond is =O; or A is pyrrolophenyl, imidazolophenyl, pyrazolophenyl, triazolophenyl, pyridinoimidazolyl, naphthyridinyl, tetrahydrocyclopentopyrazolyl, quinolinyl, pyrimidinopyrazololyl, benzothiazolyl, benzoimidazolyl, benzoxazolonyl, oxodihydrobenzoxazolyl, indolinonyl, oxadihydroquinolinyl, oxatetrahydroquinolinyl, or purinyl, each optionally substituted with 1–5 substituents, each substituent independently is —C$_{1-4}$alkyl, —C$_{3-7}$cycloalkyl, —CF$_3$, halogen, —OH, or —CN;

B is aryl(CH$_2$)$_{0-3}$—O—(CH$_2$)$_{0-2}$—C(O)—, heteroaryl(CH$_2$)$_{1-3}$—O—(CH$_2$)$_{0-2}$—C(O)—, indanyl(CH$_2$)$_{0-3}$—O—(CH$_2$)$_{0-2}$—C(O)—, aryl(CH$_2$)$_{1-3}$—C(O)—(CH$_2$)$_{0-2}$—, arylcyclopropyl-C(O)—(CH$_2$)$_{0-2}$—, heteroaryl(CH$_2$)$_{1-3}$—C(O)—, aryl(CH$_2$)$_{1-3}$—, heteroaryl(CH$_2$)$_{1-3}$—, aryl(CH$_2$)$_{1-3}$—NH—C(O)—, aryl(CH$_2$)$_{1-3}$—NH—C(NCN)—, aryl(CH$_2$)$_{1-3}$—SO$_2$—, aryl(CH$_2$)$_{0-3}$—S—(CH$_2$)$_{0-2}$—C(O)—, or heteroaryl(CH$_2$)$_{1-3}$—SO$_2$— wherein any of the aryl or heteroaryl is optionally substituted by 1–5 substituents, each substituent independently is C$_{1-4}$alkyl, C$_{3-6}$cycloalkyl, C$_{1-4}$alkoxy, trifluoromethyl, phenyl, —O—C$_{1-4}$alkylphenyl, —S(O)—C$_{1-4}$alkyl, bromo, fluoro, chloro, or 2 substituents together form methylene dioxy; any (CH$_2$) optionally is substituted with C$_{1-2}$alkyl; or B is

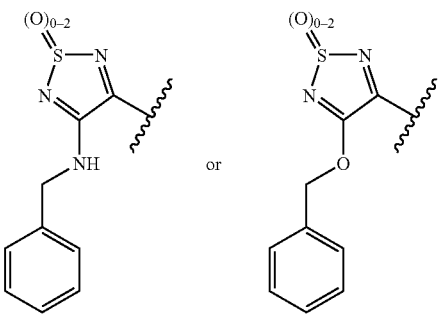

wherein the phenyl is optionally substituted by 1–3 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, —N(C$_{0-5}$alkyl)(C$_{0-5}$alkyl), phenyl, or =O.

In an embodiment of the third aspect, the compounds of this invention are represented by Formula (I) or pharmaceutically acceptable salts thereof, wherein NonAr is a nonaromatic 6 membered ring containing 2 nitrogen ring atoms, wherein the remaining ring atoms are carbon;

A is a phenyl optionally substituted with 1–5 substituents, each substituent independently is C$_{1-4}$alkyl, C$_{3-7}$cycloalkyl, —CF$_3$, halogen, —OH, —CN, imidazolyl, —C$_{0-4}$alkyl-N(C$_{0-5}$alkyl)(C$_{0-5}$alkyl), —O—C$_{1-4}$alkyl, —C(O)—C$_{0-4}$alkyl, —C(O)—O—C$_{0-4}$alkyl, —O—C(O)—C$_{0-4}$alkyl, —O—C(O)—C$_{0-4}$alkylphenyl, —C$_{0-4}$alkyl-N(C$_{0-5}$alkyl)-C(O)—C$_{0-4}$alkyl, —C$_{0-4}$alkyl-N(C$_{0-5}$alkyl)-C(O)—O—C$_{0-4}$alkyl, —C$_{0-4}$alkyl-N(C$_{0-5}$alkyl)-C(O)—O—C$_{1-4}$alkyl, or —NHSO$_2$—C$_{1-4}$alkyl, —O—C$_{1-4}$alkylphenyl, or hydroxyiminoethyl; any alkyl optionally substituted with 1-6 —OH or halogen;

B is aryl(CH$_2$)$_{0-3}$—O—(CH$_2$)$_{0-2}$—C(O)—, heteroaryl (CH$_2$)$_{1-3}$—O—(CH$_2$)$_{0-2}$—C(O)—, indanyl(CH$_2$)$_{0-3}$—O—(CH$_2$)$_{0-2}$—C(O)—, aryl(CH$_2$)$_{1-3}$—C(O)—(CH$_2$)$_{0-2}$—, arylcyclopropyl-C(O)—(CH$_2$)$_{0-2}$—, heteroaryl(CH$_2$)$_{1-3}$—C(O)—, aryl(CH$_2$)$_{1-3}$—, heteroaryl(CH$_2$)$_{1-3}$—, aryl(CH$_2$)$_{1-3}$—NH—C(O)—, aryl(CH$_2$)$_{1-3}$—NH—C(NCN)—, aryl(CH$_2$)$_{1-3}$—SO$_2$—, aryl(CH$_2$)$_{0-3}$—S—(CH$_2$)$_{0-2}$—C(O)—, or heteroaryl(CH$_2$)$_{1-3}$—SO$_2$— wherein any of the aryl or heteroaryl is optionally substituted by 1–5 substituents, each substituent independently is C$_{1-4}$alkyl, C$_{3-6}$cycloalkyl, C$_{1-4}$alkoxy, trifluoromethyl, phenyl, —O—C$_{1-4}$alkylphenyl, —S(O)—C$_{1-4}$alkyl, bromo, fluoro, chloro, or 2 substituents together form methylene dioxy; any (CH$_2$) optionally is substituted with C$_{1-2}$alkyl; or B is

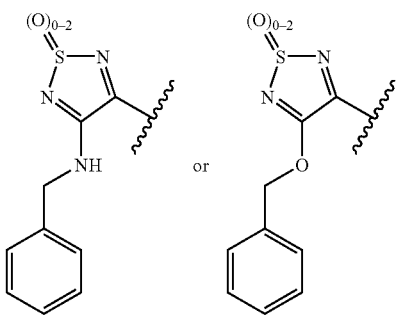

wherein the phenyl is optionally substituted by 1–3 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, —N(C$_{0-5}$alkyl)(C$_{0-5}$alkyl), phenyl, or =O.

In a fourth aspect, the compounds of this invention are represented by Formula (I) or pharmaceutically acceptable salts thereof, wherein NonAr is a nonaromatic 6 membered ring containing 1 nitrogen ring atom and 1 oxygen ring atom, wherein the remaining ring atoms are carbon;

A is a phenyl optionally substituted with 1–5 substituents, each substituent independently is C$_{1-4}$alkyl, C$_{3-7}$cycloalkyl, —CF$_3$, halogen, —OH, —CN, imidazolyl, —C$_{0-4}$alkyl-N(C$_{0-5}$alkyl)(C$_{0-5}$alkyl), —O—C$_{1-4}$alkyl, —C(O)—C$_{0-4}$alkyl, —C(O)—O—C$_{0-4}$alkyl, —O—C(O)—C$_{0-4}$alkyl, —O—C(O)—C$_{0-4}$alkylphenyl, —C$_{0-4}$alkyl-N(C$_{0-5}$alkyl)-C(O)—C$_{0-4}$alkyl, —C$_{0-4}$alkyl-N(C$_{0-5}$alkyl)-C(O)—O—C$_{0-4}$alkyl, —C$_{0-4}$alkyl-N(C$_{0-5}$alkyl)-C(O)—O—C$_{1-4}$alkyl, or —NHSO$_2$—C$_{1-4}$alkyl, —O—C$_{1-4}$alkylphenyl, or hydroxyiminoethyl; any alkyl optionally substituted with 1–6 —OH or halogen; or A is pyrrolyl, imidazolyl, pyrazolyl, triazolyl, thiophenyl, thiazolyl, thiadiazolyl, oxazolyl, or isoxazolyl, each optionally substituted with 1–3 substituents, each substituent independently is —C$_{1-4}$alkyl, —C$_{3-7}$cycloalkyl, —CF$_3$, —OH, —CN, —C$_{1-4}$alkoxyl, phenyl, —C$_{0-4}$alkyl-N(C$_{0-5}$alkyl)(C$_{0-5}$alkyl), —C$_{1-4}$hydroxyalkyl; or A is pyridyl, pyradazinyl, pyrimidinyl, or pyrazinyl, each optionally substituted with 1–5 substituents; each substituent independently is —C$_{1-4}$alkyl, —C$_{3-7}$cycloalkyl, —CF$_3$, halogen, —OH, —CN, phenyl, pyrrolidinyl, azepanyl, —C$_{1-4}$hydroxyalkyl, —C$_{1-4}$alkoxy, (CH$_3$)$_2$N—(CH$_2$)$_2$—NH—, —SO$_2$—C$_{1-4}$alkyl, —C$_{0-4}$alkyl-N(C$_{0-5}$alkyl)(C$_{0-5}$alkyl), —C$_{0-4}$alkyl-N(C$_{3-6}$cycloalkyl)(C$_{0-5}$alkyl), —C$_{0-4}$alkyl-N(C$_{0-5}$alkyl)(C$_{1-4}$alkyloxyC$_{1-4}$alkyl), —N(C$_{0-5}$alkyl)-C$_{0-4}$alkyl-phenyl(C1-4alkoxyl)$_{0-3}$, —N(C$_{0-5}$alkyl)-C$_{0-4}$alkylthiaphenyl, dimethoxyphenyl-CH$_2$—NH—; any phenyl optionally substituted with 1–5 —OH, halogen, or C$_{1-4}$alkyl; any alkyl optionally substituted with 1–5 —OH or halogen; or the substituent taken with a neighboring bond is =O; or A is pyrrolophenyl, imidazolophenyl, pyrazolophenyl, triazolophenyl, pyridinoimidazolyl, naphthyridinyl, tetrahydrocyclopentopyrazolyl, quinolinyl, pyrimidinopyrazololyl, benzothiazolyl, benzoimidazolyl, benzoxazolonyl, oxodihydrobenzoxazolyl, indolinonyl, oxadihydroquinolinyl, oxatetrahydroquinolinyl, or purinyl, each optionally substituted with 1–5 substituents, each substituent independently is —C$_{1-4}$alkyl, —C$_{3-7}$cycloalkyl, —CF$_3$, halogen, —OH, or —CN;

B is aryl(CH$_2$)$_{0-3}$—O—(CH$_2$)$_{0-2}$—C(O)—, heteroaryl (CH$_2$)$_{1-3}$—O—(CH$_2$)$_{0-2}$—C(O)—, indanyl(CH$_2$)$_{0-3}$—O—(CH$_2$)$_{0-2}$—C(O)—, aryl(CH$_2$)$_{1-3}$—C(O)—(CH$_2$)$_{0-2}$—, arylcyclopropyl-C(O)—(CH$_2$)$_{0-2}$—, heteroaryl(CH$_2$)$_{1-3}$—C(O)—, aryl(CH$_2$)$_{1-3}$—, heteroaryl(CH$_2$)$_{1-3}$—, aryl(CH$_2$)$_{1-3}$—NH—C(O)—, aryl(CH$_2$)$_{1-3}$—NH—C(NCN)—, aryl(CH$_2$)$_{1-3}$—SO$_2$—, aryl(CH$_2$)$_{0-3}$—S—(CH$_2$)$_{0-2}$—C(O)—, or heteroaryl(CH$_2$)$_{1-3}$—SO$_2$— wherein any of the aryl or heteroaryl is optionally substituted by 1–5 substituents, each substituent independently is C$_{1-4}$alkyl, C$_{3-6}$cycloalkyl, C$_{1-4}$alkoxy, trifluoromethyl, phenyl, —O—C$_{1-4}$alkylphenyl, —S(O)—C$_{1-4}$alkyl, bromo, fluoro, chloro, or 2 substituents together form methylene dioxy; any (CH$_2$) optionally is substituted with C$_{1-2}$alkyl; or B is

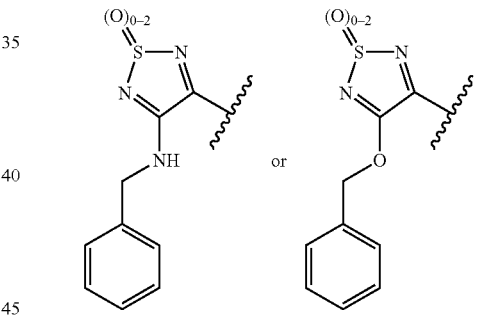

wherein the phenyl is optionally substituted by 1–3 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, —N(C$_{0-5}$alkyl)(C$_{0-5}$alkyl), phenyl, or =O.

In an embodiment of the fourth aspect, the compounds of this invention are represented by Formula (I) or pharmaceutically acceptable salts thereof, wherein NonAr is a nonaromatic 6 membered ring containing 1 nitrogen ring atom and 1 oxygen ring atom, wherein the remaining ring atoms are carbon;

A is a phenyl optionally substituted with 1–5 substituents, each substituent independently is C$_{1-4}$alkyl, C$_{3-7}$cycloalkyl, —CF$_3$, halogen, —OH, —CN, imidazolyl, —C$_{0-4}$alkyl-N(C$_{0-5}$alkyl)(C$_{0-5}$alkyl), —O—C$_{1-4}$alkyl, —C(O)—C$_{0-4}$alkyl, —C(O)—O—C$_{0-4}$alkyl, —O—C(O)—C$_{0-4}$alkyl, —O—C(O)—C$_{0-4}$alkylphenyl, —C$_{0-4}$alkyl-N(C$_{0-5}$alkyl)-C(O)—C$_{0-4}$alkyl, —C$_{0-4}$alkyl-N(C$_{0-5}$alkyl)-C(O)—O—C$_{0-4}$alkyl, —C$_{0-4}$alkyl-N(C$_{0-5}$alkyl)-C(O)—O—C$_{1-4}$alkyl, or —NHSO$_2$-C$_{1-4}$alkyl, —O—C$_{1-4}$alkylphenyl, or hydroxyiminoethyl; any alkyl optionally substituted with 1–6 —OH or halogen;

B is aryl(CH$_2$)$_{0-3}$—O—(CH$_2$)$_{0-2}$—C(O)—, heteroaryl (CH$_2$)$_{1-3}$—O—(CH$_2$)$_{0-2}$—C(O)—, indanyl(CH$_2$)$_{0-3}$—O—(CH$_2$)$_{0-2}$—C(O)—, aryl(CH$_2$)$_{1-3}$—C(O)—(CH$_2$)$_{0-2}$—, arylcyclopropyl-C(O)—(CH$_2$)$_{0-2}$—, heteroaryl(CH$_2$)$_{1-3}$—C(O)—, aryl(CH$_2$)$_{1-3}$—, heteroaryl(CH$_2$)$_{1-3}$—, aryl(CH$_2$)$_{1-3}$—NH—C(O)—, aryl(CH$_2$)$_{1-3}$—NH—C(NCN)—, aryl(CH$_2$)$_{1-3}$—SO$_2$—, aryl(CH$_2$)$_{0-3}$—S—(CH$_2$)$_{0-2}$—C(O)—, or heteroaryl(CH$_2$)$_{1-3}$—SO$_2$— wherein any of the aryl or heteroaryl is optionally substituted by 1–5 substituents, each substituent independently is C$_{1-4}$alkyl, C$_{3-6}$cycloalkyl, C$_{1-4}$alkoxy, trifluoromethyl, phenyl, —O—C$_{1-4}$alkylphenyl, —S(O)—C$_{1-4}$alkyl, bromo, fluoro, chloro, or 2 substituents together form methylene dioxy; any (CH$_2$) optionally is substituted with C$_{1-2}$alkyl; or B is

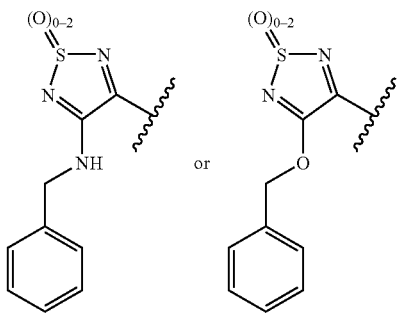

wherein the phenyl is optionally substituted by 1–3 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, —N(C$_{0-5}$alkyl)(C$_{0-5}$alkyl), phenyl, or =O.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalenyl, adamantanyl, indanyl, indenyl, fluorenyl, 1,2,3,4-tetrahydronaphthalenyl and the like. Similarly, "cycloalkenyl" means carbocycles containing no heteroatoms and at least one nonaromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "alkoxy" unless specifically stated otherwise includes an alkyl group connected to the oxy connecting atom.

The term "aryl" unless specifically stated otherwise includes multiple ring systems as well as single ring systems such as, for example, phenyl or naphthyl.

The term "aryloxy" unless specifically stated otherwise includes multiple ring systems as well as single ring systems such as, for example, phenyl or naphthyl, connected through the oxy connecting atom to the connecting site.

The term "C$_0$–C$_6$alkyl" includes alkyls containing 6, 5, 4, 3, 2, 1, or no carbon atoms. An alkyl with no carbon atoms is a hydrogen atom substituent when the alkyl is a terminus moiety. An alkyl with no carbon atoms is a direct bond when the alkyl is a bridging moiety.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The heteroatoms replace ring carbon atoms. Thus, for example, a heterocycloC$_5$alkyl is a five membered ring containing from 5 to no carbon atoms.

Examples of heteroaryl include, for example, pyridinyl, quinolinyl, isoquinolinyl, pyridazinyl, pyrimidinyl, pyrazinyl, quinoxalinyl, furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

The term "heteroaryloxy" unless specifically stated otherwise describes a heteroaryl group connected through an oxy connecting atom to the connecting site.

Examples of heteroaryl(C$_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Examples of heterocycloC$_{3-7}$alkyl include, for example, azetidinyl, pyrrolidinyl, piperidinyl, perhydroazepinyl, piperazinyl, morpholinyl, tetrahydrofuranyl, imidazolinyl, pyrolidin-2-one, piperidin-2-one, and thiomorpholinyl.

The term "N-heterocycloC$_{4-7}$alkyl" describes nonaryl heterocyclic compounds having 3–6 carbon atoms and one nitrogen atom forming the ring. Examples include azetidinyl, pyrrolidinyl, piperidinyl, and perhydroazepinyl.

Examples of aryl(C$_{1-6}$)alkyl include, for example, phenyl (C$_{1-6}$)alkyl, and naphthyl(C$_{1-6}$)alkyl.

Examples of heterocycloC$_{3-7}$alkylcarbonyl(C$_{1-6}$)alkyl include, for example, azetidinyl carbonyl(C$_{1-6}$)alkyl, pyrrolidinyl carbonyl(C$_{1-6}$)alkyl, piperidinyl carbonyl(C$_{1-6}$)alkyl, piperazinyl carbonyl(C$_{1-6}$)alkyl, morpholinyl carbonyl (C$_{1-6}$) alkyl, and thiomorpholinyl carbonyl(C$_{1-6}$)alkyl.

The term "amine" unless specifically stated otherwise includes primary, secondary and tertiary amines.

Unless otherwise stated, the term "carbamoyl" is used to include —NHC(O)OC$_1$—C$_4$alkyl, and —OC(O)NHC$_1$—C$_4$alkyl.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl(C$_{1-6}$) alkyl includes substitution on the aryl group as well as substitution on the alkyl group.

The term "oxide" of heteroaryl groups is used in the ordinary well-known chemical sense and include, for example, N-oxides of nitrogen heteroatoms.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 1 mg to about 500 mg of the active ingredient and each cachet or capsule preferably containing from about 1 to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be. preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Experimental Protocols

Assessing the Activity of Selected Compounds to Inhibit NR1A/2B NMDA Receptor Activation (FLIPR Assay)

The activity of selected compounds to inhibit NR1A/2B NMDA receptor activation measured as NR1A/2B receptor-mediated $Ca^{2+}$ influx is assessed by the following procedure:

NR1A/2B receptor transfected L(tk) cells are plated in 96-well format at $3\times10^6$ cells per plate and grown for one—two days in normal growth media (Dulbeccos MEM with Na pyruvate, 4500 mg glucose, pen/strep, glutamine, 10% FCS and 0.5 mg/mL geneticin). NR1A/2B-expression in these cells is induced by the addition of 4 nM dexamethasone in the presence of 500 μM ketamine for 16–24 hours. After receptor induction cells are washed using a Labsystem Cellwasher two times with assay buffer (Hanks balanced salt solution (HBSS-$Mg^{++}$ free) containing 20 mM HEPES, 0.1% BSA, 2 mM $CaCl_2$ and 250 μM probenecid). The cells of each 96 well cell plate are loaded with the $Ca^{++}$ sensitive dye Fluo-3 (Molecular Probes, Inc.) at 4 μM in assay buffer containing 0.5% FBS, and 0.04% pluronic F-127 (Molecular Probes, Inc.) for 1 h at 37° C. avoiding light. The cells are then washed with the Cellwasher four times with assay buffer leaving them in 100 μL buffer. Test compounds in solution are pipetted by FLIPR (Fluorometric Imaging Plate Reader) into each test well for a 2 min pretreatment. During this time the fluorescence intensity is recorded (excitation at 488 nm and emission at 530 nm). The glutamate/glycine 50 μL agonist solution (final concentration 1 μM/1 μM) is then added by FLIPR into each well already containing 150 μL of buffer (containing the test compound or vehicle) and the fluorescence is continuously monitored for 10 min. The endpoint fluorescence values are used to determine an $IC_{50}$ value comparing the agonist-stimulated signal for the vehicle alone sample and that for the cells incubated with each concentration of test compound.

Determining the Apparent Dissociation Constant (Ki) of Compounds for Human NR1A/NR2B Receptors (Binding Assay)

The radioligand binding assay is performed at room temperature in 96-well microtiter plates with a final assay volume of 1.0 mL in 20 mM HEPES buffer (pH 7.4) containing 150 mM NaCl. Solutions of test compounds were prepared in DMSO and serially diluted with DMSO to yield 20 μL of each of 10 solutions differing by 3-fold in concentration. Non-specific binding (NSB) using hot AMD-1 (10 μM final concentration) and total binding (TB) by using DMSO (2% final concentration). A solution of NR1A/NR2B receptors (40 pM final concentration) and tritiated AMD-2 (1 nM final concentration) were added to the test compounds. After 3 h of incubation at room temperature, samples are filtered through Packard GF/B filters (presoaked in 0.05% PEI, polyethyleninine Sigma P-3143) and washed 10 times with 1 mL of cold 20 mM HEPES buffer per wash. After vacuum drying of the filter plates, 40 μL of Packard Microscint-20 was added and bound radioactivity determined in a Packard TopCount. The apparent dissociation constant (Ki), the maximum percentage inhibition (% $I_{max}$), the minimum percentage inhibition (% $I_{min}$) and the hill slope (nH) were determined by a non-linear least squares fitting the bound CPM data to Equation #1 below.

$$CPM\ Bound = \frac{(SB)(\%I_{max} - \%I_{min})}{(1 + ([Drug]/(Ki[AMD-2]/K_D))^{nH})} + \quad \text{Equation \#1}$$

$$NSB + (SB)(1 - \%I_{max})$$

where, $K_D$ is the apparent dissociation constant for the radioligand for the receptor as determined by hot saturation and SB is the specifically bound CPM determined from the difference of TB and NSB.

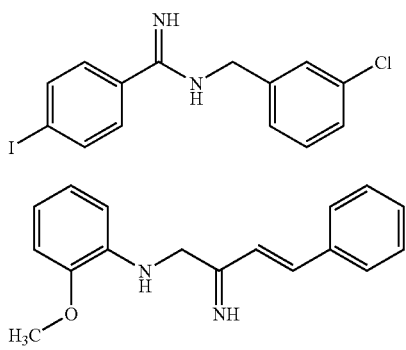

AMD-1

AMD-2

Compounds AMD-1 and AMD-2 can be synthesized in accordance with the following general reaction schemes.

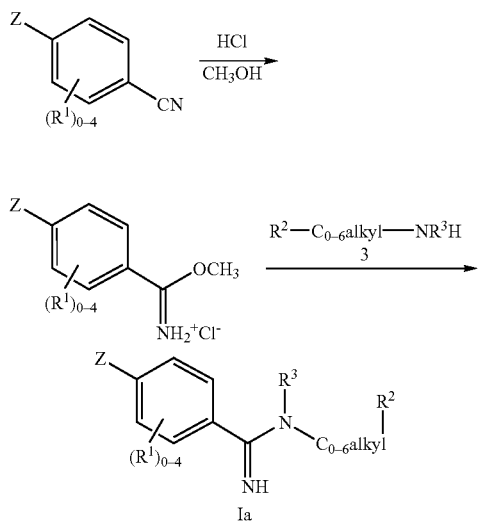

SCHEME 1

In accordance with scheme 1, hydrogen chloride is bubbled through a solution of the appropriately substituted benzonitrile 1 in methanol at room temperature. The volatiles are removed under reduced pressure and the resulting residue is triturated with ether and filtered to yield the desired imidate 2. Imidate 2 is dissolved in methanol at ambient temperature, treated with amine 3 at ambient temperature and stirred under argon. The volatiles are removed under reduced pressure and the residue purified by preparative HPLC or trituration with ether to afford amidine Ia.

SCHEME 2

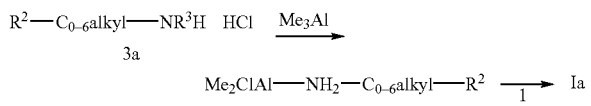

In accordance with scheme 2, at room temperature under argon, amine 3a is dissolved in ether and was treated with 1-M hydrogen chloride in ether (1 equiv.) in a single portion. The resulting precipitate is stirred vigorously for 10 minutes. The volatiles are removed under reduced pressure. The residue is suspended in toluene, cooled to 0° C. under argon, treated with 2.0-M trimethylaluminum (1.05 equiv.) in a dropwise manner, and stirred for 45 minutes at room temperature to afford intermediate 6 (not isolated). Compound 6 is added to a solution of nitrile 1 in toluene. The reaction is heated to 80° C. without stirring in a sealed tube for 18 h, cooled to ambient temperature, poured onto a silica gel column and eluted with methanol/dichloromethane to give the amidine 4.

Preparation of [$^{125}$I]AMD-1

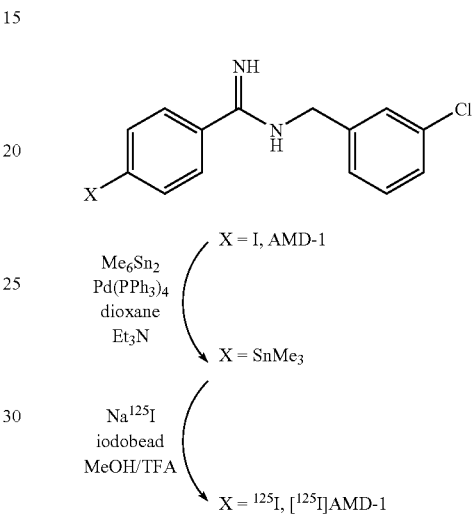

Tritiated AMD-1 was prepared by the following procedure: A mixture of AMD-1, hydrochloride salt, (5 mg, 0.012 mmol) in dioxane (0.2 mL) containing triethylamine (4 μL) was treated with hexamethylditin (5 μL), a catalytic amount of palladium catalyst and heated at 100° C. for 45 minutes. The reaction was cooled to room temperature, filtered through a glass wool plug, rinsed with methanol and concentrated in vacuo to give 10.7 mg of a brown oil. The oil was dissolved in methylene chloride and passed through a small silica column eluting with methylene chloride followed by 5% methanol/methylene chloride. Fractions containing the trimethylstannane (Rf 0.26 in 10% methanol/methylene chloride) were pooled and concentrated in vacuo to give the trimethylstannane as a clear colorless oil. This material was further purified by HPLC (C18 Econosil, 10×250 mm, 20 minute linear gradient, 30% MeCN:70% H$_2$O (0.1% TFA) to 90% MeCN, 3 mL/min, 254 nm, retention time 15 minutes) to give the trimethylstannane.

A Na$^{125}$I shipping vial (10 mCi, Amersham) was charged with a stir bar, an iodobead, 50 μL of methanol and stirred five minutes at room temperature. A solution of the trimethylstannane (0.1 mg) in 50 μL of methanol containing 5 μL of trifluoroacetic acid was added and the reaction was stirred for five minutes. The reaction was quenched with 50 μL of ammonium hydroxide and purified by HPLC (C18 Vydac protein and peptide column, 4.6×250 mm, 20 minute linear gradient, 30% MeCN:70% H$_2$O (0.1% TFA) to 90% MeCN, 1 mL/min, retention time 11 minutes). Fractions containing the radioactive product were pooled and concentrated in vacuo to give 989 μCi of [$^{125}$I]AMD-1 with a specific activity of 898 Ci/mmol as measured by UV absorbance at 272 nm.

Synthesis of Tritiated AMD-2

Tritiated AMD-2 was prepared by the following procedure: The phenol of AMD-2 (2 mg, 0.008 mmol) dissolved in dimethylformamide (0.6 mL) and potassium carbonate (1.2 mg) for 1 h. High specific activity tritiated methyl iodide (50 mCi, 0.0006 mmol, in toluene 1 mL, American Radiolabeled Chemicals) was added at room temperature and stirred for 2 hours. The reaction mixture was filtered using a Whatman PTFE 0.45 µm syringeless filter device to remove any insoluble potassium carbonate, washed with Abs. ethanol (2 mL, Pharmco), and the combined filtrates were concentrated to dryness at room temperature using a rotary evaporator; this also removed any unreacted tritiated methyl iodide. The residue was purified by HPLC chromatography on a Phenomenx Luna C8 semi-prep column (Luna 5 micro C8(2), 250×10.0 mm) using a gradient system of 20/80 acetonitrile/water with 0.1% trifluoroacetic acid to 100% acetonitrile with 0.1% trifluoroacetic acid in 20 min. Total activity of the product was 8 mCi. Further purification was effected by absorption onto a Waters C-18 Sep-Pak column (Waters Sep-Pak PLUS C18) and elution with water followed by absolute ethanol. The product was diluted with absolute ethanol (10 mL) before submission for final analysis.

The compounds of this invention exhibit $IC_{50}$'s of less than 50 µM in the FLIPR and binding assays. Thus, the compounds and pharmaceutical compositions of this invention have been found to exhibit biological activity as NMDA NR2B antagonists. Advantageously, the $IC_{50}$'s should be less than 1 µM in the FLIPR and binding assays. Even more advantageously, the $IC_{50}$'s should be less than 0.1 µM in the FLIPR and binding assays. Accordingly, another aspect of the invention is the treatment of pain, migraine, depression, anxiety, schizophrenia, Parkinson's disease, or stroke—maladies that are amenable to amelioration through inhibition of NMDA NR2B receptors—by the administration of an effective amount of the compounds of this invention. Further, another aspect of the invention is the treatment of glaucoma and tinitis—maladies that are also amenable to amelioration through inhibition of NMDA NR2B receptors—by the administration of an effective amount of the compounds of this invention.

The abbreviations used herein are as follows unless specified otherwise:

| | |
|---|---|
| BH₃*THF | Tetrahydrofuran/borane complex |
| BOC | t-Butoxycarbonyl |
| BOC₂O | t-Butoxycarbonyl anhydride |
| CBZ | Carbobenyloxy |
| CBZ-Cl | Carbobenzyl chloride |
| DCM | Dichloromethane |
| DIPEA | Diisopropylethylamine |
| DMF | N,N-Dimethylformamide |
| DMF-DMA | Dimethylformamide-Dimethylacetal |
| DMSO | Dimethylsulfoxide |
| EDC | 3-Ethyl-3-(3-dimethylaminopropyl)carbodiimide hydrochloride |
| h | hours |
| HOAt | 1-Hydroxy-7-azabenzotriazole |
| IPA | Isopropanol |
| mCPBA | meta Chloroperbenzoic acid |
| min | minutes |
| NMR | nuclear magnetic resonance |
| r.t. or rt | room temperature |
| sat. | saturated |
| TEA | Triethylamine |
| TFA | Trifluoroacetic acid |
| THF | Tetrahydrofuran |

The following examples are provided to more fully illustrate the present invention, and are not to be construed as limiting the scope of the claims in any manner.

EXAMPLES

The compounds of this invention can be prepared by procedures shown below.

Intermediates:

Intermediate 1a:

Carbonic acid 2,5-dioxo-pyrrolidin-1-yl ester 4-methyl-benzyl ester

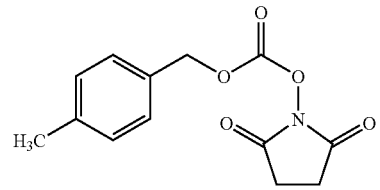

Disuccinimidyl carbonate (5.03 g, 19.65 mmol) in 30 mL MeCN and 30 mL DCM was treated with 4-methylbenzyl alcohol (2.4 g, 19.6 mmol) followed by DMAP (1.20 g, 9.82 mmol). The resulting cloudy reaction mixture was stirred overnight at rt, poured into 100 mL water, and partitioned. The organic layer was dried over anhydrous sodium sulfate and the solvent evaporated. The solid thus obtained was stirred with approx. 25 mL ether, filtered, and the resulting product was washed with a small volume of ether and dried.

Ref: *Chem. Pharm. Bull.*, 38(1):110–115(1990).

The following compounds were similarly prepared in the manner described above for INTERMEDIATE 1a:

Intermediate 1b:

Carbonic acid 2,5-dioxo-pyrrolidin-1-yl ester 4-chloro-benzyl ester

Intermediate 1c:

Carbonic acid 2,5-dioxo-pyrrolidin-1-yl ester 4-fluoro-benzyl ester

Intermediate 1d:

Carbonic acid 2,5-dioxo-pyrrolidin-1-yl ester 4-ethyl-benzyl ester

Intermediate 1e:

Carbonic acid 2,5-dioxo-pyrrolidin-1-yl ester 4-isopropyl-benzyl ester

Utilizing the carbonic acid derivatives described above as Intermediates 1a–1e, and following the procedure described below in EXAMPLE 15, step 1, the following INTERMEDIATES 2a–2e were obtained:

Intermediate 2a:

4-Methylbenzyl 4-(aminomethyl)piperidine-1-carboxylate

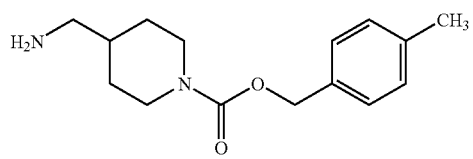

Intermediate 2b:

4-Chlorobenzyl 4-(aminomethyl)piperidine-1-carboxylate

Intermediate 2c:

4-Fluorobenzyl 4-(aminomethyl)piperidine-1-carboxylate

Intermediate 2d:

4-Ethylbenzyl 4-(aminomethyl)piperidine-1-carboxylate

Intermediate 2e:

4-Isopropylbenzyl 4-(aminomethyl)piperidine-1-carboxylate

The carboxylic acids used in the coupling steps were either commercially available or prepared according to the following references:

| Structure | Name | Reference |
|---|---|---|
| 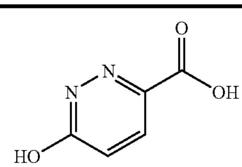 | 6-Hydroxy-pyridazine-3-carboxylic acid | M. Morishita, Chem. Pharm. Bull., 42: 371(1994). |
| 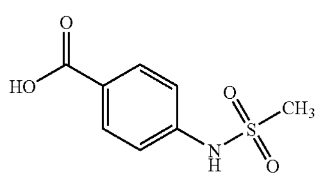 | 4-Methanesulfonylamino-benzoic acid | L. Exner, Collect Czech Chem. Comm, 35: 1371–1374(1970). |
| 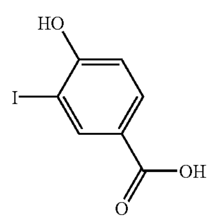 | 4-Hydroxy-3-iodo-benzoic acid | L. C. King, et al., J. Amer. Chem. Soc., 67: 2089(1945). |
| 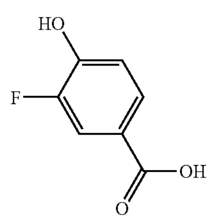 | 3-Fluoro-4-hydroxy-benzoic acid | J. Minor et al., J. Org. Chem., (1952), 17, 1425. |
| 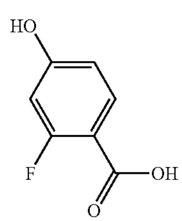 | 2-Fluoro-4-hydroxy-benzoic acid | G. Gray et al., Mol. Cryst. Liq. Cryst., 67: 1–24(1981). |

| Structure | Name | Reference |
|---|---|---|
| 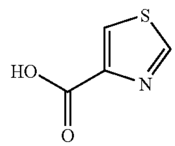 | Thiazole-4-carboxylic acid | H. Erlenmeyer et al., Helv. Chim. Acta., 28: 362(1945). |
| 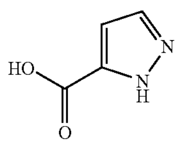 | 2H-Pyrazole-3-carboxylic acid | Sokolov et al., J. Gen. Chem. USSR (Eng.) 52: 2291(1982). |
| 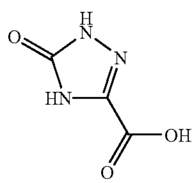 | 5-Oxo-4,5-dihydro-1H-[1,2,4]triazole-3-carboxylic acid | Gehlen Ann (1952) 577, 237–241. |
| 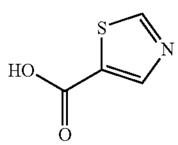 | Thiazole-5-carboxylic acid | H. Erlenmeyer et al., Helv. Chim. Acta., 30: 1865(1947). |
| 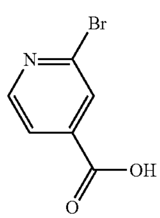 | 2-Bromo-isonicotinic acid | A. Campbell et al., Austral. J. Chem., 24: 377(1971). |
| 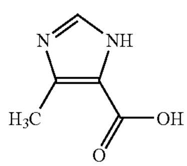 | 5-Methyl-3H-imidazole-4-carboxylic acid | G. Wellman et al., Synthesis 356(1984). |
| 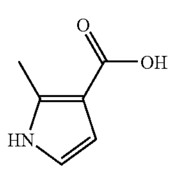 | 2-Methyl-1H-pyrrole-3-carboxylic acid | E. Benary, Chemische Berichte, 44: 493(1911). |
| 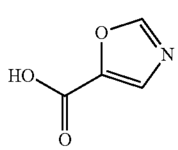 | Oxazole-5-carboxylic acid | U.S. Pat. No. 4,785,012 |
| 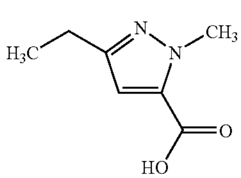 | 5-Ethyl-2-methyl-2H-pyrazole-3-carboxylic acid | H. A. DeWald et al., J. Med. Chem., 16: 1346(1973). |

-continued

| Structure | Name | Reference |
|---|---|---|
| 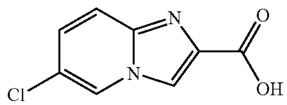 | 6-Chloro-imidazo[1,2-a]pyridine-2-carboxylic acid | WP 96/25414 |
| 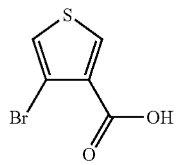 | 4-Bromo-thiophene-3-carboxylic acid | Tserng, K. et al., J. Org. Chem., 40: 172(1975). |
| 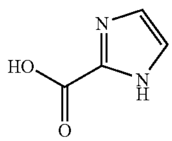 | 1H-Imidazole-2-carboxylic acid | Galeazzi, E. et al., J. Org. Chem., 60: 1090(1995). |
| 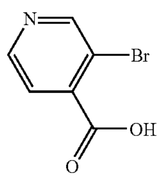 | 3-Bromo-isonicotinic acid | J. Dejardin et al., Bull. Soc. Chim. Fr., 530(1976). |
| 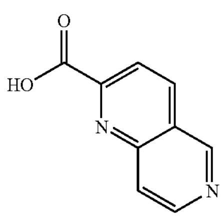 | [1,6]Naphthyridine-2-carboxylic acid | L. Chan et al., J. Med. Chem., 42: 3023(1999). |
| 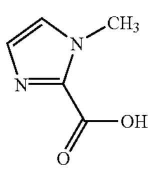 | 1-Methyl-1H-imidazole-2-carboxylic acid | Shirley, D. A. et al., J. Amer. Chem. Soc., 79: 4922(1957). |
| 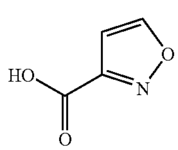 | Isoxazole-3-carboxylic acid | R. Cramer et al., J. Org. Chem., 26: 2976(1961). |
| 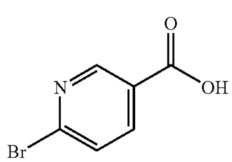 | 6-Bromo-nicotinic acid | H. H. Bradlow et al., J. Org. Chem., 14: 509(1949). |
| 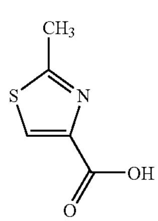 | 2-Methyl-thiazole-4-carboxylic acid | E. Jones et al., J. Chem. Soc., 87(1946). |

-continued

| Structure | Name | Reference |
|---|---|---|
| 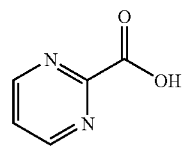 | Pyrimidine-2-carboxylic acid | A. Holland, Chem. Ind. (London), 786(1954). |
| 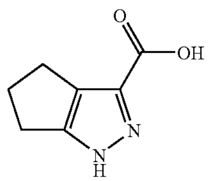 | 1,4,5,6-Tetrahydro-cyclopentapyrazole-3-carboxylic acid | N. Auwers, Justus Liebigs Annalen der Chemie, 536: 97–109(1938). |
| 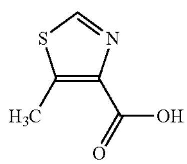 | 5-Methyl-thiazole-4-carboxylic acid | G. D. Hartman et al., Synthesis, 681(1976). |
| 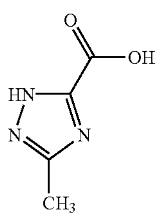 | 5-Methyl-2H-[1,2,4]triazole-3-carboxylic acid | J. Dost, Z. Chem., 26: 203(1986). |
| 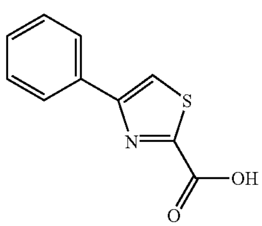 | 4-Phenyl-thiazole-2-carboxylic acid | R. Canas et al., Ann. Rev. Soc. Esp. Fis. Quim., 50: 609–614(1954). |
| 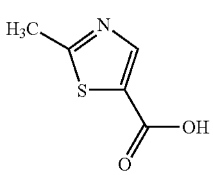 | 2-Methyl-thiazole-5-carboxylic acid | A. Schöberl et al., Ber, 73: 1240(1940). |
| 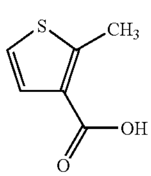 | 2-Methyl-thiophene-3-carboxylic acid | E. Bullock et al., Can. J. Chem., 55: 895(1977). |
| 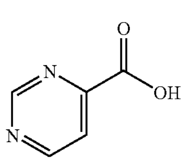 | Pyrimidine-4-carboxylic acid | G. A. Archer et al., J. Med. Chem. 16: 1312(1977). |

-continued

| Structure | Name | Reference |
|---|---|---|
| 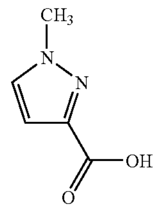 | 1-Methyl-1H-pyrazole-3-carboxylic acid | C. Wijnberger et al., J. Heterocycl. Chem., 6: 545(1969). |
| 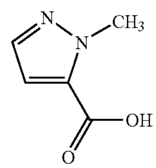 | 2-Methyl-2H-pyrazole-3-carboxylic acid | C. Wijnberger et al., J. Heterocycl. Chem., 6: 545(1969). |
| 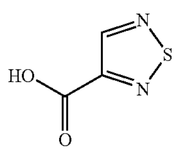 | [1,2,5]Thiadiazole-3-carboxylic acid | L. M. Weinstock et al., Adv. Heterocycl. Chem., 9: 107(1968). |
| 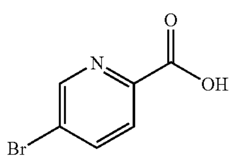 | 5-Bromo-pyridine-2-carboxylic acid | L. W. Deady et al., Austral. J. Chem., 24: 385(1971). |
| 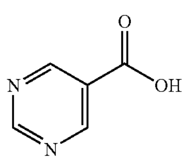 | Pyrimidine-5-carboxylic acid | H. Bredereck et al., Liebigs Ann. Chem,. (1972), 766, 73(1972). |
| 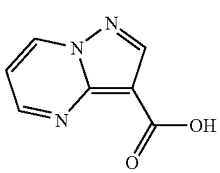 | Pyrazolo[1,5-a]pyrimidine-3-carboxylic acid | Khan et al., J. Heterocycl. Chem., 7: 247(1970). |
| 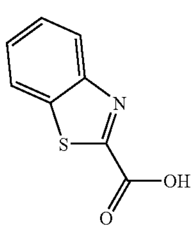 | Benzothiazole-2-carboxylic acid | A. Buraway et al., J. Chem. Soc., 648(1956). |
| 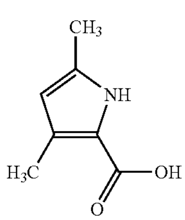 | 3,5-Dimethyl-1H-pyrrole-2-carboxylic acid | H. Fischer et al., Chemische Berichte, 56: 1194(1923). |

| Structure | Name | Reference |
|---|---|---|
| 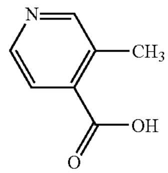 | 3-Methyl-isonicotinic acid | R.S. Miu et al., Chem. Abstract., 84: 150463(1976). |
| 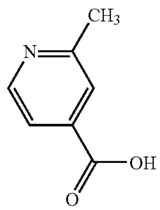 | 2-Methyl-isonicotinic acid | R. Adams et al., J. Amer. Chem. Soc., 76: 3168(1954). |
| 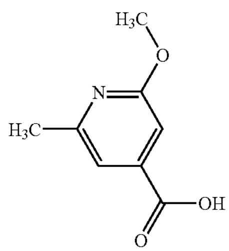 | 2-Methoxy-6-methyl-isonicotinic acid | WO 00/17163 |
| 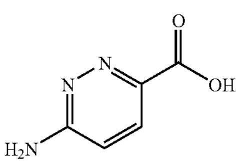 | 6-Amino-pyridazine-3-carboxylic acid | S. Mitsui, Chem. Abstract., 5275(1959). |
| 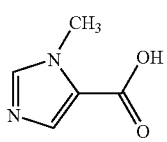 | 3-methyl-3H-imidazole-4-carboxylic acid | EP 0306868 |

Example 1

4-[(4-Hydroxy-benzoylamino)-methyl]-piperidine-1-carboxylic acid benzyl ester

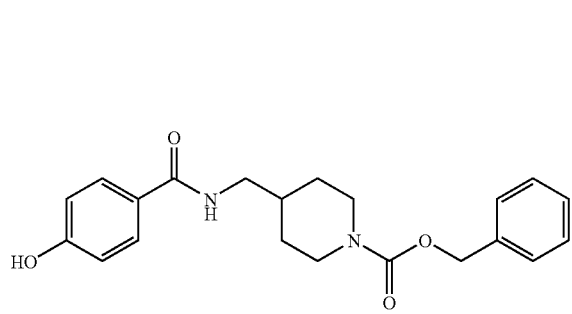

Step 1:

Preparation of Benzyl 4-(aminomethyl)piperidine-1-carboxylate

4-Aminomethylpiperidine (40 g, 350 mmol) and benzaldehyde (37.3 mL, 368 mmol) in toluene (600 mL) were heated to reflux under dean stark conditions for 2 h. The resulting reaction mixture was cooled to room temperature and 500 mL dichloromethane was added. The resulting solution was cooled to 5° C. and treated with N-(benzyloxycarbonyloxy)succinimide (91.7 g, 368 mmol). After 10 min, the cooling bath was removed and the reaction mixture stirred for 1 h. The solvents were evaporated and the resulting residue was stirred with 400 mL THF and 400 mL 2 M HCl for 1 h. The mixture was concentrated to remove organics and was then extracted with ether (3×300 mL). The aqueous phase was adjusted to pH14 with 50% NaOH and extracted with ethyl acetate. The organic layer was washed with water and brine, dried over anhydrous sodium sulfate, and the solvent evaporated to give benzyl 4-(aminomethyl) piperidine-1-carboxylate as an oil.

$^1$HNMR 500 MHz (δ, CDCl$_3$) δ: 7.4–7.2 (m, 5H); 5.12 (s, 2H); 4.20 (brs, 2H); 2.77 (brs, 2H); 2.58 (d, J=6.6 Hz, 2H) 1.9–1.7 (m, 2H); 1.0–1.5 (m, 5H).

Step 2:

Preparation of 4-[(4-Hydroxy-benzoylamino)-methyl]-piperidine-1-carboxylic acid benzyl ester

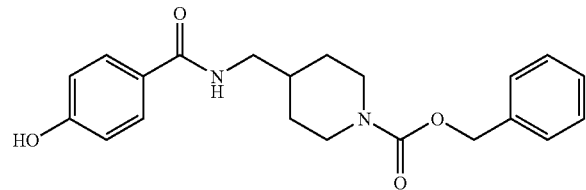

To a mixture of 4-hydroxybenzoic acid (2.5 g, 0.0182 mol), 1-hydroxybenzotriazole hydrate (3.33 g, 0.0218 mol), benzyl 4-(aminomethyl)piperidine-1-carboxylate (4.5 g, 0.0182 mol) and triethylamine (3.03 mL, 0.0218 mol) in DMF (30mL) was added 1-ethyl-3-(3-dimethylaminopropyl)carbodiimide hydrochloride (4.2 g, 0.0218 mol) and the mixture allowed to stir at rt for 18 h. The mixture was quenched into water (200 mL) and extracted with ethyl acetate (200 nL). The ethyl acetate extract was washed with 10% aqueous sodium bicarbonate (100 mL), brine (50 mL), dried over sodium sulfate, and filtered. The filtrate was concentrated in vacuo and the residue chromatographed on silica using 10–20% acetone/dichloromethane to give 6.3 g of 4-[(4-hydroxy-benzoylamino)-methyl]-piperidine-1-carboxylic acid benzyl ester as a foam. The foam was dissolved in hot isopropyl acetate (125 mL), filtered, and allowed to cool and crystallize. The reaction volume was reduced in vacuo to 50 mL, allowed to stir overnight at rt and filtered. The resulting solid was dried in vacuo (50° C.) yielding the 4-[(4-hydroxy-benzoylamino)-methyl]-piperidine-1-carboxylic acid benzyl ester.

M.P. 122–123° C. M.S(M+1): 369.

$^1$H NMR 300 MHz (δ, CDCl$_3$) δ: 7.64 (d, 2H); 7.4–7.2 (m, 5H); 6.86 (d, 2H); 6.18 (m, 1H); 5.85 (s, 1H1); 5.15 (s, 2H); 4.20 (brs, 2H); 3.35 (brs, 2H); 2.77 (brs, 2H); 1.9–1.7 (m, 3H); 1.3–1.1 (m, 2H).

Analysis Calcd. for $C_{21}H_{24}N_2O_4$: C, 68.46; H, 6.57; N, 7.60;

Found: C, 68.23; H, 6.61; N, 7.48.

The following compounds were prepared in a manner similar to that used above for the preparation of 4-[(4-hydroxy-benzoylamino)-methyl]-piperidine-1-carboxylic acid benzyl ester, using the appropriate acid in place of the 4-hydroxybenzoic acid. References or experimental procedures are shown for the preparation of non-commercially available acids. Appropriately substituted benzyl 4-(aminomethyl)piperidine-1-carboxylates were prepared in a similar manner to that described above in EXAMPLE 1, step 1, with the necessary N-(benzyloxycarbonyloxy)succinimides prepared as previously described (Chem. Pharm Bull 1990, 38(1) 110–115).

| EX. | Name | Structure | Data |
|---|---|---|---|
| 2. | 4-{[(Pyrazine-2-carbonyl)-amino]-methyl}-piperidine-1-carboxylic acid benzyl ester | 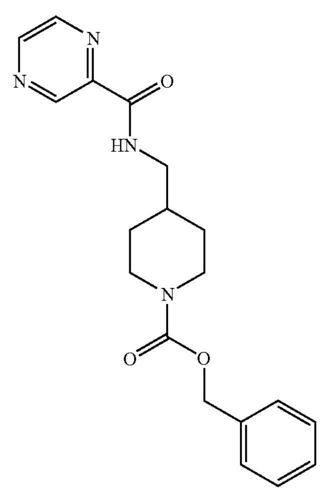 | M.S(M+1): 370 $^1$H NMR 300 MHz(δ, CDCl$_3$) δ: 12.10(brs, 1H); 8.02(d, 1H, J=2.5 Hz); 7.77(dd, 1H, J=7.7 and 2.5 Hz); 7.4–7.2(m, 5H); 6.59(d, 2H, J=7.7 Hz); 6.12(m, 1H); 5.12(s, 2H); 4.20(brs, 2H); 3.30(brs, 2H); 2.77(brs, 2H); 2.0–1.8(m, 3H); 1.3–1.1(m, 2H). |

| EX. | Name | Structure | Data |
|---|---|---|---|
| 3. | 4-{[(3-Amino-pyridine-4-carbonyl)-amino]-methyl}-piperidine-1-carboxylic acid benzyl ester | 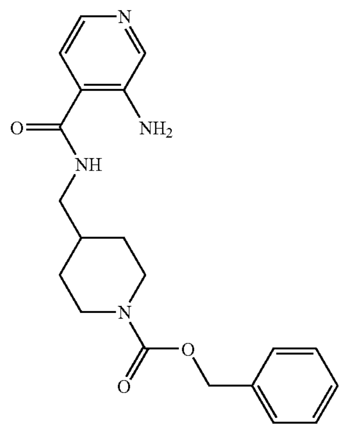 | M.S(M+1): 369 NMR(300 MHz, CDCl$_3$) δ: all broad |
| 4. | 4-{[(6-Hydroxy-pyridazine-3-carbonyl)-amino]-methyl}-piperidine-1-carboxylic acid benzyl ester | 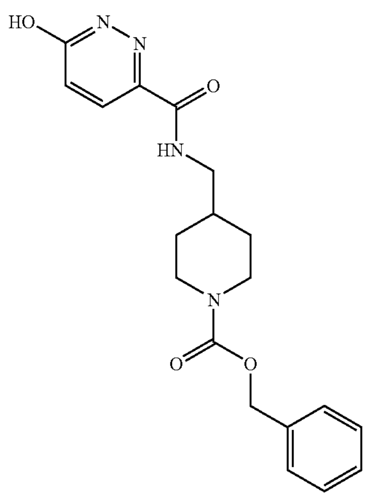 | M.S(M+1): 371 NMR(300 MHz, CDCl$_3$) δ: 11.55(brs, 1H); 8.04(d, 1H, J=9.8 Hz); 7.4–7.1(m, 5H); 7.04(d, 1H, 9.8 Hz); 5.12(s, 2H); 4.22(brs, 2H); 3.30(brs, 2H); 2.80(m, 2H); 1.8–1.6(m, 3H); 1.3–1.1(m, 2H) |
| 5. | 4-[(4-Methanesulfonylamino-benzoylamino)-methyl]-piperidine-1-carboxylic acid benzyl ester | 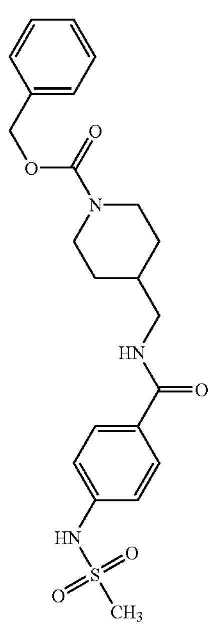 | M.S(M+1): 446 NMR (300 MHz, CDCl$_3$)) δ: 7.75(d, 2H, J=8.6 Hz); 7.4–7.2(m, 5H); 7.25(d, 2H, J=8.6 Hz); 6.95(brs, 1H); 6.25(brs, 1H); 5.12(s, 2H); 4.21(brs, 2H); 4.36(brs, 2H); 3.05(s, 3H); 2.78(brs, 2H); 1.9–1.6(m, 3H); 1.3–1.1(m, 2H). |

| EX. | Name | Structure | Data |
|---|---|---|---|
| 6. | 4-[(2,4-Dihydroxy-benzoylamino)-methyl]-piperidine-1-carboxylic acid benzyl ester | 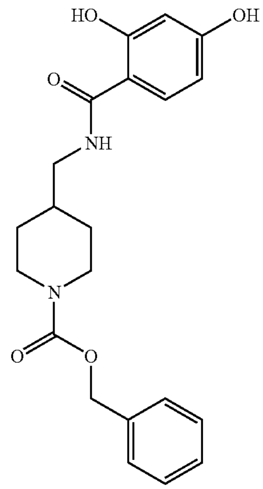 | M.S(M+1): 385 NMR (300 MHz, CDCl₃)) δ: 12.55(s, 1H); 7.5–7.3(m, 5H); 7.22(d, 1H, J=8.6 Hz); 6.41(d, 1H, J=2.5 Hz); 6.34(dd, 1H, J=8.6 and 2.5 Hz); 6.22(m, 1H); 5.13(s, 2H); 4.22(brs, 2H); 3.33(brs, 2H); 2.79(brs, 2H); 1.8–1.6(m, 3H); 1.3–1.0(m, 2H). |
| 7. | 4-[(3,4-Dihydroxy-benzoylamino)-methyl]-piperidine-1-carboxylic acid benzyl ester | 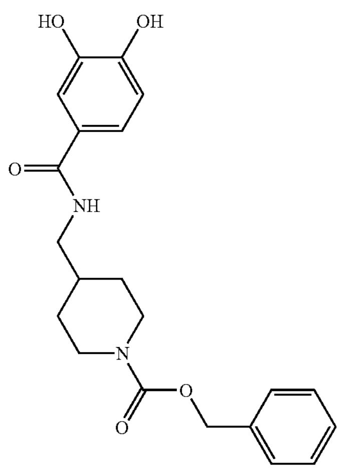 | M.S(M+1): 385 NMR (300 MHz, CDCl₃)) δ: 7.57(d, 1H, J=1.6 Hz); 7.5–7.3(m, 5H); 7.10(dd, 1H, J=8.2 and 1.6Hz); 6.86(d, 1H, J=8.2 Hz); 6.30(m, 1H); 5.12(s, 2H); 4.18(brs, 2H); 3.32(brs, 2H); 2.76(brs, 2H); 1.8–1.4(m, 3H); 1.3–1.0(m, 2H). |
| 8. | 4-[(4-Hydroxy-3-iodo-benzoylamino)-methyl]-piperidine-1-carboxylic acid benzyl ester | 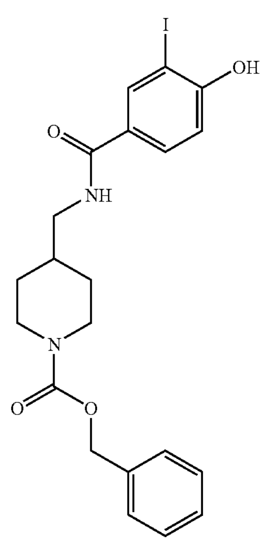 | M.S(M+1): 495 NMR(300 MHz, CDCl₃)) δ: 8.11(d, 1H, J=2.1 Hz); 7.63(dd, 1H, J=8.4 and 2.1 Hz); 7.5–7.3(m, 5H); 7.00(d, 1H, J=8.4 Hz); 6.10(m, 1H); 5.12(s, 2H); 4.21(brs, 2H); 3.33(brs, 2H); 2.78(brs, 2H); 1.8–1.6(m, 3H); 1.3–1.0(m, 2H). |

-continued

| EX. | Name | Structure | Data |
|---|---|---|---|
| 9. | 4-[(3-Fluoro-4-hydroxy-benzoylamino)-methyl]-piperidine-1-carboxylic acid benzyl ester | 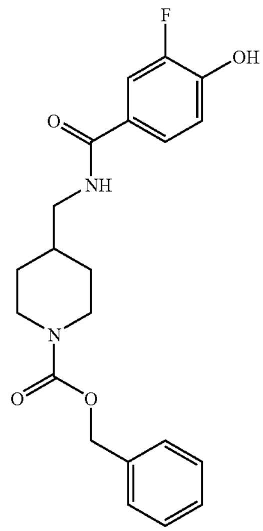 | M.S(M+1): 387 NMR(300 MHz, CDCl$_3$)) δ: 7.56(dd, 1H, J=11.0 and 1.9 Hz); 7.5–7.3(m, 6H); 7.03(t, 1H, J=8.4 Hz); 6.16(m, 1H); 5.12(s, 2H); 4.20(brs, 2H); 3.33(brs, 2H); 2.78(brs, 2H); 1.9–1.6(m, 3H); 1.3–1.0(m, 2H). |
| 10. | 4-[(2-Fluoro-4-hydroxy-benzoylamino)-methyl]-piperidine-1-carboxylic acid benzyl ester | 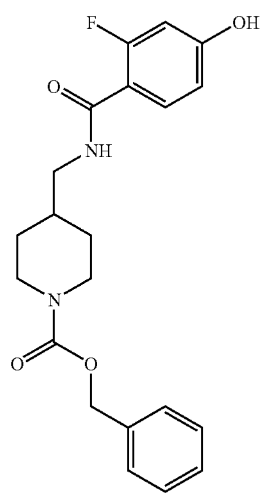 | M.S(M+1): 387 NMR (300 MHz, CDCl$_3$)) δ: 7.94(t, 1H, J=9.0 Hz); 7.5–7.2(m, 5H); 6.78(m, 1H); 7.73(dd, 1H, J=8.7 and 2.4 Hz); 6.61(dd, 1H, J=13.8 and 2.2 Hz); 5.13(s, 2H); 4.20(brs, 2H); 3.37(brs, 2H); 2.78(brs, 2H); 1.9–1.6(m, 3H); 1.3–1.0(m, 2H). |
| 11. | 4-{[(1H-Benzoimidazole-5-carbonyl)-amino]-methyl}-piperidin-1-carboxylic acid benzyl ester | 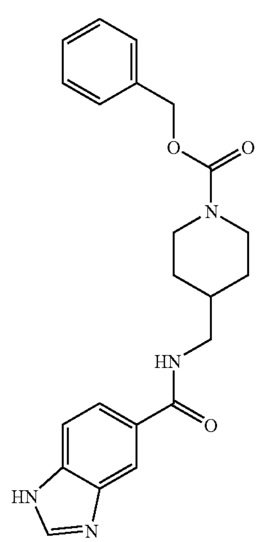 | MS Exact mass: 393.1940. Experimental for C$_{21}$H$_{24}$N$_4$O$_3$: 393.1921. $^1$H NMR (400 MHz, δ, CDCl$_3$): 8.13–8.11(m, 2H), 7.67(brs, 2H), 7.35–7.28(m, 5H), 6.52(d, J=5.98 Hz, 2H), 5.13(s, 2H), 4.21(brs, 2H), 3.39(brs, 2H), 2.79(brs, 2H), 1.90–1.78(m, 1H), 1.78–1.62(m, 2H), 1.29–1.16(m, 2H). |

-continued

| EX. | Name | Structure | Data |
|---|---|---|---|
| 12. | 4-{[(1H-Benzotriazole-5-carbonyl)-amino]-methyl}-piperidine-1-carboxylic acid benzyl ester | 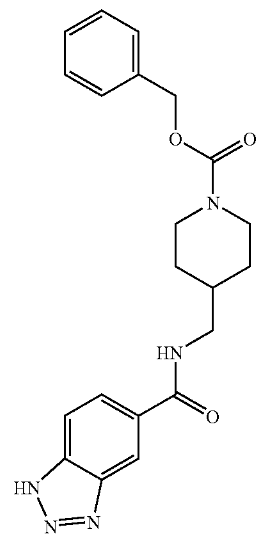 | MS Exact mass: 394.1896. Experimental for $C_{21}H_{23}N_5O_3$: 394.1874. $^1$H NMR (400 MHz, δ, CDCl$_3$): 8.37(s, 1H), 7.78(d, J=8.68 Hz, 2H), 7.66–7.64(m, 2H), 7.31–7.22(m, 5H), 6.65(vbs, 2H), 5.09(s, 2H), 4.13(brd, J=11.06, 2H), 3.35(brs, 2H), 2.71(brs, 2H), 1.90–1.77(m, 1H), 1.71(brd, J=11.61Hz, 2H), 1.26–1.12(m, 2H). |
| 13. | 4-[(4-Cyano-benzoylamino)-methyl]-piperidine-1-carboxylic acid benzyl ester | 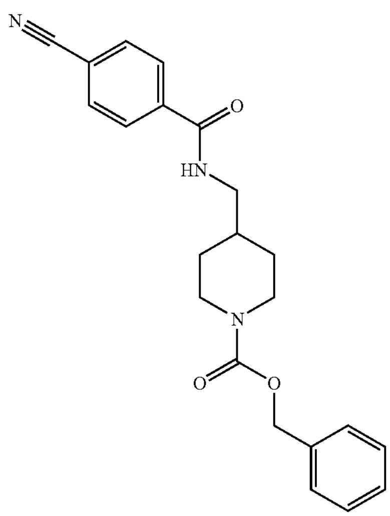 | $^1$H NMR(δ, CDCl$_3$): 7.86(d, J=8.05 Hz, 2H), 7.74(d, J=8.05 Hz, 2H), 7.25–7.4(m, 5H), 6.31(brt, J=5.61 Hz, 1H), 5.12(s, 2H), 4.22(brs, 2H), 3.37(brs, 2H), 2.79(brs, 2H), 1.7–1.9(m, 3H), 1.23(m, 2H). |
| 14. | 4-{[(6-Hydroxy-pyridine-3-carbonyl)-amino]-methyl}-piperidine-1-carboxylic acid 4-methyl-benzyl ester | 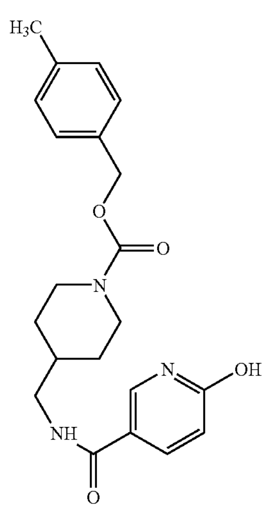 | M.S(M+1): 384 NMR(300 MHz, CDCl$_3$) δ: 12.20(brs, 1H); 8.02(d, 1H, J=2.5 Hz); 7.75(dd, 1H, J=9.6 and 2.5 Hz); 7.24(d, 2H, J=7.9 Hz); 7.15(d, 2H, J=7.9 Hz); 6.56(d, 1H, J=9.6 Hz); 6.20(m, 1H); 5.07(s, 2H); 4.20(brs, 2H); 3.30(brs, 2H); 2.35(brs, 2H); 1.8–1.6(m, 3H); 1.3–1.1(m, 2H). |

-continued

| EX. | Name | Structure | Data |
|---|---|---|---|
| 15. | 4-{[(6-Hydroxy-pyridazine-3-carbonyl)-amino]-methyl}-piperidine-1-carboxylic acid 4-methyl-benzyl ester | 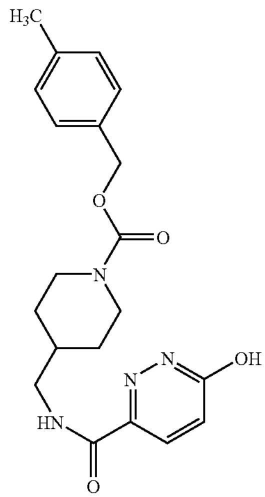 | M.S(M+1): 385 NMR(300 MHz, CDCl$_3$)) δ: 11.9(s, 1H); 8.05(d, 1H, J=9.9 Hz); 7.25(d, 2H, J=7.9 Hz); 7.16(d, 2H, J=7.9 Hz); 7.04(d, 1H, J=9.9 Hz); 5.08(s, 2H); 4.20(brs, 2H); 3.32(brs, 2H); 2.76(m, 2H); 2.35(s, 3H); 1.8–1.6(m, 3H); 1.3–1.1(m, 2H). |
| 16. | 4-{[(6-Hydroxy-pyridine-3-carbonyl)-amino]-methyl}-piperidine-1-carboxylic acid 4-fluoro-benzyl ester | 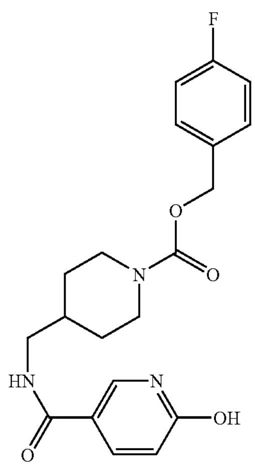 | M.S(M+1): 388 NMR(300 MHz, CDCl$_3$)) δ: 12.2(s, 1H); 8.03(d, 1H, J=2.6 Hz); 7.77(dd, 1H, J=9.6 and 2.6 Hz); 7.34(m, 2H); 7.03(t, 2H, J=8.6 Hz); 6.57(d, 1H, J=9.6 Hz); 5.07(s, 2H); 4.20(brs, 2H); 3.31(brs, 2H); 2.76(brs, 2H); 2.35(s, 3H); 1.8–1.6(m, 3H); 1.3–1.1(m, 2H). |
| 17. | 4-{[(6-Hydroxy-pyridine-3-carbonyl)-amino]-methyl}-piperidine-1-carboxylic acid 4-chloro-benzyl ester | 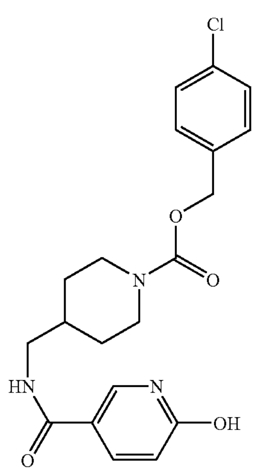 | M.S(M+1): 404 NMR(300 MHz, CDCl$_3$)) δ: 11.8(brs, 1H); 8.02(d, 1H, J=2.4 Hz); 7.74(dd, 1H, J=9.6 and 2.4 Hz); 7.4–7.2(m, 4H); 6.58(d, 1H, J=9.6 Hz); 6.03(m, 1H); 5.08(s, 2H); 4.20(brs, 2H); 3.31(brs, 2H); 2.78(brs, 2H); 1.8–1.4(m, 3H); 1.3–1.1(m, 2H). |

-continued

| EX. | Name | Structure | Data |
|---|---|---|---|
| 18. | 4-{[(6-Hydroxy-pyridine-3-carbonyl)-amino]-methyl}-piperidine-1-carboxylic acid indan-2-yl ester | 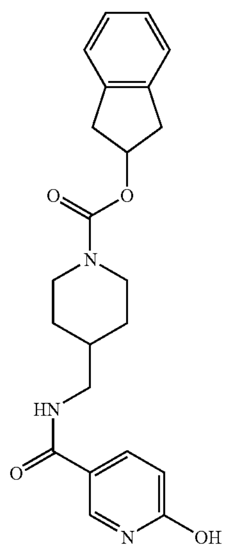 | M.S(M+1): 396 NMR(300 MHz, CDCl$_3$)) δ: 12.0(brs, 1H); 8.01(d, 1H, J=2.5 Hz); 7.74(dd, 1H, J=9.6 and 2.5 Hz); 7.3–7.1(m, 4H); 6.57(d, 1H, J=9.6 Hz); 6.04(m, 1H); 5.46(m, 1H); 4.3–4.1(m, 2H); 3.32(m, 4H); 3.04(d, 1H, J=3.2 Hz); 3.00(d, 1H, J=3.2Hz); 2.72(m, 2H); 1.8–1.6(m, 3H); 1.3–1.0(m,2H). |
| 19. | 4-[(4-Hydroxy-benzoylamino)-methyl]-piperidine-1-carboxylic acid 4-fluoro-benzyl ester | 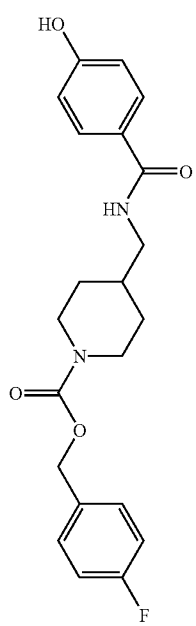 | M.S(M+1): 387 NMR (300 MHz, CDCl$_3$)) δ: 7.65(d, 2H, J=8.6 Hz); 7.33(m, 2H); 7.03(t, 2H, J=8.6 Hz); 6.86(d, 2H, J=8.6 Hz); 6.64(s, 1H); 6.22(m, 1H); 5.08(s, 2H); 4.14(brs, 2H); 3.33(brs, 2H); 2.67(brs, 2H); 1.8–1.6(m, 3H); 1.3–1.0(m, 2H). |

-continued

| EX. | Name | Structure | Data |
|---|---|---|---|
| 20. | 4-[(4-Hydroxy-benzoylamino)-methyl]-piperidine-1-carboxylic acid 4-chloro-benzyl ester | 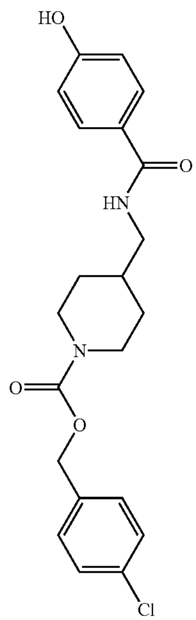 | M.S(M+1): 403 NMR(300 MHz, CDCl$_3$)) δ: 7.66(d, 2H, J=8.6 Hz); 7.30(m, 4H); 6.86(d, 2H, J=8.6 Hz); 6.33(s, 1H); 6.22(m, 1H); 5.08(s, 2H); 4.14(brs, 2H); 3.33(brs, 2H); 2.77(brs, 2H); 1.8–1.6(m, 3H); 1.3–1.0(m, 2H). |
| 21. | 4-[(4-Hydroxy-benzoylamino)-methyl]-piperidine-1-carboxylic acid indan-2-yl ester | 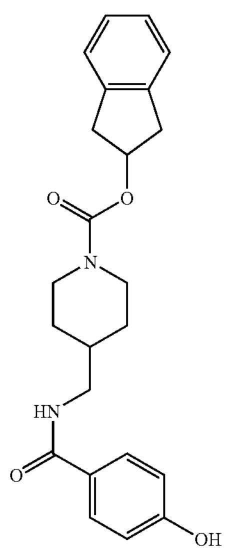 | M.S(M+1): 395 NMR (300 MHz, CDCl$_3$)) δ: 7.63(d, 2H, J=8.6 Hz); 7.3–7.1(m, 4H); 6.85(d, 2H, J=8.6 Hz); 6.27(m, 1H); 5.46(m, 1H); 4.3–3.8(m, 2H); 3.3(dd, 4H, J=16.9 and 6.6 Hz); 3.0(dd, 2H, J=7.0 and 3.2 Hz); 2.69(dt, 2H, J=13.2 and 2.7 Hz); 1.8–1.6(m, 3H); 1.3–1.0(m, 2H). |

-continued

| EX. | Name | Structure | Data |
|---|---|---|---|
| 22. | 4-[(4-Hydroxy-benzoylamino)-methyl]-piperidine-1-carboxylic acid 4-methyl-benzyl ester | 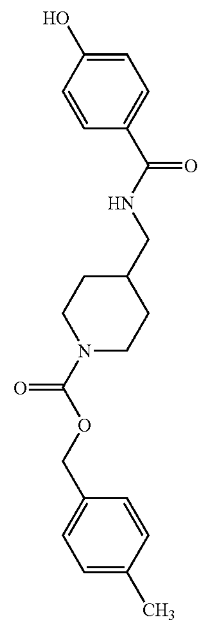 | M.S(M+1): 383 NMR(300 MHz, CDCl$_3$)) δ: 7.64(d, 2H, J=8.8 Hz); 7.24(d, 1H, J=8.0 Hz); 7.15(d, 1H, J=8.0 Hz); 6.86(d, 2H, J=8.8 Hz); 6.24(m, 1H); 5.08(s, 2H); 4.18(brs, 2H); 3.32(brs, 2H); 2.75(brs, 2H); 2.34(s, 3H); 1.8–1.6(m, 3H); 1.3–1.0(m, 2H). |
| 23. | 4-{[(Pyridine-4-carbonyl)-amino]-methyl}-piperidine-1-carboxylic acid 4-methyl-benzyl ester | 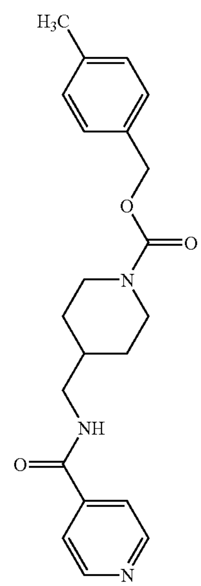 | $^1$H NMR(δ, CDCl$_3$): 8.75(d, J=5.86Hz, 2H), 7.60(d, J=4.89 Hz, 2H), 7.25(d, J=8.05 Hz, 2H), 7.16(d, J=8.05 Hz, 2H), 6.32(brt, 1H), 5.08(s, 2H), 4.22(brs, 2H), 3.37(brs, 2H), 2.77(brs, 2H), 2.35(s, 3H), 1.7–1.9(m, 3H), 1.21(m, 2H). |

| EX. | Name | Structure | Data |
|---|---|---|---|
| 24. | 4-{[(Pyridine-4-carbonyl)-amino]-methyl}-piperidine-1-carboxylic acid 4-chloro-benzyl ester | 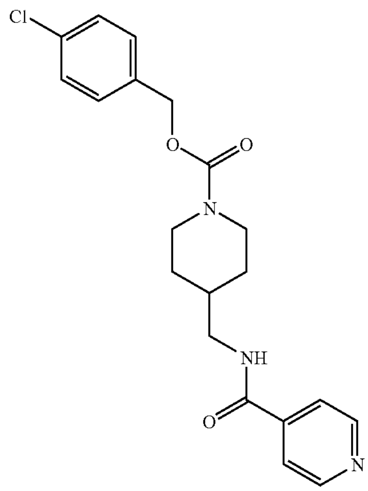 | ¹H NMR (δ, CDCl₃): 8.75(d, J=4.64 Hz, 2H), 7.60(d, J=5.13 Hz, 2H), 7.32(d, J=8.05 Hz, 2H), 7.28(d, J=8.55 Hz, 2H), 6.35(brt, 1H), 5.08(s, 2H), 4.22(brd, 2H), 3.37(brd, 2H), 2.79(brs, 2H), 1.7–1.9(m, 3H), 1.23(m, 2H). |
| 25. | 4-{[(Pyridine-4-carbonyl)-amino]-methyl}-piperidine-1-carboxylic acid 4-fluoro-benzyl ester | 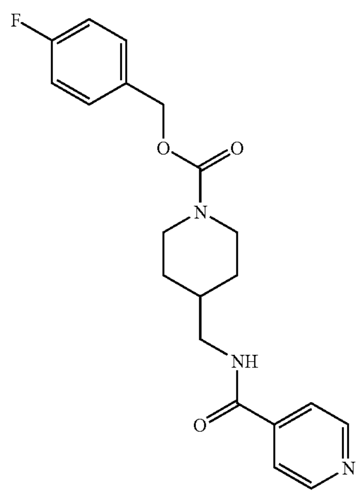 | ¹H NMR (δ, CDCl₃): 8.75(d, J=5.61 Hz, 2H), 7.60(d, J=6.11 Hz, 2H), 7.28(dd, J=5.62, 8.3 Hz, 2H), 7.04(t, J=8.8 Hz, 2H), 6.33(brt, 1H), 5.08(s, 2H), 4.23(brd, 2H), 3.38(brd, 2H), 2.78(brs, 2H), 1.7–1.9(m, 3H), 1.22(m, 2H). |
| 26. | 4-[(4-Hydroxy-3-methyl-benzoylamino)-methyl]-piperidine-1-carboxylic acid benzyl ester | 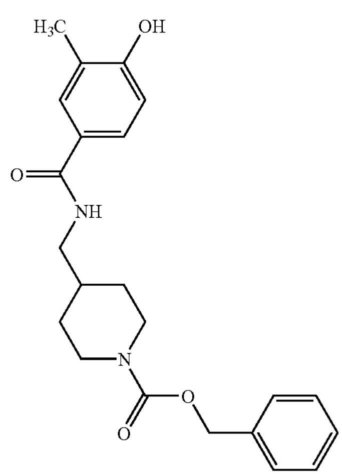 | ¹H NMR (δ, CDCl₃): 7.56(brs, 1H), 7.49(dd, J=2.2, 8.3 Hz, 1H), 7.25–7.4(m, 5H), 6.79(d, J=8.3 Hz, 1H), 6.13(brt, 1H), 5.55(s, 1H), 5.12(s, 2H), 4.22(brs, 2H), 3.33(brs, 2H), 2.78(brs, 2H), 2.28(s, 3H), 1.7–1.9(m, 3H), 1.23(m, 2H). |

-continued

| EX. | Name | Structure | Data |
|---|---|---|---|
| 27. | 4-[(3-Chloro-4-hydroxy-benzoylamino)-methyl]-piperidine-1-carboxylic acid benzyl ester | 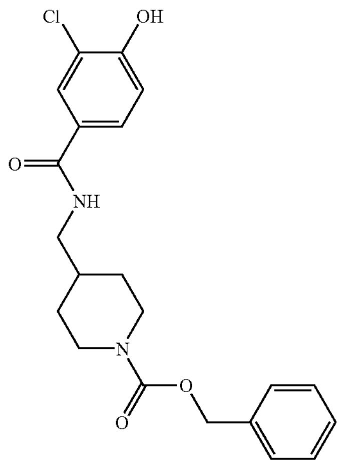 | $^1$H NMR ($\delta$, CDCl$_3$): 7.80(d, J=2.2 Hz, 1H), 7.57(dd, J=2.2, 8.55 Hz, 1H), 7.25–7.4(m, 5H), 7.05(d, J=8.55 Hz, 1H), 6.13(brt, 1H), 6.04(brs, 1H), 5.12(s, 2H), 4.22(brs, 2H), 3.33(brs, 2H), 2.78(brs, 2H), 1.7–1.9(m, 3H), 1.23(m, 2H). |
| 28. | 4-{[(Thiophene-3-carbonyl)-amino]-methyl}-piperidine-1-carboxylic acid benzyl ester | 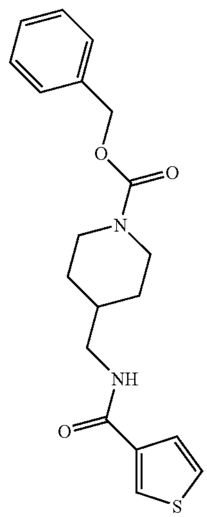 | $^1$H NMR ($\delta$, CDCl$_3$): 7.84(s, 1H), 7.41–7.27(m, 7H), 6.24(brt, 1H), 5.06(s, 2H), 4.19(brd, 2H), 3.30(brs, 2H), 2.77(brt, 2H), 1.9–1.7(m, 3H), 1.18(m, 2H). |
| 29. | 4-{[(Thiazole-4-carbonyl)-amino]-methyl}-piperidine-1-carboxylic acid benzyl ester | 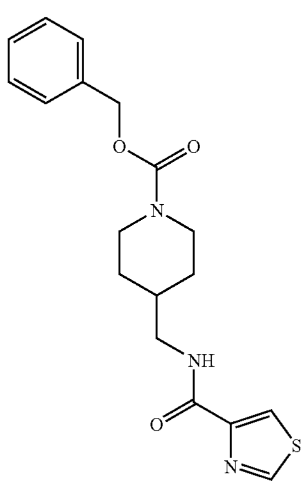 | $^1$H NMR ($\delta$, CDCl$_3$): 8.74(d, 1H), 8.17(d, 1H), 7.50(brt, 1H), 7.26(m, 5H), 5.11(s, 2H), 4.19(brs, 2H), 3.35(brs, 2H), 2.78(brt, 2H), 1.9–1.7(m, 3H), 1.21(m, 2H). |

-continued

| EX. | Name | Structure | Data |
|---|---|---|---|
| 30. | 4-{[(2H-Pyrazole-3-carbonyl)-amino]-methyl}-piperidine-1-carboxylic acid benzyl ester | 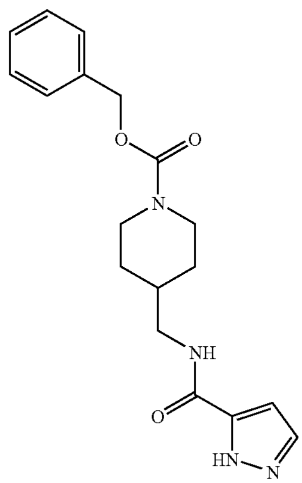 | $^1$H NMR (δ, CDCl$_3$): 7.59(d, J=1.3 Hz, 1H), 7.36–7.28(m, 5H), 7.07(brt, 1H), 6.82(d, J=1.3 Hz, 1H), 5.13(s, 2H), 4.20(brs, 2H), 3.37(brs, 2H), 2.78(brt, 2H), 1.9–1.7(m, 3H), 1.21(m, 2H). |
| 31. | 4-{[(5-Oxo-4,5-dihydro-1H-[1,2,4]triazole-3-carbonyl)-amino]-methyl}-piperidine-1-carboxylic acid benzyl ester | 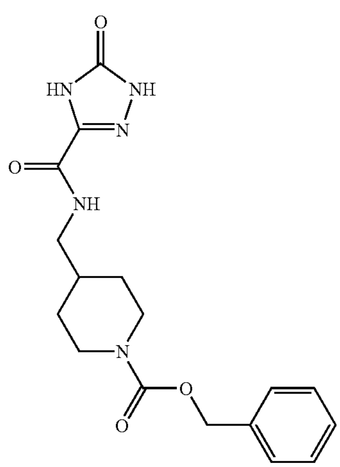 | $^1$H NMR (500 MHz, δ, CDCl$_3$): 11.55(s, br, 2H), 7.45–7.30(m, 6H), 5.12(s, 2H), 4.19(s, 2H), 3.25(m, 2H), 2.75(m, 2H), 1.85–1.65(m, 3H), 1.15(m, 2H). |
| 32. | 4-{[(2H-[1,2,4]Triazole-3-carbonyl)-amino]-methyl}-piperidine-1-carboxylic acid benzyl ester | 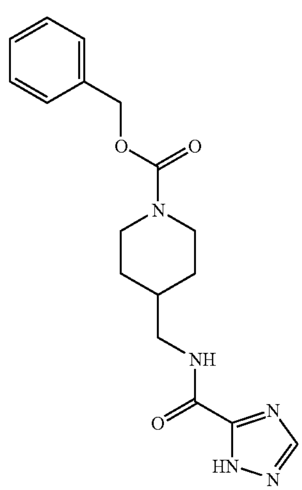 | $^1$H NMR (500 MHz, δ, DMSO-d$_6$): 14.60(s, br, 1H), 8.80–8.30(s, br, 2H), 7.40–7.30(m, 5H), 5.07(s, 2H), 3.98(d, 2H), 3.15(t, 2H), 2.77(m, br, 2H), 1.77(m, 1H), 1.63(d, 2H), 1.05(m, 2H). |

| EX. | Name | Structure | Data |
|---|---|---|---|
| 33. | 4-{[(Thiazole-5-carbonyl)-amino]-methyl}-piperidine-1-carboxylic acid benzyl ester | 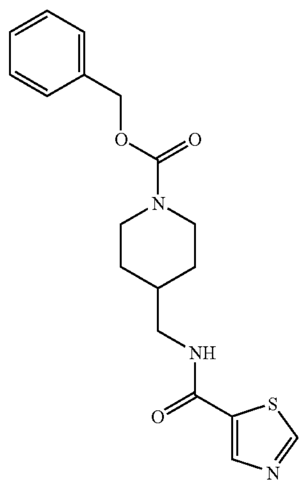 | ¹H NMR (500 MHz, δ, DMSO-d₆): 9.21(s, 1H), 8.74(m, 1H), 8.46(s, 1H), 7.40–7.28(m, 5H), 5.09(s, 2H), 4.00(d, 2H), 3.12(t, 2H), 2.90–2.70(m, br, 2H), 1.80–1.65(m, 3H), 1.05(m, 2H). |
| 34. | 4-{[(1H-Pyrazole-4-carbonyl)-amino]-methyl}-piperidine-1-carboxylic acid benzyl ester | 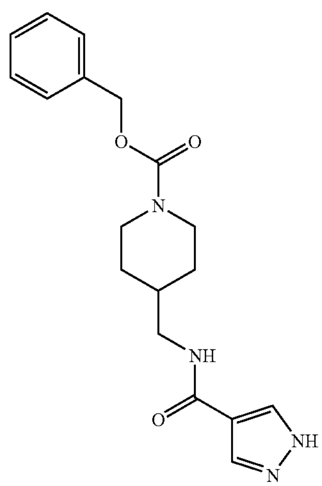 | ¹H NMR (500 MHz, δ, CD₃OD): 8.2–7.8(s, br, 2H), 7.36–7.25(m, 5H), 5.11(s, 2H), 4.15(m, 2H), 3.23(m, 2H), 2.90–2.75(s, br, 2H), 1.90–1.70(m, 3H), 1.20–1.10(m, 2H). |
| 35. | 4-{[(2-Bromo-pyridine-4-carbonyl)-amino]-methyl}-piperidine-1-carboxylic acid benzyl ester | 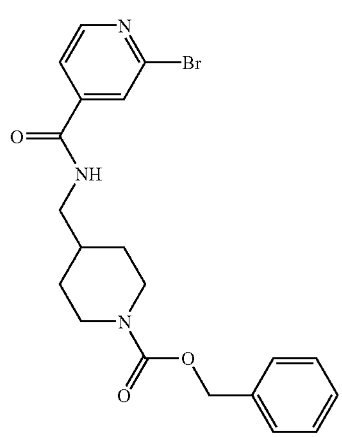 | ¹H NMR (500 MHz, δ, DMSO-d₆): 8.88(m, 1H), 8.54(d, 1H), 7.99(s, 1H), 7.78(d, 1H), 7.38–7.28(m, 5H), 5.07(s, 1H), 4.00(d, 2H), 3.16(t, 2H), 2.90–2.70(m, 2H), 1.80–1.65(m, 3H), 1.09(m, 2H). |

-continued

| EX. | Name | Structure | Data |
|---|---|---|---|
| 36. | 4-{[(1H-Pyrrole-2-carbonyl)-amino]-methyl}-piperidine-1-carboxylic acid benzyl ester | 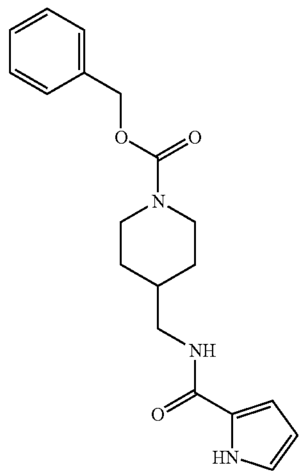 | $^1$H NNR (δ, CDCl$_3$): 9.55(brs, 1H), 7.39–7.28(m, 5H), 6.92(m, 1H), 6.57(m, 1H), 6.22(m, 1H), 6.01(brt, 1H), 5.08(s, 2H), 4.20(brs, 2H), 3.28(brs, 2H), 2.77(brt, 2H), 1.9–1.7(m, 3H), 1.21(m, 2H). |
| 37. | 4-{[(1H-Imidazole-4-carbonyl)-amino]-methyl}-piperidine-1-carboxylic acid benzyl ester | 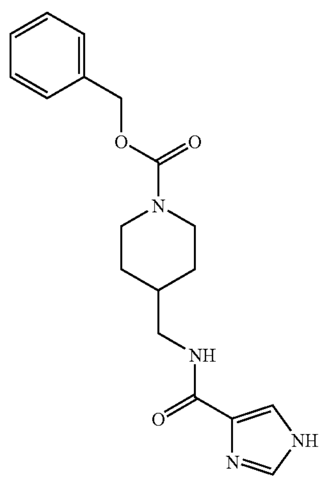 | $^1$H NMR (δ, CDCl$_3$): 7.58(m, 2H), 7.38–7.27(m, 5H), 5.10(s, 2H), 4.20(brd, 2H), 3.37(brs, 2H), 2.77(brt, 2H), 1.9–1.7(m, 3H), 1.21(m, 2H). |
| 38. | 4-{[(1-Methyl-1H-pyrrole-2-carbonyl)-amino]-methyl}-piperidine-1-carboxylic acid benzyl ester | 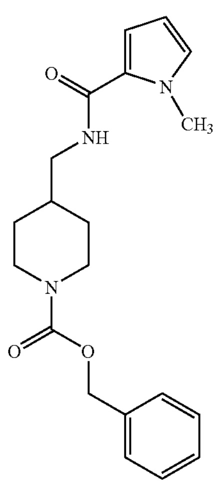 | $^1$H NMR (δ, CDCl$_3$): 7.38–7.25(m, 5H), 6.71(m, 1H), 6.50(m, 1H), 6.08(m, 1H), 6.00(brt, 1H), 5.11(s, 2H), 4.22(brs, 2H), 3.94(s, 3H), 3.26(brs, 2H), 2.77(brt, 2H), 1.9–1.7(m, 3H), 1.21(m, 2H). |

-continued

| EX. | Name | Structure | Data |
|---|---|---|---|
| 39. | 4-{[(5-Methyl-3H-imidazole-4-carbonyl)-amino]-methyl}-piperidine-1-carboxylic acid benzyl ester | 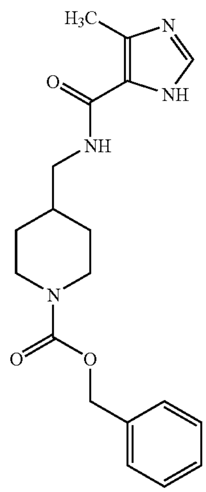 | $^1$H NMR ($\delta$, CDCl$_3$): 9.62(brs, 1H), 7.40(s, 1H), 7.31(m, 6H), 5.12(s, 2H), 4.19(brd, 2H), 3.25(brs, 2H), 2.77(brt, 2H), 2.59(s, 3H), 1.9–1.7(m, 3H), 1.21(m, 2H). |
| 40. | 4-{[(1H-Pyrrole-3-carbonyl)-amino]-methyl}-piperidine-1-carboxylic acid benzyl ester | 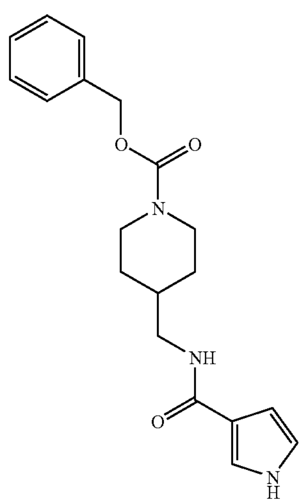 | $^1$H NMR ($\delta$, CDCl$_3$): 8.55(brs, 1H), 7.28(m, 6H), 6.78(s, 1H), 6.40(s, 1H), 5.88(brt, 1H), 5.10(s, 2H), 4.19(brs, 2H), 3.30(brs, 2H), 2.77(brt, 2H), 1.9–1.7(m, 3H), 1.20(m, 2H). |
| 41. | 4-{[(Thiophene-3-carbonyl)-amino]-methyl}-piperidine-1-carboxylic acid 4-methyl-benzyl ester | 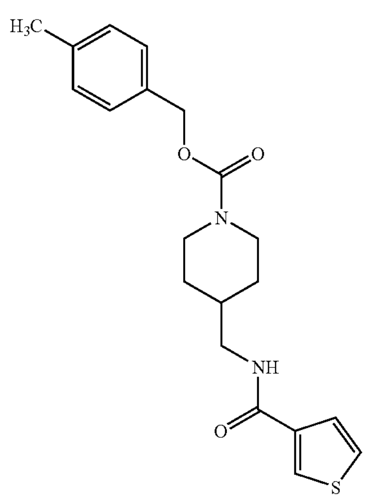 | $^1$H NMR ($\delta$, CDCl$_3$): 7.83(m, 1H), 7.38(m, 2H), 7.24(d, 2H), 7.18(d, 2H), 6.19(brt, 1H), 5.02(s, 2H), 4.20(brs, 2H), 3.30(brs, 2H), 2.77(brt, 2H), 2.35(s, 3H), 1.9–1.7(m, 3H), 1.21(m, 2H). |

-continued

| EX. | Name | Structure | Data |
|---|---|---|---|
| 42. | 4-{[(2H-Pyrazole-3-carbonyl)-amino]-methyl}-piperidine-1-carboxylic acid 4-fluoro-benzyl ester | 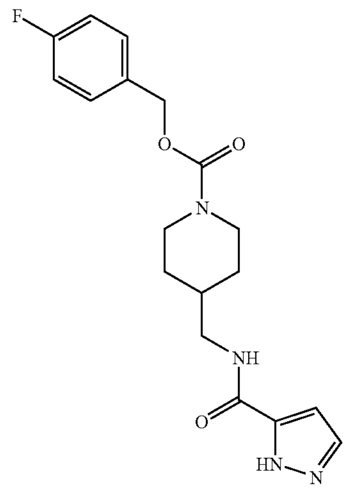 | $^1$H NMR (δ, CDCl$_3$): 7.60(d, 1H), 7.30(d, 2H), 7.04(m, 3H), 6.82(d, 1H), 5.04(s, 2H), 4.18(brs, 2H), 3.33(brs, 2H), 2.77(brt, 2H), 1.9–1.7(m, 3H), 1.21(m, 2H). |
| 43. | 4-{[(2H-Pyrazole-3-carbonyl)-amino]-methyl}-piperidine-1-carboxylic acid 4-chloro-benzyl ester | 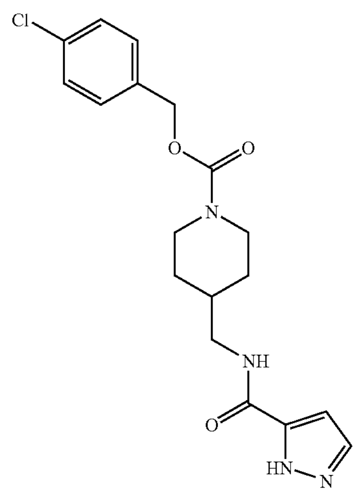 | $^1$H NMR (δ, CDCl$_3$): 7.58(d, 1H), 7.27(m, 4H), 7.04(brt, 1H), 6.82(d, 1H), 5.05(s, 2H), 4.18(brs, 2H), 3.36(brs, 2H), 2.77(brt, 2H), 1.9–1.7(m, 3H), 1.21(m, 2H). |
| 44. | 4-{[(2H-Pyrazole-3-carbonyl)-amino]-methyl}-piperidine-1-carboxylic acid 4-methyl-benzyl ester | 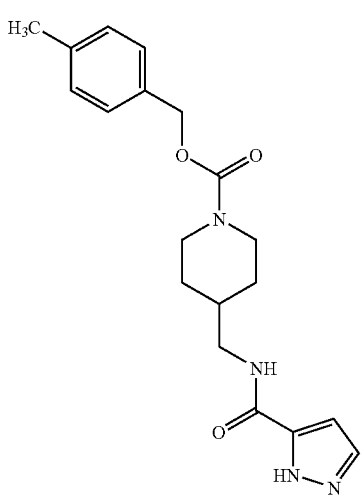 | $^1$H NMR (δ, CDCl$_3$): 7.60(d, 1H), 7.22(d, 2H), 7.17 d, 2H), 6.97(brt, 1H), 6.84(d, 1H),, 5.04(s, 2H), 4.20(brs, 2H), 3.35(brs, 2H), 2.77(brt, 2H), 2.37(m, 3H), 1.9–1.7(m, 3H), 1.21(m, 2H). |

| EX. | Name | Structure | Data |
|---|---|---|---|
| 45. | 4-{[(1H-Pyrazole-4-carbonyl)-amino]-methyl}-piperidine-1-carboxylic acid 4-fluoro-benzyl ester | 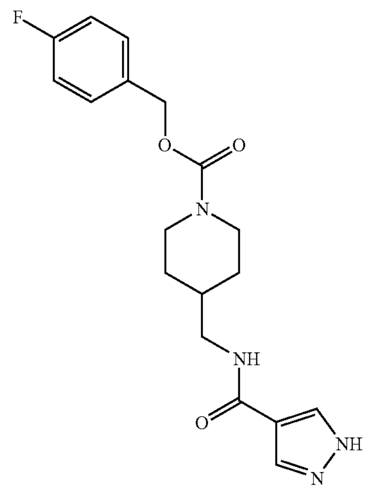 | $^1$H NMR (δ, CDCl$_3$): 7.94(s, 2H), 7.30(m, 2H), 7.01(m, 2H), 6.60(brs, 1H), 5.03(s, 2H), 4.16(brd, 2H), 3.24(brs, 2H), 2.75(brs, 2H), 1.9–1.7(m, 3H), 1.15(m, 2H). |
| 46. | 4-{[(1H-Pyrazole-4-carbonyl)-amino]-methyl}-piperidine-1-carboxylic acid 4-chloro-benzyl ester | 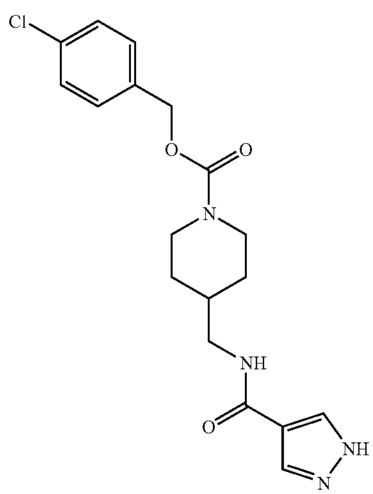 | $^1$H NMR (δ, CDCl$_3$): 7.94(s, 2H), 7.26(m, 4H), 6.43(brs, 1H), 5.03(s, 2H), 4.17(brs, 2H), 3.25(brs, 2H), 2.77(brs, 2H), 1.9–1.7(m, 3H), 1.15(m, 2H). |
| 47. | 4-{[(1H-Pyrazole-4-carbonyl)-amino]-methyl}-piperidine-1-carboxylic acid 4-methyl-benzyl ester | 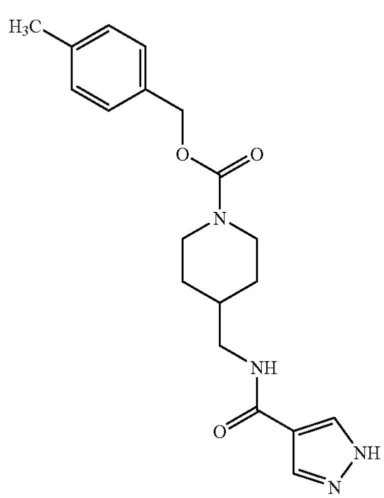 | $^1$H NMR (δ, CDCl$_3$): 7.94(s, 2H), 7.25(d, 2H), 7.16(d, 2H), 6.03(brt, 1H), 5.06(s, 2H), 4.20(brs, 2H), 3.30(brs, 2H), 2.77(brt, 2H), 2.37(s, 3H), 1.9–1.7(m, 3H), 1.20(m, 2H). |

| EX. | Name | Structure | Data |
|---|---|---|---|
| 48. | 4-{[(1H-Pyrazole-4-carbonyl)-amino]-methyl}-piperidine-1-carboxylic acid indan-2-yl ester | 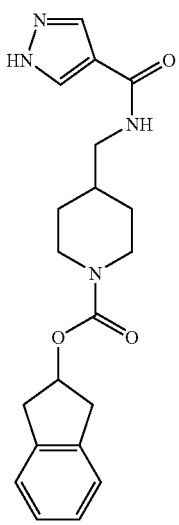 | ¹H NMR (δ, CDCl₃): 7.94(s, 2H), 7.20(m, 4H), 6.15(brt, 1H), 5.42(m, 1H), 4.10(brd, 2H), 3.30(m, 4H), 3.00(dd, 2H), 2.70(t, 2H), 1.8–1.6(m, 3H), 1.18(m, 2H). |
| 49. | 4-{[(1H-Pyrrole-2-carbonyl)-amino]-methyl}-piperidine-1-carboxylic acid 4-methyl-benzyl ester | 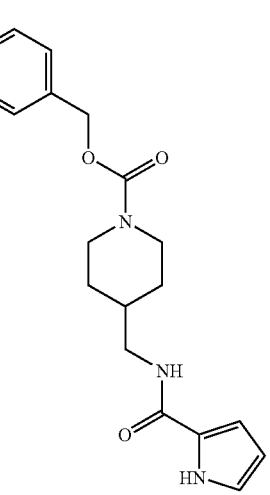 | ¹H NMR (δ, CDCl₃): 9.43(brs, 1H), 7.24(d, 2H), 7.17(d, 2H), 6.91(s, 1H), 6.55(s, 1H), 6.22(m, 1H), 5.95(brt, 1H), 5.06(s, 2H), 4.19(brs, 2H), 3.30(brs, 2H), 2.77(brt, 2H), 2.36(s, 3H), 1.9–1.7(m, 3H), 1.18(m, 2H). |

| EX. | Name | Structure | Data |
|---|---|---|---|
| 50. | 4-{[(1H-Imidazole-4-carbonyl)-amino]-methyl}-piperidine-1-carboxylic acid 4-chloro-benzyl ester | 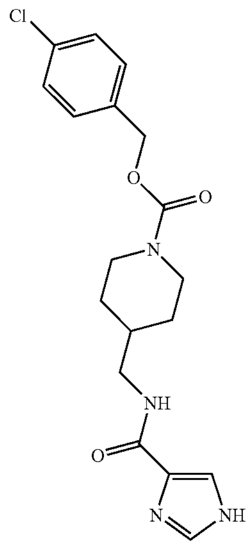 | $^1$H NMR(δ, CDCl$_3$): 7.59(s, 2H), 7.30(m, 5H), 5.06(s, 2H), 4.18(brs, 2H), 3.33 (brs, 2H), 2.77(brt, 2H), 1.9–1.7(m, 3H), 1.21(m, 2H). |
| 51. | 4-{[(1-Methyl-1H-pyrrole-2-carbonyl)-amino]-methyl}-piperidine-1-carboxylic acid 4-fluoro-benzyl ester | 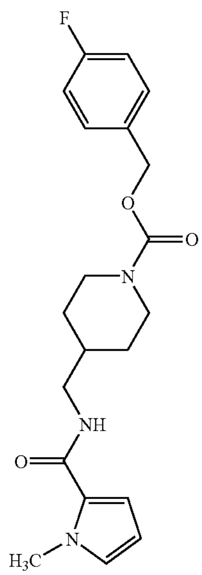 | $^1$H NMR(δ, CDCl$_3$): 7.31(dd, 2H), 7.02 (dd, 2H), 6.72(s, 1H), 6.50(m, 1H), 6.08(m, 1H), 6.00 (brt, 1H), 5.04(s, 2H), 4.18(brs, 2H), 3.93(s, 3H), 3.25 (brs, 2H), 2.77(brt, 2H), 1.9–1.7(m, 3H), 1.18(m, 2H). |

-continued

| EX. | Name | Structure | Data |
|---|---|---|---|
| 52. | 4-{[(1H-Pyrrole-2-carbonyl)-amino]-methyl}-piperidine-1-carboxylic acid 4-chloro-benzyl ester | 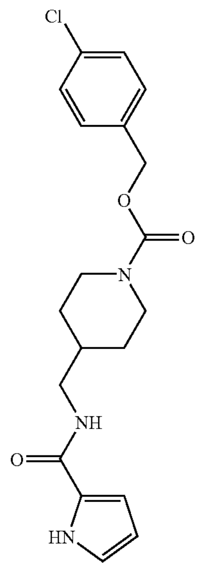 | $^1$H NMR($\delta$, CDCl$_3$): 9.37(brs, 1H), 7.24 (m, 4H), 6.92(s, 1H), 6.53(s, 1H), 6.22(m, 1H), 5.93(brt, 1H), 5.06(s, 2H), 4.20 (brs, 2H), 3.31(brs, 2H), 2.77(brt, 2H), 1.9–1.7(m, 3H), 1.18 (m, 2H). |
| 53. | 4-{[(2-Methyl-1H-pyrrole-3-carbonyl)-amino]-methyl}-piperidine-1-carboxylic acid 4-methyl-benzyl ester | 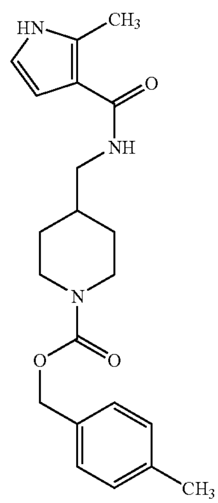 | $^1$H NMR($\delta$, CDCl$_3$): 8.10(brs, 1H), 7.25 (d, 2H), 7.17(d, 2H), 6.59(m, 1H), 6.23 (m, 1H), 5.81(brt, 1H), 5.06(s, 2H), 4.20(brs, 2H), 3.26 (brs, 2H), 2.77(brt, 2H), 2.55(s, 3H), 2.36(s, 3H), 1.9–1.7 (m, 3H), 1.20(m, 2H). |

| EX. | Name | Structure | Data |
|---|---|---|---|
| 54. | 4-{[(1H-Pyrrole-3-carbonyl)-amino]-methyl}-piperidine-1-carboxylic acid 4-methyl-benzyl ester | 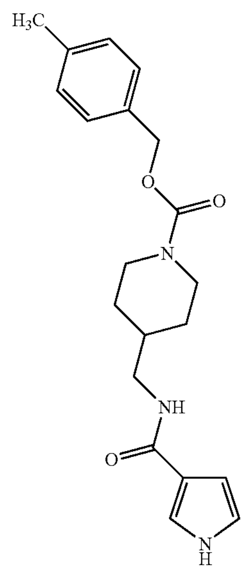 | $^1$H NMR(δ, CDCl$_3$): 8.55(brs, 1H), 7.36 (m, 1H), 7.25(d, 2H), 7.17(d, 2H), 6.77(m, 1H), 6.40(m, 1H), 5.86(brt, 1H), 5.06 (s, 2H), 4.19(brs, 2H), 3.29(brs, 2H), 2.77(brt, 2H), 2.36(s, 3H), 1.9–1.7(m, 3H), 1.18(m, 2H). |
| 55. | 4-{[(Thiazole-5-carbonyl)-amino]-methyl}-piperidine-1-carboxylic acid 4-methyl-benzyl ester | 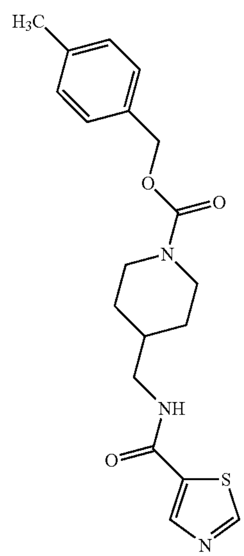 | $^1$H NMR(δ, CDCl$_3$): 8.90(s, 1H), 8.24(s, 1H), 7.24(d, 2H), 7.16(d, 2H), 6.24 (brt, 1H), 5.05(s, 2H), 4.20(brs, 2H), 3.35(brs, 2H), 2.77 (brt, 2H), 2.36(s, 3H), 1.9–1.7(m, 3H), 1.21(m, 2H). |

-continued
| EX. | Name | Structure | Data |
|---|---|---|---|
| 56. | 4-{[(Oxazole-5-carbonyl)-amino]-methyl}-piperidine-1-carboxylic acid 4-methyl-benzyl ester | 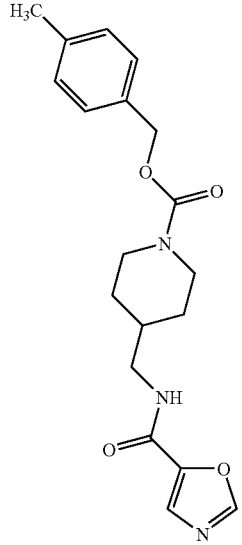 | $^1$H NMR($\delta$, CDCl$_3$): 7.90(s, 1H), 7.72(s, 1H), 7.23(d, 2H), 7.17(d, 2H), 6.35 (brt, 1H), 5.05(s, 2H), 4.20(brs, 2H), 3.33(brs, 2H), 2.77 (brt, 2H), 2.35(s, 3H), 1.9–1.7(m, 3H), 1.20(m, 2H). |
| 57. | 4-{[(1H-Pyrazole-4-carbonyl)-amino]-methyl}-piperidine-1-carboxylic acid 4-isopropyl-benzyl ester | 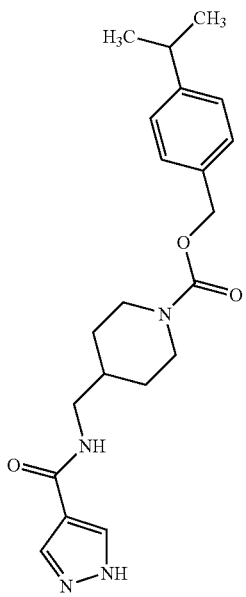 | $^1$H NMR($\delta$, CDCl$_3$): 7.93(s, 2H), 7.25(m, 4H), 6.62(brt, 1H), 5.07(s, 2H), 4.16 (brd, 2H), 3.26(brs, 2H), 2.89(m, 1H), 2.71(brt, 2H), 1.9–1.7 (m, 3H), 1.23(d, 6H), 1.18(m, 2H). |

| EX. | Name | Structure | Data |
|---|---|---|---|
| 58. | 4-{[(1H-Pyrazole-4-carbonyl)-amino]-methyl}-piperidine-1-carboxylic acid thiophen-3-ylmethyl ester | 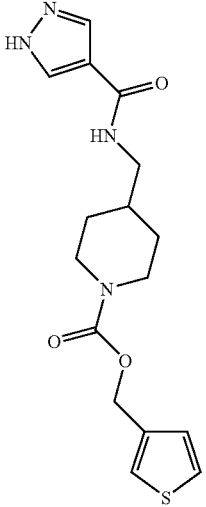 | $^1$H NMR($\delta$, CDCl$_3$): 10.50(brs, 1H), 7.94 (s, 2H), 7.28(m, 2H), 7.08(m, 1H), 5.93 (brt, 1H), 5.11(s, 2H), 4.19(brs, 2H), 3.31(brs, 2H), 2.77 (brt, 2H), 1.9–1.7(m, 3H), 1.19(m, 2H). |
| 59. | 4-[(4-Hydroxy-benzoylamino)-methyl]-piperidine-1-carboxylic acid 4-isopropyl-benzyl ester | 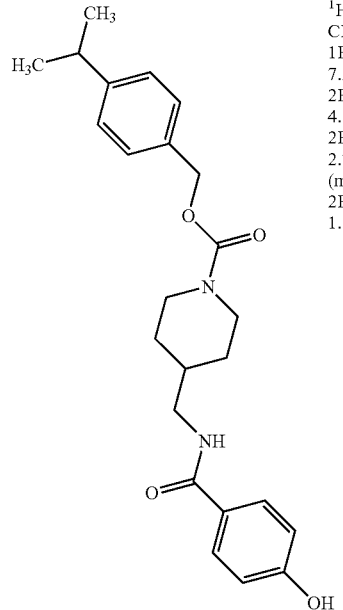 | $^1$H NMR($\delta$, CD$_3$OD): 8.24(brd, 1H) 7.68(d, 2H), 7.20(m, 4H), 6.79(d, 2H), 5.02(s, 2H), 4.10(d, 2H), 3.20(t, 2H), 2.81(m, 1H), 2.77(brs, 2H), 1.77 (m, 1H), 1.70(brd, 2H), 1.20(d, 6H), 1.16(m, 2H). |

| EX. | Name | Structure | Data |
|---|---|---|---|
| 60. | 4-[(4-Hydroxy-benzoylamino)-methyl]-piperidine-1-carboxylic acid thiophen-3-ylmethyl ester | 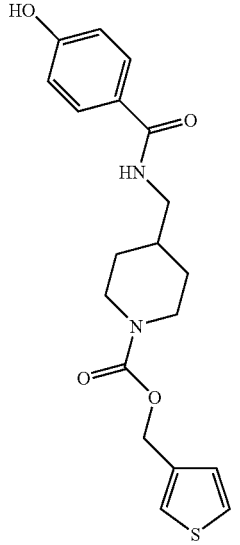 | $^1$H NMR($\delta$, CDCl$_3$): 7.94(s, 2H), 7.26(m, 4H), 7.09(d, 1H), 5.92 (brt, 1H), 5.14 (s, 2H), 4.19(brs, 2H), 3.30(brs, 2H), 2.77(brt, 2H), 1.9–1.7 (m, 3H), 1.20(m, 2H). |
| 61. | 4-{[(Pyridine-4-carbonyl)-amino]-methyl}-piperidine-1-carboxylic acid 4-isopropyl-benzyl ester | 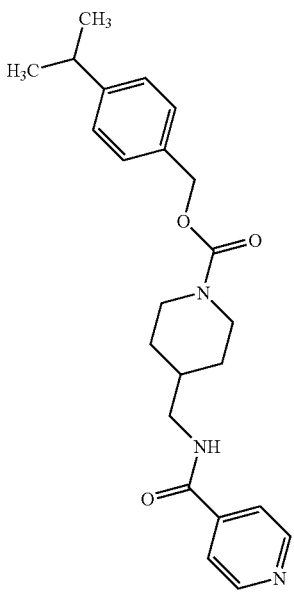 | $^1$H NMR($\delta$, CDCl$_3$): 8.72(d, 2H), 7.60(d, 2H), 7.22(m, 4H), 6.55(brt, 1H), 5.06 (s, 2H), 4.21(brd, 2H), 3.33(brs, 2H), 2.90(m, 1H), 2.77 (brt, 2H), 1.9–1.7(m, 3H), 1.21(d, 6H), 1.18(m, 2H). |

| EX. | Name | Structure | Data |
|---|---|---|---|
| 62. | 4-{[(2H-Pyrazole-3-carbonyl)-amino]-methyl}-piperidine-1-carboxylic acid 4-isopropyl-benzyl ester | 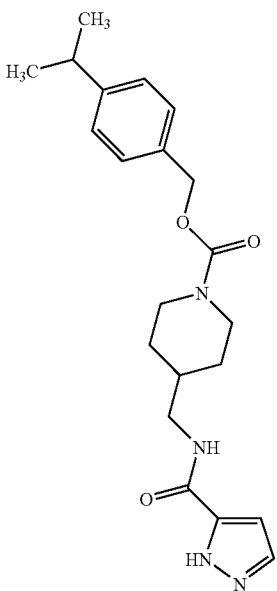 | ¹H NMR(δ, CDCl₃): 7.57(m, 1H), 7.23 (m, 4H), 7.02(brt, 1H), 6.83(m, 1H), 5.06(s, 2H), 4.19 (brs, 2H), 3.33(brs, 2H), 2.90(m, 1H), 2,77(brt, 2H), 1.9–1.7 (m, 3H), 1.21(d, 6H), 1.18(m, 2H). |
| 63. | 4-{[(1H-Pyrrole-3-carbonyl)-amino]-methyl}-piperidine-1-carboxylic acid 4-isopropyl-benzyl ester | 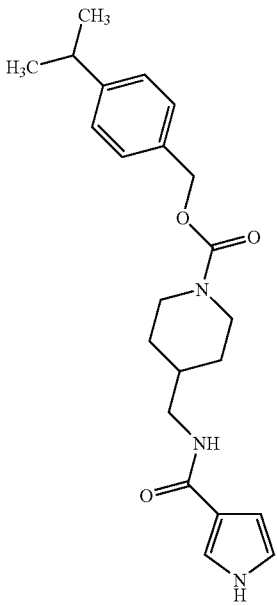 | ¹H NMR(δ, CDCl₃): 9.79(brs, 1H), 7.30–7.15(m, 5H), 6.70(s, 1H), 6.42(s, 1H), 6.30(brt, 1H), 5.06 (s, 2H), 4.17(brs, 2H), 3.25(brs, 2H), 2.90(m, 1H), 2.75 (brs, 2H), 1.9–1.7(m, 3H), 1.22(d, 6H), 1.17(m, 2H). |

-continued

| EX. | Name | Structure | Data |
|---|---|---|---|
| 64. | 4-Hydroxy-N-[1-(3-phenyl-propionyl)-piperidin-4-ylmethyl]-benzamide | 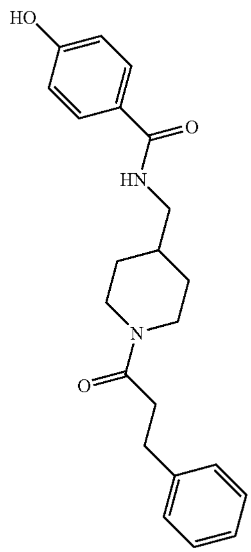 | $^1$H NMR($\delta$, CDCl$_3$): 8.80(brs, 1H), 7.63 (d, 2H), 7.3–7.1(m, 5H), 6.89(d, 2H), 6.69(brt, 1H), 4.58 (d, 1H), 3.76(d, 1H), 3.35–3.18(m, 2H), 2.90(m, 3H), 2.60(t, 2H), 2.49(t, 1H), 1.9–1.7(m, 3H), 1.1–0.9 (m, 2H). |
| 65. | 4-{[(2-Chloro-pyridine-4-carbonyl)-amino]-methyl}-piperidine-1-carboxylic acid benzyl ester | 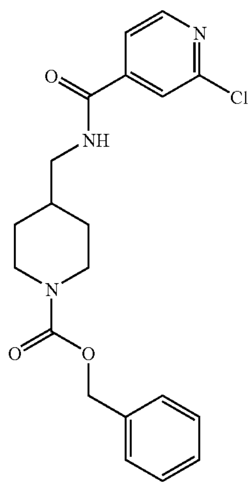 | M.S. (M$^+$ + 1) 388 |
| 66. | 4-{[(6-Amino-pyridine-3-carbonyl)-amino]-methyl}-piperidine-1-carboxylic acid benzyl ester | 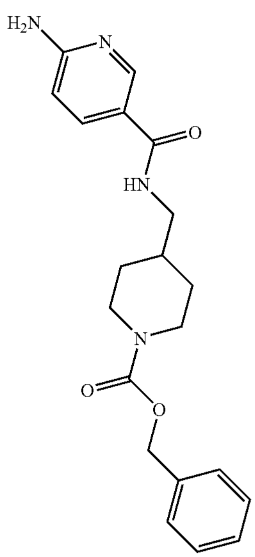 | M.S. (M$^+$ + 1) 369 |

| EX. | Name | Structure | Data |
|---|---|---|---|
| 67. | 4-(Benzoylamino-methyl)-piperidine-1-carboxylic acid benzyl ester | 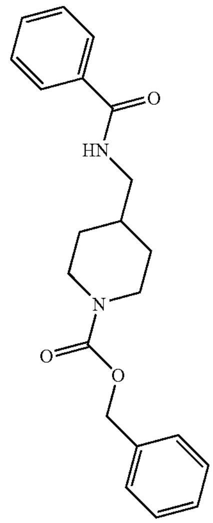 | M.S. (M$^+$ + 1) 353 |
| 68. | 4-[(3-Cyano-benzoylamino)-methyl]-piperidine-1-carboxylic acid benzyl ester | 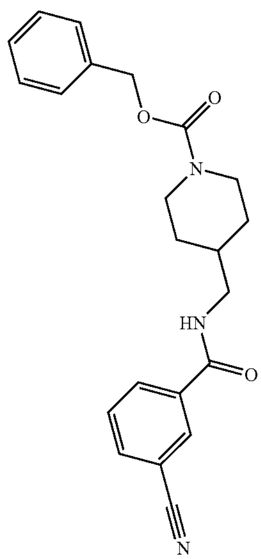 | M.S. (M$^+$ + 1) 378 |
| 69. | 4-{[(Pyridine-4-carbonyl)-amino]-methyl}-piperidine-1-carboxylic acid indan-2-yl ester | 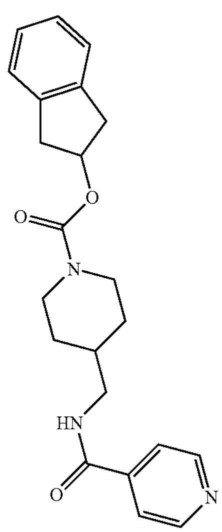 | M.S. (M$^+$ + 1) 380 |

| EX. | Name | Structure | Data |
|---|---|---|---|
| 70. | 4-{[(2-Amino-pyridine-3-carbonyl)-amino]-methyl}-piperidine-1-carboxylic acid benzyl ester | 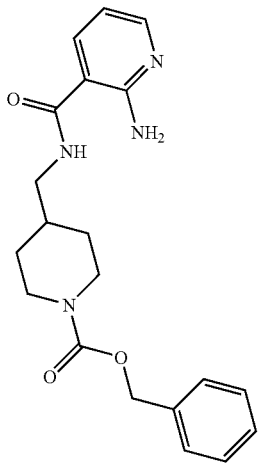 | M.S. (M⁺ + 1) 369 |
| 71. | 4-[(4-Methylamino-benzoylamino)-methyl]-piperidine-1-carboxylic acid benzyl ester | 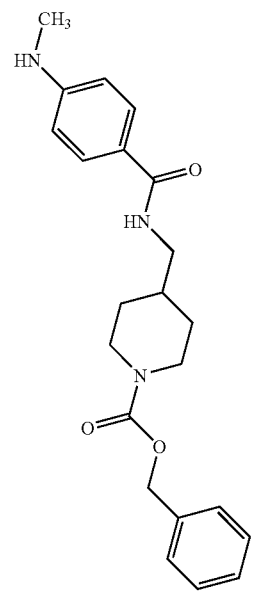 | M.S. (M⁺ + 1) 382 |

| EX. | Name | Structure | Data |
|---|---|---|---|
| 72. | 4-[(4-Amino-benzoylamino)-methyl]-piperidine-1-carboxylic acid benzyl ester | 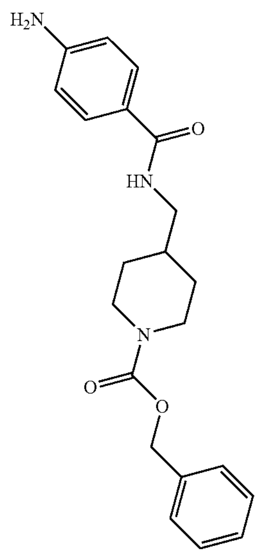 | M.S. (M⁺ + 1) 368 |
| 73. | 4-[(4-Trifluoromethoxy-benzoylamino)-methyl]-piperidine-1-carboxylic acid benzyl ester | 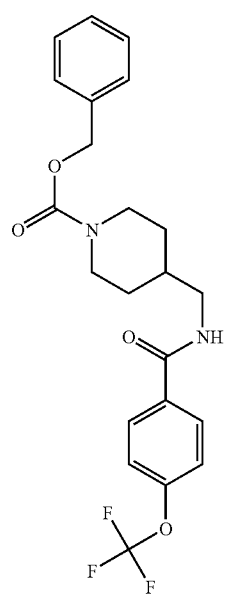 | M.S. (M⁺ + 1) 437 |

-continued

| EX. | Name | Structure | Data |
|---|---|---|---|
| 74. | 4-[(4-Fluoro-benzoylamino)-methyl]-piperidine-1-carboxylic acid benzyl ester | 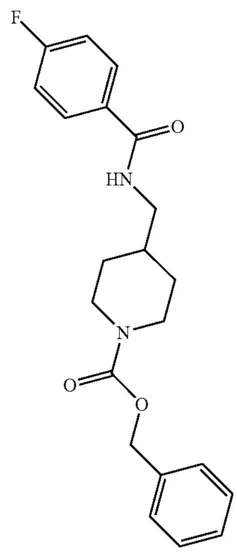 | M.S. (M$^+$ + 1) 371 |
| 75. | 4-[(2-Amino-benzoylamino)-methyl]-piperidine-1-carboxylic acid benzyl ester | 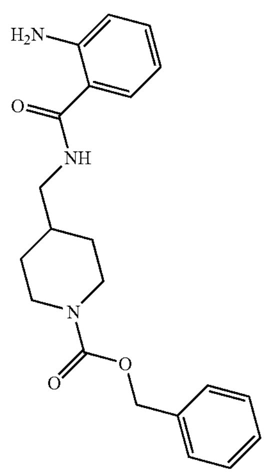 | M.S. (M$^+$ + 1) 368 |
| 76. | 4-{[(5-Ethyl-2-methyl-2H-pyrazole-3-carbonyl)-amino]-methyl}-piperidine-1-carboxylic acid benzyl ester | 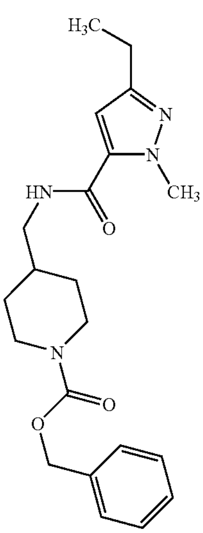 | M.S. (M$^+$ + 1) 385 |

| EX. | Name | Structure | Data |
|---|---|---|---|
| 77. | 4-{[(6-Chloro-imidazo[1,2-a]pyridine-2-carbonyl)-amino]-methyl}-piperidine-1-carboxylic acid benzyl ester | 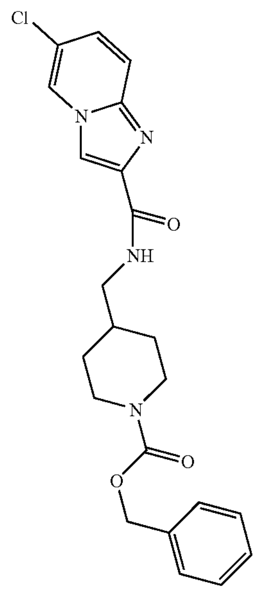 | M.S. (M$^+$ + 1) 427 |
| 78. | 4-{[(4-Bromo-thiophene-3-carbonyl)-amino]-methyl}-piperidine-1-carboxylic acid benzyl ester | 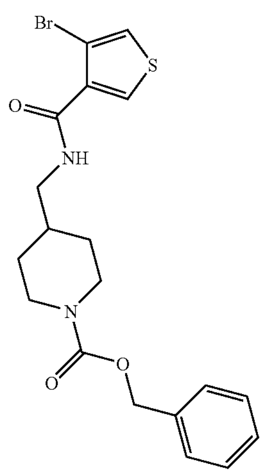 | M.S. (M$^+$ + 1) 438 |
| 79. | 4-{[(Isoxazole-5-carbonyl)-amino]-methyl}-piperidine-1-carboxylic acid benzyl ester | 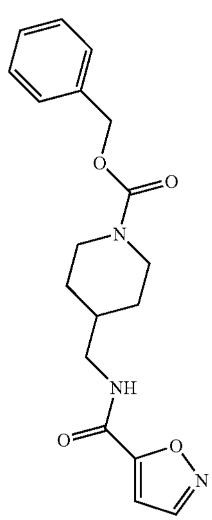 | M.S. (M$^+$ + 1) 344 |

| EX. | Name | Structure | Data |
|---|---|---|---|
| 80. | 4-{[(1H-Imidazole-2-carbonyl)-amino]-methyl}-piperidine-1-carboxylic acid benzyl ester | 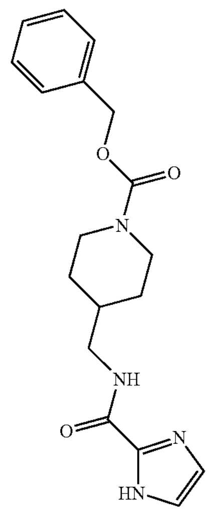 | M.S. (M+ + 1) 343 |
| 81. | 4-{[(3-Bromo-pyridine-4-carbonyl)-amino]-methyl}-piperidine-1-carboxylic acid benzyl ester | 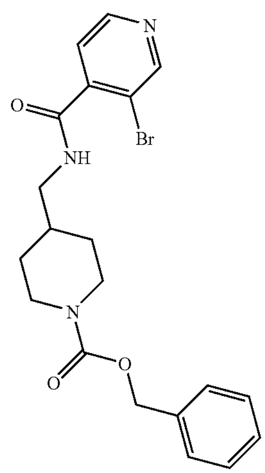 | M.S. (M+ + 1) 433 |
| 82. | 4-{[([1,6]-Naphthyridine-2-carbonyl)-amino]-methyl}-piperidine-1-carboxylic acid benzyl ester | 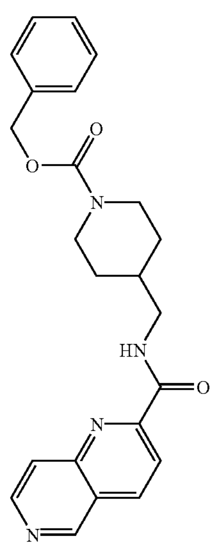 | M.S. (M+ + 1) 405 |

| EX. | Name | Structure | Data |
|---|---|---|---|
| 83. | 4-{[(1-Methyl-1H-imidazole-2-carbonyl)-amino]-methyl}-piperidine-1-carboxylic acid benzyl ester | 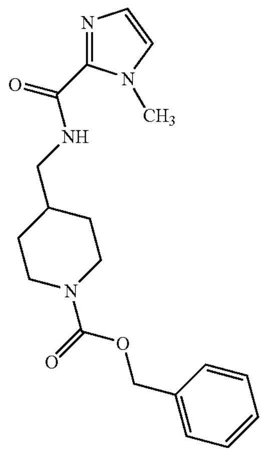 | M.S. (M⁺ + 1) 357 |
| 84. | 4-{[(5-Bromo-pyridine-3-carbonyl)-amino]-methyl}-piperidine-1-carboxylic acid benzyl ester | 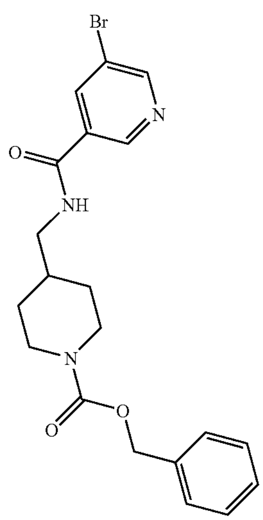 | M.S. (M⁺ + 1) 432 |
| 85. | 4-{[(Isoxazole-3-carbonyl)-amino]-methyl}-piperidine-1-carboxylic acid benzyl ester | 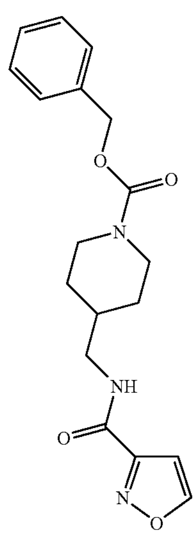 | M.S. (M⁺ + 1) 344 |

-continued
| EX. | Name | Structure | Data |
|---|---|---|---|
| 86. | 4-{[(6-Bromo-pyridine-3-carbonyl)-amino]-methyl}-piperidine-1-carboxylic acid benzyl ester | 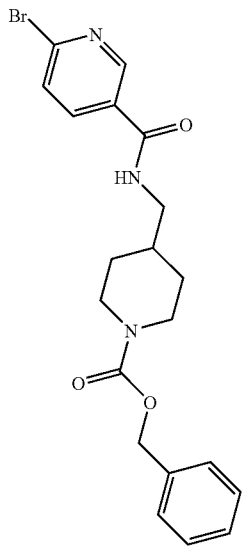 | M.S. (M$^+$ + 1) 432 |
| 87. | 4-{[(2-Methyl-thiazole-4-carbonyl)-amino]-methyl}-piperidine-1-carboxylic acid benzyl ester | 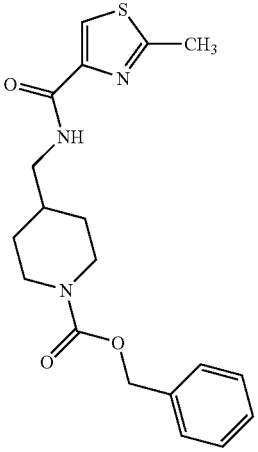 | M.S. (M$^+$ + 1) 374 |
| 88. | 4-{[(Oxazole-5-carbonyl)-amino]-methyl}-piperidine-1-carboxylic acid benzyl ester | 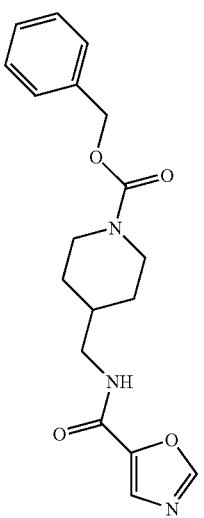 | M.S. (M$^+$ + 1) 344 |

-continued

| EX. | Name | Structure | Data |
|---|---|---|---|
| 89. | 4-{[(Pyrimidine-2-carbonyl)-amino]-methyl}-piperidine-1-carboxylic acid benzyl ester | 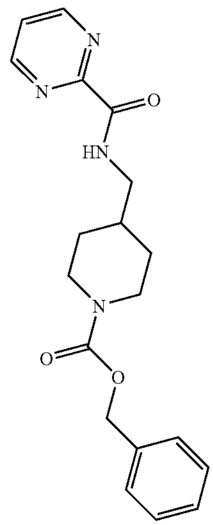 | M.S. (M$^+$ + 1) 355 |
| 90. | 4-{[(1,4,5,6-Tetrahydro-cyclopentapyrazole-3-carbonyl)-amino]-methyl}-piperidine-1-carboxylic acid benzyl ester | 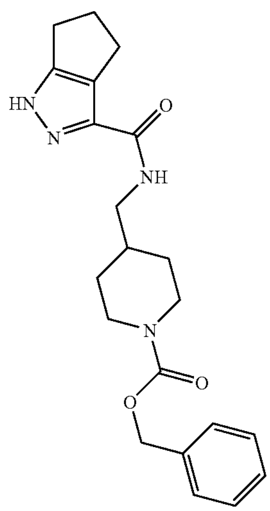 | M.S. (M$^+$ + 1) 383 |
| 91. | 4-{[(2-Methylsulfanyl-thiazole-4-carbonyl)-amino]-methyl}-piperidine-1-carboxylic acid benzyl ester | 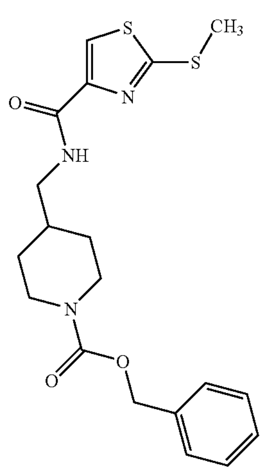 | M.S. (M$^+$ + 1) 406 |

| EX. | Name | Structure | Data |
|---|---|---|---|
| 92. | 4-{[(5-Methyl-thiazole-4-carbonyl)-amino]-methyl}-piperidine-1-carboxylic acid benzyl ester | 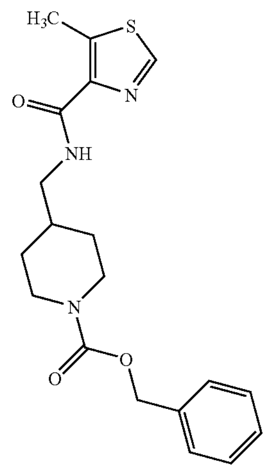 | M.S. (M$^+$ + 1) 374 |
| 93. | 4-{[(5-Methyl-2H-[1,2,4]triazole-3-carbonyl)-amino]-methyl}-piperidine-1-carboxylic acid benzyl ester | 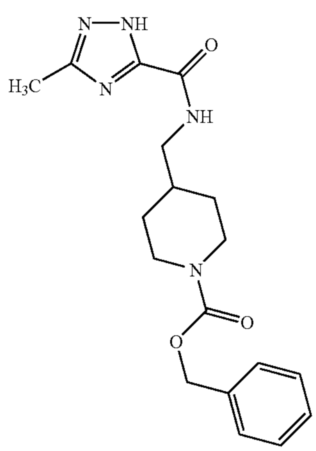 | M.S. (M$^+$ + 1) 358 |
| 94. | 4-{[(4-Phenyl-thiazole-2-carbonyl)-amino]-methyl}-piperidine-1-carboxylic acid benzyl ester | 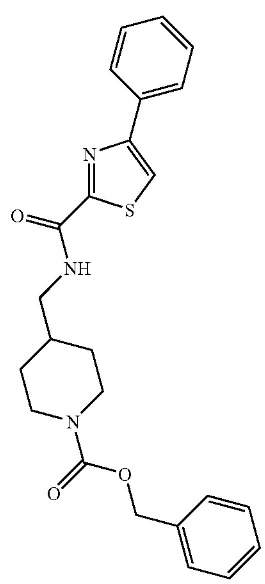 | M.S. (M$^+$ + 1) 436 |

| EX. | Name | Structure | Data |
|---|---|---|---|
| 95. | 4-{[(5-Hydroxymethyl-3H-imidazole-4-carbonyl)-amino]-methyl}-piperidine-1-carboxylic acid benzyl ester | 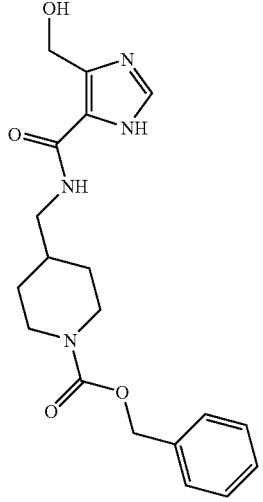 | M.S. (M⁺ + 1) 373 |
| 96. | 4-{[(2-Methyl-thiazole-5-carbonyl)-amino]-methyl}-piperidine-1-carboxylic acid benzyl ester | 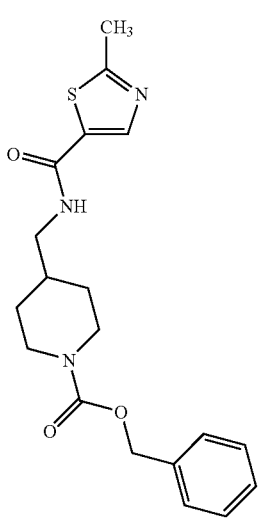 | M.S. (M⁺ + 1) 374 |
| 97. | 4-{[(2-Methyl-1H-pyrrole-3-carbonyl)-amino]-methyl}-piperidine-1-carboxylic acid benzyl ester | 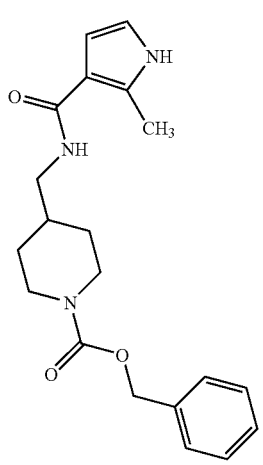 | M.S. (M⁺ + 1) 356 |

-continued

| EX. | Name | Structure | Data |
|---|---|---|---|
| 98. | 4-{[(2-Methyl-thiophene-3-carbonyl)-amino]-methyl}-piperidine-1-carboxylic acid benzyl ester | 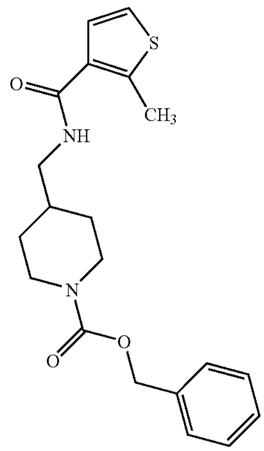 | M.S. (M$^+$ + 1) 373 |
| 99. | 4-{[(Thiophene-3-carbonyl)-amino]-methyl}-piperidine-1-carboxylic acid 4-fluoro-benzyl ester | 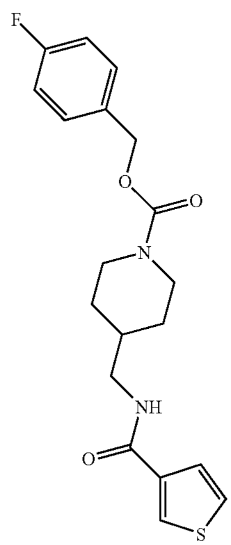 | M.S. (M$^+$ + 1) 377 |
| 100. | 4-{[(Thiophene-3-carbonyl)-amino]-methyl}-piperidine-1-carboxylic acid 4-chloro-benzyl ester | 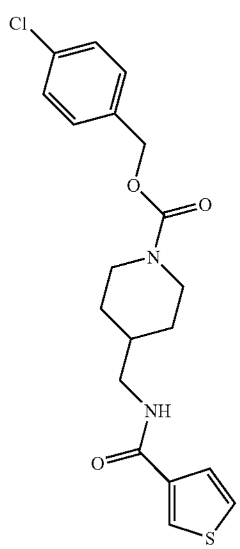 | M.S. (M$^+$ + 1) 393 |

-continued

| EX. | Name | Structure | Data |
|---|---|---|---|
| 101. | 4-{[(Thiophene-3-carbonyl)-amino]-methyl}-piperidine-1-carboxylic acid indan-2-yl ester | 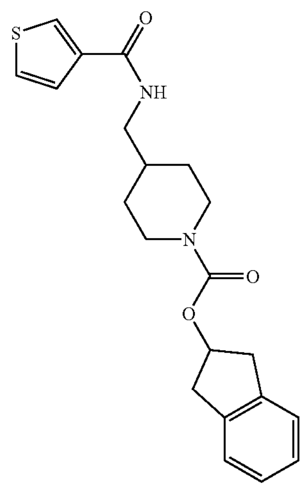 | M.S. (M⁺ + 1) 385 |
| 102. | 4-{[(2H-Pyrazole-3-carbonyl)-amino]-methyl}-piperidine-1-carboxylic acid indan-2-yl ester | 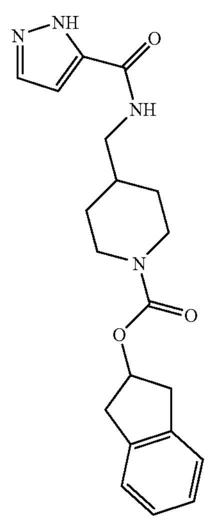 | M.S. (M⁺ + 1) 369 |
| 103. | 4-{[(1H-Imidazole-4-carbonyl)-amino]-methyl}-piperidine-1-carboxylic acid 4-methyl-benzyl ester | 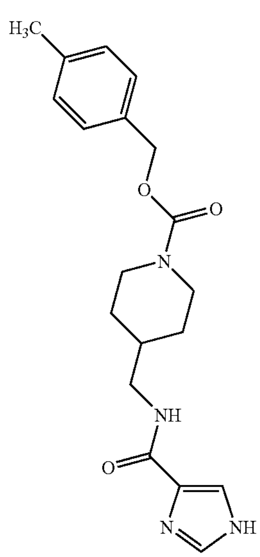 | M.S. (M⁺ + 1) 357 |

| EX. | Name | Structure | Data |
|---|---|---|---|
| 104. | 4-{[(1-Methyl-1H-pyrrole-2-carbonyl)-amino]-methyl}-piperidine-1-carboxylic acid 4-methyl-benzyl ester | 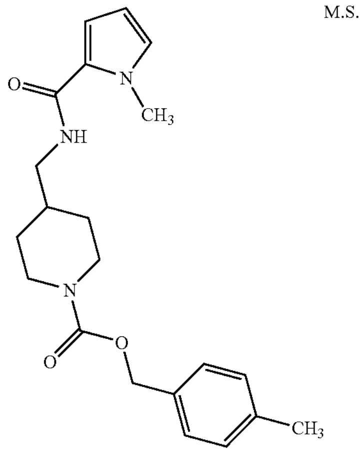 | M.S. (M⁺ + 1) 370 |
| 105. | 4-{[(1H-Imidazole-4-carbonyl)-amino]-methyl}-piperidine-1-carboxylic acid 4-fluoro-benzyl ester | 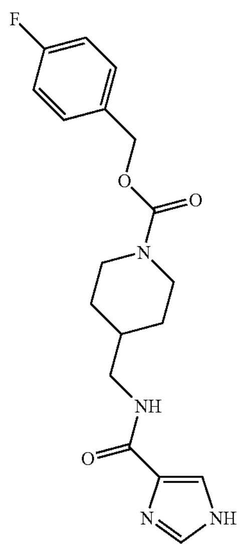 | M.S. (M⁺ + 1) 361 |
| 106. | 4-{[(1H-Imidazole-4-carbonyl)-amino]-methyl}-piperidine-1-carboxylic acid indan-2-yl ester | 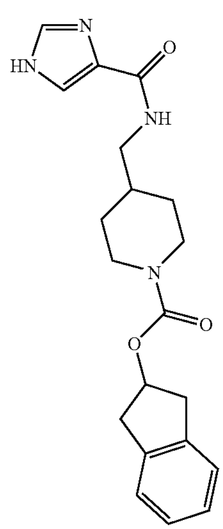 | M.S. (M⁺ + 1) 369 |

-continued

| EX. | Name | Structure | Data |
|---|---|---|---|
| 107. | 4-{[(1-Methyl-1H-pyrrole-2-carbonyl)-amino]-methyl}-piperidine-1-carboxylic acid 4-chloro-benzyl ester | 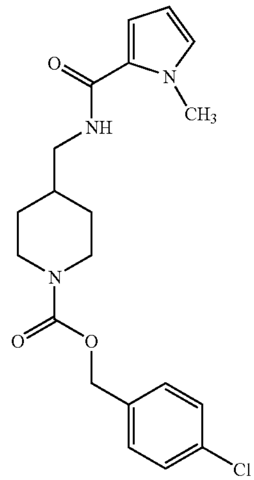 | M.S. (M$^+$ + 1) 390 |
| 108. | 4-{[(1-Methyl-1H-pyrrole-2-carbonyl)-amino]-methyl}-piperidine-1-carboxylic acid indan-2-yl ester | 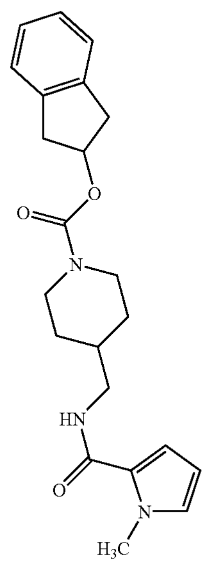 | M.S. (M$^+$ + 1) 382 |
| 109. | 4-{[(1H-Pyrrole-2-carbonyl)-amino]-methyl}-piperidine-1-carboxylic acid 4-fluoro-benzyl ester | 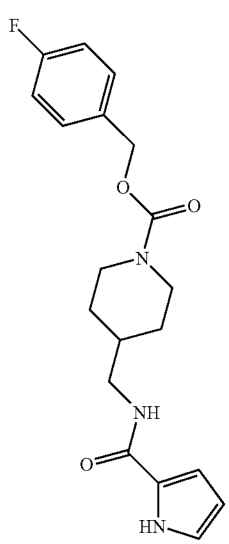 | M.S. (M$^+$ + 1) 360 |

-continued
| EX. | Name | Structure | Data |
|---|---|---|---|
| 110. | 4-{[(1H-Pyrrole-2-carbonyl)-amino]-methyl}-piperidine-1-carboxylic acid indan-2-yl ester | 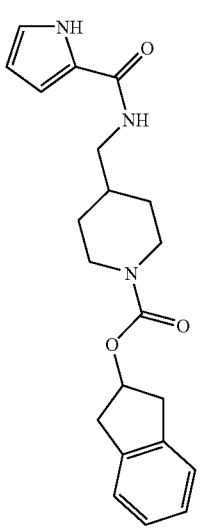 | M.S. (M+ + 1) 368 |
| 111. | 4-{[(1H-Pyrazole-4-carbonyl)-amino]-methyl}-piperidine-1-carboxylic acid 4-bromo-thiophen-3-ylmethyl ester | 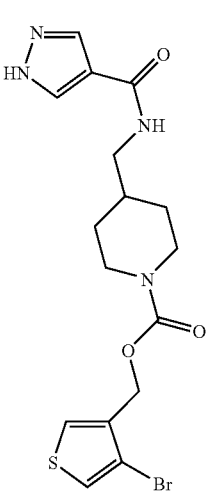 | M.S. (M+ + 1) 427 |
| 112. | 4-{[(Pyrazine-2-carbonyl)-amino]-methyl}-piperidine-1-carboxylic acid benzyl ester | 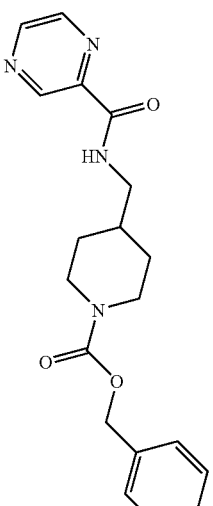 | M.S. (M+ + 1) 355 |

| EX. | Name | Structure | Data |
|---|---|---|---|
| 113. | 4-{[(Quinoline-4-carbonyl)-amino]-methyl}-piperidine-1-carboxylic acid benzyl ester | 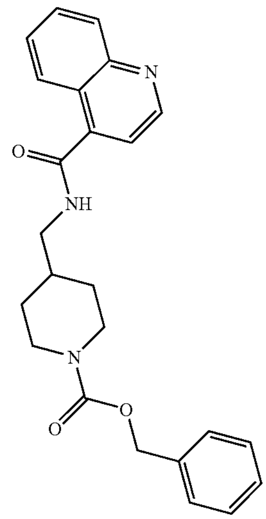 | M.S. (M+ + 1) 404 |
| 114. | 4-{[(2,6-Dihydroxy-pyridine-4-carbonyl)-amino]-methyl}-piperidine-1-carboxylic acid benzyl ester | 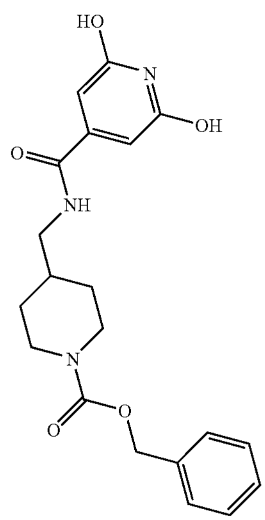 | M.S. (M+ + 1) 386 |
| 115. | 4-{[(1-Oxy-pyridine-4-carbonyl)-amino]-methyl}-piperidine-1-carboxylic acid benzyl ester | 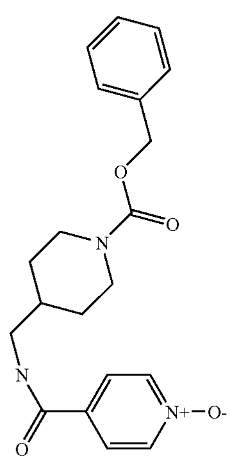 | M.S. (M+ + 1) 370 |

| EX. | Name | Structure | Data |
|---|---|---|---|
| 116. | 4-{[(Pyrimidine-4-carbonyl)-amino]-methyl}-piperidine-1-carboxylic acid benzyl ester | 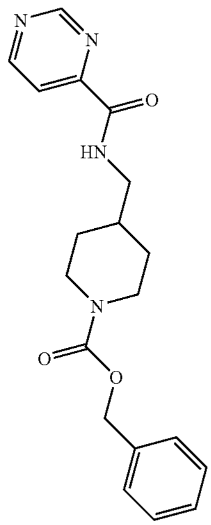 | M.S. (M+ + 1) 355 |
| 117. | 4-{[(1-Methyl-1H-pyrazole-3-carbonyl)-amino]-methyl}-piperidine-1-carboxylic acid benzyl ester | 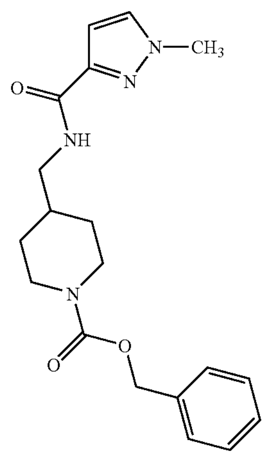 | M.S. (M+ + 1) 357 |
| 118. | 4-{[(2-Methyl-2H-pyrazole-3-carbonyl)-amino]-methyl}-piperidine-1-carboxylic acid benzyl ester | 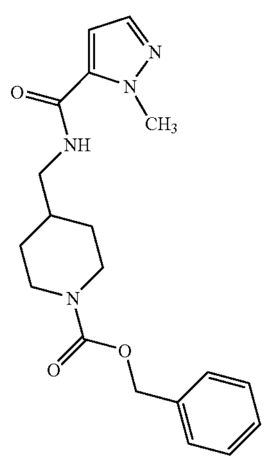 | M.S. (M+ + 1) 357 |

-continued

| EX. | Name | Structure | Data |
|---|---|---|---|
| 119. | 4-{[(1-Methyl-1H-pyrazole-4-carbonyl)-amino]-methyl}-piperidine-1-carboxylic acid benzyl ester | 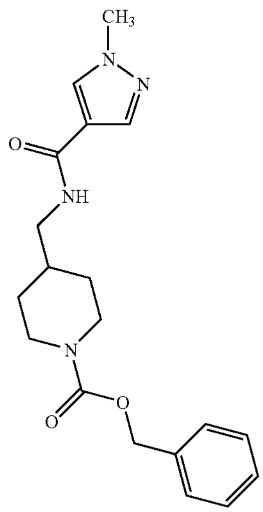 | M.S. (M$^+$ + 1) 357 |
| 120. | 4-{[([1,2,5]-Thiadiazole-3-carbonyl)-amino]-methyl}-piperidine-1-carboxylic acid benzyl ester | 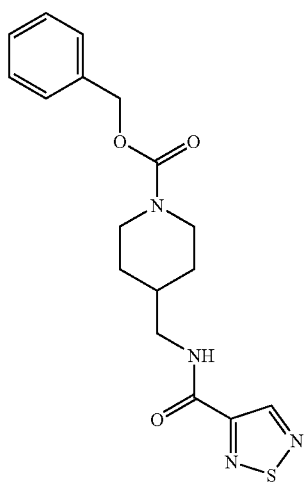 | M.S. (M$^+$ + 1) 361 |
| 121. | 4-{[(5-Bromo-pyridine-2-carbonyl)-amino]-methyl}-piperidine-1-carboxylic acid benzyl ester | 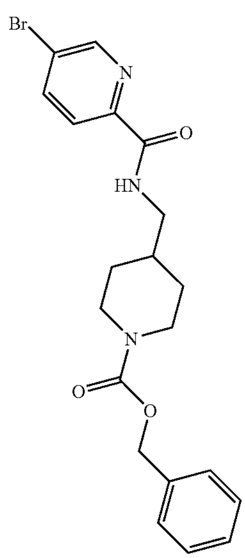 | M.S. (M$^+$ + 1) 432 |

| EX. | Name | Structure | Data |
|---|---|---|---|
| 122. | 4-{[(Pyrimidine-5-carbonyl)-amino]-methyl}-piperidine-1-carboxylic acid benzyl ester | 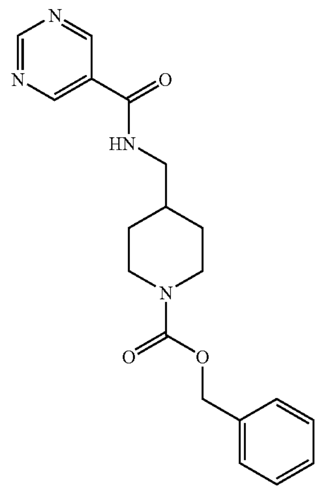 | M.S. (M$^+$ + 1) 355 |
| 123. | 4-{[(Pyrazolo[1,5-a]-pyrimidine-3-carbonyl)-amino]-methyl}-piperidine-1-carboxylic acid benzyl ester | 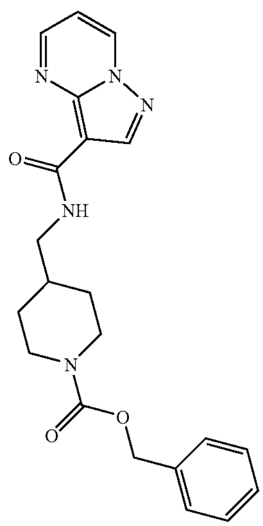 | M.S. (M$^+$ + 1) 394 |
| 124. | 4-{[(6-Bromo-pyridine-2-carbonyl)-amino]-methyl}-piperidine-1-carboxylic acid benzyl ester | 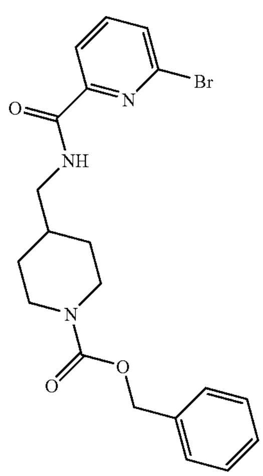 | M.S. (M$^+$ + 1) 432 |

-continued

| EX. | Name | Structure | Data |
|---|---|---|---|
| 125. | 4-{[(Benzothiazole-2-carbonyl)-amino]-methyl}-piperidine-1-carboxylic acid benzyl ester | 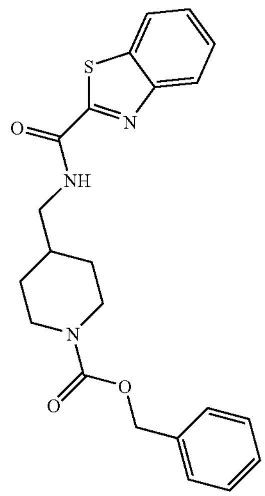 | M.S. (M$^+$ + 1) 410 |
| 126. | 4-{[(3,5-Dimethyl-1H-pyrrole-2-carbonyl)-amino]-methyl}-piperidine-1-carboxylic acid benzyl ester | 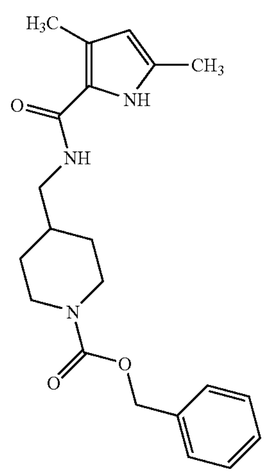 | M.S. (M$^+$ + 1) 370 |
| 127. | 4-{[(3-Methyl-pyridine-4-carbonyl)-amino]-methyl}-piperidine-1-carboxylic acid benzyl ester | 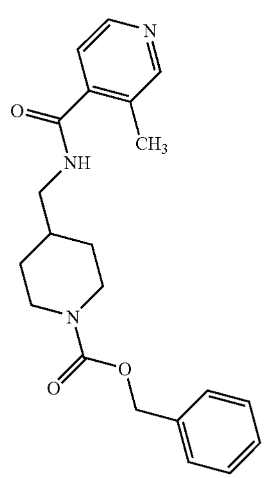 | M.S. (M$^+$ + 1) 368 |

| EX. | Name | Structure | Data |
|---|---|---|---|
| 128. | 4-{[(6-Cyano-pyridine-3-carbonyl)-amino]-methyl}-piperidine-1-carboxylic acid benzyl ester | 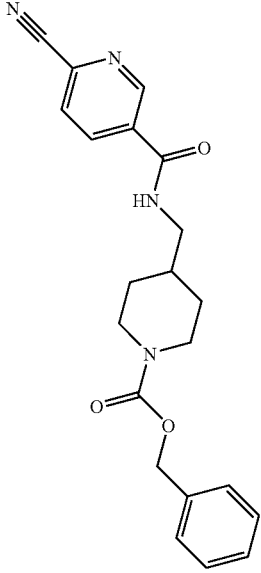 | M.S. (M+ + 1) 379 |
| 129. | 4-{[(2-Methyl-pyridine-4-carbonyl)-amino]-methyl}-piperidine-1-carboxylic acid benzyl ester | 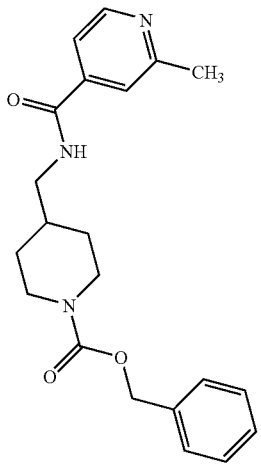 | M.S. (M+ + 1) 368 |
| 130. | 4-{[(2-Methoxy-6-methyl-pyridine-4-carbonyl)-amino]-methyl}-piperidine-1-carboxylic acid benzyl ester | 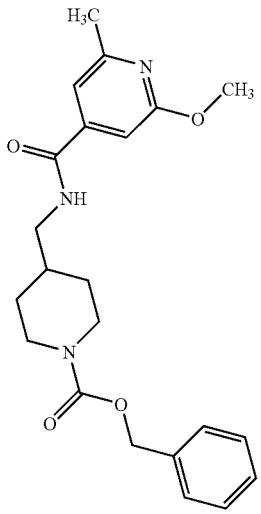 | M.S. (M+ + 1) 398 |

-continued

| EX. | Name | Structure | Data |
|---|---|---|---|
| 131. | 4-{[(2-Chloro-6-methyl-pyridine-4-carbonyl)-amino]-methyl}-piperidine-1-carboxylic acid benzyl ester | 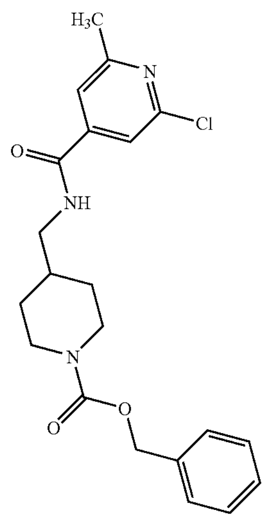 | M.S. (M⁺ + 1) 402 |
| 132. | 4-{[(6-Amino-pyridazine-3-carbonyl)-amino]-methyl}-piperidine-1-carboxylic acid benzyl ester | 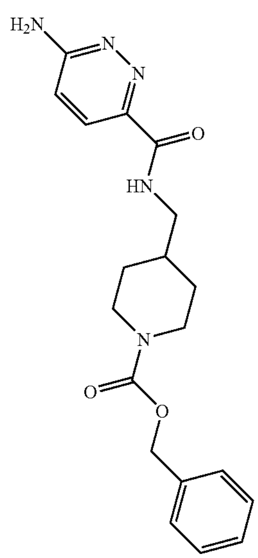 | M.S. (M⁺ + 1) 370 |
| 133. | 4-[(2-Hydroxy-benzoylamino)-methyl]-piperidine-1-carboxylic acid benzyl ester | 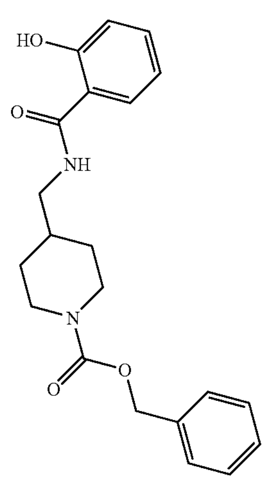 | M.S. (M⁺ + 1) 369 |

-continued

| EX. | Name | Structure | Data |
|---|---|---|---|
| 134. | 4-[(3-Hydroxy-benzoylamino)-methyl]-piperidine-1-carboxylic acid benzyl ester | 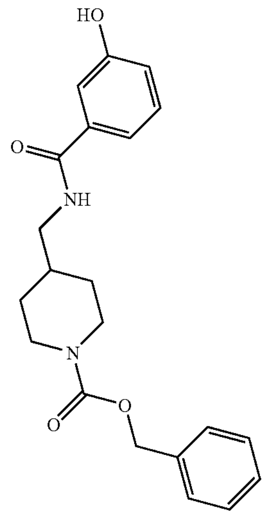 | M.S. (M$^+$ + 1) 369 |
| 135. | 4-[(2,5-Dihydroxy-benzoylamino)-methyl]-piperidine-1-carboxylic acid benzyl ester | 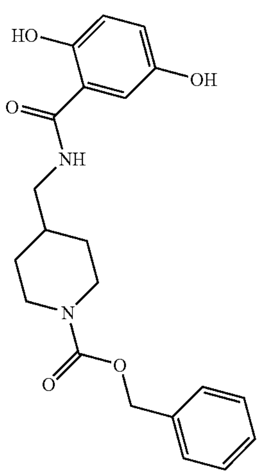 | M.S. (M$^+$ + 1) 385 |
| 136. | 4-[(4-Hydroxy-3,5-diiodo-benzoylamino)-methyl]-piperidine-1-carboxylic acid benzyl ester | 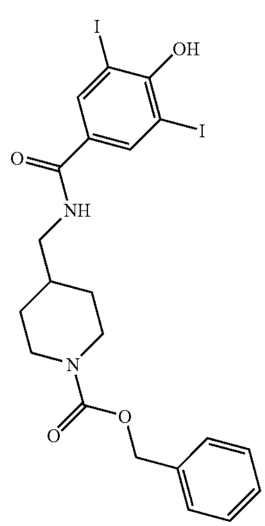 | M.S. (M$^+$ + 1) 621 |

Example 137

1H-Pyrazole-4-carboxylic acid [1-(3-phenyl-propionyl)-piperidin-4-ylmethyl]-amide

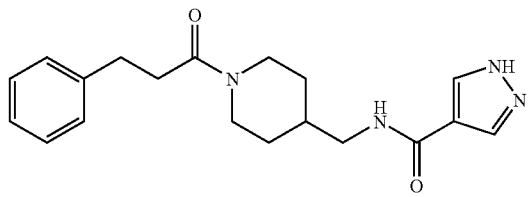

Step 1:

1H-Pyrazole-4-carboxylic acid (piperidin-4-ylmethyl)-amide

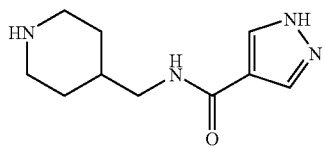

4-{[(1H-Pyrazole-4-carbonyl)-amino]-methyl}-piperidine-1-carboxylic acid benzyl ester (EXAMPLE 34) (600 mg, 1.75 mmol), 10% palladium on Carbon (150 mg) and ethanol (15 mL) were combined in a Parr® jar and hydrogenated at 50 psi for 24 h. The reaction mixture was filtered through Celite® and the filtrate was evaporated in vacuo to give the product as a white foam.

Step 2:

1H-Pyrazole-4-carboxylic acid [1-(3-phenyl-propionyl)-piperidin-4-ylmethyl]-amide

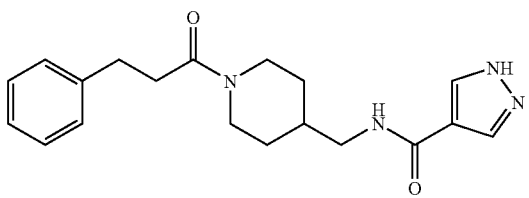

1H-Pyrazole-4-carboxylic acid (piperidin-4-ylmethyl)-amide (352 mg, 1.69 mmol), hydrocinnamoyl chloride (503 µL, 3.38 mmol), diisopropylethylamine (294 µL, 1.69 mmol) and DMF (4 mL) were combined under Nitrogen and stirred at 25° C. for 24 h. Sodium hydroxide (1 mL, 2N) was added and the mixture was stirred 1 h. Water was added and the contents of the reaction flask were extracted with EtOAc (3×50 mL). The combined organic extracts were dried with $Na_2SO_4$ and filtered. The filtrate was removed in vacuo and the remaining residue was purified using an ISCO® normal phase silica chromatography system ($CH_2Cl_2$ (100%) to $CH_2Cl_2$:MeOH:$NH_4OH$ 90:10:1). Fractions containing the desired product were combined and the solvent was removed in vacuo to give a colorless oil. Addition of EtOAc followed by 1N HCl/$Et_2O$ gave the product as a white solid.

$^1$H NMR (500 MHz, δ, DMSO-$d_6$): 8.10 (m, 1H), 8.04 (s, 2H), 7.28–7.20 (m, 4H), 7.18–7.14 (m, 1H), 4.38 (m, 1H), 3.85 (m, 1H), 3.06 (m, 2H), 2.90 (m, 1H), 2.80 (t, 2H), 2,60 (m, 2H), 1.75–1.60 (m, 4H), 0.95 (m, 2H).

The following compounds were prepared by substituting the appropriate acid chloride for the hydrocinnamoyl chloride in the above procedure.

| EX. | Name | Structure | Analytical Data |
|---|---|---|---|
| 138 | 1H-Pyrazole-4-carboxylic acid [1-(2-phenyl-cyclopropane-carbonyl)-piperidin-4-ylmethyl]-amide | 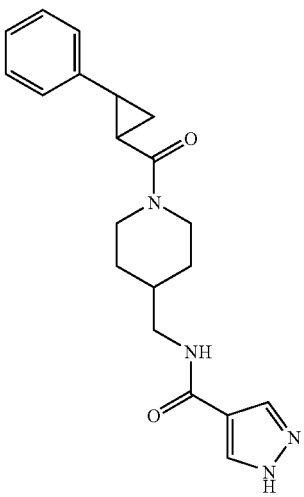 | $^1$H NMR(500MHz, δ, DMSO-$d_6$): 8.08–7.98(m, 3H), 7.26 (m, 2H), 7.17(m, 3H), 4.38(m, 1H), 4.16(m, 1H), 3.15–2.97(m, 3H), 2.58 (m, 1H), 2.26(m, 2H), 1.80–1.60(m, 3H), 1.30(m, 1H), 1.20–0.95(m, 3H). |

| EX. | Name | Structure | Analytical Data |
|---|---|---|---|
| 139 | 1H-Pyrazole-4-carboxylic acid [1-(3-phenyl-acryloyl)-piperidin-4-ylmethyl]-amide | 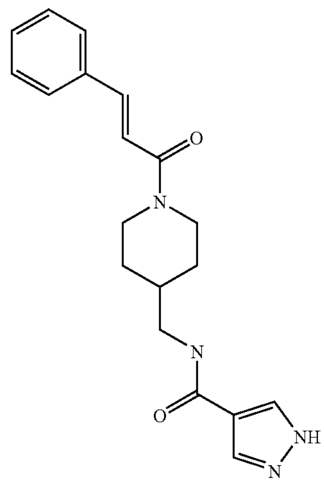 | $^1$H NMR(500MHz, δ, DMSO-d$_6$): 8.16 (s, br, 1H), 8.07(m, 1H), 7.88(s, br, 1H), 7.70(m, 2H), 7.48–7.34(m, 4H), 7.26 (m, 2H), 4.48(m, 1H), 4.29(m, 1H), 3.17–3.00(m, 3H), 2.65(m, 1H), 1.85–1.69(m, 3H), 1.15–1.00(m, 2H). |

The following examples were prepared from 1H-pyrazole4-carboxylic acid (piperidin-4-ylmethyl)-amide as described in Example 1 Step 2.

| EX. | Name | Structure | Analytical Data |
|---|---|---|---|
| 140 | [1-Benzyl-2-oxo-2-(4-{[(1H-pyrazole-4-carbonyl)-amino]-methyl}-piperidin-1-yl)-ethyl]-carbamic acid tert-butyl ester | 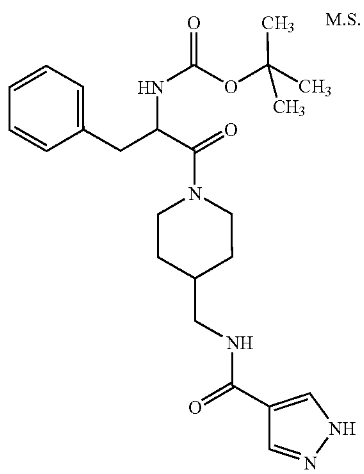 | M.S. (M$^+$ + 1) 456 |

-continued

| EX. | Name | Structure | Analytical Data |
|---|---|---|---|
| 141 | [1-(4-Chloro-benzyl)-2-oxo-2-(4-{[(1H-pyrazole-4-carbonyl)-amino]-methyl}-piperidin-1-yl)-ethyl]-carbamic acid tert-butyl ester | 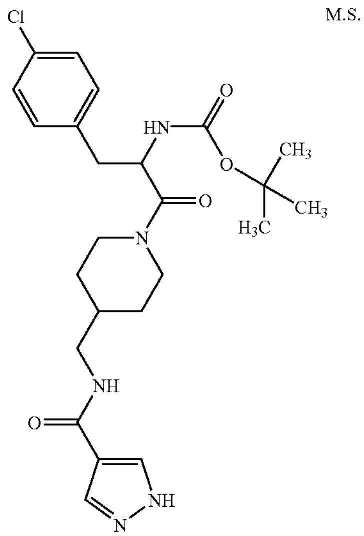 | M.S. (M$^+$ + 1) 490 |
| 142 | 1H-Pyrazole-4-carboxylic acid [1-(2-hydroxy-3-phenyl-propionyl)-piperidin-4-ylmethyl]-amide | 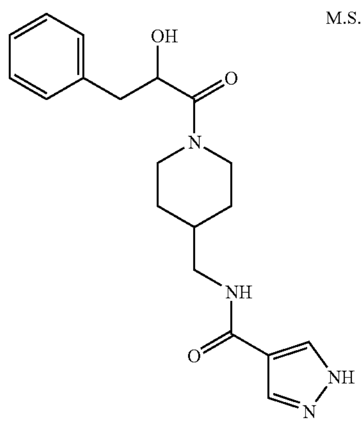 | M.S. (M$^+$ + 1) 357 |
| 143 | 1H-Pyrazole-4-carboxylic acid [1-(2-methyl-3-phenyl-propionyl)-piperidin-4-ylmethyl]-amide | 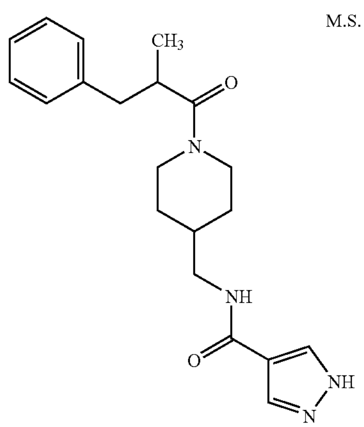 | M.S. (M$^+$ + 1) 355 |

-continued

| EX. | Name | Structure | Analytical Data |
|---|---|---|---|
| 144 | 1H-Pyrazole-4-carboxylic acid {1-[2-hydroxy-3-(4-hydroxy-phenyl)-propionyl]-piperidin-4-ylmethyl}-amide | 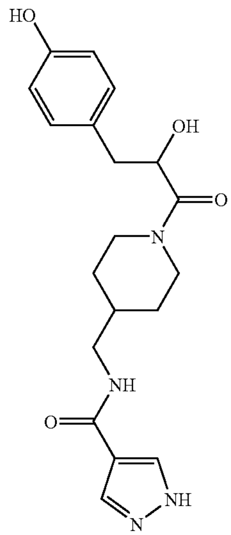 | M.S. (M$^+$ + 1) 373 |
| 145 | 1H-Pyrazole-4-carboxylic acid [1-(2-phenyl-cyclopropane-carbonyl)-piperidin-4-ylmethyl]-amide | 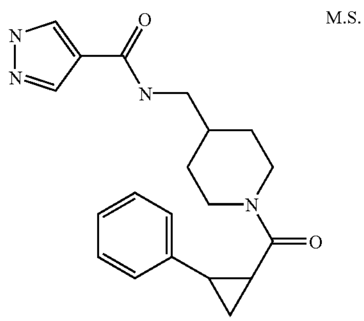 | M.S. (M$^+$ + 1) 353 |

The following two compounds were prepared from EXAMPLES 140 and 141 respectively by treatment with trifluoroacetic acid in dichloromethane.

| EX. | Name | Structure | Analytical Data |
|---|---|---|---|
| 146 | 1H-Pyrazole-4-carboxylic acid [1-(2-amino-3-phenyl-propionyl)-piperidin-4-ylmethyl]-amide | 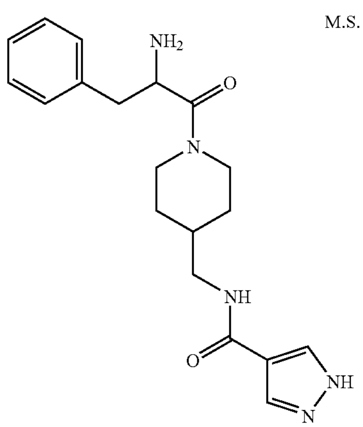 | M.S. (M$^+$ + 1) 356 |

| EX. | Name | Structure | Analytical Data |
|---|---|---|---|
| 147 | 1H-Pyrazole-4-carboxylic acid {1-[2-amino-3-(4-chloro-phenyl)-propionyl]-piperidin-4-yl-methyl}-amide | 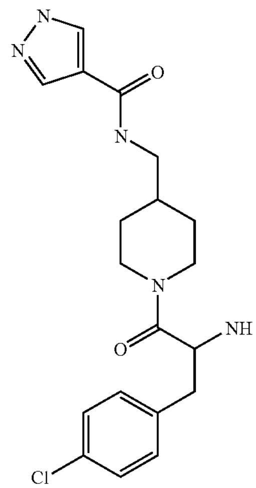 | M.S. (M⁺ + 1) 390 |

Example 148

Trans 1H-Pyrazole-4-carboxylic acid [1-(2-phenyl-cyclopropylmethyl)-piperidin-4-ylmethyl]-amide

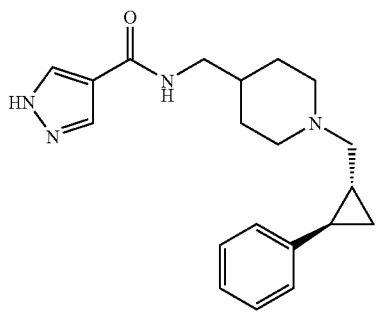

A solution of 1H-pyrazole-4-carboxylic acid (piperidin-4-ylmethyl)-amide (290 mg, 1.39 mmol), trans-2-phenylcyclopropanecarbaldehyde (224 mg, 1.53 mmol) and sodium triacetoxyborohydride (590 mg, 2.78 mmol) in MeOH (15 mL) was heated to 50° C. and stirred for 1 h. The resulting reaction mixture was concentrated and purified by silica gel chromatography (gradient: $CH_2Cl_2$ to 80:20:2 $CH_2Cl_2$:MeOH:$NH_4OH$) to give the trans 1H-pyrazole-4-carboxylic acid [1-(2-phenyl-cyclopropylmethyl)-piperidin-4-ylmethyl]-amide product.

$^1$H NMR (δ, $CDCl_3$): 7.86 (s, 2H), 7.23 (d, 2H), 7.17 (t, 1H), 7.02 (d, 2H), 5.94 (brt, 1H), 3.35 (m, 2H), 3.10 (brt, 2H), 2.55 (dd, 1H), 2.39 (dd, 1H), 2.30 (q, 2H), 1.70–1.55 (m, 4H), 1.41 (m, 2H), 1.22 (m, 1H), 0.95 (m, 1H), 0.82 (m, 1H).

The following compounds were prepared similarly to the procedure described above for EXAMPLE 148 but substituting the appropriate aldehyde for the trans-2-phenylcyclopropanecarbaldehyde.

| EX. | Name | Structure | Analytical Data |
|---|---|---|---|
| 149 | 1H-Pyrazole-4-carboxylic acid [1-(3-phenyl-propyl)-piperidin-4-ylmethyl]-amide | 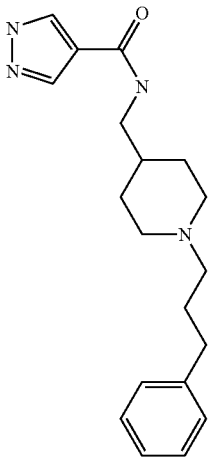 | $^1$H NMR($\delta$, CDCl$_3$): 7.93(s, 2H), 7.3–7.15(m, 5H), 6.30 (brt, 1H), 3.35(t, 2H), 3.04(brd, 2H), 2.61(t, 2H), 2.46 (dd, 2H), 2.04(t, 2H), 1.88(m, 2H), 1.70(m, 2H), 1.47 (m, 2H), 1.27(t, 1H). |
| 150 | 1H-Pyrazole-4-carboxylic acid [1-(4-phenyl-butyl)-piperidin-4-ylmethyl]-amide | 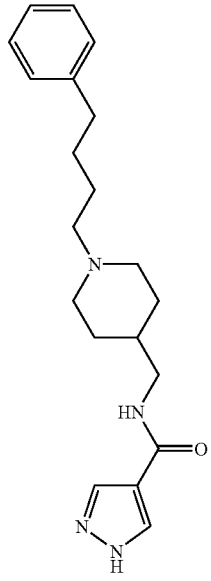 | $^1$H NMR($\delta$, CD$_3$-OD): 8.03(s, 2H), 7.3–7.1(m, 5H), 3.21(d, 2H), 2.97 (brd, 2H), 2.63(t, 2H), 2.40(dd, 2H), 2.01(t, 2H), 1.76 (brd, 2H), 1.7–1.5 (m, 5H), 1.30(m, 2H). |
| 151 | 1H-Pyrazole-4-carboxylic acid (1-phenethyl-piperidin-4-ylmethyl)-amide | 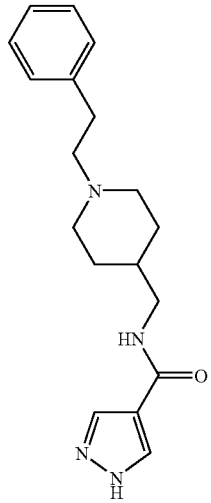 | M.S. (M$^+$ + 1) 313 |

-continued

| EX. | Name | Structure | Analytical Data |
|---|---|---|---|
| 152 | 1H-Pyrazole-4-carboxylic acid [1-(2-phenyl-cyclopropyl-methyl)-piperidin-4-ylmethyl]-amide | 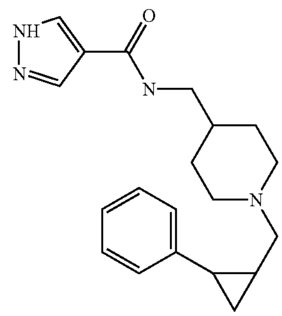 | M.S. (M$^+$ + 1) 339 |
| 153 | 1H-Pyrazole-4-carboxylic acid [1-(2-phenyl-cyclopropyl-methyl)-piperidin-4-ylmethyl]-amide | 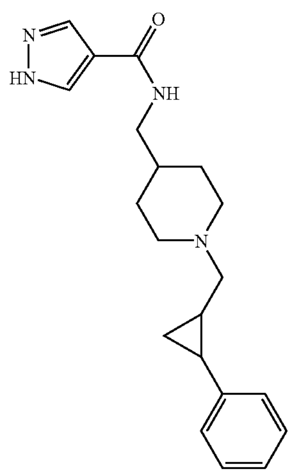 | $^1$H NMR(δ, CDCl$_3$): 7.86(s, 2H), 7.23(d, 2H), 7.17(t, 1H), 7.00(d, 2H), 6.61 (brs, 1H), 3.30(m, 2H), 3.10(brt, 2H), 2.55(dd, 1H), 2.39 (dd, 1H), 2.03(q, 2H), 1.70–1.55(m, 4H), 1.41(m, 2H), 1.22(m, 1H), 0.95 (m, 1H), 0.82(m, 1H). |

The following compounds were prepared as described above for EXAMPLE 148, but replacing 1H-pyrazole-4-carboxylic acid (piperidin-4-ylmethyl)-amide with, for example, 4-hydroxy-N-piperidin-4-ylmethyl-benzamide, which was prepared from 4-[(4-hydroxy-benzoylamino)-methyl]-piperidine-1-carboxylic acid benzyl ester as described in EXAMPLE 137, step 1.

| EX. | Name | Structure | Analytical Data |
|---|---|---|---|
| 154 | 4-Hydroxy-N-[1-(2-phenyl-cyclopropyl-methyl)-piperidin-4-ylmethyl]-benzamide | 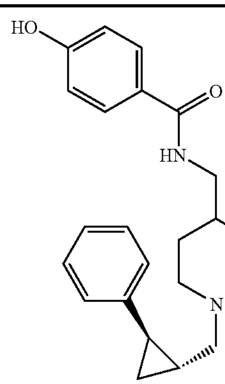 | $^1$H NMR(δ, CDCl$_3$): 7.43(d, 2H), 7.3–7.1 (m, 3H), 7.00(d, 2H), 6.65(d, 2H), 6.39(brt, 1H), 3.35 (m, 2H), 3.14(brt, 2H), 2.58(dd, 1H), 2.41(dd, 1H), 2.08 (q, 2H), 1.7–1.5(m, 4H), 1.41(m, 2H), 1.22(m, 1H), 0.96 (m, 1H), 0.82(m, 1H). |

| EX. | Name | Structure | Analytical Data |
|---|---|---|---|
| 155 | 4-Hydroxy-N-[1-(3-phenyl-propyl)-piperidin-4-ylmethyl]-benzamide | 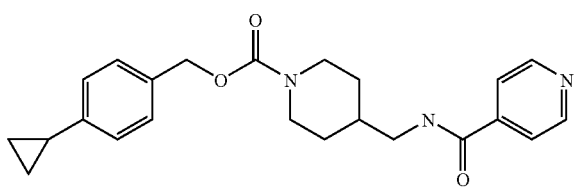 | $^1$H NMR($\delta$, CD$_3$-OD): 7.70(d, 2H), 7.3–7.1(m, 5H), 6.80(d, 2H), 3.23 (d, 2H), 3.02(brd, 2H), 2.61(dd, 2H), 2.42(dd, 2H), 2.08 (brt, 2H), 1.9–1.6 (m, 5H), 1.35(m, 2H). |

Example 156

4-{[(Pyridine-4-carbonyl)-amino]-methyl}-piperidine-1-carboxylic acid 4-cyclopropyl-benzyl ester

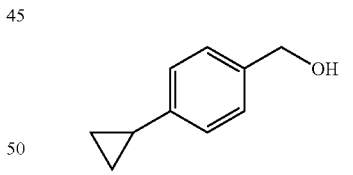

Step 1:

4-Cyclopropyl-benzoic acid ethyl ester

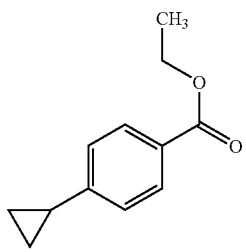

Indium trichloride (2.2 g, 10 mmol) and THF (50 mL) were combined under nitrogen and cooled to −70° C. Cyclopropylmagnesium bromide solution (33 mL, 30 mmol, 0.92M) was added dropwise while maintaining the reaction temperature ≦−60° C. After the addition was complete the reaction was stirred 0.5 h with cooling then 0.5 h with the cooling bath removed. The resulting solution was added via cannula to a refluxing solution of ethyl-4-iodobenzoate (5.5 g, 20 mmol), trans-dichlorobis(triphenylphosphine)palladium(II) (421 mg, 0.60 mmol) and THF (100 mL) under nitrogen. After 24 h, the contents of the reaction flask were cooled and the solvent was removed in vactio. Water (100 mL) and 5% KHSO$_4$ were added and the mixture was extracted with CH$_2$Cl$_2$ (3×100 mL). The combined organic extracts were washed with brine, dried with Na$_2$SO$_4$ and filtered. The filtrate was removed in vacuo and the remaining residue was purified by flash column chromatography (hexane:EtOAc 95:5) to give the 4-cyclopropyl-benzoic acid ethyl ester as an orange oil.

Step 2:

(4-Cyclopropyl-phenyl)-methanol

4-Cyclopropyl-benzoic acid ethyl ester (2.46 g, 13 mmol), and THF (250 mL) were combined under nitrogen and cooled in an IPA/dry ice bath to −70° C. Lithium aluminum hydride solution (20 mL, 20 mmol, 1.0M) was added dropwise. After 2 h excess lithium aluminum hydride was quenched by adding EtOAc dropwise. The reaction was warmed to 25° C. then the solvent was removed in vacuo. Water (200 mL) and a few drops of HCl(aq, 6N) were added. The mixture was extracted with EtOAc (3×100 mL). The combined organic extracts were washed with brine, dried with Na$_2$SO$_4$ and filtered. The filtrate was removed in vacuo and the remaining residue was purified by flash column chromatography (hexane:EtOAc 40:60) to give the (4-cyclopropyl-phenyl)-methanol as a colorless oil.

Step 3:

Carbonic acid 4-cyclopropyl-benzyl ester 2,5-dioxo-pyrrolidin-1-yl ester

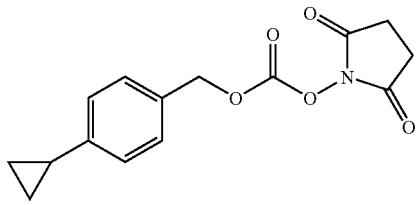

The title compound was prepared from (4-Cyclopropyl-phenyl)-methanol as described above for similar compounds (*Chem. Pharm. Bull.*, 38(1):110–115 (1990)).

Step 4:

4-Aminomethyl-piperidine-1-carboxylic acid 4-cyclopropyl-benzyl ester

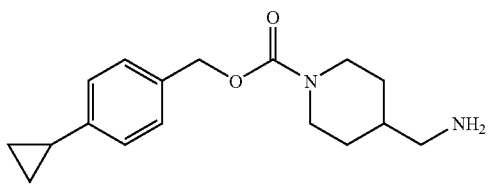

The title compound was prepared from carbonic acid 4-cyclopropyl-benzyl ester 2,5-dioxo-pyrrolidin-1-yl ester as described in EXAMPLE 1, Step 1.

Step 5:

4-{[(Pyridine-4-carbonyl)amino]-methyl}-piperidine-1-carboxylic acid 4-cyclopropyl-benzyl ester

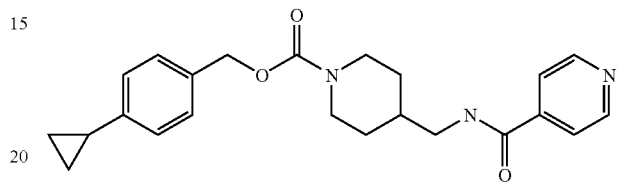

The title compound was prepared from 4-aminomethyl-piperidine-1-carboxylic acid 4-cyclopropyl-benzyl ester as described above in EXAMPLE 1, Step 2.

M.S. (M$^+$+1) 394

The following compounds were prepared from 4-aminomethyl-piperidine-1-carboxylic acid 4-cyclopropyl-benzyl ester as described above in EXAMPLE 1, step 2.

| EX. | Name | Structure | Analytical Data |
|---|---|---|---|
| 157 | 4-[(4-Hydroxy-benzoylamino)-methyl]-piperidine-1-carboxylic acid 4-cyclopropyl-benzyl ester | 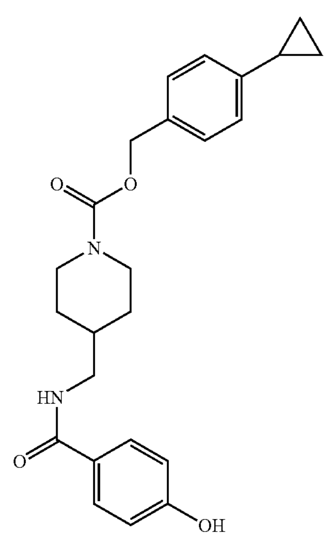 | M.S. (M$^+$ + 1) 409 |

-continued
| EX. | Name | Structure | Analytical Data |
|---|---|---|---|
| 158 | 4-{[(1H-Pyrazole-3-carbonyl)-amino]-methyl}-piperidine-1-carboxylic acid 4-cyclopropyl-benzyl ester | 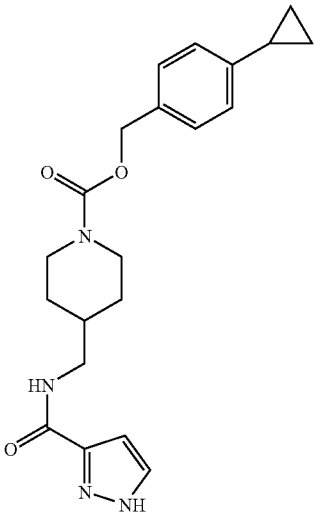 | M.S. (M$^+$ + 1) 383 |
| 159 | 4-{[(1H-Pyrazole-4-carbonyl)-amino]-methyl}-piperidine-1-carboxylic acid 4-cyclopropyl-benzyl ester | 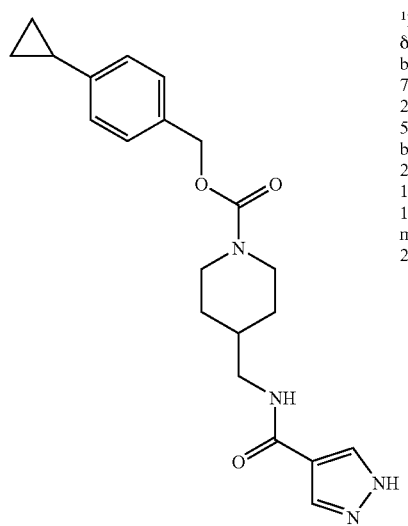 | $^1$H NMR(500MHz δ, CDCl$_3$): 10.70(s, br, 1H), 7.95(s, 2H), 7.25(d, 2H), 7.05(d, 2H), 600(m, 1H), 5.06(s, 2H), 4.20(s, br, 2H), 3,30(s, br, 2H), 2.75(s, br, 2H), 1.90(m, 1H), 1.85–1.50(m, 3H), 1.20 m, 2H), 0.97(m, 2H), 0.68(m, 2H). |

The following compounds were prepared from 4-hydroxy-N-piperidin-4-ylmethyl-benzamide (prepared from 4-[(4-hydroxy-benzoylamino)-methyl]-piperidine-1-carboxylic acid benzyl ester as described in EXAMPLE 137, step 1) as described in EXAMPLE 1, Step 2.

| EX. | Name | Structure | Analytical Data |
|---|---|---|---|
| 160 | 4-Hydroxy-N-[1-(2-phenyl-cyclopropane-carbonyl)-piperidin-4-ylmethyl]-benzamide | 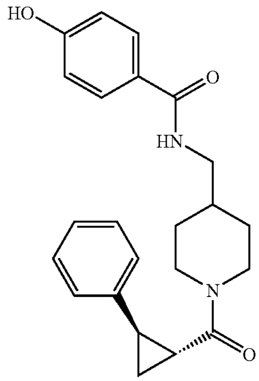 | $^1$H NMR9 ($\delta$, CDCl$_3$): 8.72 (brs, 1H), 7.61 (d, 2H), 7.24 (m, 2H), 7.19 (t, 1H), 7.06 (d, 2H), 6.93 (d, 2H), 6.72 (brs, 1H), 4.55 (brd, 1H), 4.10 (brd, 1H) 3.3–3.1 (m, 2H), 3.01 (q, 1H), 2.58 (brt, 1H), 2.41 (brs, 1H), 2.0–1.6 (m, 5H), 1.3–1.1 (m, 3H). |
| 161 | 4-Hydroxy-N-[1-(2-phenyl-cyclopropane-carbonyl)-piperidin-4-ylmethyl]-benzamide | 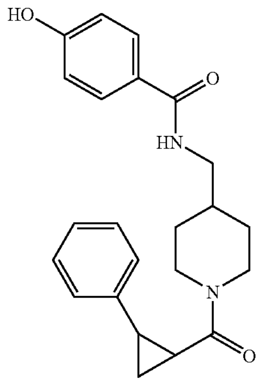 | M.S. (M$^+$ + 1) 379 |

Example 162

1H-Pyrazole-4-carboxylic acid (1-benzylthiocarbamoyl-piperidin-4-ylmethyl)-amide

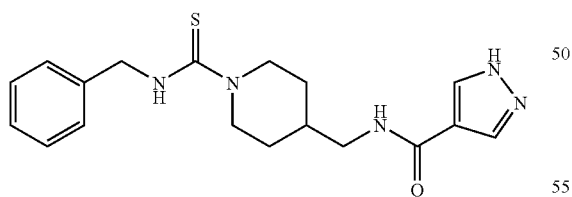

1H-Pyrazole-4-carboxylic acid (piperidin-4-ylmethyl)-amide (EXAMPLE 137, Step 1) (50 mg, 0.24 mmol), benzyl isothiocyanate (35 μL, 0.264 mmol) and DMF (1 mL) were combined and stirred under Nitrogen for 1 h. The contents of the reaction flask were poured into water and sodium hydroxide (2 mL, 2N) was added. The resulting mixture was extracted with EtOAc (3×50 mL) and the combined organic extracts were dried with Na$_2$SO$_4$. The filtrate was removed in vacuo and the remaining residue was purified by Gilson® reverse phase preparative HPLC. The fraction containing the desired product was evaporated in vacuo to give a colorless oil. Trituration with EtOAc/EtOH afforded the EXAMPLE 162 as a white solid.

$^1$H NMR (500 MHz, $\delta$, DMSO-d$_6$): 13.10 (s, 1H), 8.20 (m, 2H), 8.10 (m, 1H), 7.90 (m, 1H), 7.32–7.18 (m, 5H), 4.80 (d, 2H), 4.65 (d, 2H), 3.10 (t, 2H), 2.97 (t, 2H), 1.80 (m, 1H), 1.67 (m, 2H), 1.10 (m, 2H).

Example 163

4-{[(1H-Pyrazole-4-carbonyl)-amino]-methyl}-piperidine-1-carboxylic acid benzylamide

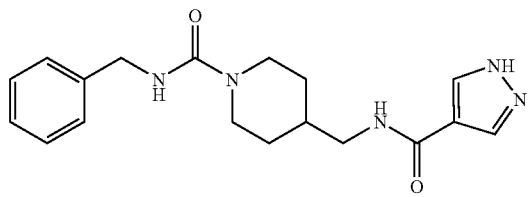

The title compound was prepared as described in EXAMPLE 162 except that benzyl isocyanate was used instead of benzyl isothiocyanate.

¹H NMR (500 MHz, δ, DMSO-d₆): 13.10 (s, 1H), 8.16 (s, 1H), 8.04 (m, 1H), 7.88 (s, 1H), 7.30–7.16 (m, 4H), 7.02 (m, 1H), 4.21 (d, 2H), 3.99 (d, 2H), 3.10 (t, 2H), 2.65 (m, 2H), 1.72–1.58 (m, 3H), 1.05–0.95 (m, 2H).

Example 164

1H-Pyrazole-4-carboxylic acid [1-(2-hydroxy-3-phenyl-propyl)-piperidin-4-ylmethyl]-amide

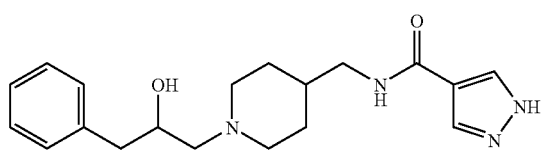

To a solution of 2-benzyloxirane (0.01 mL, 0.07 mmol) in iso-propyl alcohol (5 mL) was added 1H-pyrazole-4-carboxylic acid (piperidin-4-ylmethyl)-amide (EXAMPLE 137, Step 1) (15 mg, 0.07 mmol). The resulting reaction mixture was heated to 60° C. for 24 h. The reaction mixture was concentrated, partitioned between EtOAc and aqueous sodium bicarbonate. The organic phase was dried, the solvent evaporated, and the crude product purified by reverse phase HPLC to give 1H-Pyrazole-4-carboxylic acid [1-(2-hydroxy-3-phenyl-propyl)-piperidin-4-ylmethyl]-amide.

M.S. (M⁺+1) 343

Example 165

4-{[(2-Oxo-1,2-dihydro-pyridine-4-carbonyl)-amino]-methyl}-piperidine-1-carboxylic acid benzyl ester

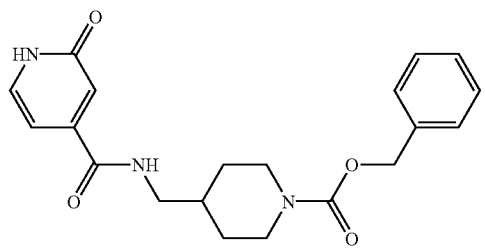

To 4-{[(-oxy-pyridine-4-carbonyl)-amino]-methyl}-piperidine-1-carboxylic acid benzyl ester (EXAMPLE 115) (200 mg, 0.542 mmol) was added acetic anhydride (5 mL) and the mixture heated to reflux for 24 h. The reaction was concentrated and chromatographed on silica using ethyl acetate to give an oil (40 mg). The crude material was dissolved in methanol (10 mL) and treated with solid potassium carbonate (40 mg) for 0.5 h. Concentration of the reaction and extraction into dichloromethane (20 mL) from aqueous sodium bicarbonate (20 mL) followed by concentration and precipitation of the solid from ether gave the 4-{[(2-Oxo-1,2-dihydro-pyridine-4-carbonyl)-amino]-methyl}-piperidine-1-carboxylic acid benzyl ester.

M.S. (M+1): 370

Example 166

4-{[(2-Methylaminomethyl-pyridine-4-carbonyl)-amino]-methyl}-piperidine-1-carboxylic acid benzyl ester

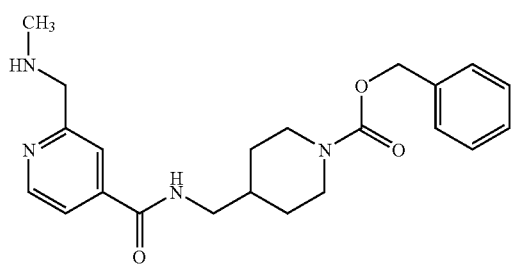

Step 1:

Preparation of 2,4-pyridinedicarboxcyclic acid diethyl ester

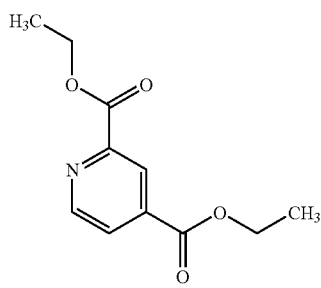

To a mixture of 2,4-pyridinedicarboxylic acid (23 g, 0.138 mol) in ethanol (500 mL) was bubbled anhydrous hydrogen chloride gas over a period of 6 h. The resulting reaction mixture was concentrated in vacuo and extracted into dichloromethane (500 mL) from 10% aqueous sodium bicarbonate (500 mL). The organic extract was dried over sodium sulfate, and concentrated in vacuo to give 2,4-pyridinedicarboxcyclic acid diethyl ester as an oil.

M.S. (M+1): 224

Step 2:

Preparation of 2-Formyl-isonicotinic acid ethyl ester

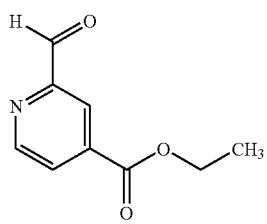

To a solution of 2,4-pyridinedicarboxcyclic acid diethyl ester (25 g, 0.112 mol) in tetrahydrofuran (IL) at −78° C. and under nitrogen was slowly added a solution of 1.0M diisobutylaluminum hydride in TF (11 mL). The reaction was stirred at −78° C. for 5 h and then quenched by addition of a solution of tetrahydrofuran-acetic acid-water (174 mL, 62 mL, 15 mL) and the reaction allowed to warm to room temperature. Diethyl ether (500 mL) and 10% aqueous sodium bicarbonate (1 L) were added and the mixture stirred for 0.5 h. The ether layer was removed and the aqueous layer extracted with ethyl acetate (4×500 mL) The combined organic extracts were washed with saturated sodium chloride and concentrated to an oil which was purified by silica gel column chromatography using 30%ethyl acetate/hexane as eluent to give 2-formyl-isonicotinic acid ethyl ester as an oil.

M.S. (M+1): 180

Step 3:

Preparation of 2-Diethoxymethyl-isonicotinic acid ethyl ester

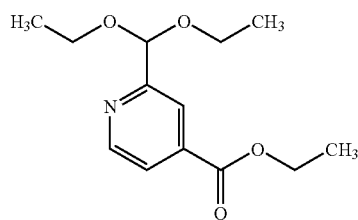

To a solution of 2-formyl-isonicotinic acid ethyl ester (5.0 g, 0.027 mol) in ethanol (9 mL) was added triethyl orthoformate (6.2 mL, 0.037 mol) followed by a solution of 6N hydrochloric acid in ethanol (1.5 mL). The mixture was heated to 110° C. (reflux) for 1.5 h, cooled to rt and solid potassium carbonate (1.80 g) added. The mixture was stirred for 5 min, concentrated in vacuo, and redissolved in diethyl ether (100 mL). The reaction was filtered through silica and the resulting cake washed with diethyl ether (50 mL). The filtrated was concentrated in vacuo to give 2-diethoxymethyl-isonicotinic acid ethyl ester as an oil.

M.S. (M+1): 254

Step 4:

Preparation of 2-Diethoxymethyl-isonicotinic acid

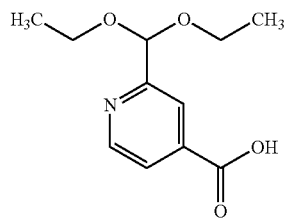

To a solution of 2-diethoxymethyl-isonicotinic acid ethyl ester (3.0 g, 0.012 mol) in tetrahydrofuran (100 mL) was added 1N sodium hydroxide (24 mL, 0.024 mol) and mixture allowed to stir for 2 h at rt. The reaction was concentrated in vacuo to give a pasty solid of 2-diethoxymethyl-isonicotinic acid, which was used in the next step as is.

M.S. (M+1): 226

Step 5:

Preparation of 4-{[(2-Diethoxymethyl-pyridine-4-carbonyl)-amino]-methyl}-piperidine-1-carboxylic acid benzyl ester

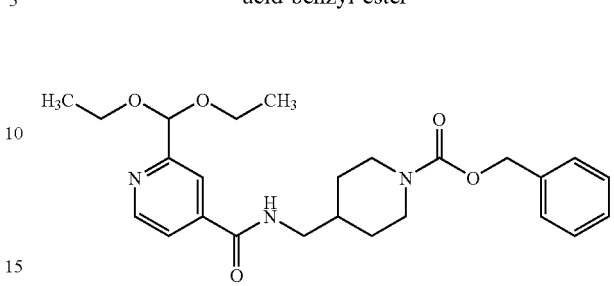

4-{[(2-Diethoxymethyl-pyridine-4-carbonyl)-amino]-methyl}-piperidine-1-carboxylic acid benzyl ester was prepared in a similar manner as described in EXAMPLE 1, Step 2.

M.S. (M+1): 456

Step 6:

Preparation of 4-{[(2-Formyl-pyridine-4-carbonyl)-amino]-methyl}-piperidine-1-carboxylic acid benzyl ester

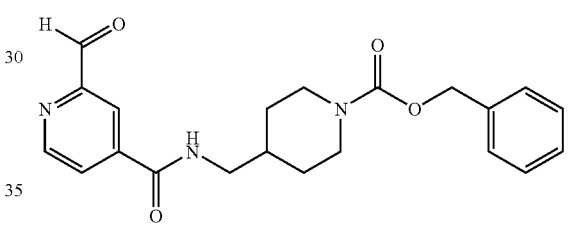

To a solution of 4-{[(2-diethoxymethyl-pyridine-4-carbonyl)-amino]-methyl}-piperidine-1-carboxylic acid benzyl ester (1.3 g, 0.0029 mol) in dioxane (20 mL) was added 1N hydrochloric acid (40 mL) and the mixture was warmed to 50° C. for 1.5 h. The reaction was cooled, diluted with ethyl acetate (100 mL) and 10% aqueous sodium bicarbonate (100 mL), and stirred well. The organic layer was removed, dried over sodium sulfate, filtered and concentrated in vacuo to give 4-{[(2-formyl-pyridine-4-carbonyl)-amino]-methyl}-piperidine-1-carboxylic acid benzyl ester as an oil.

M.S. (M+1): 382

Step 7:

Prep of 4-{[(2-Methylaminomethyl-pyridine-4-carbonyl)-amino]-methyl}-piperidine-1-carboxylic acid benzyl ester

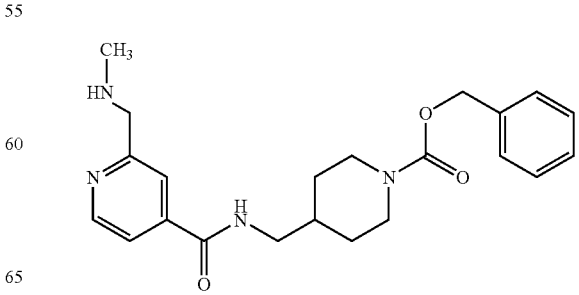

To a solution of 4-{[(2-formyl-pyridine-4-carbonyl)-amino]-methyl}-piperidine-1-carboxylic acid benzyl ester (50 mg, 0.13 mmol) in dichloroethane (0.5 mL) was added acetic acid (8 μL, 0.13 mmol), 2.0 M methylamine in TEF (72 μL, 0.14 mmol) followed by sodium triacetoxyborohydride (42 mg, 0.20 mmol). The resulting mixture was stirred for 5 h. The reaction was concentrated in vactio and the residue chromatographed (reverse phase C-18 using acetonitrile/0.1% trifluoroacetic acid in water) to give upon concentration in vacuo 4-{[(2-methylaminomethyl-pyridine-4-carbonyl)-amino]-methyl}-piperidine-1-carboxylic acid benzyl ester as the trifluoroacetic acid salt.

M.S. (m+1) 397

The following compounds were prepared as described above for 4-{[(2-methylaminomethyl-pyridine-4-carbonyl)-amino]-methyl}-piperidine-1-carboxylic acid benzyl ester, replacing methylamine with the appropriate amine in step 7, EXAMPLE 166.

| EX. | Name | Structure | Analytical Data |
|---|---|---|---|
| 167 | 4-{[(2-Dimethyl-aminomethyl-pyridine-4-carbonyl)-amino]-methyl}-piperidine-1-carboxylic acid benzyl ester | 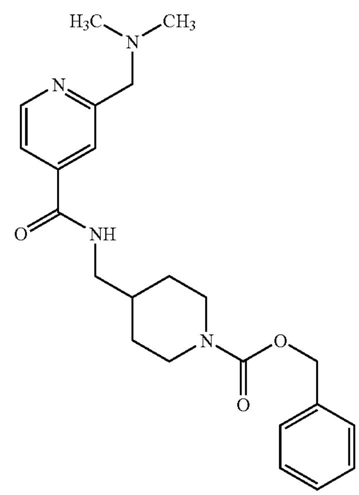 | M.S. (M$^+$ + 1) 411 |
| 168 | 4-{[(2-Aminomethyl-pyridine-4-carbonyl)-amino]-methyl}-piperidine-1-carboxylic acid benzyl ester | 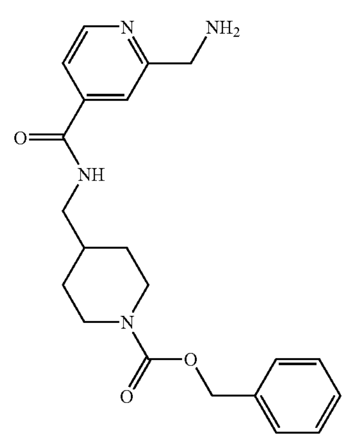 | M.S. (M$^+$ + 1) 383 |

Example 169

4-{[(2-Hydroxymethyl-pyridine-4-carbonyl)-amino]-methyl}-piperidine-1-carboxylic acid benzyl ester

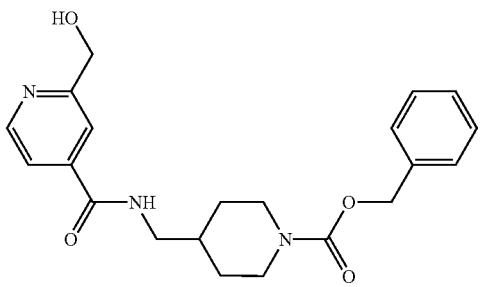

To a solution of 4-{[(2-formyl-pyridine-4-carbonyl)-amino]-methyl}-piperidine-1-carboxylic acid benzyl ester (EXAMPLE 166, Step 6) (50 mg, 0.131 mmol) in ethanol (2 mL) was added sodium borohydride (5 mg) and the mixture stirred for 0.5 h. The reaction was diluted with 10% aqueous sodium bicarbonate (10 mL) and extracted with ethyl acetate (25 mL). The ethyl acetate extract was concentrated and chromatographed (reverse phase C-18 using acetonitrile/ 0.1% trifluoroacetic acid in water) to give upon concentration in vacuo the 4-{[(2-hydroxymethyl-pyridine-4-carbonyl)-amino]-methyl}-piperidine-1-carboxylic acid benzyl ester as the trifluoroacetic acid salt.

M.S. (M+1): 384

Example 170

4-({[2-(1-Hydroxy-ethyl)-pyridine-4-carbonyl]-amino}-methyl)-piperidine-1-carboxylic acid benzyl ester

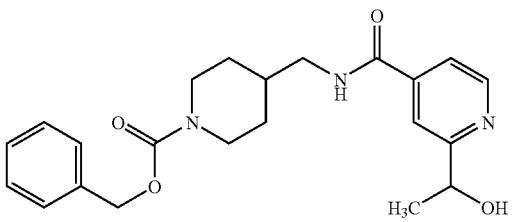

To a solution of 4-{[(2-formyl-pyridine-4-carbonyl)-amino]-methyl}-piperidine-1-carboxylic acid benzyl ester (EXAMPLE 166, Step 6) (50 mg, 0.131 mmol) in TBF (2 mL) at −78° C. was added 3.0M methylmagnesium chloride (45 μL, 0.135 mmol). The mixture was stirred for 5 min and allowed to warm to rt. The reaction was diluted with 10% aqueous sodium bicarbonate (10 mL) and extracted with ethyl acetate (25 mL). The ethyl acetate extract was concentrated and chromatographed on silica using 100% ethyl acetate to ethyl acetate/methanol (95/5) to give the 4-({[2-(1-hydroxy-ethyl)-pyridine-4-carbonyl]-amino}-methyl)-piperidine-1-carboxylic acid benzyl ester.

M.S. (M$^+$+1) 398

Example 171

4-({[2-(2,4-Dimethoxy-benzylamino)-pyridine-4-carbonyl]-amino}-methyl)-piperidine-1-carboxylic acid benzyl ester

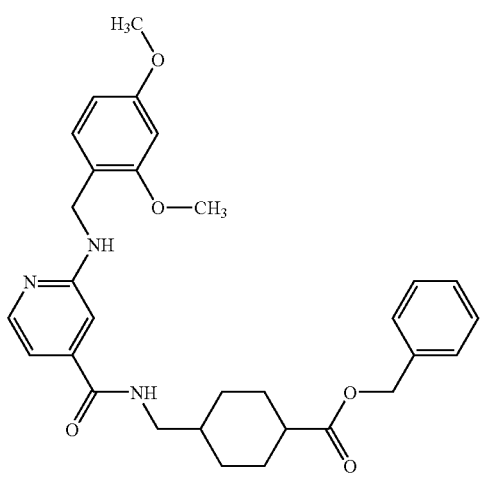

A mixture of 4-{[(2-chloro-pyridine-4-carbonyl)-amino]-methyl}-piperidine-1-carboxylic acid benzyl ester (EXAMPLE 65) (310 mg, 0.8 mmol) and 2,4-dimethoxybenzylamnine (1 mL) were heated to 140° C. for 18 h, cooled to rt, and partitioned between pH5.2 citrate buffer and EtOAc. The organic layer was dried and the solvent evaporated to give the crude product, purified by chromatography on silica (1:1 hexane EtOAc to 5% MeOH EtOAc to give the 4-({[2-(2,4-Dimethoxy-benzylamino)-pyridine4-carbonyl]-amino}-methyl)-piperidine-1-carboxylic acid benzyl ester.

M.S. (M$^+$+1) 519

Example 172

4-{[(2-Amino-pyridine-4-carbonyl)-amino]-methyl}-piperidine-1-carboxylic acid benzyl ester

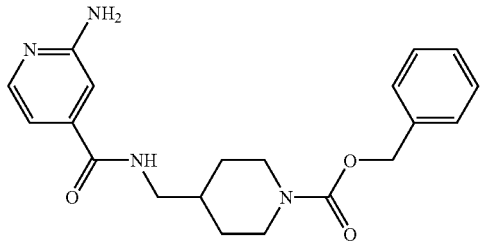

4-({[2-(2,4-Dimethoxy-benzylamino)-pyridine-4-carbonyl]-amino}-methyl)-piperidine-1-carboxylic acid benzyl ester (EXAMPLE 171) (124 mg) in dichloromethane (5 mL) was treated with trifluoroacetic acid (0.5 mL). After 30 min, the reaction mixture was partitioned between EtOAc and dilute sodium bicarbonate solution. The organic layer was washed with brine, dried and the solvent evaporated to give the crude product which was stirred with ether (3mL) and filtered to give the 4-{[(2-amino-pyridine-4-carbonyl)-amino]-methyl}-piperidine-1-carboxylic acid benzyl ester as a white solid.

M.S. (M$^+$+1) 369

Example 173

4-({[2-(2-Dimethylamino-ethylamino)-pyridine-4-carbonyl]-amino}-methyl)-piperidine-1-carboxylic acid benzyl ester

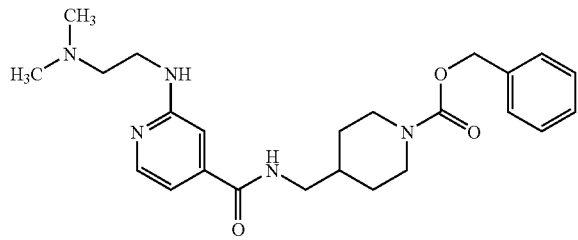

A mixture of 4-{[(2-chloro-pyridine-4-carbonyl)-amino]-methyl}-piperidine-1-carboxylic acid benzyl ester (EXAMPLE 65) (50 mg, 0.8 mmol) and N,N-dimethylethylenediamine (0.2 mL) were heated to 100 C for 18 hours, cooled to room temperature. The reaction mixture was then purified by reverse phase BPLC to give the 4-({[2-(2-dimethylamino-ethylamino)-pyridine-4-carbonyl]-amino}-methyl)-piperidine-1-carboxylic acid benzyl ester as its trifluoroacetate salt.

M.S. (M$^+$+1) 440

Example 174

N-[1-(2-Phenyl-ethanesulfonyl)-piperidin-4-ylmethyl]-isonicotinamide

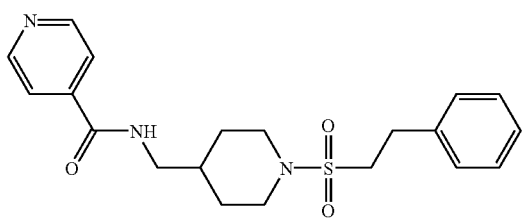

Step 1:

4-Aminomethyl-piperidine-1-carboxylic acid tert-butyl ester

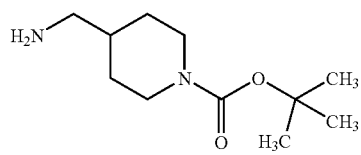

To a mixture of 15 g of 4-aminomethylpiperidine in 250 mL of anhydrous tetrahydrofuran cooled to −78° C. was added dropwise over 45 min a solution of 24 g of di-tert-butyl di-carbonate in 100 mL of anhydrous tetrahydrofuran. After stirring for 1 h at −78° C., the mixture was allowed to warm to rt and stirred overnight. The mixture was concentrated to near dryness and diluted with 200 mL of 10% aqueous citric acid. The mixture was extracted with 3×100 mL of ether, then made basic with sodium hydroxide pellets and extracted with 3×200 mL of chloroform. The combined chloroform extracts were dried over magnesium sulfate and concentrated to dryness under reduced pressure. The resulting oil was homogeneous by TLC (development with 90:10 chloroform saturated with ammonia: methanol).

$^1$H NMR (400 MHz, CDCl$_3$): 4.1 (br s, 2 H), 2.7 (br m, 2H), 2.6 (d, 2H), 1.7 (m, 3H), 1.42 (s, 9H), 1.1 (m, 2H).

Step 2:

4-(Benzyloxycarbonylamino-methyl)-piperidine-1-carboxylic acid tert-butyl ester

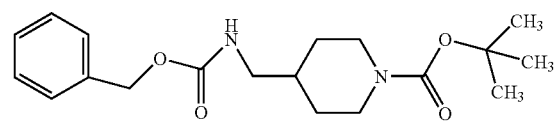

To a solution of 21 g of 4-aminomethyl-piperidine-1-carboxylic acid tert-butyl ester in 100 mL of ethyl acetate cooled to 0° C. was added 100 mL of saturated sodium carbonate and 17 g of benzyl chloroformate. The solution was stirred for 3 h, then separated. The organic layer was dried over magnesium sulfate and concentrated under reduced pressure. Drying under vacuum gave the product as an oil:

$^1$H NMR (400 MHz, CDCl$_3$): 7.35 (m, 5H), 5.3 (d, 1H), 5.1 (s, 2H), 4.1 (br s, 2 H), 3.0 (br m, 2H), 2.6 (br m, 2H), 1.7 (m, 3H), 1.42 (s, 9H), 1.1 (m, 2H).

Step 3:

Piperidin-4-ylmethyl-carbamic acid benzyl ester

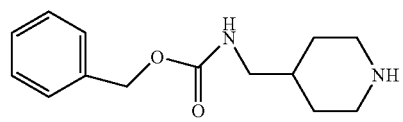

A mixture of 35 g of 4-(benzyloxycarbonylamino-methyl)-piperidine-1-carboxylic acid tert-butyl ester and 50 mL of 4N HCl in dioxane was stirred at rt for 3 h, then diluted with 200 mL of ether and filtered. The piperidin-4-ylmethyl-carbamic acid benzyl ester hydrochloride salt was obtained as a white fluffy solid. The free base was obtained by partitioning the hydrochloride between 50 mL chloroform and 50 mL saturated aqueous Na$_2$CO$_3$.

MS (m+1)=249;

$^1$H NMR (400 MHz, CDCl$_3$)): 7.35 (m, 5H), 5.15 (s, 2H), 4.9 (br s, 1 H), 3.1 (m, 2H), 2.6 (m, 3H), 1.7 (m, 2H), 1.6 (m, 2H), 1.1 (m, 2H).

Step 4:

[1-(2-Phenyl-ethenesulfonyl)-piperidin-4-ylmethyl]-carbamic acid benzyl ester

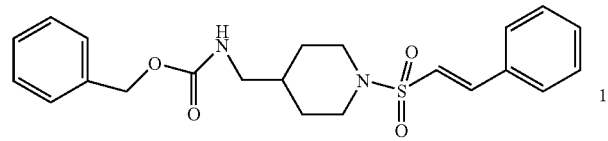

A mixture of 2 g of piperidin-4-ylmethyl-carbamic acid benzyl ester hydrochloride, 25 mL of dichloromethane, 1.5 grams of trans-2-styrenesulfonyl chloride, and 3 mL of N,N-diisopropylethylamine was stirred at rt overnight, then diluted with 200 mL of chloroform, and washed with 100 mL of saturated sodium carbonate. The chloroform extracts were dried over magnesium sulfate and concentrated. The [1-(2-phenyl-ethenesulfonyl)-piperidin-4-ylmethyl]-carbamic acid benzyl ester was obtained as a white solid.

MS (m+1)=415;
$^1$H NMR (400 MHz, CDCl$_3$) ): 7.5–7.2 (m, 10H), 6.65 (m, 1H), 5.15 (s, 2H), 4.8 (br s, 1H), 3.8 (d, 2H), 3.1 (dd, 2H), 2.6 (dd, 2H), 1.8 (d, 2H), 1.6 (m, 2H), 1.35 (m, 2H).

Step 5:

C-[1-(2-Phenyl-ethanesulfonyl)-piperidin-4-yl]-methylamine

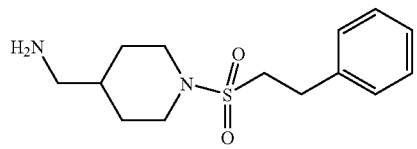

A mixture of 2.5 g of [1-(2-phenyl-ethenesulfonyl)-piperidin-4-ylmethyl]-carbamic acid benzyl ester, 1 g of 20% palladium hydroxide on carbon, 200 mL of methanol and 50 mL of tetrahydrofuran were shaken under 50 psi of hydrogen for 2 days at rt. The catalyst was filtered off and washed with 250 mL of methanol. Concentration under reduced pressure gave the C-[1-(2-phenyl-ethanesulfonyl)-piperidin-4-yl]-methylamine as a white solid.

MS (m+1)=283;
$^1$H NMR (400 MHz, CDCl$_3$) ): 7.4–7.2 (m, 5H), 5.1 (s, 2H), 3.8 (d, 2H), 3.1 (m, 4H), 2.7 (dd, 2H), 1.8 (d, 2H), 1.6 (m, 5H), 1.3 (m, 2H).

Step 6:

N-[1-(2-Phenyl-ethanesulfonyl)-piperidin-4-ylmethyl]-isonicotinamide

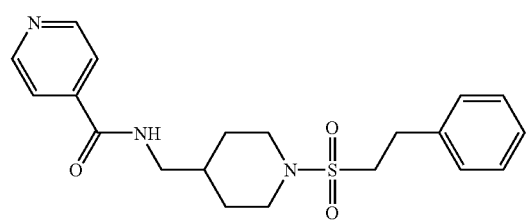

The N-[1-(2-Phenyl-ethanesulfonyl)-piperidin-4-ylmethyl]-isonicotinamide was prepared from C-[1-(2-phenyl-ethanesulfonyl)-piperidin-4-yl]-methylamine and isonicotinic acid as described above in EXAMPLE 1, Step 2.

MS (m+1)=388.

Example 175

N-{1-[2-(4-Fluoro-phenyl)-ethanesulfonyl]-piperidin-4-ylmethyl}-4-hydroxy-benzamide

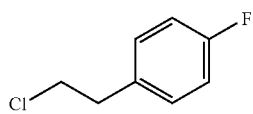

Step 1:

1-(2—Chloro-ethyl)-4-fluoro-benzene

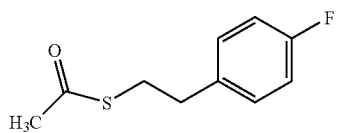

A mixture of 7 g of 2-(4-fluoro-phenyl)-ethanol, 25 mL of chlorobenzene, 42 mL of 37% HCl, and 0.9 g of Aliquat® 336 (tricaprylylmethyl ammonium chloride) was heated to reflux for 3 days, cooled and extracted into 3×100 mL of hexane. The combined extracts were dried over magnesium sulfate and concentrated under reduced pressure. The resulting oil was a crude product of 1-(2-chloro-ethyl)-4-fluoro-benzene:

$^1$H NMR (400 MHz, CDCl$_3$): 7.3 (dd, 2H), 7.0 (dd, 2H), 3.7 (t, 2H), 3.05 (t, 2H).

Step 2:

Thioacetic acid S-[2-(4-fluoro-phenyl)-ethyl] ester

A mixture of 2.4 g of 1-(2-chloro-ethyl)-4-fluoro-benzene, 30 mL of DMF, and 2.5 g of potassium thioacetate was stirred under nitrogen for 24 h. The mixture was diluted with 200 mL of water and extracted with 3×50 mL of dichloromethane. The combined organic layers were dried over magnesium sulfate and concentrated under reduced pressure. Drying under vacuum gave the product as an oil:

$^1$H NMR (400 MHz, CDCl$_3$): 7.18 (dd, 2H), 6.98 (dd, 2H), 3.08 (t, 2H), 2.81 (t, 2H), 2.32 (s, 3H).

Step 3:

2-(4-Fluoro-phenyl)-ethanesulfonyl chloride

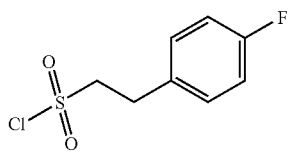

A stream of chlorine gas was dispersed into a stirred, ice cold mixture of 2.5 g of thioacetic acid S-[2-(4-fluoro-phenyl)-ethyl] ester, 30 mL of dichloromethane and 30 mL of water over 1 h. The mixture was diluted with 200 mL of dichloromethane, shaken and separated. The combined organic layers were dried over magnesium sulfate and concentrated under reduced pressure. Trituration with hexane gave a white solid:

$^1$H NMR (400 MHz, CDCl$_3$): 7.2 (dd, 2H), 7.0 (dd, 2H), 3.1 (dd, 2H), 3.3 (dd, 2H), 2.32 (s, 3H).

Step 4:

4-(tert-Butoxycarbonylamino-methyl)-piperidine-1-carboxylic acid benzyl ester

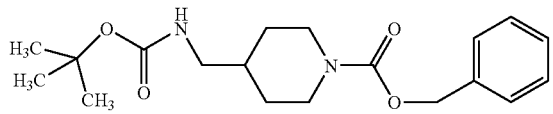

To an ice cold, stirred solution of 21 g of 4-aminomethyl-piperidine-1-carboxylic acid benzyl ester in 250 mL of dichloromethane was added 18 g of di-tert-butyldicarbonate in 100 mL of dichloromethane over 30 min. After stirring overnight, the mixture was concentrated to dryness. Trituration with hexane gave a white solid:

$^1$H NMR (400 MHz, CDCl$_3$): 7.4 (m, 5H), 5.15 (s, 2H), 4.6 (br s, 1H), 4.2 (br s, 2H), 3.0 (br s, 2H), 2.8 ((m, 2H), 1.7 (m, 3H), 1.42 (s, 9H), 1.15 (m, 2H).

Step 5:

Piperidin-4-ylmethyl-carbamic acid tert-butyl ester

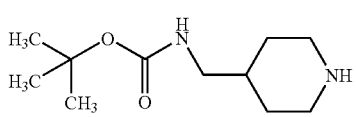

A mixture of 28 g of 4-(tert-butoxycarbonylamino-methyl)-piperidine-1-carboxylic acid benzyl ester, 1 g of 10% palladium on carbon, 100 mL of THF and 200 mL of methanol was stirred under an atmosphere of hydrogen for 2 days. The mixture was filtered concentrated under reduced pressure. Drying under reduced pressure gave a white solid:

$^1$H NMR (400 MHz, CDCl$_3$): 4.8 (br s, 1H), 3.05 (d, 2H), 2.9 (dd, 2H), 2.6 (m, 3H), 1.6 (d, 2H), 1.5 (m, 1H), 1.4 (s, 9H), 1.05 (m, 2H).

Step 6:

{1-[2-(4-Fluoro-phenyl)-ethanesulfonyl]-piperidin-4-ylmethyl}-carbamic acid tert-butyl ester

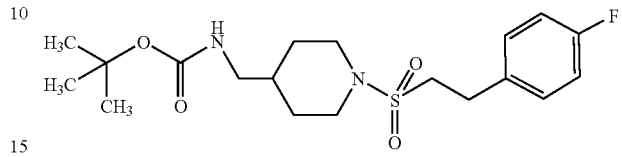

To an ice cold, stirred solution of 0.2 g of piperidin-4-ylmethyl-carbamic acid tert-butyl ester and 0.2 mL of N,N-diisopropylethyl amine in 20 mL of dichloromethane was added 0.3 g of 2-(4-fluoro-phenyl)-ethanesulfonyl chloride. After stirring overnight, the mixture was diluted with 50 mL of chloroform, washed with 50 mL of saturated sodium carbonate, dried over magnesium sulfate and concentrated to dryness under reduced pressure. Trituration with hexane gave a white solid:

$^1$H NMR (400 MHz, CDCl$_3$): 7.2 (m, 2H), 7.0 (dd, 2H), 4.6 (br m, 1H), 3.8 (d, 2H), 3.1 (m, 3H), 3.0 (m, 2H), 2.7 (dd, 2H), 1.8 (d, 2H), 1.6 (br m, 2H), 1.42 (s, 9H), 1.3 (m, 2H).

Step 7:

C-{1-[2-(4-Fluoro-phenyl)-ethanesulfonyl]-piperidin-4-yl}-methylamine

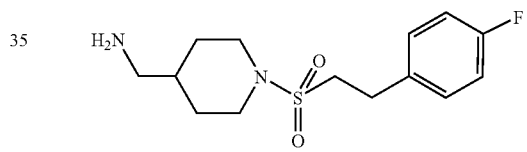

A mixture of 0.4 g of {1-[2-(4-fluoro-phenyl)-ethanesulfonyl]-piperidin-4-ylmethyl}-carbamic acid tert-butyl ester and 5 mL of 4N HCl in dioxane was stirred at rt for 3 h, then diluted with 50 mL of chloroform, washed with 50 mL of saturated sodium carbonate, dried over magnesium sulfate and concentrated to dryness under reduced pressure. The product was a white solid:

MS (m+1)=301;

$^1$H NMR (400 MHz, CDCl$_3$): 7.2 (m, 2H), 7.0 (dd, 2H), 3.92 (d, 2H), 3.1 (s, 4H), 2.7 (dd, 2H), 2.6 (d, 2H), 1.8 (d, 2H), 1.5 (br m, 3H), 1.3 (m, 2H).

Step 8:

N-{1-[2-(4-Fluoro-phenyl)-ethanesulfonyl]-piperidin-4-ylmethyl}-4-hydroxy-benzamide

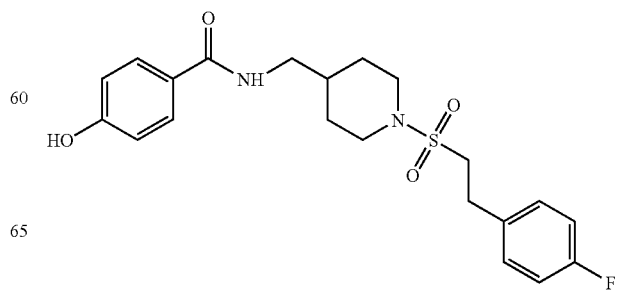

N-{1-[2-(4-Fluoro-phenyl)-ethanesulfonyl]-piperidin-4-ylmethyl}-4-hydroxy-benzamide was prepared from C-{1-[2-(4-fluoro-phenyl)-ethanesulfonyl]-piperidin-4-yl}-methylamine and 4-hydroxybenzoic acid as described above in EXAMPLE 1, Step 2
MS (m+1)=421.

The following compounds were prepared as described in EXAMPLE 175, but replacing the 4-fluorophenethyl alcohol with the appropriately substituted phenethyl alcohol in Step 1 and using the appropriate carboxylic acid in Step 8.

| EX. | Name | Structure | Analytical Data |
|---|---|---|---|
| 176 | N-[1-(2-p-Tolyl-ethanesulfonyl)-piperidin-4-ylmethyl]-isonicotinamide | 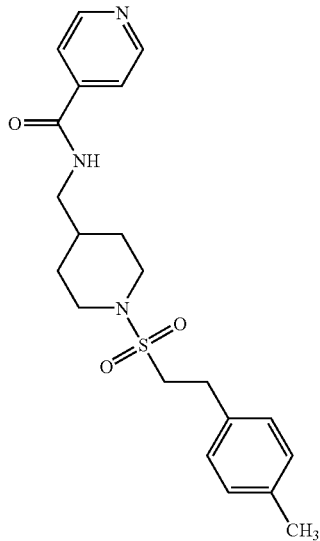 | MS (m + 1) = 402.5. |
| 177 | 3H-Benzoimidazole-5-carboxylic acid [1-(2-phenyl-ethane-sulfonyl)-piperidin-4-ylmethyl]-amide | 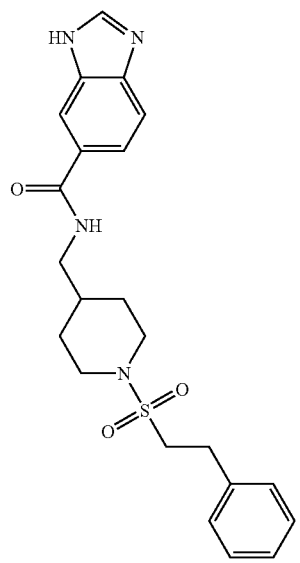 | MS (m + 1) = 427.5. |

-continued

| EX. | Name | Structure | Analytical Data |
|---|---|---|---|
| 178 | Pyrimidine-4-carboxylic acid [1-(2-phenyl-ethane-sulfonyl)-piperidin-4-ylmethyl]-amide | 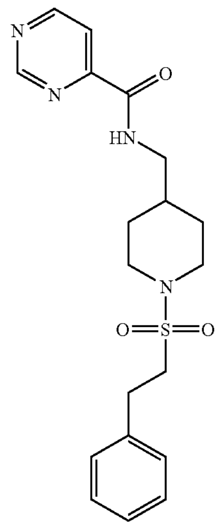 | MS (m + 1) = 389. |
| 179 | 2-Amino-pyrimidine-5-carboxylic acid [1-(2-phenyl-ethane-sulfonyl)-piperidin-4-ylmethyl]-amide | 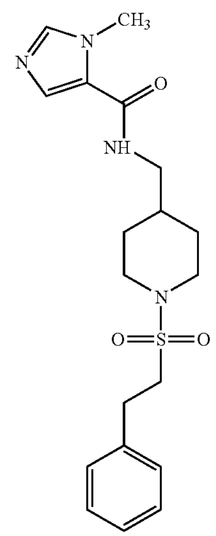 | MS (m + 1) = 391 |
| 180 | Pyrazine-2-carboxylic acid [1-(2-phenyl-ethane-sulfonyl)-piperidin-4-ylmethyl]-amide | 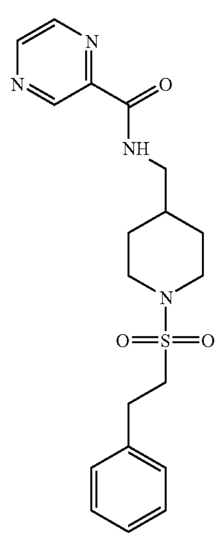 | MS (m + 1) = 389 |

| EX. | Name | Structure | Analytical Data |
|---|---|---|---|
| 181 | 3-Amino-pyrazine-2-carboxylic acid [1-(2-phenyl-ethane-sulfonyl)-piperidin-4-ylmethyl]-amide | 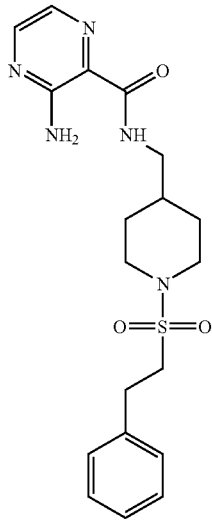 | MS (m + 1) = 404 |
| 182 | Pyrimidine-5-carboxylic acid [1-(2-phenyl-ethane-sulfonyl)-piperidin-4-ylmethyl]-amide | 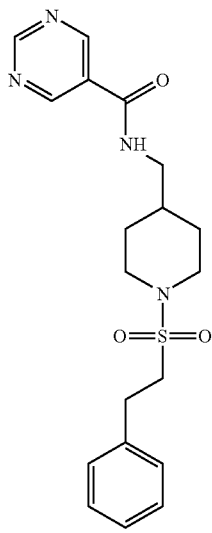 | MS (m + 1) = 389 |

-continued
| EX. | Name | Structure | Analytical Data |
|---|---|---|---|
| 183 | Pyrimidine-4-carboxylic acid [1-(2-p-tolyl-ethane-sulfonyl)-piperidin-4-ylmethyl]-amide | 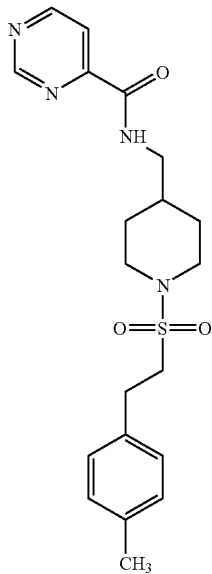 | MS (m + 1) = 389 |
| 184 | 9H-Purine-6-carboxylic acid [1-(2-phenyl-ethane-sulfonyl)-piperidin-4-ylmethyl]-amide | 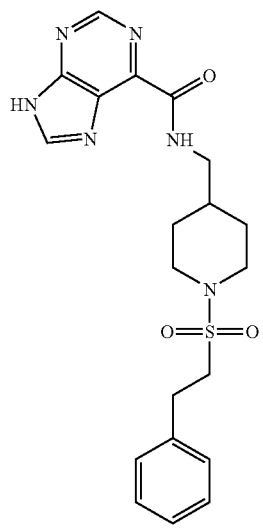 | MS (m + 1) = 429 |

-continued
| EX. | Name | Structure | Analytical Data |
|---|---|---|---|
| 185 | N-{1-[2-(4-Chloro-phenyl)-ethane-sulfonyl]-piperidin-4-ylmethyl}-4-hydroxy-benzamide | 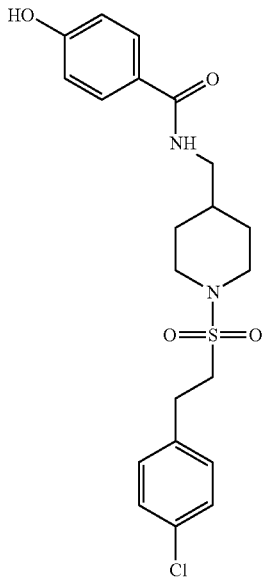 | MS (m + 1) = 437 |
| 186 | N-{1-[2-(2-Fluoro-phenyl)-ethane-sulfonyl]-piperidin-4-ylmethyl}-4-hydroxy-benzamide | 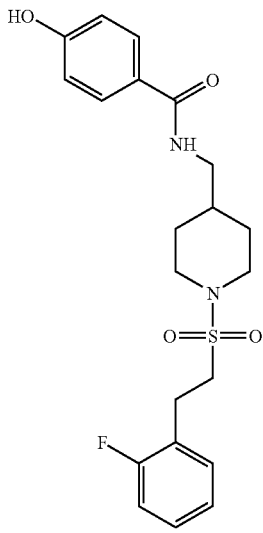 | MS (m + 1) = 421 |

-continued
| EX. | Name | Structure | Analytical Data |
|---|---|---|---|
| 187 | 6-Hydroxy-N-[1-(2-phenyl-ethane-sulfonyl)-piperidin-4-ylmethyl]-nicotinamide | 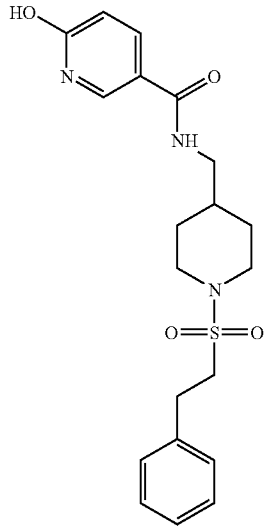 | MS (m + 1) = 404 |
| 188 | 4-Hydroxy-N-[1-(2-phenyl-ethane-sulfonyl)-piperidin-4-ylmethyl]-benzamide | 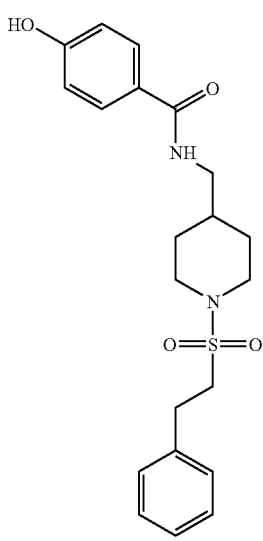 | MS (m + 1) = 403 |

| EX. | Name | Structure | Analytical Data |
|---|---|---|---|
| 189 | Pyridazine-4-carboxylic acid [1-(2-phenyl-ethane-sulfonyl)-piperidin-4-ylmethyl]-amide | 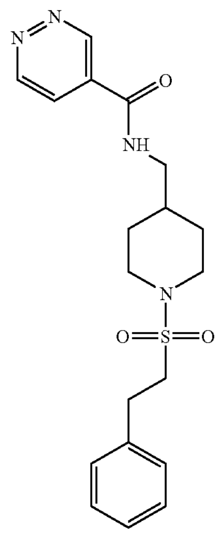 | MS (m + 1) = 389 |

Example 190

(R,S) 3-[(4-Hydroxy-benzoylamino)-methyl]-pyrrolidine-1-carboxylic acid benzyl ester

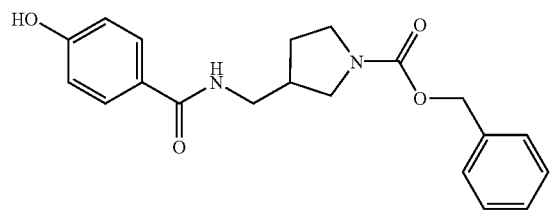

Step 1:

1-Benzyl-pyrrolidine-3-carboxylic acid amide

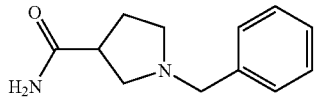

To a mixture of 4.4 g of 1-benzyl-pyrrolidine-3-carboxylic acid methyl ester (M. J. Kornet et al., *J. Org. Chem.*, 33:3637–3639(1968)) and 3 g of formamide in 10 mL of anhydrous DMF heated to 100° C. was added a solution of sodium methoxide, from 0.33 g of sodium dissolved in methanol, dropwise over 20 min. After stirring for 1 h at 100° C., the mixture was allowed to cool to rt and added to 100 mL of isopropanol. The mixture was concentrated to dryness. The resulting residue was triturated with 200 mL of chloroform, filtered and concentrated to dryness under reduced pressure. The resulting oil was fairly homogeneous by TLC (development with 90:10 chloroform saturated with ammonia: methanol):

$^1$H NMR (400 MHz, CDCl$_3$): 7.1 (5H), 4.3 (br s, 2 H), 3.5 (d, 2H), 3.4 (m, 1H), 2.6 (m, 2H), 2.5 (m, 1H), 2.25 (m, 1H), 1.9 (m, 1H).

Step 2:

3-Carbamoyl-pyrrolidine-1-carboxylic acid benzyl ester

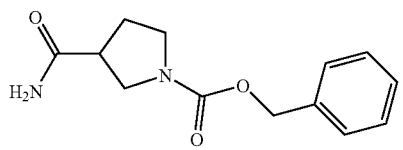

A mixture of 4.5 g of 1-benzyl-pyrrolidine-3-carboxylic acid amide, 200 mL of THF, 20 mL of methanol, and 1 g of 20% palladium hydroxide on carbon was shaken under 50 psi of hydrogen for 12 h. The catalyst was filtered off and the filtrate concentrated under reduced pressure. Drying under vacuum gave 3 g of an oil. To a stirred solution of the crude residue in 500 mL of chloroform was added 5.5 g of N-(benzyloxycarbonyloxy)succinimide and 2.2 mL of triethylamine. The mixture was allowed to stir overnight and washed with 50 mL of saturated sodium carbonate dried over magnesium sulfate and concentrated to dryness. Purification by chromatography on silica gel, eluting with 90:10 ethyl acetate: methanol, gave the product as a resin:

$^1$H NMR (400 MHz, CDCl$_3$): 7.35 (m, 5H), 5.6 (br m, 2H), 3.6 (m, 3H), 3.4 (m, 1H), 2.9 (br m, 1H), 2.1 (m, 2H).

Step 3:

3-Aminomethyl-pyrrolidine-1-carboxylic acid benzyl ester

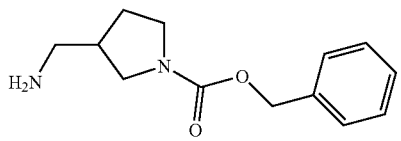

A mixture of 1 g of 3-carbamoyl-pyrrolidine-1-carboxylic acid benzyl ester and 24 mL of 1M borane-THF was stirred at room temperature for 24 h, then quenched with 50 mL of 3N HCl. The mixture was concentrated under reduced pressure, followed by being partitioned between 50 mL chloroform and 25 mL saturated aqueous sodium carbonate. Concentration of the combined extracts after drying over magnesium sulfate gave the product as a resin:

$^1$H NMR (400 MHz, CDCl$_3$)): 7.35 (m, 5H), 5.15 (s, 2H), 3.7–4 (complex, 4H), 2.7 (m, 1H), 2.4–2.0 (complex, 2H), 1.6 (m, 4H).

Step 4:

(R,S) 3-[(4-Hydroxy-benzoylamino)-methyl]-pyrrolidine-1-carboxylic acid benzyl ester

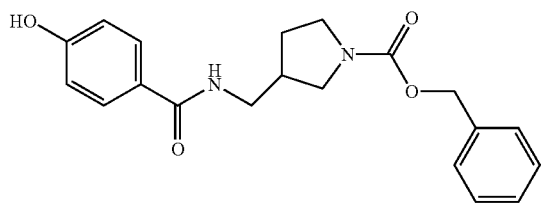

(R,S) 3-[(4-Hydroxy-benzoylamino)-methyl]-pyrrolidine-1-carboxylic acid benzyl ester was prepared from 3-aminomethyl-pyrrolidine-1-carboxylic acid benzyl ester and 4-hydroxybenzoic acid as described above in EXAMPLE 1, Step 2.

MS (m+1)=395.

Example 191

(R) 3-[(4-Hydroxy-benzoylamino)-methyl]-pyrrolidine-1-carboxylic acid benzyl ester and (S) 3-[(4-Hydroxy-benzoylamino)-methyl]-pyrrolidine-1-carboxylic acid benzyl ester

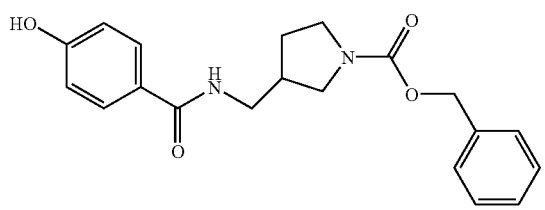

Resolution of (R,S) 3-[(4-hydroxy-benzoylamino)-methyl]-pyrrolidine-1-carboxylic acid benzyl ester (EXAMPLE 190) was performed on a Chirapak® preparative chiral KPLC column:

MS (m+1)=395.

Example 192

2-Amino-pyrimidine-5-carboxylic acid [1-(2-phenyl-ethanesulfonyl)-piperidin-4-ylmethyl]-amide

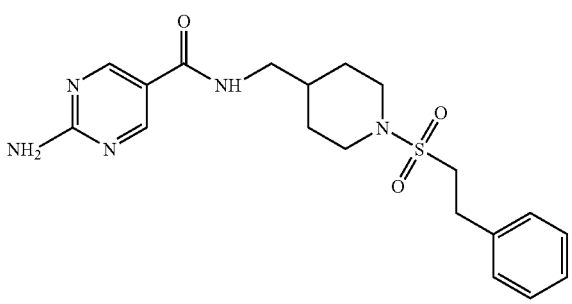

Step 1:

(5-{[1-(2-Phenyl-ethanesulfonyl)-piperidin-4-ylmethyl]carbamoyl}-pyrimidin-2-yl)-carbamic acid tert-butyl ester

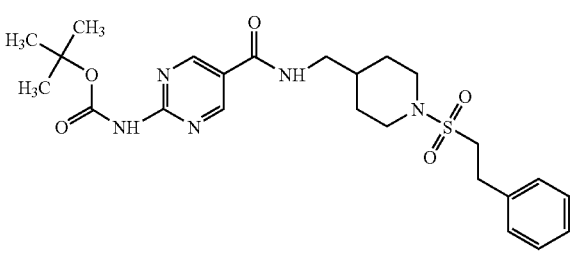

(5-{[1-(2-Phenyl-ethanesulfonyl)-piperidin-4-ylmethyl]-carbamoyl}-pyrimidin-2-yl)-carbamic acid tert-butyl ester was prepared from C-[1-(2-phenyl-ethanesulfonyl)-piperidin-4-yl]-methylamine and 2-tert-butoxycarbonylamino-pyrimidine-5-carboxylic acid (prepared by BOC protection of ethyl 2-amino-5-pyrimidine carboxylate [prepared as described by P. Schenone, et al., *J. Heterocyclic Chem.,* 27:295–305(1990)] using di-tert-butyl dicarbonate and 4-dimethylaminopyridine in acetonitrile, followed by saponification with sodium hydroxide and neutralization with dilute aqueous HCl) as described in EXAMPLE 1, Step 2:

MS (m+1)=504.

Step 2:

2-Amino-pyrimidine-5-carboxylic acid [1-(2-phenyl-ethanesulfonyl)-piperidin-4-ylmethyl]-amide

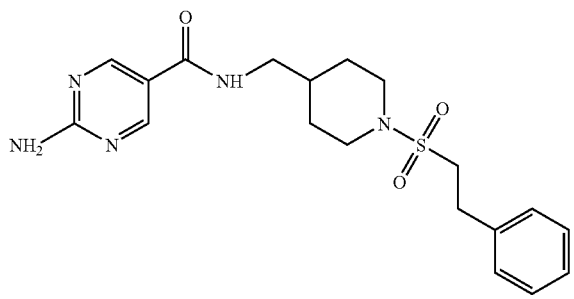

2-Amino-pyrimidine-5-carboxylic acid [1-(2-phenyl-ethanesulfonyl)-piperidin-4-ylmethyl]-amide was prepared from (5-{[1-(2-phenyl-ethanesulfonyl)-piperidin-4-ylmethyl]-carbamoyl}-pyrimidin-2-yl)-carbamic acid tert-butyl ester by stirring at rt for 3 h in 4N HCl in dioxane. The product was precipitated as the hydrochloride salt by dilution with ether and filtration.

MS (m+1)=404.

Example 193

2-Amino-pyrimidine-5-carboxylic acid [1-(2-p-tolyl-ethanesulfonyl)-piperidin-4-ylmethyl]-amide

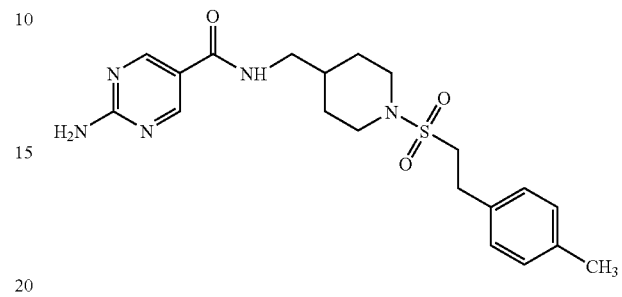

The title compound was prepared from C-[1-(2-p-tolyl-ethanesulfonyl)-piperidin-4-yl]-methylamine and 2-tert-butoxycarbonylamino-pyrimidine-5-carboxylic acid, followed by treatment with 4N HCl in dioxane as described in EXAMPLE 192.

MS (m+1)=418.

The following compounds were prepared by coupling 4-aminomethyl-piperidine-1-carboxylic acid benzyl ester (EXAMPLE 1, Step 1) with the appropriate acid as described in EXAMPLE 1, Step 2.

| EX. | Name | Structure | Analytical Data |
|---|---|---|---|
| 194 | 4-{[(3-Methyl-3H-imidazole-4-carbonyl)-amino]-methyl}-piperidine-1-carboxylic acid benzyl ester | 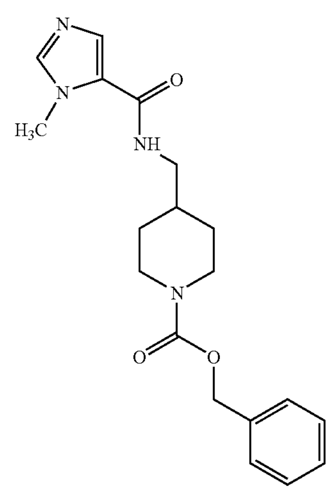 | MS (m + 1) = 357 |

| EX. | Name | Structure | Analytical Data |
|---|---|---|---|
| 195 | 4-{[(3-Methyl-3H-imidazole-4-carbonyl)-amino]-methyl}-piperidine-1-carboxylic acid 4-methyl-benzyl ester | 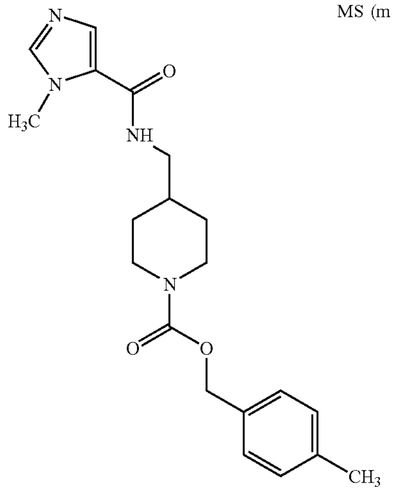 | MS (m + 1) = 371 |
| 196 | 4-{[(9H-Purine-6-carbonyl)-amino]-methyl}-piperidine-1-carboxylic acid benzyl ester | 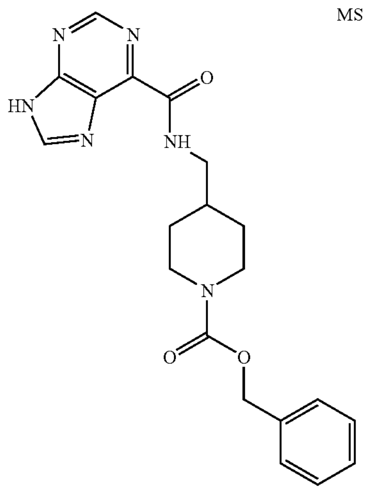 | MS (m + 1) = 395 |

Example 197

3-Hydroxy-4-[(4-hydroxy-benzoylamino)-methyl]-piperidine-1-carboxylic acid benzyl ester Step 1:

1-Benzyl-4-hydroxymethyl-piperidin-3-ol

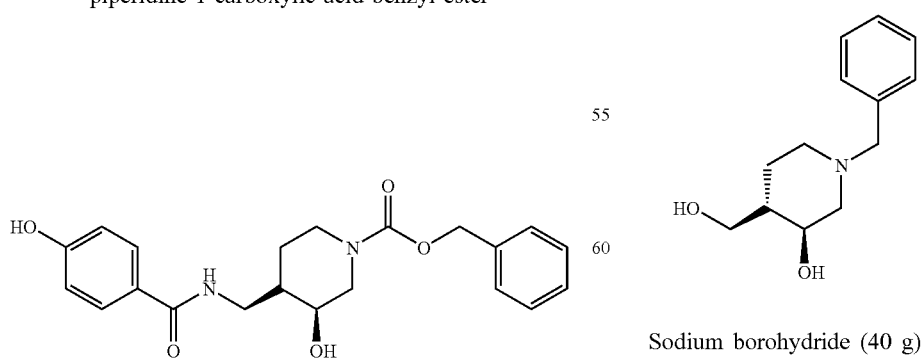

Sodium borohydride (40 g) was added in portions to a stirred solution of ethyl N-benzyl-3-oxopiperidine-4-carboxylate hydrochloride in methanol (500 mL), over 2 h.

Water (300 mL) was added slowly, the mixture stirred for 15 min, and then the organics were evaporated. The resulting residue was partitioned between DCM and water (×3), the combined organic layers dried over anhydrous sodium sulfate, and the solvent evaporated to give the product as a cis trans mixture, used in the next step without further purification.

M.S. (M+1): 222.

Step 2:

3-Hydroxy-4-hydroxymethyl-piperidine-1-carboxylic acid benzyl ester

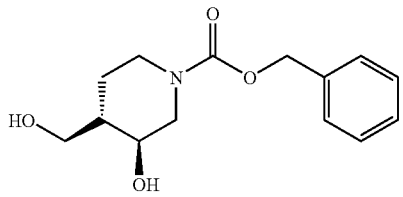

A solution of the 1-Benzyl-4-hydroxymethyl-piperidin-3-ol from Step 1 above (13.5 g) in methanol (450 mL) was hydrogenated at 50 psi over 20% palladium hydroxide on charcoal (10 g) for 48 h in three batches. The combined reaction mixtures were filtered and the filtrate evaporated to give an oil. This oil was dissolved in water (100 mL) and dioxane (100 mL), cooled to 5° C., and benzyl chloroformate (7.8 mL) was added slowly. 1M NaOH was added to maintain pH of 10–11. After 30 min, the cooling bath was removed and reaction mixture stirred for 30 min. The reaction mixture was concentrated to remove dioxane and the residue extracted with EtOAc (×3). The combined extracts were washed with brine, dried over anhydrous sodium sulfate and solvent evaporated to give a mixture of cis and trans products. Purified by flash column chromatography (80% EtOAc hexane to 5% MeOH EtOAc) gave the upper Rf cis isomer and the lower Rf trans isomer.

M.S. (M+1): 266.

Step 3:

Cis 3-Hydroxy-4-(toluene-4-sulfonyloxymethyl)-piperidine-1-carboxylic acid benzyl ester

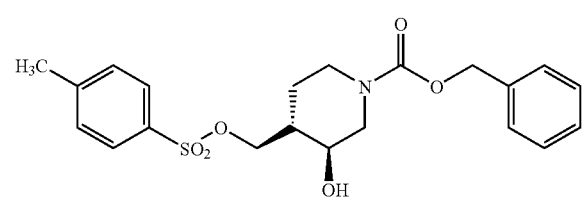

A solution of the 3-Hydroxy-4-hydroxymethyl-piperidine-1-carboxylic acid benzyl ester diol from Step 2 above (7.65 g) in chloroform (200 mL) was treated with pyridine (2.6 mL) and 4-toluenesulfonyl chloride (6.05 g) and the reaction mixture heated to 60° C. for 18 h. Additional pyridine (0.85 mL) and 4-toluenesulfonyl chloride (2.0 g) were added to the cooled reaction and heating continued for a further 24 h. The reaction mixture was cooled to rt and washed with 10% aqueous citric acid solution and water, dried over anhydrous sodium sulfate and the solvent evaporated to give, after flash column chromatography, the Cis 3-Hydroxy-4-(toluene-4-sulfonyloxymethyl)-piperidine-1-carboxylic acid benzyl ester.

Step 4:

Cis 4-Aminomethyl-3-hydroxy-piperidine-1-carboxylic acid benzyl ester

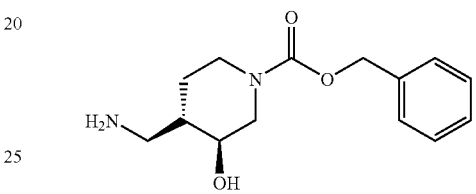

A solution of the cis 3-Hydroxy-4-(toluene-4-sulfonyloxymethyl)-piperidine-1-carboxylic acid benzyl ester (6.80 g) from Step 3 above was dissolved in DME (50 mL) and treated with sodium azide (3.16 g). The reaction mixture was then heated to 50° C. for 48 h, cooled to rt, and partitioned between dilute aqueous sodium bicarbonate and EtOAc. The organic layer was washed with brine, dried over anhydrous sodium sulfate and solvent evaporated to give the azide, which was dissolved in THF (50 mL) and treated with triphenylphosphine (14.07 g) and water (3.25 mL). The reaction mixture was stirred for 18 h at rt, the volatiles evaporated, and the residue purified by flash column chromatography (DCM to 80/20/2 DCM MeOH NH$_4$OH) to give the cis 4-Aminomethyl-3-hydroxy-piperidine-1-carboxylic acid benzyl ester as an oil.

M.S. (M+1): 265.

Step 4:

3-Hydroxy-4-[(4-hydroxy-benzoylamino)-methyl]-piperidine-1-carboxylic acid benzyl ester

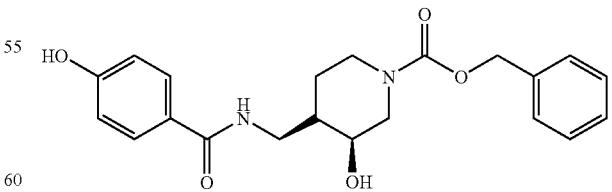

The 3-Hydroxy-4-[(4-hydroxy-benzoylamino)-methyl]-piperidine-1-carboxylic acid benzyl ester was prepared from the cis 4-Aminomethyl-3-hydroxy-piperidine-1-carboxylic acid benzyl ester (Step 3 above) and 4-hydroxybenzoic acid as described in EXAMPLE 1, Step 2.

Example 198

3-[(4-Hydroxy-benzoylamino)-methyl]-piperidine-1-carboxylic acid benzyl ester

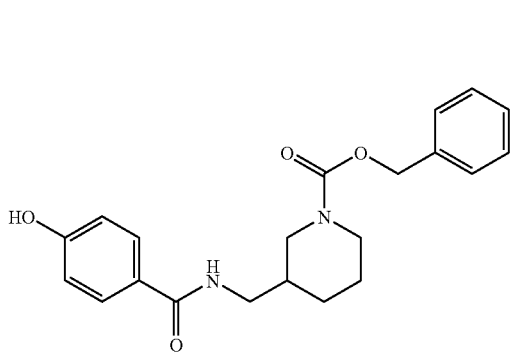

Step 1:

4-Hydroxy-N-pyridin-3-ylmethyl-benzamide

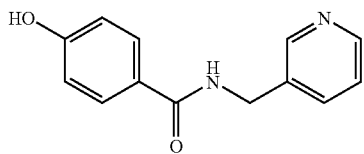

The 4-hydroxy-N-pyridin-3-ylmethyl-benzamide was prepared from 3-(2-aminomethyl)pyridine and 4-hydroxybenzoic acid in as described in EXAMPLE 1, Step 2.

M.S. (M+1): 229.

Step 2:

4-Hydroxy-N-piperidin-3-ylmethyl-benzamide

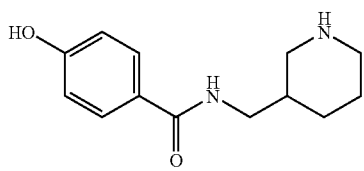

To a solution of 4-hydroxy-N-pyridin-3-ylmethyl-benzamide (2.0 g, 0.0088 mol) in acetic acid (135 mL) was added platinum oxide (200 mg) and the mixture stirred under hydrogen for 3 h. The reaction was filtered and concentrated in vacuo to give an oil.

M.S. (M+1): 235.

Step 3:

3-[(4-Hydroxy-benzoylamino)-methyl]-piperidine-1-carboxylic acid benzyl ester

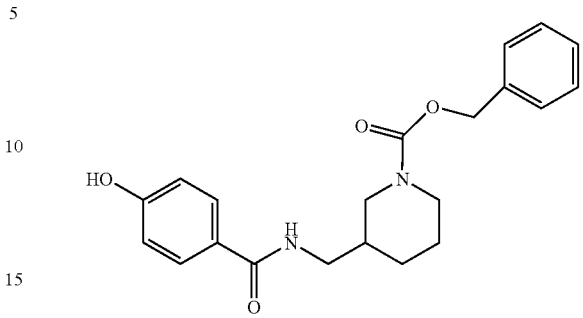

To a mixture of 4-hydroxy-N-piperidin-3-ylmethyl-benzamide (135 mg, 0.580 mmol) in tetrahydrofuran (5 mL) was added triethylamine (100 μL) and N-benzyloxycarbonyloxysuccinamide (144 mg, 0.580 mmol) and the mixture stirred at rt for 3 h. The reaction was concentrated in vacuo and chromatographed on silica using 50–100% ethyl acetate/hexane to give 3-[(4-hydroxy-benzoylamino)-methyl]-piperidine-1-carboxylic acid benzyl ester as a foam.

M.S. (M+1): 369.

Example 199

3-[(4-Hydroxy-benzoylamino)-methyl]-piperazine-1-carboxylic acid benzyl ester

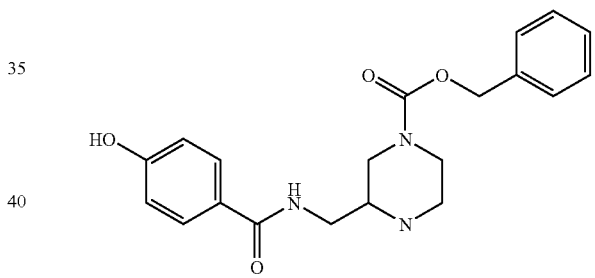

Step 1:

1,4-Dibenzyl-2-chloromethyl-piperazine

The above compound was prepared according to the procedure described in Bihan, G. et. al., *J. Med. Chem.*, 42:1587–1603(1999).

Step 2:

2-Azidomethyl-1,4-dibenzyl-piperazine

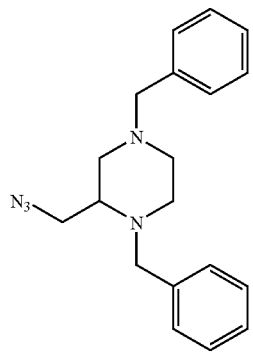

To a solution of 1,4-dibenzyl-2-chloromethyl-piperazine (8.8 g, 0.028 mol) in dimethylformamide (90 mL) under nitrogen was added sodium azide (5.5 g) and the reaction stirred at 50° C. for 18 h. The reaction was cooled and diluted with 10% aqueous sodium bicarbonate (100 mL) and water (250 mL) and the mixture extracted with ethyl acetate (2×200 mL). The organic extracts were washed with 10% sodium bicarbonate, brine, dried over sodium sulfate and concentrated to an oil.

M.S. (M+1): 322.

Step 3:

C-(1,4-Dibenzyl-piperazin-2-yl)-methylamine

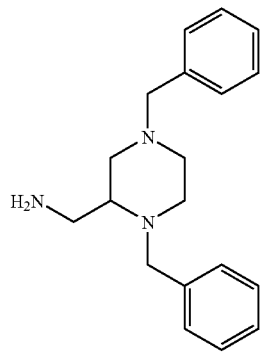

To a solution of 2azidomethyl-1,4-dibenzyl-piperazine (9.0 g, 0.028 mol) in TBFE (90 mL) and water (5 mL) was added triphenylphosphine (22.3 g, 0.085 mol) and the mixture stirred for 18 h. The reaction was concentrated to an oil, dissolved in 1N hydrochloric acid (100 mL) and washed with ethyl acetate (2×100 mL). The acidic aqueous layer was cooled to 0° C. and the pH adjusted to 8.5 with 3N sodium hydroxide. The mixture was extracted with ethyl acetate (2×100 mL) and extracts dried over sodium sulfate and concentrated to an oil.

M.S. (M+1): 296.

Step 4:

N-(1,4-Dibenzyl-piperazin-2-ylmethyl)-4-hydroxy-benzamide

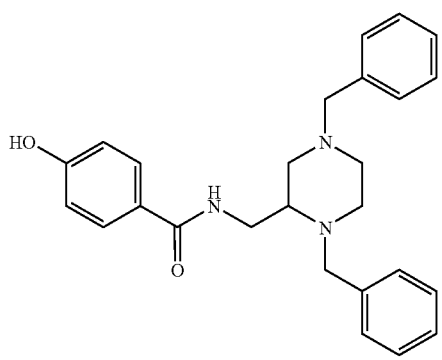

The N-(1,4-Dibenzyl-piperazin-2-ylmethyl)-4-hydroxy-benzamide was prepared from C-(1,4-Dibenzyl-piperazin-2-yl)-methylamine and 4-hydroxybenzoic acid as described in EXAMPLE 1, Step 2.

M.S. (M+1): 416.

Step 5:

4-Hydroxy-N-piperazin-2-ylmethyl-benzamide

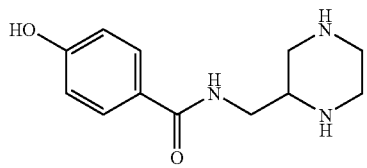

The 4-Hydroxy-N-piperazin-2-ylmethyl-benzamide was prepared according to the procedure described in EXAMPLE 198, Step 2, using 10% Palladium/Carbon as catalyst in ethanol/12N HCl at 50° C. for 5 h.

M.S. (M+1): 236.

Step 6:

3-[(4-Hydroxy-benzoylamino)-methyl]-piperazine-1-carboxylic acid benzyl ester

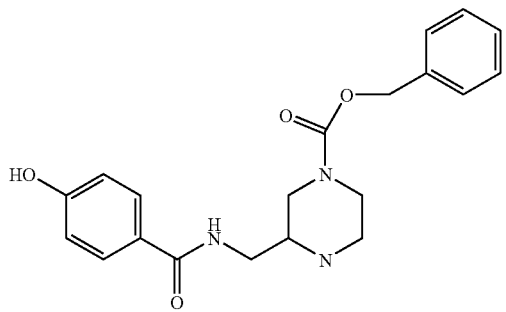

The 3-[(4-Hydroxy-benzoylamino)-methyl]-piperazine-1-carboxylic acid benzyl ester was prepared according to the procedure described in EXAMPLE 198, Step 3. Dilution of reaction with 10% aqueous sodium bicarbonate and extraction with ethyl acetate followed by concentration and purification by silica gel chromatography using 95/5/1 to 90/10/2 (dichloromethane/methanol/NH$_4$OH) gave the 3-[(4-Hydroxy-benzoylamino)-methyl]-piperazine-1-carboxylic acid benzyl ester as a solid.

M.S. (M+1): 370.

Example 200

4-Hydroxy-N-[4-(3-phenyl-propionyl)-piperazin-2-ylmethyl]-benzamide

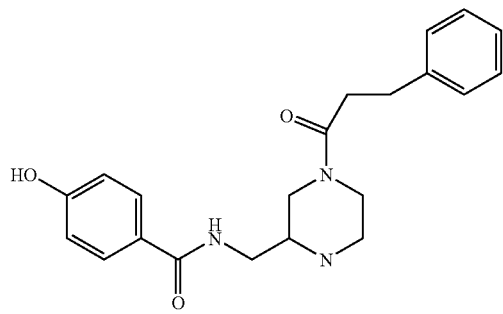

The title compound was prepared in a similar manner as described in EXAMPLE 1, Step 2, from 4-hydroxy-N-piperazin-2-ylmethyl-benzamide and 4-hydroxybenzoic acid.

M.S. (M+1): 368.

Example 201

4-Hydroxy-N-[4-(3-phenyl-propyl)-piperazin-2-ylmethyl]-benzamide

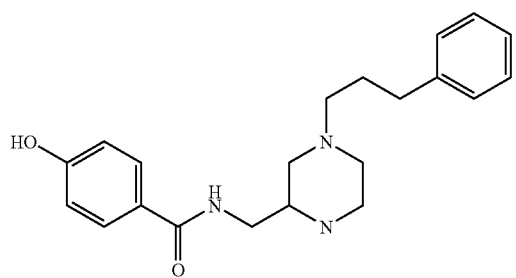

The title compound was prepared in a similar manner as described in EXAMPLE 148, Step 1, from 4-Hydroxy-N-piperazin-2-ylmethyl-benzamide and propionaldehyde in dichlorethane as solvent.

M.S. (M+1): 354.

Example 202

2-[(4-Hydroxy-benzoylamino)-methyl]-morpholine-4-carboxylic acid benzyl ester

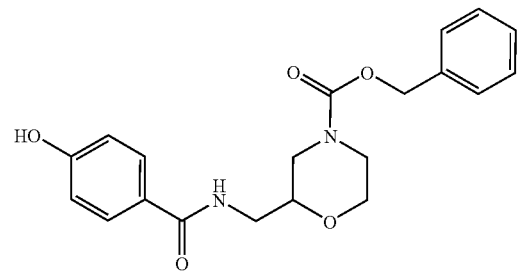

Step 1:

N-(4-Benzyl-morpholin-2-ylmethyl)-4-hydroxy-benzamide

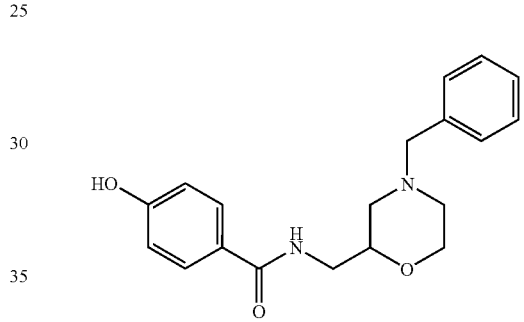

The N-(4-Benzyl-morpholin-2-ylmethyl)-4-hydroxy-benzamide was prepared from C-(4-benzyl-morpholin-2-yl)-methylamine (S. Kato et al., *J. Med Chem.*, 33:1406(1990)) similarly to the procedure described in EXAMPLE 1, Step 2.

M.S. (M+1): 327

Step 2:

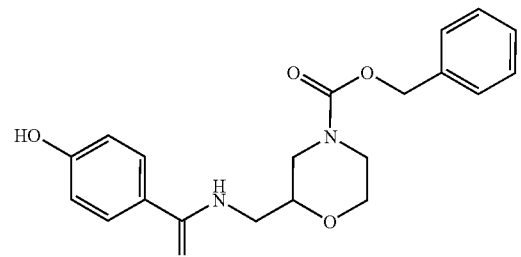

A solution of N-(4-benzyl-morpholin-2-ylmethyl)-4-hydroxy-benzamide (Step 1 above) (320 mg) was dissolved in ethanol (20 mL) and hydrogenated at 1 atm over 20% Pd(OH)$_2$/C (250 mg) for 18 h. The catalyst was removed by filtration, washed with ethanol, and the filtrate evaporated, to give a solid. A portion (21 mg) of this material was dissolved in DMF (0.5 mL) and N-(benzyloxycarbonyloxy)succinimide (27 mg) was added. The reaction mixture was stirred for 10 min, one drop of water was added and the solution was purified by preparative reverse phase HPLC to give the 2-[(4-Hydroxy-benzoylamino)-methyl]-morpholine4-carboxylic acid benzyl ester compound.

M.S. (M+1): 371

Example 203

4-Hydroxy-N-[4-(3-phenyl-propyl)-morpholin-2-ylmethyl]-benzamide

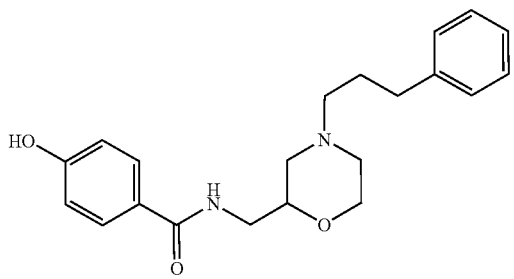

A solution of N-(4-benzyl-morpholin-2-ylmethyl)-4-hydroxy-benzamide (EXAMPLE 202, Step 1) (55 mg) was dissolved in acetic acid (3 mL) and hydrogenated at 1 atm over 10% Pd/C (50 mg) for 18 h. The catalyst was removed by filtration, washed with acetic acid and the filtrate evaporated, to give an oil. A portion of this oil (21 mg) was dissolved in methanol (1 mL) and treated with phenylpropionaldehyde (24 mg) and sodium cyanoborohydride (25 mg). The resulting reaction was stirred for 15 min and the crude reaction mixture purified by preparative reverse phase IPLC to give the 4-Hydroxy-N-[4-(3-phenyl-propyl)-morpholin-2-ylmethyl]-benzamide compound.

M.S. (M+1): 355

Acid Intermediates:

4-(1-Hydroxyethyl)benzoic acid

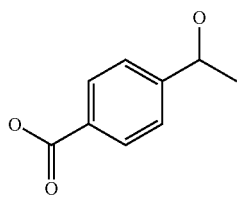

To a solution of methyl 4-(1-hydroxyethylbenzoate (150 mg, 0.83 mmol) in TBF (1 mL) was added 1M LiOH (1 mL). The reaction mixture was heated to 60° C. and stirred for 1 h. After cooling, the reaction was acidified with 1M HCl, and extracted with EtOAc twice. The organic layer was dried over Na$_2$SO$_4$, filtered and concentrated to give 4-(1-hydroxyethyl)benzoic acid as a white solid which was used without further purification.

4-(2-Hydroxyethyl)benzoic acid

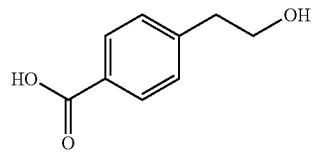

To a solution of 0.5 g (3.40 mmol) of the nitrile and 20 mL ethanol was added 7 mL of 2N NaOH. The solution was heated at 98° C. for 18 h., cooled, then evaporated. The remaining oil was dissolved into EtOAc and aqueous sodium bicarbonate. The organic layer was discarded. The aqueous layer was acidified with 6N HCl, extracted into EtOAc, dried over Na$_2$SO$_4$, filtered and evaporated to yield the hydroxy acid as a white solid.

4-(1H-Imidazol-2-yl)benzoic acid

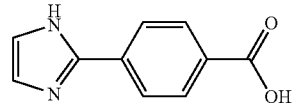

Ammonia gas was bubbled into a solution of 4-carboxybenzaldehyde (2.0 g, 13.32 mmol) in water (15 mL) for 10 min. To clear soln was added glyoxal (2.9 mL, 19.98 mmol) in water (10 mL) dropwise over 15 min and the reaction mixture was stirred for 3 h. The solution was neutralized with 6N HCl and filtered to give a white paste. Trituration with acetone followed by evaporation gave 4-(1H-imidazol-2-yl)benzoic acid as a white solid.

2-(Hydroxymethyl)-1,3-thiazole-4-carboxylic acid

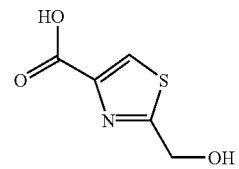

Step 1:

Preparation of 2-{[(2,2-dimethylpropanoyl)oxy]methyl}-1,3-thiazole-4-carboxylic acid

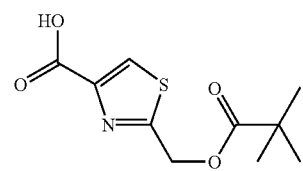

To a solution of bromopyruvic acid (0.37 g, 2.22 mmol) and 2-(tert-butylcarbonyloxy)thioacetamide (0.41 g, 2.22 mmol) in ethanol (20 ml) was added 4 A molecular sieves (2 g). After stirring for 15 h, 20 mL of dichloromethane was added. The mixture was stirred 5 min and filtered to give the product as a yellow solid.

Step 2:

Preparation of 2-(hydroxymethyl)-1,3-thiazole-4-carboxylic acid

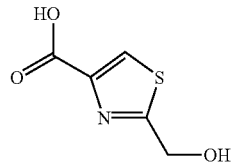

To the protected alcohol acid (0.36 g, 1.48 mmol) in MeOH (20 mL) and water (6 mL) was added potassium carbonate (0.36 g, 0.26 mmol). The mixture was heated at reflux for 2 h. The methanol was removed in vacuo and the remaining aqueous reaction mixture was extracted with hot EtbAc (2×100 mL). The combined organic layers were dried over $Na_2SO_4$, filtered and evaporated to a yellow oil. Diethyl ether (20 mL) was added, and the mixture was decanted and dried in vacuo to give the product as a brown powder.

Example 204

4-Methylbenzyl 4-({[4-(1-hydroxy-1-methylethyl) benzoyl]amino}methyl)piperidine-1-carboxylate

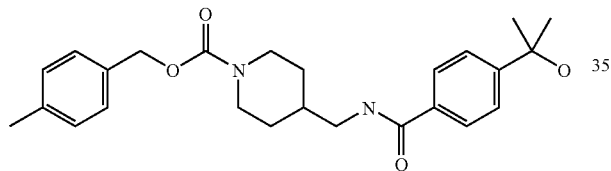

To a 0° C. solution of 4-methylbenzyl 4-({[4-(methoxycarbonyl)benzoyl]-amino}methyl)-piperidine-1-carboxylate (EXAMPLE 538) (100 mg, 0.24 mmol) in THF (3 mL) was added methyl magnesiumbromide (0.39 mL, 1.18 mmol, 3.0M in $Et_2O$). The reaction mixture was warmed to rt, quenched with $H_2O$ and extracted with EtOAc. The organic layer was dried over $Na_2SO_4$, filtered and concentrated. The residue was chromatographed on silica gel (gradient elution, 2:1 hexane:EtOAc to EtOAc) to give 4-methylbenzyl 4-({[4-(1-hydroxy-1-methylethyl)benzoyl]amino}methyl)piperidine-1-carboxylate.

$(M+H)^+=425.5$

Example 205

4-Methylbenzyl 4-({[3-(hydroxymethyl)benzoyl] amino}methyl)piperidine-1-carboxylate

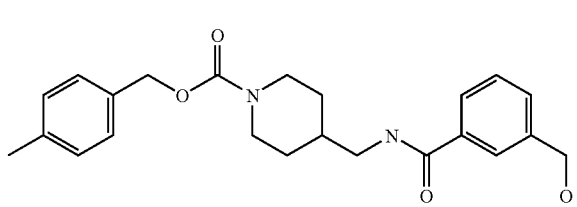

To a solution of 4-methylbenzyl 4-({[3-(methoxycarbonyl)benzoyl]amino}methyl)piperidine-1-carboxylate (EXAMPLE 540) (100 mg, 0.24 mmol) in MeOH (2 mL) was added sodium borohydride (0.18 mg, 4.7 mmol). The solution was stirred at rt for 2 h, quenched with saturated $NH_4Cl$ (aq) and extracted with EtOAc. The organic layer was dried over $NaSO_4$, filtered and concentrated. The residue was chromatographed on silica gel (gradient elution, 2:1 hexane: EtOAc to EtOAc) to give 4-methylbenzyl 4-({[3-(hydroxymethyl)benzoyl]amino}methyl)piperidine-1-carboxylate.

$(M+H)^+=397.5$

Example 206

4-Methylbenzyl 4-[({[3-(hydroxymethyl)-1H-pyrazol-5-yl]carbonyl}amino)methyl]piperidine-1-carboxylate

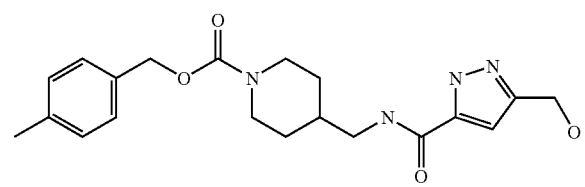

To 5-({[(1-{[(4-methylbenzyl)oxy]carbonyl}piperidin-4-yl)methyl]amino}carbonyl)-1H-pyrazole-3-carboxylic acid (50 mg, 0.13 mmol) was added $BH_3$-THF solution (2.5 mL, 2.5 mmol, 1.0M in THE). The solution was stirred at rt for 1 h, quenched with HCl (1M) and extracted with EtOAc. The organic layer was washed with $H_2O$ dried over $Na_2SO_4$, filtered and concentrated. The residue was chromatographed on silica gel (gradient elution, EtOAc to 10% MeOH/ EtOAc) to give 4-methylbenzyl 4-[({[3-(hydroxymethyl)-1H-pyrazol-5-yl]carbonyl}amino)methyl]piperidine-1-carboxylate.

$(M+H)^+=387.5$

Example 207

Benzyl 4-({[(2-aminopyrinmidin-4-yl)carbonyl] amino}-methyl)piperidine-1-carboxylate

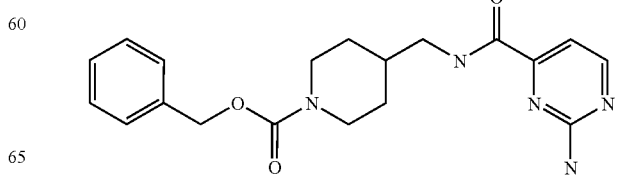

Step 1:

Preparation of 1-bromo-2-(methylthio)pyrimidine-4-carboxylic acid

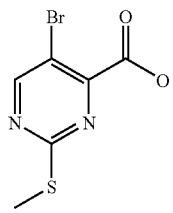

To a stirring solution of mucobromic acid (28.1 g, 109 mmol) and 2-methyl-2-thiopseudourea sulfate (21.4 g, 109 mmol) in water (400 mL) under an argon atmosphere was added triethylamine (45.6 mL, 327 mmol) via a syringe pump (~3 mL/h). After 18 h, conc. HCl (14 mL) was added to the dark brown solution, stirred 30 min, then filtered. The resulting solid was washed with water and dried to yield a brown solid. The solid was dissolved in 400 mL water, and the pH was adjusted to ~8 with solid sodium bicarbonate slowly to form a solution. To the solution, 10 g of Norit decolorizing charcoal was added and the suspension was heated for 1.25 h. at 100° C., cooled, then filtered through a pad of Celite. The pH of the solution was adjusted to ~0.3 with conc. HCl, allowed to stir in an ice bath for 30 min then filtered to yield 16.0 g of yellow solid after drying in air.

Step 2:

Preparation of 2-(methylthio)pyrimidine-4-carboxylic acid

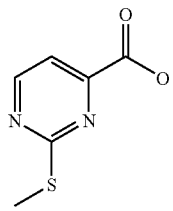

A solution of 5-bromo-2-(methylthio)pyrimidine-4-carboxylic acid (8.0 g, 32.1 mmol) and potassium hydroxide (4.4 g, 32.1 mmol) in MeOH (175 mL) was transferred to a Parr hydrogenation jar. After purging the solution with nitrogen gas, of 5% Pd on barium sulfate (3.93 g) was added then hydrogenated on Parr Hydrogenation Apparatus for 2 h at 40 psi. The mixture was filtered through a Celite pad. The resulting yellow solution was evaporated to ~30 mL, then conc HCl was added to pH~0.3, yielding a yellow solid carboxylic acid after filtration and air drying.

Step 3:

Preparation of 2-(methylsulfonyl)pyrimidine-4-carboxylic acid

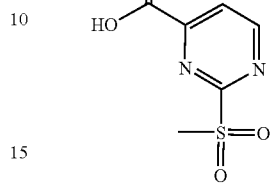

To a solution of 2-(methylthio)pyrimidine-4-carboxylic acid (1.88 g, 11.1 mmol) in THf (200 mL) was added Oxone (20.4 g, 33.1 mmol) in water (50 mL). The suspension was stirred for 24 h, then evaporated to dryness. The resulting white paste was extracted 5× each 100 mL EtOAc and 5% MeOH in EtOAc. The combined extracts were dried over anhydrous MgSO$_4$, filtered and concentrated to give the sulfone as a white solid.

Step 4:

Preparation of benzyl 4-[({[2-(methylsulfonyl)pyrimidin-4-yl]carbonyl}amino)methyl]piperidine-1-carboxylate

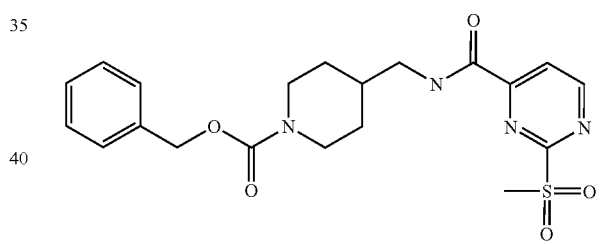

2-(Methylsulfonyl)pyrimidine-4-carboxylic acid was coupled to benzyl 4-(aminomethyl)piperidine-1-carboxylate according to the procedure for EXAMPLE 1.

Step 5:

Preparation of benzyl 4-({[(2-aminopyrimidin-4-yl)carbonyl]amino}-methyl)piperidine-1-carboxylate

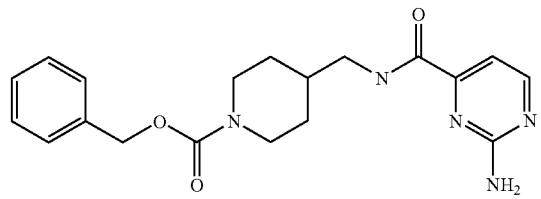

Ammonia gas was bubbled through a solution of benzyl 4-[({[2-(methylsulfonyl)pyrimidin4-yl]carbonyl}amino)methyl]piperidine-1-carboxylate (EXAMPLE 207, Step 4)

(1.30 g, 3.01 mmol) in EtOAc (75 mL) for 10 min. The resulting solution was heated in a sealed pressure tube for 18 h. at 65° C. The white suspension was then concentrated in vacuo. The mixture was recrystallized using ~20 mL EtOAc, and a minimal amount of MeOH, providing EXAMPLE 207 as a white solid. (M+H)$^+$=370.4

Example 208

Benzyl 4-[({[2-(methylamino)pyrimidin-4-yl]carbonyl}amino)methyl]piperidine-1-carboxylate

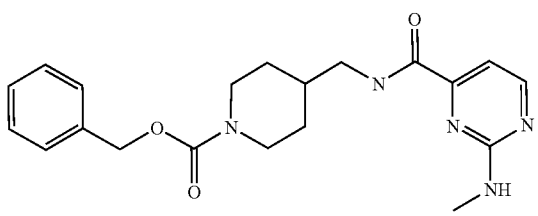

To a solution of benzyl 4-[({[2-(methylsulfonyl)pyrimidin-4-yl]carbonyl}amino)methyl]piperidine-1-carboxylate (EXAMPLE 207, Step 4) (0.90 g, 3.01 mmol) in THF (75 mL) was added 40% aqueous methylamine (0.45 g). The resulting solution was heated for 18 h at 65° C., evaporated to dryness and purified by silica gel chromatography (gradient elution, 30 to 100% ethyl acetate in hexane) to provide EXAMPLE 208 as a yellow gum. (M+H)$^+$=384.3

Example 209

Benzyl 4-[({[2-(dimethylamino)pyrimidin-4-yl]carbonyl}amino)methyl]piperidine-1-carboxylate

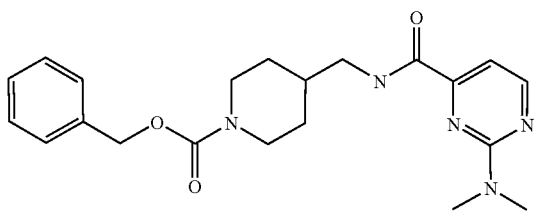

To a solution of benzyl 4-[({[2-(methylsulfonyl)pyrimidin-4-yl]carbonyl}amino)methyl]piperidine-1-carboxylate (EXAMPLE 207, Step 4) (43 mg, 0.01 mmol) in THF (10 mL) was added dimethylamine hydrochloride (23.6 mg, 0.3 mmol). The resulting solution was heated for 18 h at 80° C. and evaporated to dryness. Ethyl acetate was added, and washed with sat'd aqueous sodium bicarbonate, water then brine. The organic layer was dried over Na$_2$SO$_4$, filtered and concentrated. The resulting oil was purified by silica gel chromatography (gradient elution, 20 to 100% ethyl acetate in hexane) to provide EXAMPLE 209 as a white foam. (M+H)$^+$=398.3

Example 210

Benzyl 4-({[(2-hydroxypyrimidin-4-yl)carbonyl]amino}methyl)piperidine-1-carboxylate

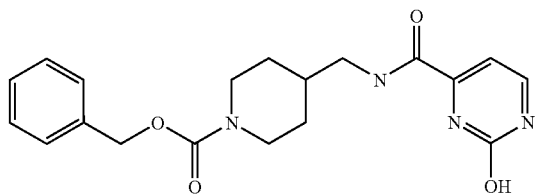

To a solution of benzyl 4-[({[2-(methylsulfonyl)pyrimidin-4-yl]carbonyl}amino)methyl]piperidine-1-carboxylate (EXAMPLE 207, Step 4) (70 mg, 0.20 mmol) in THF (3 mL) was added NH$_4$OH (0.5 mL). The solution was stirred at rt for 2 h. The solution was evaporated, water was added then extracted 2× with EtOAc, dried over Na$_2$SO$_4$, and evaporated to an oil. Silica gel column chromatography using a 95:5:0.5 to 90:10:1 CH$_2$Cl$_2$:MeOH:NH$_4$OH gradient provided EXAMPLE 210 as a white solid. (M+H)$^+$=371.4

Example 211

Benzyl 4-({[(2-methoxypyrimidin-4-yl)carbonyl]amino}methyl)piperidine-1-carboxylate

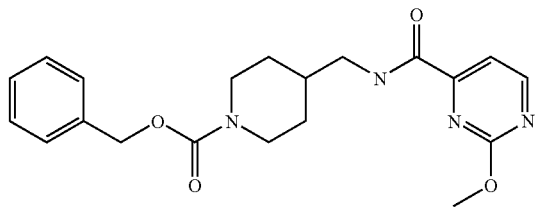

A solution of benzyl 4-[({[2-(methylsulfonyl)pyrimidin-4-yl]carbonyl}amino)methyl]piperidine-1-carboxylate (EXAMPLE 207, Step 4) (70 mg, 0.20 mmol) in MeOH (3 mL) was heated at 60° C. for 18 h. The solution was evaporated, water was added then extracted 2× with EtOAc, dried over Na$_2$SO$_4$, and evaporated to an oil. Silica gel column chromatography using a 95:5:0.5 to 90:10:1 CH$_2$Cl$_2$:MeOH:NH$_4$OH gradient provided EXAMPLE 211 as a white solid. (M+H)$^+$=385.4

Example 212

4-Methylbenzyl 4-({[4-(2,2,2-trifluoro-1-hydroxyethyl)benzoyl]amino}methyl)piperidine-1-carboxylate

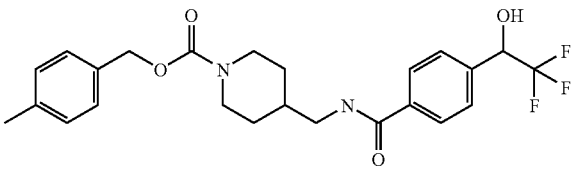

To a solution of 4-methylbenzyl 4-({[4-(trifluoroacetyl)benzoyl]amino}methyl)piperidine-1-carboxylate (EXAMPLE 543) (250 mg, 0.54 mmol) in methanol (10 mL) was added sodium borohydride (20.5 mg, 0.54 mmol). After 1 h., water (10 mL) was added and the organics evaporated. The aqueous suspension was extracted 2× with EtOAc. The organics were dried over Na$_2$SO$_4$, filtered and evaporated to a clear oil. Silica gel chromatography (gradient elution, 30 to 100% ethyl acetate in hexane), provided EXAMPLE 212 as a white foam. (M+H)$^+$=465.4

Example 213

4-Methylbenzyl 4-({[4-(aminomethyl)benzoyl]amino}methyl)piperidine-1-carboxylate

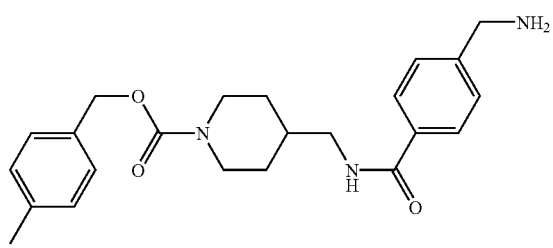

4-Methylbenzyl 4-{[(4-{[(tert-butoxycarbonyl)amino]methyl}benzoyl)amino]methyl}piperidine-1-carboxylate (EXAMPLE 544) (200 mg, 0.40 mmol) was dissolved in EtOAc (10 mL), cooled to 0° C., and gaseous HCl was bubbled in for 10 min. After 30 min., the mixture was evaporated to give a fine white powder of the hydrochloride salt of EXAMPLE 213.

(M+H)$^+$=396.4

Example 214

4-Methylbenzyl 4-[({4-[(acetylamino)methyl]benzoyl}amino)methyl]piperidine-1-carboxylate

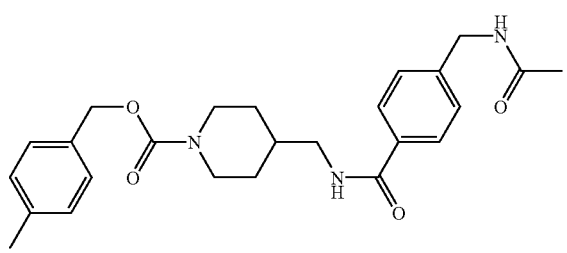

To a solution of EXAMPLE 213 (20 mg, 0.05 mmol), in CH$_2$Cl$_2$ (10 mL) was added triethylamine (14 μL, 0.10 mmol) and acetyl chloride (7.2 μL, 0.092 mmol). After 5 min, water was added and the product was extracted into CH$_2$Cl$_2$. Evaporation gave EXAMPLE 214 as a white solid. (M+H)$^+$=438.3

Example 215

4-methylbenzyl 4-{[(4-{[(methoxycarbonyl)amino]methyl}benzoyl)amino]methyl}piperidine-1-carboxylate

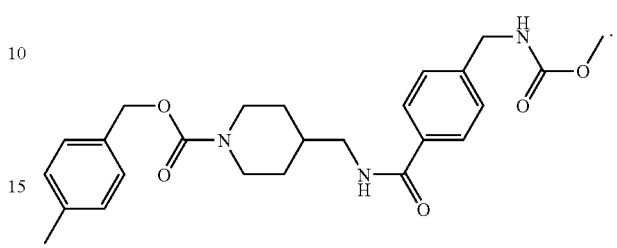

To a solution of EXAMPLE 213 (30 mg, 0.069mmol) in THF (5 mL) was added triethylamine (19.3 μL) and methylchloroformate (5.3 μL). The reaction mixture was stirred for 3 h then concentrated. Water and saturated sodium bicarbonate was added and the aqueous layer was extracted with EtOAc. The organic layer was dried over Na$_2$SO$_4$, filtered and concentrated to a white solid. Silica gel chromatography (75% ethyl acetate in hexane to 95:5:0.5 ethyl acetate:MeOH:NH$_4$OH) provided EXAMPLE 215 as a white solid. (M+H)$^+$=454.4

Example 216

Benzyl 4-fluoro-4-{[(4-hydroxybenzoyl)amino]methyl}piperidine-1-carboxylate

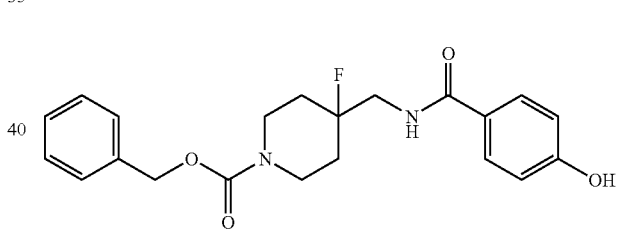

Step 1:

Preparation of tert-butyl 1-oxa-6-azaspiro[2.5]octane-6-carboxylate

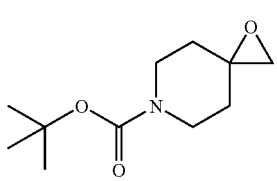

To a solution of tert-butyl 4-oxopiperidine-1-carboxylate (0.50 g, 2.51 mmol) in THF/DME (2:1, 6 mL) at 60° C. was added trimethylsulfoxonium iodide (0.58 g, 2.63 mmol) and sodium t-butoxide (0.25 g, 2.63 mmol). The reaction mixture was stirred at 60° C. for 30 min, cooled to rt and concentrated. Water was added and the mixture was extract with EtOAc twice. The combined organics were dried over Na₂SO₄, filtered and concentrated. Purification on silica gel (3:1, hexanes:EtOAc) gave tert-butyl 1-oxa-6-azaspiro[2.5]octane-6-carboxylate as a clear oil that solidified upon standing.

Step 2:

Preparation of benzyl 4-fluoro-4-(hydroxymethyl)piperidine-1-carboxylate

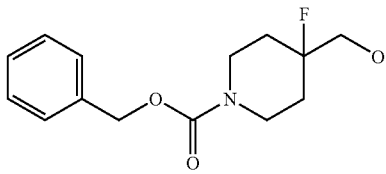

To a solution of tert-butyl 4-oxopiperidine-1-carboxylate (7.0 g, 32.8 mmol) in CH₂Cl₂ (14 mL) at −10° C. was added HF-pyridine (11.6 mL, 82.1 mmol) portionwise. The reaction mixture was stirred for 10 min at −10° C., warmed to rt. After stirring for 16 h, the reaction was carefully quenched with aqueous NaCO₃, and extracted with CH₂Cl₂. The aquoues layer was concentrated to a white paste that was suspended in CH₂Cl₂ (100 mL). BOCOS (8.2 g, 32.8 mmol) was added and the mixture was stirred at RT for 3 h. The reaction mixture was partitioned between EtOAc and H₂O, the organic layer was dried over Na₂SO₄, filtered and concentrated. Purification on silica gel (10:1 to 1:1 hexanes:EtOAc) gave benzyl 4-fluoro-4-(hydroxymethyl)piperidine-1-carboxylate as a clear oil.

Step 3:

Preparation of benzyl 4-fluoro-4-{[(methylsulfonyl)oxy]methyl}piperidine-1-carboxylate

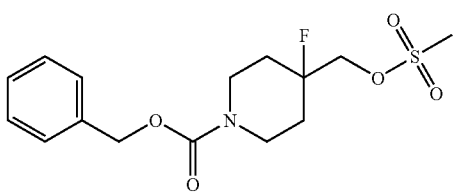

To a solution of benzyl 4-fluoro-4-(hydroxymethyl)piperidine-1-carboxylate (1.0 g, 3.7 mmol) in CH₂Cl₂ (10 mL) at RT was added MsCl (0.29 mL, 3.7 mmol) and TEA (1.04 mL, 7.5 mmol). The reaction mixture was stirred at RT for 5 min, and partitioned between EtOAc and H₂O. The organic layer was dried over Na2SO4, filtered, concentrated and purified on silica gel (10:1 to 1:2 hexanes:EtOAc) togive benzyl 4-fluoro-4-{[(methylsulfonyl)oxy]methyl}piperidine-1-carboxylate.

Step 4:

Preparation of benzyl 4-(azidomethyl)-4-fluoropiperidine-1-carboxylate

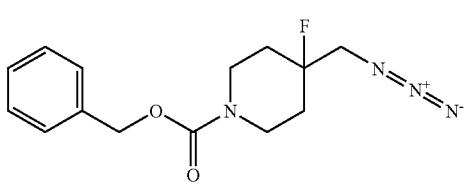

To a solution of benzyl 4-fluoro-4-{[(methylsulfonyl)oxy]methyl}piperidine-1-carboxylate (1.3 g, 3.7 mmol) in DMF (10 mL) at RT was added NaN₃ (2.4 g, 37.0 mmol). The reaction mixture was heated to 110° C. and stirred for 60 h, cooled and partitioned between EtOAc and H₂O. The organic layer was dried over Na₂SO₄, filtered, concentrated and purified on silica gel (10:1 to 1:2 hexanes:EtOAc) to give benzyl 4-(azidomethyl)-4-fluoropiperidine-1-carboxylate.

Step 5:

Preparation of benzyl 4-(aminomethyl)-4-fluoropiperidine-1-carboxylate

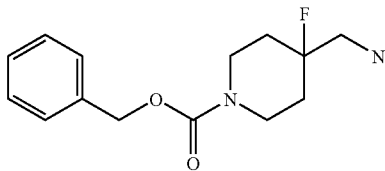

To a solution of benzyl 4-(azidomethyl)-4-fluoropiperidine-1-carboxylate (1.5 g, 5.1 mmol) in THF (10 mL) at RT with added water (0.92 mL, 0.92 mmol) and triphenylphosphine (4.3 g, 15.4 mmol). The reaction mixture was stirred for 60 h, concentrated, dissolved in HCl (1M) and extracted with Et₂O four times. The aqueous layer was basified to pH 11 and extracted with EtOAc twice. The organic layer was dried over Na₂SO₄, filtered and concentrated. The crude mixture was chromatographed on silica gel (CH₂Cl₂ to 80:20:2 CH₂C12:MeOH:NH4OH) to give benzyl 4-(aminomethyl)-4-fluoropiperidine-1-carboxylate.

Step 6:

Benzyl 4-fluoro-4-{[(4-hydroxybenzoyl)amino]methyl}piperidine-1-carboxylate

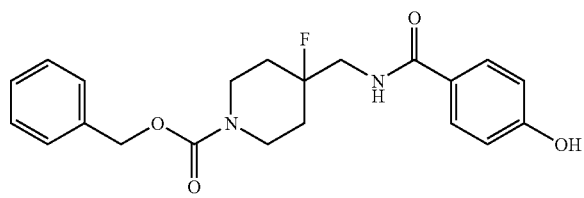

4-Hydroxy benzoic acid was coupled to benzyl 4-(aminomethyl)-4-fluoropiperidine-1-carboxylate according to the procedure for EXAMPLE 1.

(M+H)⁺=387.3

Example 217

Benzyl 4-({[(2-amino-1,3-thiazol-5-yl)carbonyl]amino}methyl)piperidine-1-carboxylate

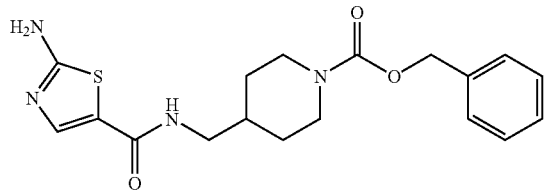

Step 1:

Preparation of ethyl 2-amino-1,3-thiazole-5-carboxylate

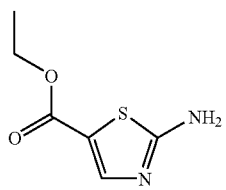

To a mixture of B-ethoxyacrylic acid ethyl ester (2.0 g, 13.9 mmol) in 1:1 dioxane/water (15 mL) at −10°0 C. was added NBS (2.72 g, 15.3 mmol). Thiourea (1.06 g, 13.9 mmol) was added and the mixture was heated to 80° C. and stirred for 1.5 h. The reaction mixture was cooled to 0° C. and 5 mL of saturated ammonium hydroxide was added. A precipitate formed in 15 min. The solid was filtered, washed with water and dried under vacuum, yielding a light orange solid.

Step 2:

Preparation of 2-[(tert-butoxycarbonyl)amino]-1,3-thiazole-5-carboxylic acid

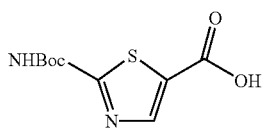

To a solution of ethyl 2-amino-1,3-thiazole-5-carboxylate (1.88 g, 10.9 mmol) in dioxane (100 mL) was added di-t-butyl dicarbonate (2.43 g, 12.0 mmol) and 2N NaOH (16.4 mL, 32.8 mmol). The reaction mixture was stirred 18 h. then concentrated in vacuo. The paste was partitioned between ethyl acetate and water, the layers were separated, and the aqueous re-extracted twice with ethyl acetate. The combined organics were dried over anhydrous sodium sulfate and concentrated to give an oil. The product was preabsorbed onto silica gel and column chromatography (10 to 30% ethyl acetate in hexanes) afforded 3 g white solid.

The solid was added to a solution of lithium hydroxide (0.5 g) in water/TBF (1:1, 100 mL). The mixture was heated at 45° C. for 3d. The organics were evaporated, and the product was partitioned between ethyl acetate and water. The aqueous layer was then acidified to pH ~4 with 6N HCl and filtered to obtain an off white solid.

Step 3:

Preparation of benzyl 4-{[({2-[(tert-butoxycarbonyl)amino]-1,3-thiazol-5-yl}carbonyl)amino]methyl}piperidine-1-carboxylate

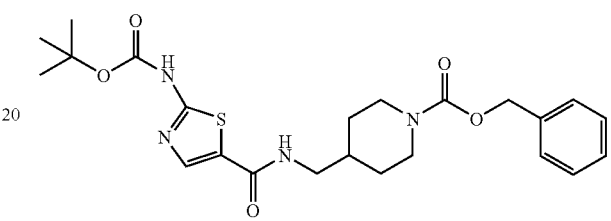

2-[(tert-Butoxycarbonyl)amino]-1,3-thiazole-5-carboxylic acid was coupled to benzyl 4-(aminomethyl)piperidine-1-carboxylate according to the procedure for EXAMPLE 1.

Step 4:

Benzyl 4-({[(2-amino-1,3-thiazol-5-yl)carbonyl]amino}methyl)piperidine-1-carboxylate

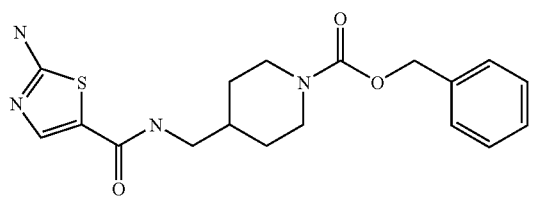

EXAMPLE 217 was prepared from benzyl 4-{[({2-[(tert-butoxycarbonyl)amino]-1,3-thiazol-5-yl}carbonyl)amino]methyl}piperidine-1-carboxylate using the procedure for EXAMPLE 174, Step 3.

$(M+H)^+=375.3$

Example 218

4-Hydroxy-N-{[1(4-methylbenzyl)piperidin-4-yl]methyl}benzamide

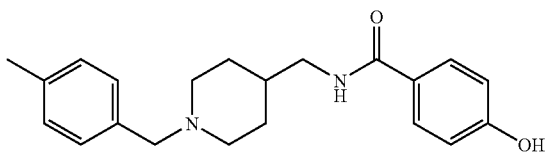

To a solution of 4-hydroxy-N-piperidin-4-ylmethyl-benzamide (EXAMPLE 154, Step 1) (50 mg, 0.21 mmol) in MeOH (3 mL) was added 4-methylbenzaldehyde (25 mg, 0.21 mmol) and sodium cyanoborohydride (40 mg, 0.64 mmol). The reaction mixture was stirred at rt for 15 h, concentrated and purified by reverse-phase HPLC. (M+H)$^+$= 339.2

The following Examples were prepared utilizing appropriate procedures from examples described above.

| EX. | Structure | Name | MS (M$^+$ + 1) |
|---|---|---|---|
| 219. | 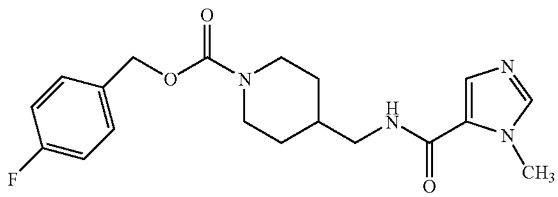 | 4-{[(3-Methyl-3H-imidazole-4-carbonyl)-amino]-methyl}-piperidine-1-carboxylic acid 4-fluoro-benzyl ester | 375.3 |
| 220. | 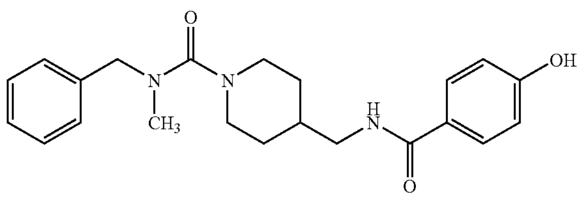 | 4-[(4-Hydroxy-benzoylamino)-methyl]-piperidine-1-carboxylic acid benzyl-methyl-amide | 382.4 |
| 221. | 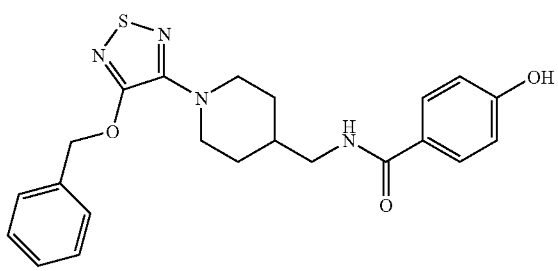 | N-[1-(4-Benzyloxy-[1,2,5]thiadiazol-3-yl)-piperidin-4-ylmethyl]-4-hydroxy-benzamide | 425.2 |
| 222. | 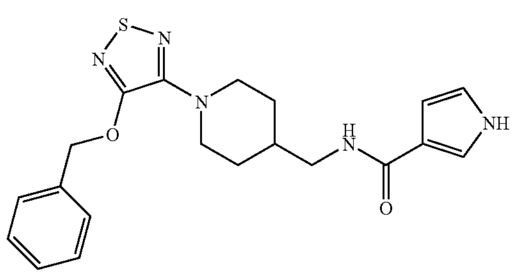 | 1H-Pyrrole-3-carboxylic acid [1-(4-benzyloxy-[1,2,5]thiadiazol-3-yl)-piperidin-4-ylmethyl]-amide | 398.2 |
| 223. | 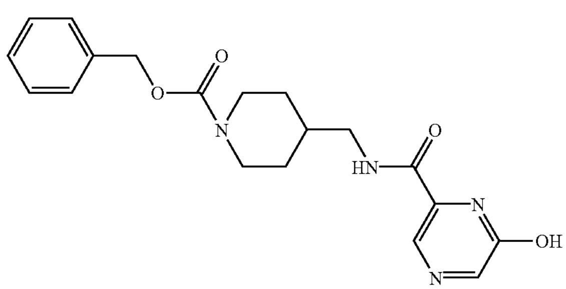 | 4-{[(6-Hydroxy-pyrazine-2-carbonyl)-amino]-methyl}-piperidine-1-carboxylic acid benzyl ester | 371.3 |

-continued

| EX. | Structure | Name | MS (M⁺ + 1) |
|---|---|---|---|
| 224. | 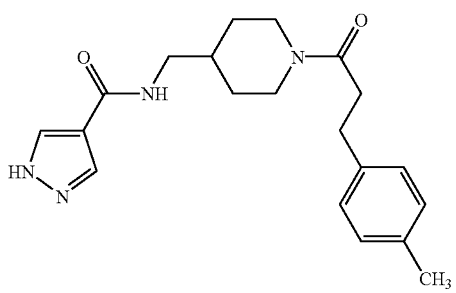 | 1H-Pyrazole-4-carboxylic acid [1-(3-p-tolyl-propionyl)-piperidin-4-ylmethyl]-amide | 355.3 |
| 225. | 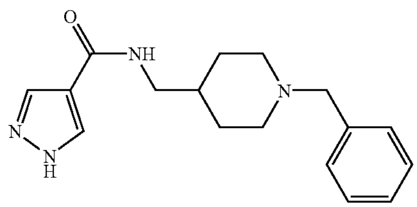 | 1H-Pyrazole-4-carboxylic acid (1-benzyl-piperidin-4-ylmethyl)-amide | 299.3 |
| 226. | 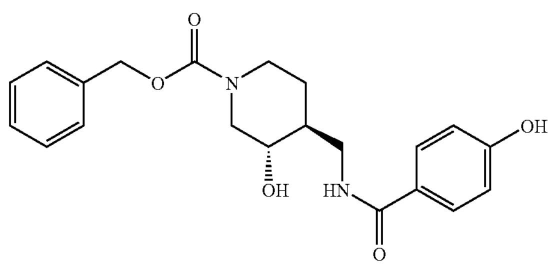 | 3-Hydroxy-4-[(4-hydroxy-benzoylamino)-methyl]-piperidine-1-carboxylic acid benzyl ester | 385.3 |
| 227. | 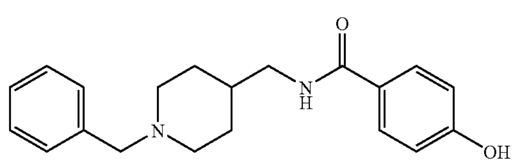 | N-(1-Benzyl-piperidin-4-ylmethyl)-4-hydroxy-benzamide | 325.3 |
| 228. | 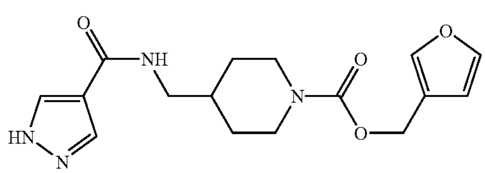 | 4-{[(1H-Pyrazole-4-carbonyl)-amino]-methyl}-piperidine-1-carboxylic acid furan-3-ylmethyl ester | 333.2 |
| 229. | 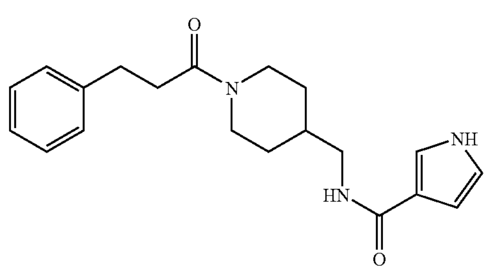 | 1H-Pyrrole-3-carboxylic acid [1-(3-phenyl-propionyl)-piperidin-4-ylmethyl]-amide | 340.3 |
| 230. | 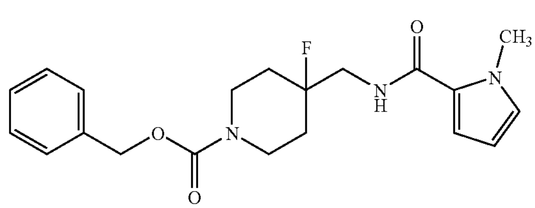 | 4-Fluoro-4-{[(1-methyl-1H-pyrrole-2-carbonyl)-amino]-methyl}-piperidine-1-carboxylic acid benzyl ester | 374.3 |

-continued

| EX. | Structure | Name | MS (M+ + 1) |
|---|---|---|---|
| 231. | 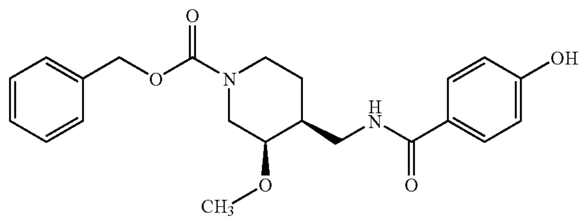 | 4-[(4-Hydroxy-benzoylamino)-methyl]-3-methoxy-piperidine-1-carboxylic acid benzyl ester | 399.3 |
| 232. | 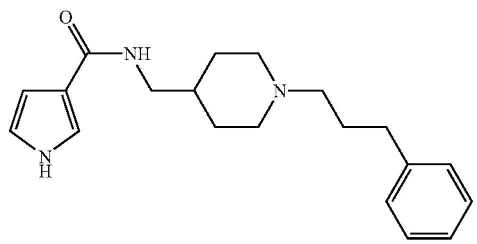 | 1H-Pyrrole-3-carboxylic acid [1-(3-phenyl-propyl)-piperidin-4-ylmethyl]-amide | 326.3 |
| 233. | 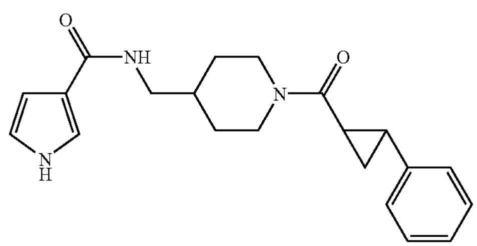 | 1H-Pyrrole-3-carboxylic acid [1-(2-phenyl-cyclopropanecarbonyl)-piperidin-4-ylmethyl]-amide | 352.3 |
| 234. | 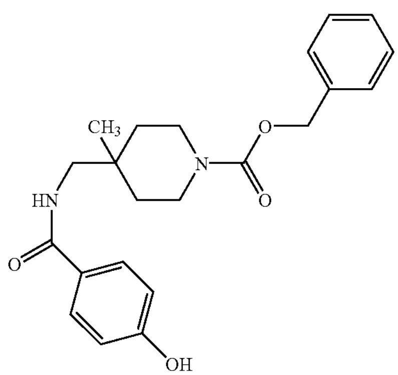 | 4-[(4-Hydroxy-benzoylamino)-methyl]-4-methyl-piperidine-1-carboxylic acid benzyl ester | 383.3 |
| 235. | 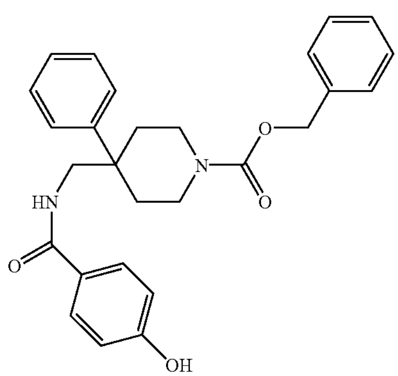 | 4-[(4-Hydroxy-benzoylamino)-methyl]-4-phenyl-piperidine-1-carboxylic acid benzyl ester | 445.3 |

-continued

| EX. | Structure | Name | MS (M⁺ + 1) |
|---|---|---|---|
| 236. | 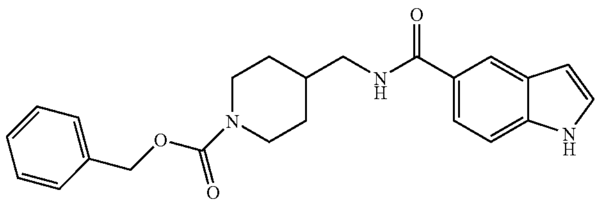 | 4-{[(1H-Indole-5-carbonyl)-amino]-methyl}-piperidine-1-carboxylic acid benzyl ester | 392.3 |
| 237. | 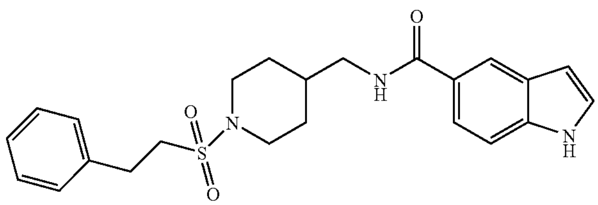 | 1H-Indole-5-carboxylic acid [1-(2-phenyl-ethanesulfonyl)-piperidin-4-ylmethyl]-amide | 426.3 |
| 238. | 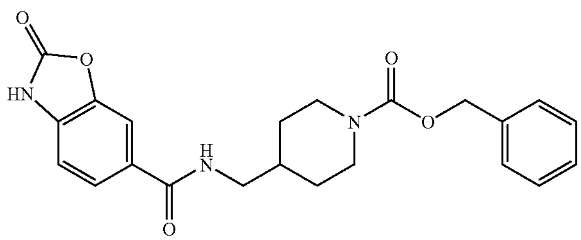 | 4-{[(2-Oxo-2,3-dihydro-benzooxazole-6-carbonyl)-amino]-methyl}-piperidine-1-carboxylic acid benzyl ester | |
| 239. | 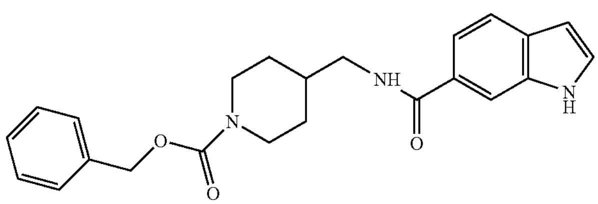 | 4-{[(1H-Indole-6-carbonyl)-amino]-methyl}-piperidine-1-carboxylic acid benzyl ester | 392.3 |
| 240. | 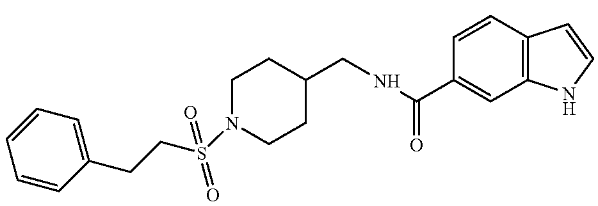 | 1H-Indole-6-carboxylic acid [1-(2-phenyl-ethanesulfonyl)-piperidin-4-ylmethyl]-amide | 426.3 |
| 241. | 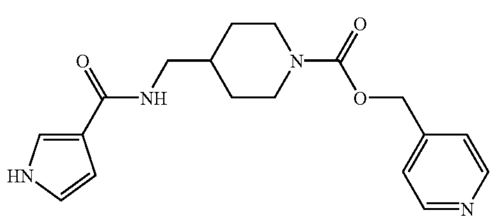 | 4-{[(1H-Pyrrole-3-carbonyl)-amino]-methyl}-piperidine-1-carboxylic acid pyridin-4-ylmethyl ester | 343.2 |
| 242. | 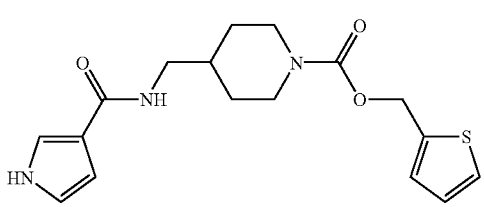 | 4-{[(1H-Pyrrole-3-carbonyl)-amino]-methyl}-piperidine-1-carboxylic acid thiophen-2-ylmethyl ester | 348.2 |

-continued

| EX. | Structure | Name | MS (M⁺ + 1) |
|---|---|---|---|
| 243. | 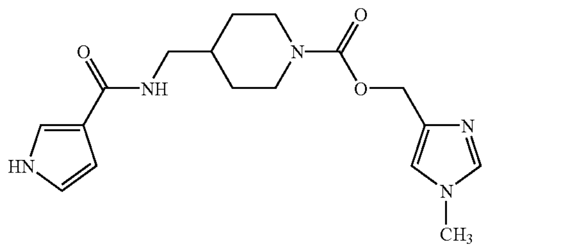 | 4-{[(1H-Pyrrole-3-carbonyl)-amino]-methyl}-piperidine-1-carboxylic acid 1-methyl-1H-imidazol-4-yl methyl ester | 346.2 |
| 244. | 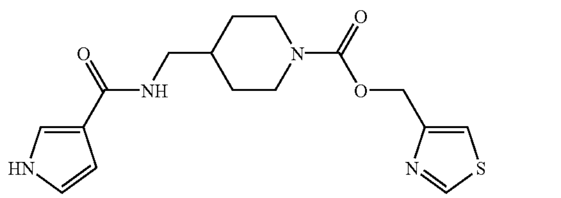 | 4-{[(1H-Pyrrole-3-carbonyl)-amino]-methyl}1-piperidine-1-carboxylic acid thiazol-4-ylmethyl ester | 349.2 |
| 245. | 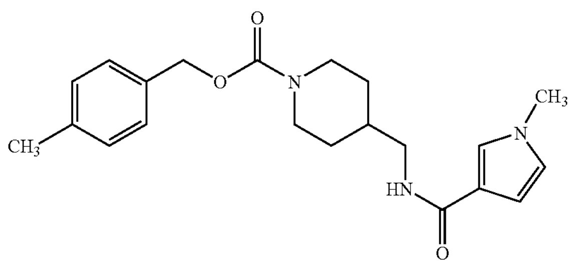 | 4-{[(1-Methyl-1H-pyrrole-3-carbonyl)-amino]-methyl}-piperidine-1-carboxylic acid 4-methyl-benzyl ester | 370.3 |
| 246. | 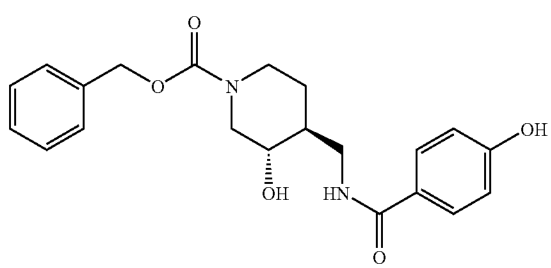 | 3-Hydroxy-4-[(4-hydraxy-benzoylamino)-methyl]-piperidine-1-carboxylic acid benzyl ester | 385.3 |
| 247. | 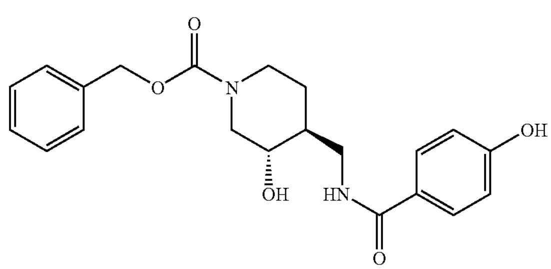 | 3-Hydroxy-4-[(4-hydroxy-benzoylamino)-methyl]-piperidine-1-carboxylic acid benzyl ester | 385.3 |
| 248. | 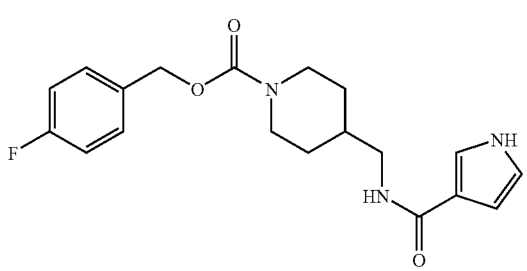 | 4-}[(1H-Pyrrole-3-carbonyl)-amino]-methyl}-piperidine-1-carboxylic acid 4-fluoro-benzyl ester | 360.2 |

-continued

| EX. | Structure | Name | MS (M⁺ + 1) |
|---|---|---|---|
| 249. | 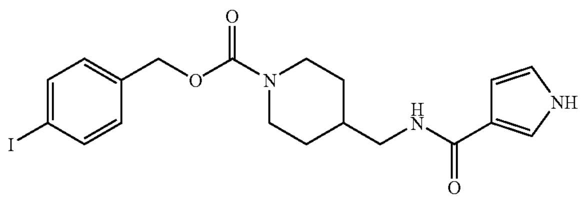 | 4-}[(1H-Pyrrole-3-carbonyl)-amino]-methyl}-piperidine-1-carboxylic acid 4-iodo-benzyl ester | 468.2 |
| 250. | 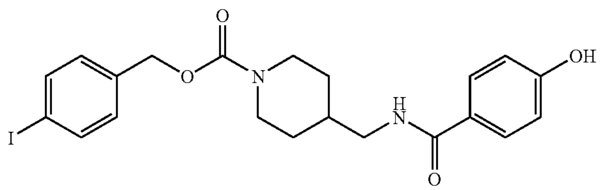 | 4-[(4-Hydroxy-benzoylamino)-methyl]-piperidine-1-carboxylic acid 4-iodo-benzyl ester | 495.2 |
| 251. | 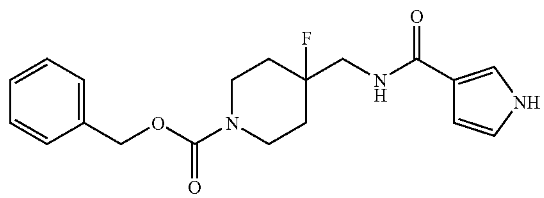 | 4-Fluoro-4-{[(1H-pyrrole-3-carbonyl)-amino]-methyl}-piperidine-1-carboxylic acid benzyl ester | 360.2 |
| 252. | 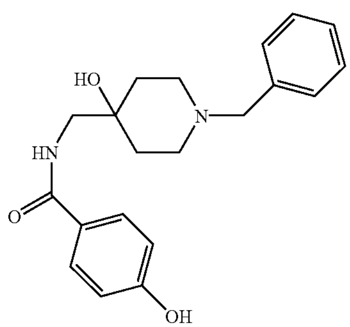 | N-(1-Benzyl-4-hydroxy-piperidin-4-ylmethyl)-4-hydroxy-benzamide | 341.2 |
| 253. | 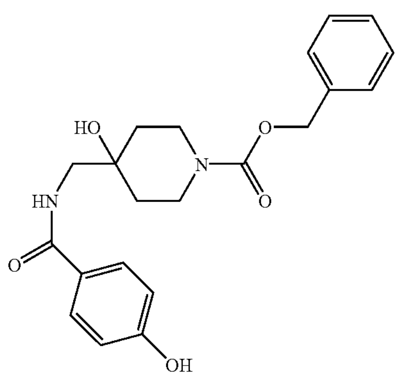 | 4-Hydroxy-4-[(4-hydroxy-benzoylamino)-methyl]-piperidine-1-carboxylic acid benzyl ester | 385.2 |
| 254. | 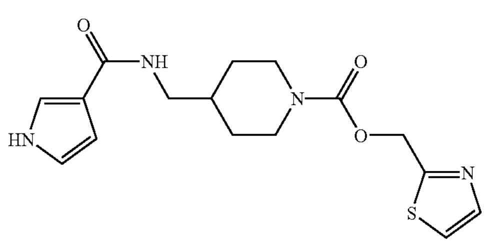 | 4-{[(1H-Pyrrole-3-carbonyl)-amino]-methyl}-piperidine-1-carboxylic acid thiazol-2-ylmethyl ester | 349.2 |

-continued

| EX. | Structure | Name | MS (M⁺ + 1) |
|---|---|---|---|
| 255. | 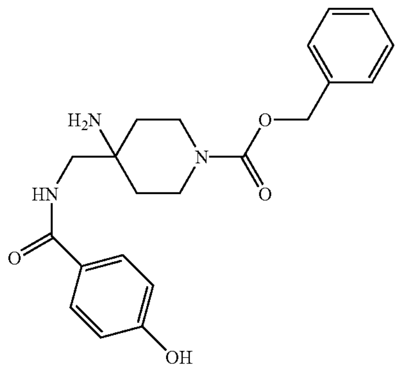 | 4-Amino-4-[(4-hydroxy-benzoylamino)-methyl]-piperidine-1-carboxylic acid benzyl ester | 384.3 |
| 256. | 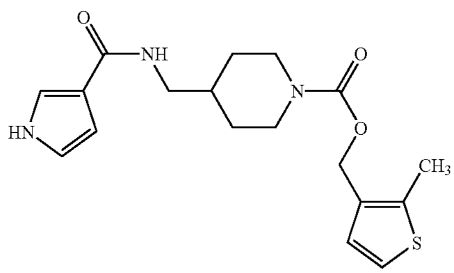 | 4-{[(1H-Pyrrole-3-carbonyl)-amino]-methyl}-piperidine-1-carboxylic acid 2-methyl-thiophen-3-ylmethyl ester | 362.2 |
| 257. | 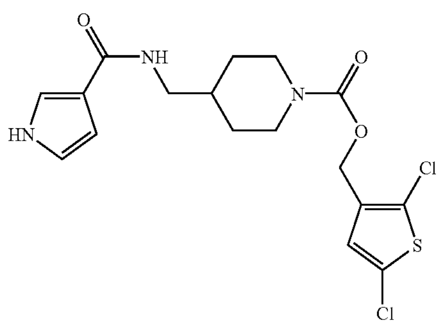 | 4-{[(1H-Pyrrole-3-carbonyl)-amino]-methyl}-piperidine-1-carboxylic acid 2,5-dichloro-thiophen-3-yl methyl ester | 416.1 |
| 258. | 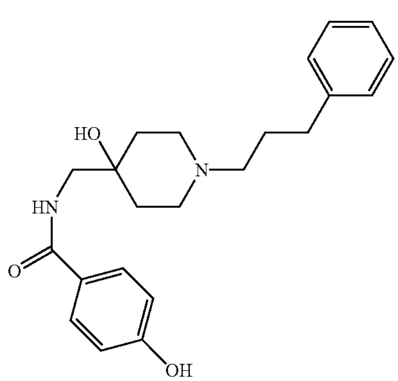 | 4-Hydroxy-N-[4-hydroxy-1-(3-phenyl-propyl)-piperidin-4-ylmethyl]-benzamide | 369.2 |

| EX. | Structure | Name | MS (M⁺ + 1) |
|---|---|---|---|
| 259. | 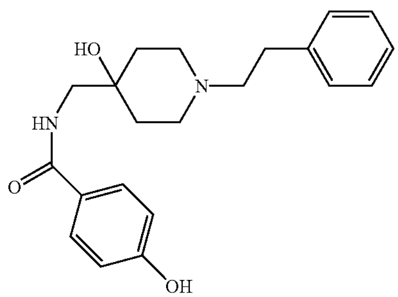 | 4-Hydroxy-N-(4-hydroxy-1-phenethyl-piperidin-4-ylmethyl)-benzamide | 355.2 |
| 260. | 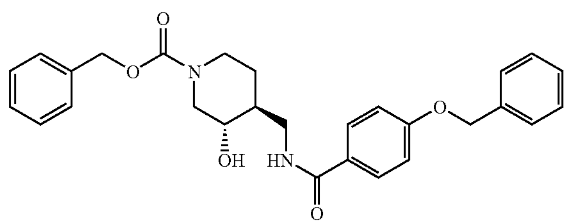 | 4-[(4-Benzyloxy-benzoylamino)-methyl]-3-hydroxy-piperidine-1-carboxylic acid benzyl ester | 475.3 |
| 261. | 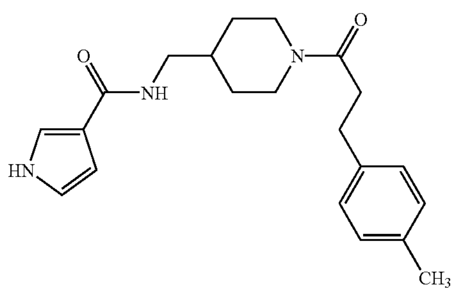 | 1H-Pyrrole-3-carboxylic acid [1-(3-p-tolyl-propionyl)-piperidin-4-ylmethyl]-amide | 354.3 |
| 262. | 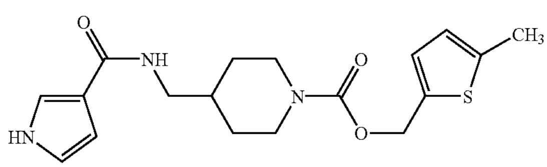 | 4{[(1H-Pyrrole-3-carbonyl)-amino]-methyl}-piperidine-1-carboxylic acid 5-methyl-thiophen-2-ylmethyl ester | 362.2 |
| 263. | 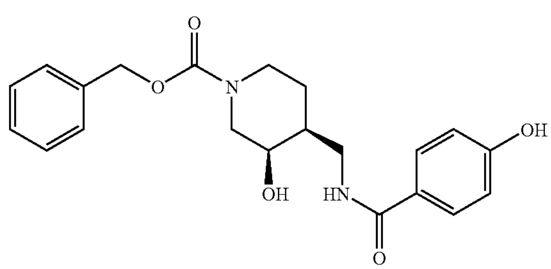 | 3-Hydroxy-4-[(4-hydroxy-benzoylamino)-methyl]-piperidine-1-carboxylic acid benzyl ester | 385.2 |
| 264. | 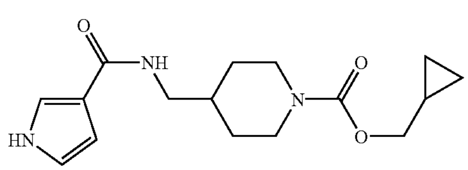 | 4-{[(1H-Pyrrole-3-carbonyl)-amino]-methyl}-piperidine-1-carboxylic acid cyclopropylmethyl ester | 306.2 |

-continued

| EX. | Structure | Name | MS (M⁺ + 1) |
|---|---|---|---|
| 265. | 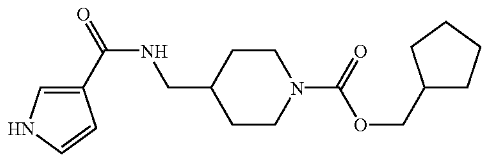 | 4-{[(1H-Pyrrole-3-carbonyl)-amino]-methyl}-piperidine-1-carboxylic acid cyclopentylmethyl ester | 334.2 |
| 266. | 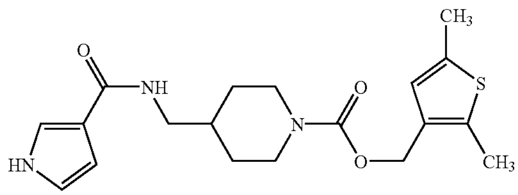 | 4-{[(1H-Pyrrole-3-carbonyl)-amino]-methyl}-piperidine-1-carboxylic acid 2,5-dimethyl-thiophen-3-yl methyl ester | 376.1 |
| 267. | 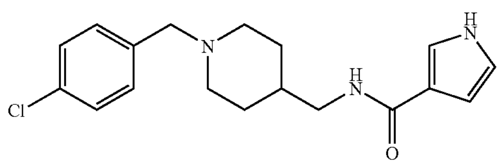 | 1H-Pyrrole-3-carboxylic acid [1-(4-chloro-benzyl)-piperidin-4-ylmethyl]-amide | 332.2 |
| 268. | 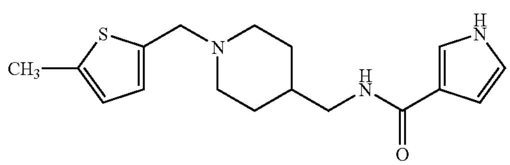 | 1H-Pyrrole-3-carboxylic acid [1-(5-methyl-thiophen-2-ylmethyl)-piperidin-4-ylmethyl]-amide | 318.2 |
| 269. | 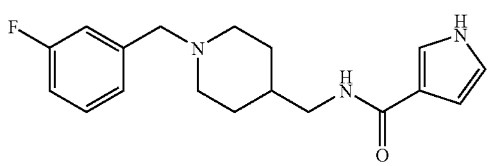 | 1H-Pyrrole-3-carboxylic acid [1-(3-fluoro-benzyl)-piperidin-4-ylmethyl]-amide | 316.2 |
| 270. | 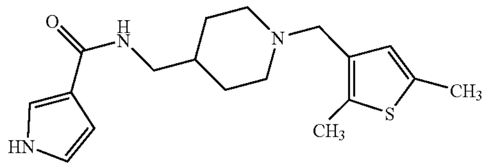 | 1H-Pyrrole-3-carboxylic acid [1-(2,5-dimethyl-thiophen-3-ylmethyl)-piperidin-4-ylmethyl]-amide | 332.2 |
| 271. | 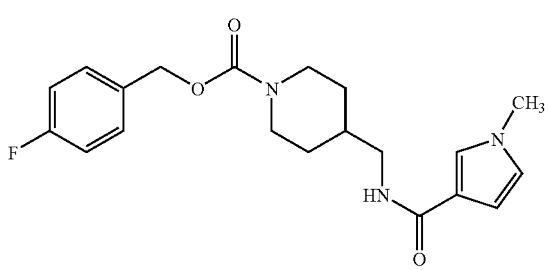 | 4-{[(1-Methyl-1H-pyrrole-3-carbonyl)-amino]-methyl}-piperidine-1-carboxylic acid 4-fluoro-benzyl ester | 374.2 |
| 272. | 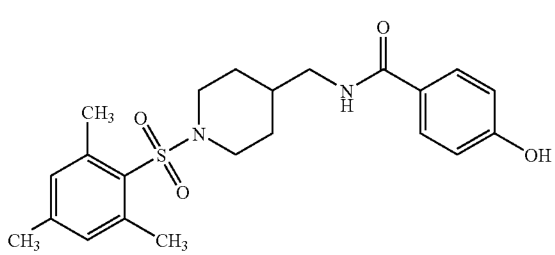 | 4-Hydroxy-N-[1-(2,4,6-trimethyl-benzenesulfonyl)-piperidin-4-ylmethyl]-benzamide | 416.2 |

-continued

| EX. | Structure | Name | MS (M⁺ + 1) |
|---|---|---|---|
| 273. | 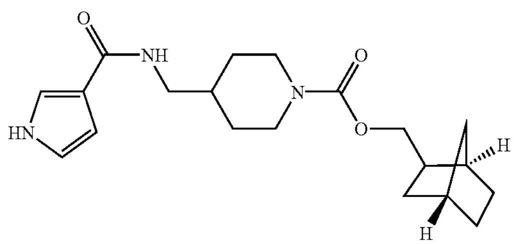 | 4-{[(1H-Pyrrole-3-carbonyl)-amino]-methyl}-piperidine-1-carboxylic acid bicyclo[2.2.1]hept-2-ylmethyl ester | 360.2 |
| 274. | 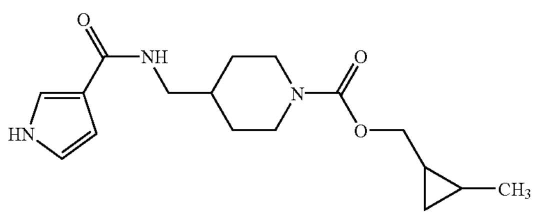 | 4-{[(1H-Pyrrole-3-carbonyl)-amino]-methyl}-piperidine-1-carboxylic acid 2-methyl-cyclopropylmethyl ester | 320.2 |
| 275. | 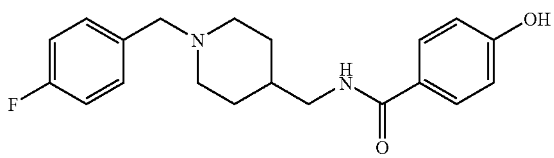 | N-[1-(4-Fluoro-benzyl)-piperidin-4-ylmethyl]-4-hydroxy-benzamide | 343.2 |
| 276. | 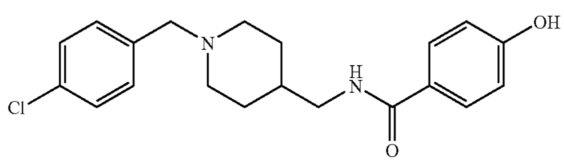 | N-[1-(4-Chloro-benzyl)-piperidin-4-ylmethyl]-4-hydroxy-benzamide | 359.1 |
| 277. | 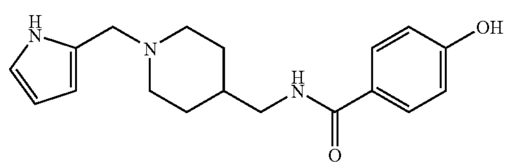 | 4-Hydroxy-N-[1-(1H-pyrrol-2-ylmethyl)-piperidin-4-ylmethyl]-benzamide | 314.2 |
| 278. | 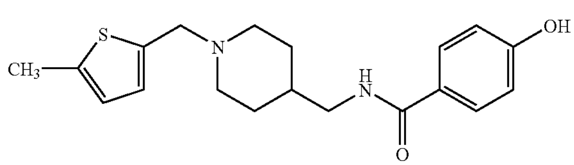 | 4-Hydroxy-N-[1-(5-methyl-thiophen-2-ylmethyl)-piperidin-4-ylmethyl]-benzamide | 345.2 |
| 279. | 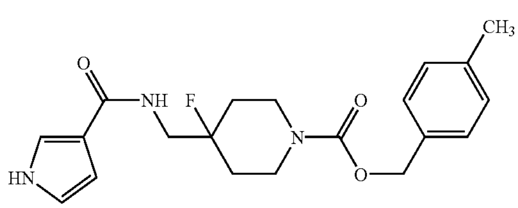 | 4-Fluoro-4-{[(1H-pyrrole-3-carbonyl)-amino]-methyl}-piperidine-1-carboxylic acid 4-methyl-benzyl ester | 374.2 |

-continued

| EX. | Structure | Name | MS (M⁺ + 1) |
|---|---|---|---|
| 280. | 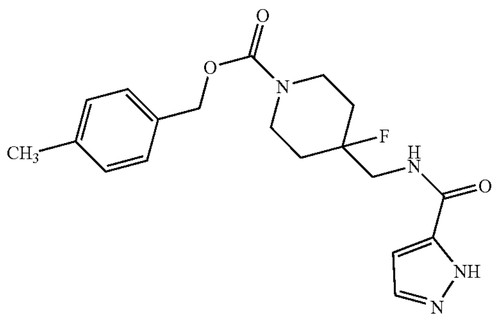 | 4-Fluoro-4-{[(2H-pyrazole-3-carbonyl)-amino]-methyl}-piperidine-1-carboxylic acid 4-methyl-benzyl ester | 375.2 |
| 281. | 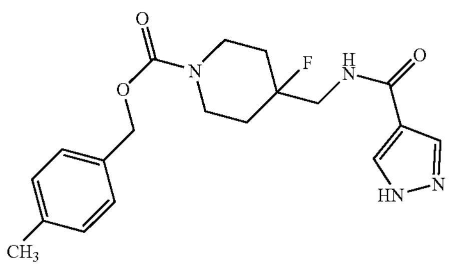 | 4-Fluoro-4-{[(1H-pyrazole-4-carbonyl)-amino]-methyl}-piperidine-1-carboxylic acid 4-methyl-benzyl ester | 375.2 |
| 282. | 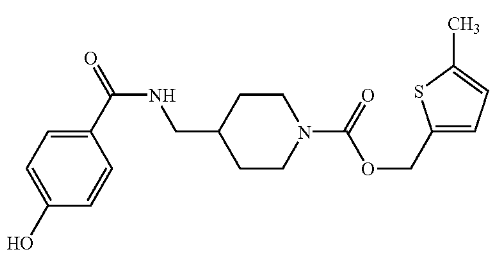 | 4-[(4-Hydroxy-benzoylamino)-methyl]-piperidine-1-carboxylic acid 5-methyl-thiophen-2-ylmethyl ester | 411.2 |
| 283. | 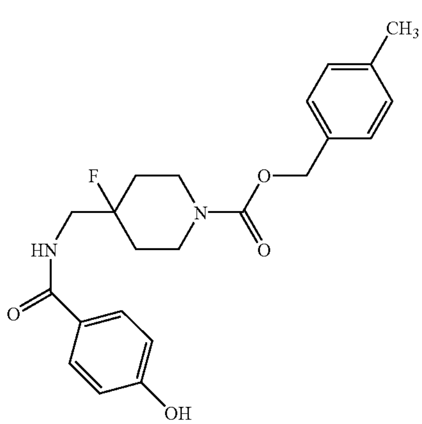 | 4-Fluoro-4-[(4-hydroxy-benzoylamino)-methyl]-piperidine-1-carboxylic acid 4-methyl-benzyl ester | 401.2 |

-continued

| EX. | Structure | Name | MS (M⁺ + 1) |
|---|---|---|---|
| 284. | 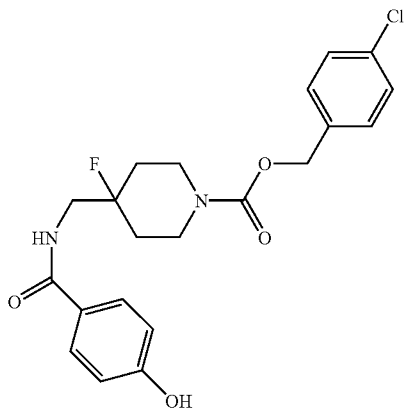 | 4-Fluoro-4-[(4-hydroxy-benzoylamino)-methyl]-piperidine-1-carboxylic acid 4-chloro-benzyl ester | 421.2 |
| 285. | 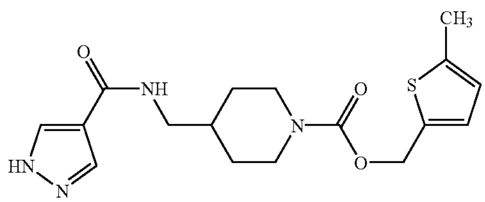 | 4-{[(1H-Pyrazole-4-carbonyl)-amino]-methyl}-piperidine-1-carboxylic acid 5-methyl-thiophen-2-ylmethyl ester | 363.1 |
| 286. | 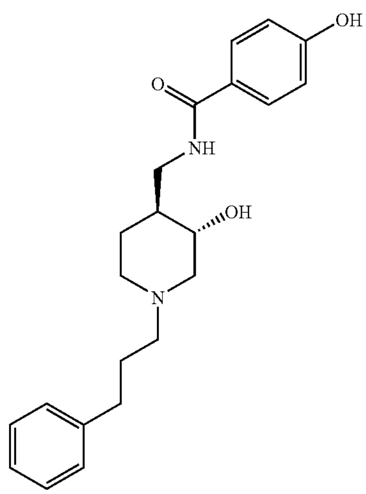 | 4-Hydroxy-N-[3-hydroxy-1-(3-phenyl-propyl)-piperidin-4-ylmethyl]-benzamide | 369.2 |
| 287. | 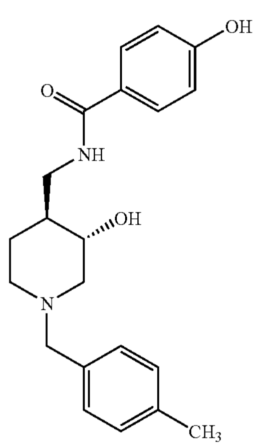 | 4-Hydroxy-N-[3-hydroxy-1-(4-methyl-benzyl)-piperidin-4-ylmethyl]-benzamide | 355.2 |

-continued

| EX. | Structure | Name | MS (M⁺ + 1) |
|---|---|---|---|
| 288. | 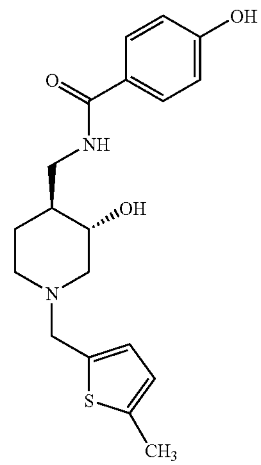 | 4-Hydroxy-N-[3-hydroxy-1-(5-methyl-thiophen-2-ylmethyl)-piperidin-4-ylmethyl]-benzamide | 361.1 |
| 289. | 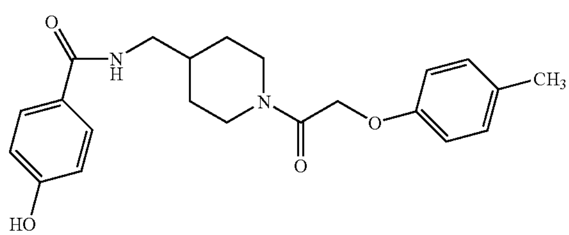 | 4-Hydroxy-N-[1-(2-p-tolyloxy-acetyl)-piperidin-4-ylmethyl]-benzamide | 383.2 |
| 290. | 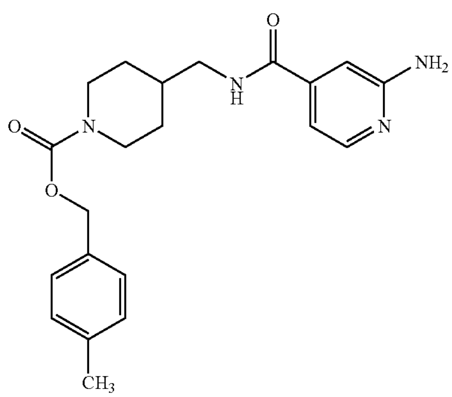 | 4-{[(2-Amino-pyridine-4-carbonyl)-amino]-methyl}-piperidine-1-carboxylic acid 4-methyl-benzyl ester | 383.2 |
| 291. | 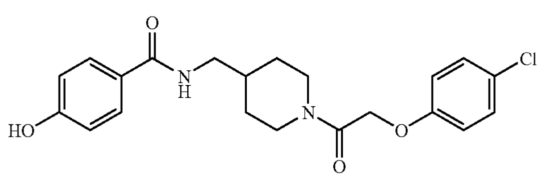 | N-{1-[2-(4-Chloro-phenoxy)-acetyl]-piperidin-4-ylmethyl}-4-hydroxy-benzamide | 403.2 |
| 292. | 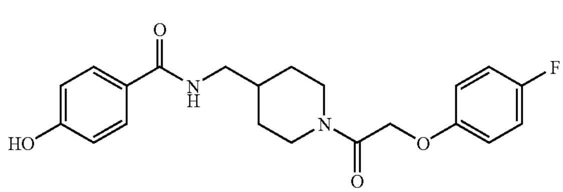 | N-{1-[2-(4-Fluoro-phenoxy)-acetyl]-piperidin-4-ylmethyl}-4-hydroxy-benzamide | 387.3 |

| EX. | Structure | Name | MS (M⁺ + 1) |
|---|---|---|---|
| 293. | 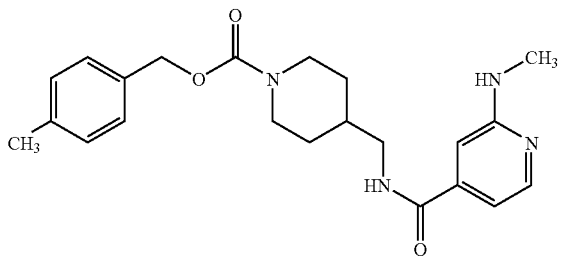 | 4-{[(2-Methylamino-pyridine-4-carbonyl)-amino]-methyl}-piperidine-1-carboxylic acid 4-methyl-benzyl ester | 397.2 |
| 294. | 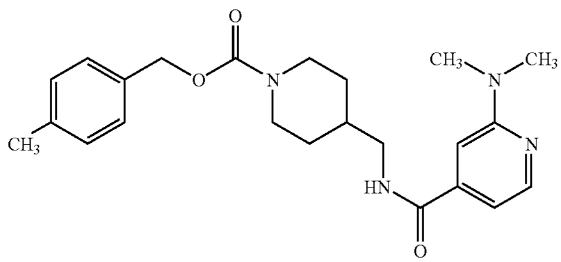 | 4-{[(2-Dimethylamino-pyridine-4-carbonyl)-amino]-methyl}-piperidine-1-carboxylic acid 4-methyl-benzyl ester | 411.3 |
| 295. | 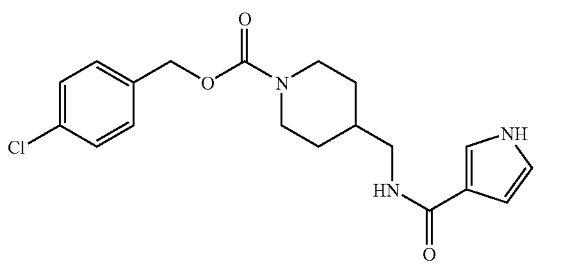 | 4-{[(1H-Pyrrole-3-carbonyl)-aminol]-methyl}-piperidine-1-carboxylic acid 4-chloro-benzyl ester | 376.3 |
| 296. | 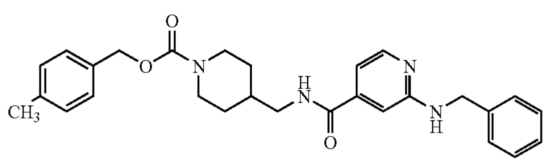 | 4-{[(2-Benzylamino-pyridine-4-carbonyl)-amino]-methyl}-piperidine-1-carboxylic acid 4-methyl-benzy ester | 473.3 |
| 297. | 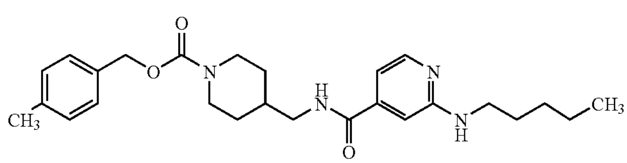 | 4-{[(2-Pentylamino-pyridine-4-carbonyl)-amino]-methyl}-piperidine-1-carboxylic acid 4-methyl-benzyl ester | 453.4 |
| 298. | 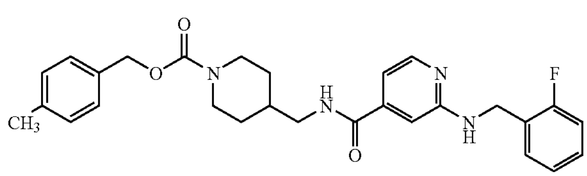 | 4-({[2-(2-Fluoro-benzylamino)-pyridine-4-carbonyl]-amino}-methyl)-piperidine-1-carboxylic acid 4-methyl-benzyl ester | 491.3 |
| 299. | 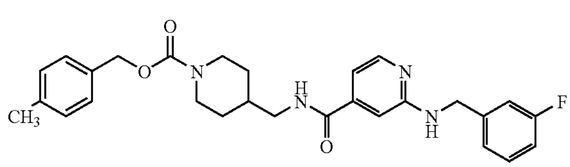 | 4-({[2-(3-Fluoro-benzylamino)-pyridine-4-carbonyl]-amino}-methyl)-piperidine-1-carboxylic acid 4-methyl-benzyl ester | 491.3 |

| EX. | Structure | Name | MS (M⁺ + 1) |
|---|---|---|---|
| 300. | 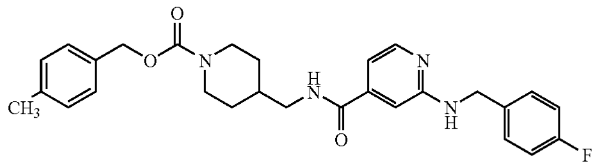 | 4-({[2-(4-Fluoro-benzylamino)-pyridine-4-carbonyl]-amino}-methyl)-piperidine-1-carboxylic acid 4-methyl-benzyl ester | 491.3 |
| 301. | 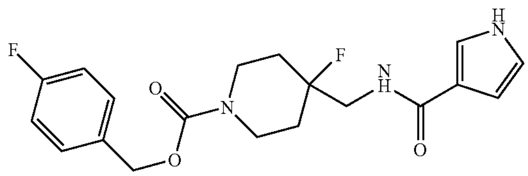 | 4-Fluoro-4-{[(1H-pyrrole-3-carbonyl)-amino]-methyl}-piperidine-1-carboxylic acid 4-fluoro-benzyl ester | 378.2 |
| 302. | 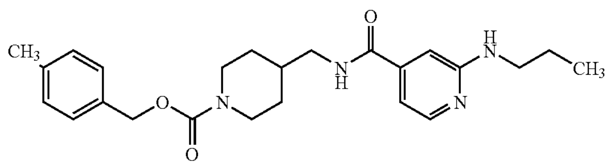 | 4-{[(2-Propylamino-pyridine-4-carbonyl)-amino]-methyl}-piperidine-1-carboxylic acid 4-methyl-benzyl ester | 425.3 |
| 303. | 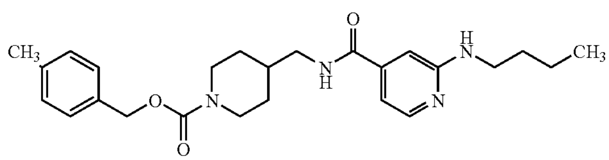 | 4-{[(2-Butylamino-pyridine-4-carbonyl)-amino]-methyl}-piperidine-1-carboxylic acid 4-methyl-benzyl ester | 439.3 |
| 304. | 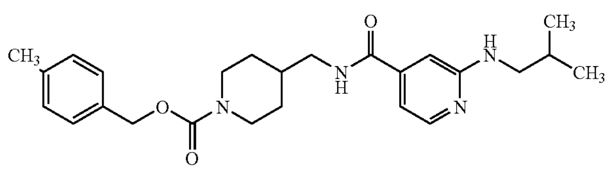 | 4-{[(2-Isobutylamino-pyridine-4-carbonyl)-aminol]-methyl}-piperidine-1-carboxylic acid 4-methyl-benzyl ester | 439.3 |
| 305. | 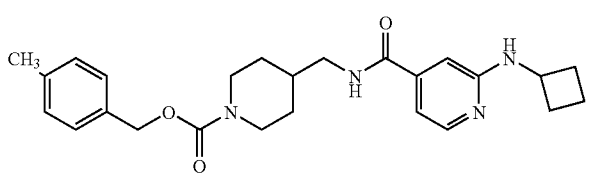 | 4-{[(2-Cyclobutylamino-pyridine-4-carbonyl)-amino]-methyl}-piperidine-1-carboxylic acid 4-methyl-benzyl ester | 437.3 |
| 306. | 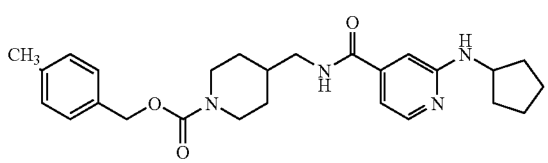 | 4-{[(2-Cyclopentylamino-pyridine-4-carbonyl)-amino]-methyl}-piperidine-1-carboxylic acid 4-methyl-benzyl ester | 451.3 |
| 307. | 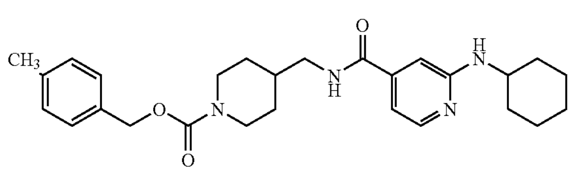 | 4-{[(2-Cyclohexylamino-pyridine-4-carbonyl)-amino]-methyl}-piperidine-1-carboxylic acid 4-methyl-benzyl ester | 465.3 |
| 308. | 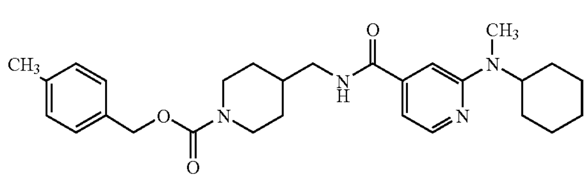 | 4-({[2-(Cyclohexyl-methyl-amino)-pyridine-4-carbonyl]-amino}-methyl)-piperidine-1-carboxylic acid 4-methyl-benzyl ester | 479.3 |

-continued

| EX. | Structure | Name | MS (M⁺ + 1) |
|---|---|---|---|
| 309. | 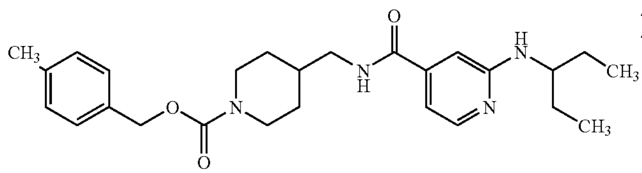 | 4-({[2-(1-Ethyl-propylamino)-pyridine-4-carbonyl]-amino}-methyl)-piperidine-1-carboxylic acid 4-methyl-benzyl ester | 453.3 |
| 310. | 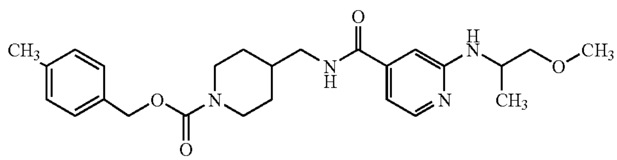 | 4-({[2-(2-Methoxy-1-methyl-ethylamino)-pyridine-4-carbonyl]-amino}-methyl)-piperidine-1-carboxylic acid 4-methyl-benzyl ester | 455.3 |
| 311. | 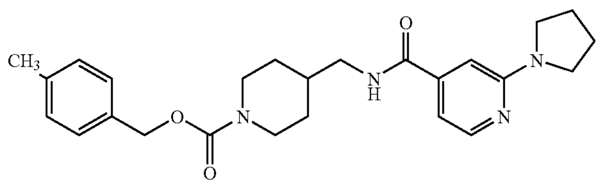 | 4-{[(2-Pyrrolidin-1-yl-pyridine-4-carbonyl)-amino]-methyl}-piperidine-1-carboxylic acid 4-methyl-benzyl ester | 437.3 |
| 312. | 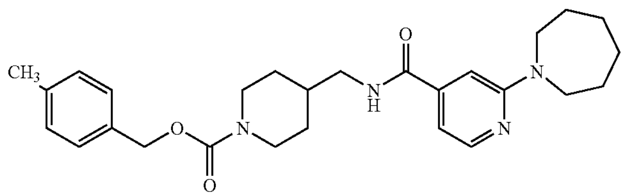 | 4-{[(2-Azepan-1-yl-pyridine-4-carbonyl)-amino]-methyl}-piperidine-1-carboxylic acid 4-methyl-benzyl ester | 465.3 |
| 313. | 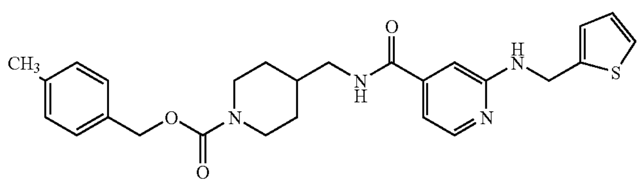 | 4-((({2-[(Thiophen-2-ylmethyl)-amino]-pyridine-4-carbonyl}-amino)-methyl]-piperidine-1-carboxylic acid 4-methyl-benzyl ester | 479.2 |
| 314. | 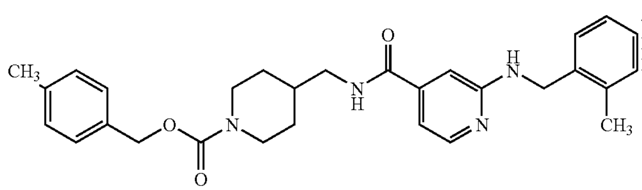 | 4-({[2-(2-Methyl-benzylamino)-pyridine-4-carbonyl]-amino}-methyl)-piperidine-1-carboxylic acid 4-methyl-benzyl ester | 487.3 |
| 315. | 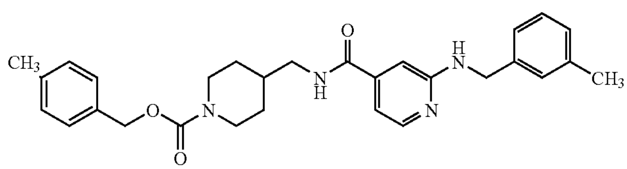 | 4-({[2-(3-Methyl-benzylamino)-pyridine-4-carbonyl]-amino}-methyl)-piperidine-1-carboxylic acid 4-methyl-benzyl ester | 487.3 |
| 316. | 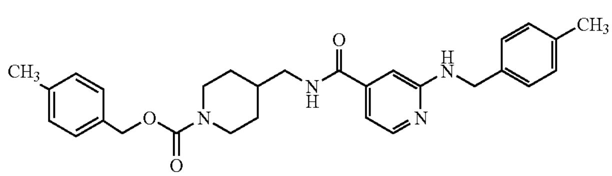 | 4-({[2-(4-Methyl-benzylamino)-pyridine-4-carbonyl]-amino}-methyl)-piperidine-1-carboxylic acid 4-methyl-benzyl ester | 487.3 |

-continued

| EX. | Structure | Name | MS (M⁺ + 1) |
|---|---|---|---|
| 317. | 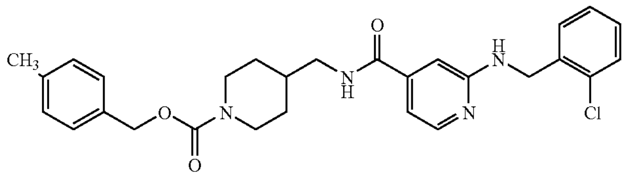 | 4-({[2-(2-Chloro-benzylamino)-pyridine-4-carbonyl]-amino}-methyl)-piperidine-1-carboxylic acid 4-methyl-benzyl ester | 507.3 |
| 318. | 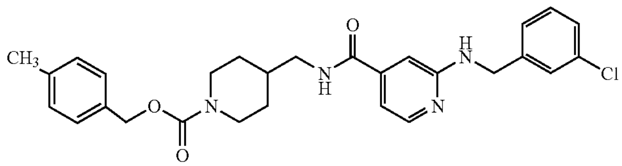 | 4-({[2-(3-Chloro-benzylamino)-pyridine-4-carbonyl]-amino}-methyl)-piperidine-1-carboxylic acid 4-methyl-benzyl ester | 507.3 |
| 319. | 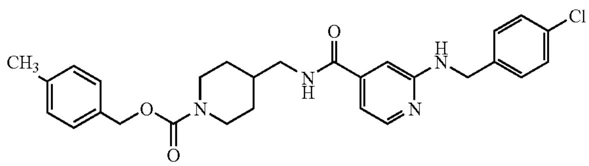 | 4-({[2-(4-Chloro-benzylamino)-pyridine-4-carbonyl]-amino}-methyl)-piperidine-1-carboxylic acid 4-methyl-benzyl ester | 507.3 |
| 320. | 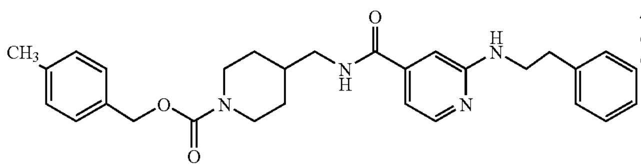 | 4-{[(2-Phenethylamino-pyridine-4-carbonyl)-amino]-methyl}-piperidine-1-carboxylic acid 4-methyl-benzyl ester | 487.3 |
| 321. | 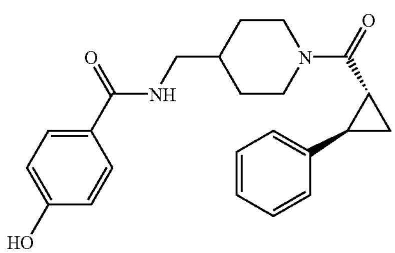 | 4-Hydroxy-N-[1-(2-phenyl-cyclopropanecarbonyl)-piperidin-4-ylmethyl]-benzamide | 379.3 |
| 322. | 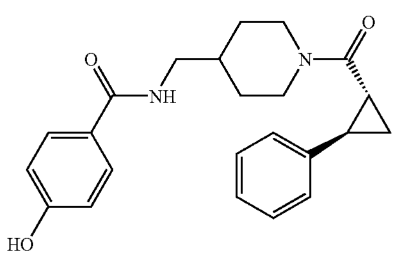 | 4-Hydroxy-N-[1-(2-phenyl-cyclopropanecarbonyl)-piperidin-4-ylmethyl]-benzamide | 379.3 |
| 323. | 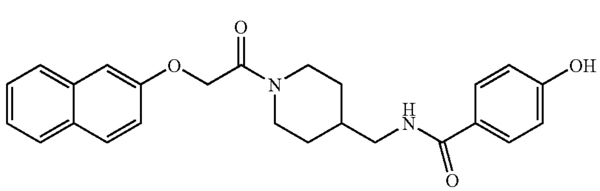 | 4-Hydroxy-N-{1-[2-(naphthalen-2-yloxy)-acetyl]-piperidin-4-ylmethyl}-benzamide | 419.4 |

-continued

| EX. | Structure | Name | MS (M⁺ + 1) |
|---|---|---|---|
| 324. | 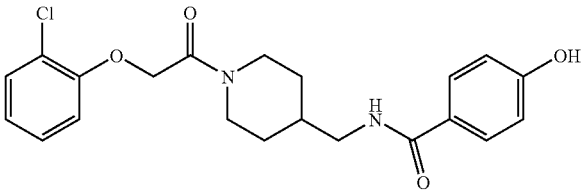 | N-{1-[2-(2-Chloro-phenoxy)-acetyl]-piperidin-4-ylmethyl}-4-hydroxy-benzamide | 403.3 |
| 325. | 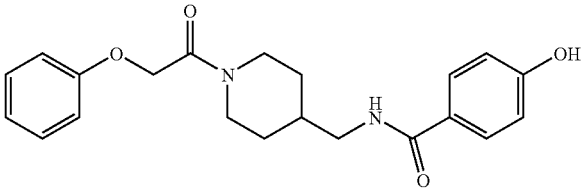 | 4-Hydroxy-N-[1-(2-phenoxy-acetyl)-piperidin-4-ylmethyl]-benzamide | 369.4 |
| 326. | 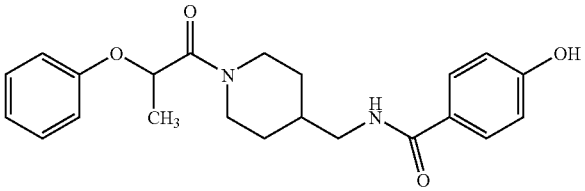 | 4-Hydroxy-N-[1-(2-phenoxy-propionyl)-piperidin-4-ylmethyl]-benzamide | 383.4 |
| 327. | 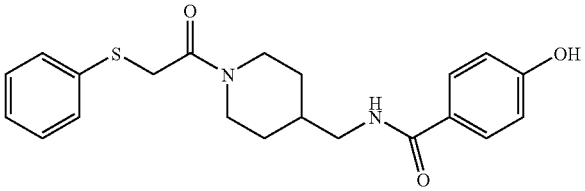 | 4-Hydroxy-N-[1-(2-phenylsulfanyl-acetyl)-piperidin-4-ylmethyl]-benzamide | 385.3 |
| 328. | 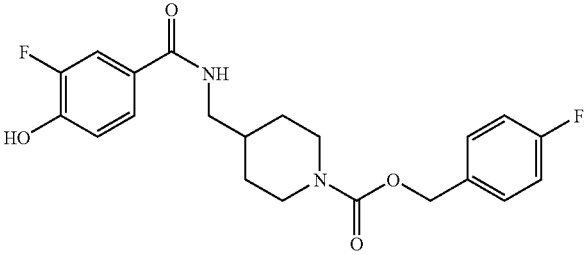 | 4-[(3-Fluoro-4-hydroxy-benzoylamino)-methyl]-piperidine-1-carboxylic acid 4-fluoro-benzyl ester | 405.3 |
| 329. | 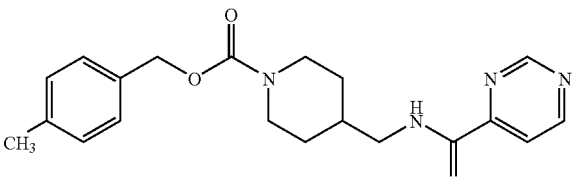 | 4-{[(Pyrimidine-4-carbonyl)-amino]-methyl}-piperidine-1-carboxylic acid 4-methyl-benzyl ester | 369.4 |
| 330. | 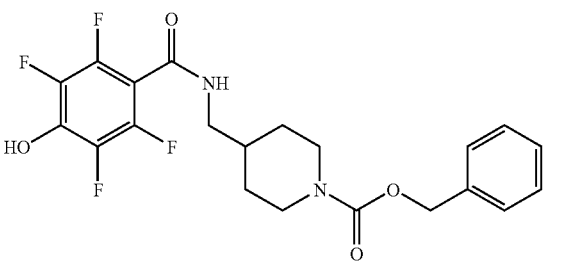 | 4-[(2,3,5,6-Tetrafluoro-4-hydroxy-benzoylamino)-methyl]-piperidine-1-carboxylic acid benzyl ester | 441.3 |

-continued

| EX. | Structure | Name | MS (M⁺ + 1) |
|---|---|---|---|
| 331. | 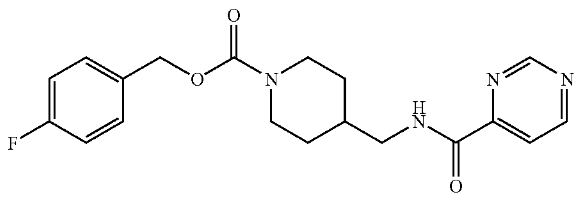 | 4-{[(Pyrimidine-4-carbonyl)-amino]-methyl}-piperidine-1-carboxylic acid 4-fluoro-benzyl ester | 373.4 |
| 332. | 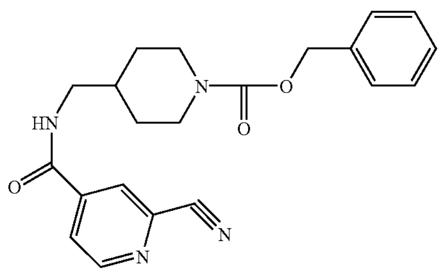 | 4-{[(2-Cyano-pyridine-4-carbonyl)-amino]-methyl}-piperidine-1-carboxylic acid benzyl ester | 379.4 |
| 333. | 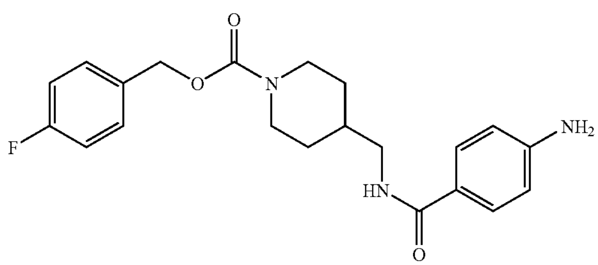 | 4-[(4-Amino-benzoylamino)-methyl]-piperidine-1-carboxylic acid 4-fluoro-benzyl ester | 386.4 |
| 334. | 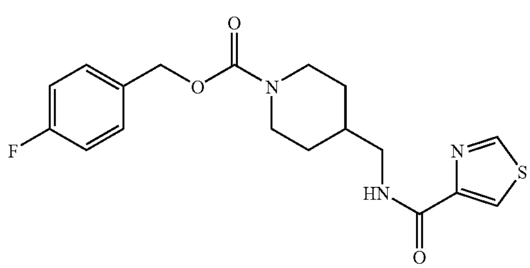 | 4-{[(Thiazole-4-carbonyl)-amino]-methyl}-piperidine-1-carboxylic acid 4-fluoro-benzyl ester | 378.4 |
| 335. | 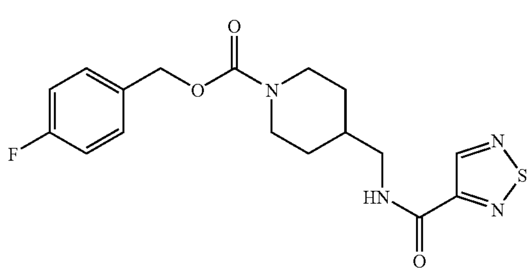 | 4-{[([1,2,5]Thiadiazole-3-carbonyl)-amino]-methyl}-piperidine-1-carboxylic acid 4-fluoro-benzyl ester | 379.4 |

-continued

| EX. | Structure | Name | MS (M⁺ + 1) |
|---|---|---|---|
| 336. | 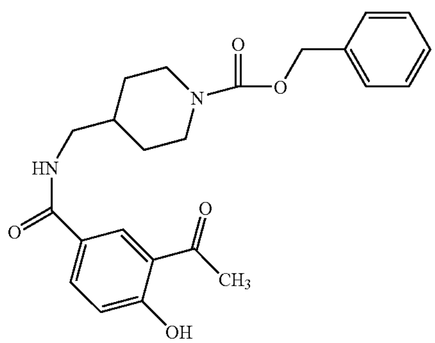 | 4-[(3-Acetyl-4-hydroxy-benzoylamino)-methyl]-piperidine-1-carboxylic acid benzyl ester | 411.4 |
| 337. | 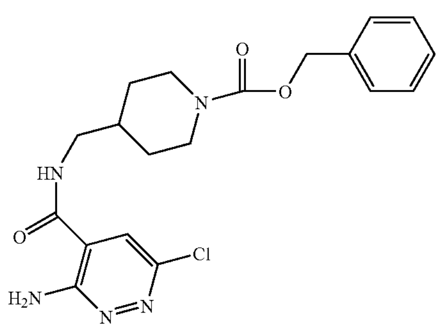 | 4-{[(3-Amino-6-chloro-pyridazine-4-carbonyl)-amino]-methyl}-piperidine-1-carboxylic acid benzyl ester | 404.4 |
| 338. | 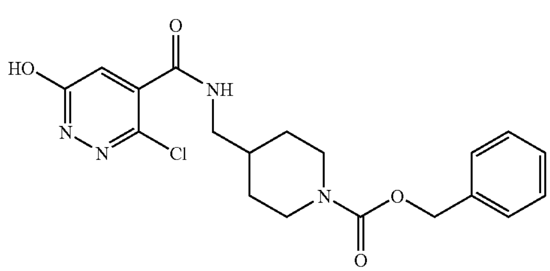 | 4-{[(3-Chloro-6-hydroxy-pyridazine-4-carbonyl)-amino]-methyl}-piperidine-1-carboxylic acid benzyl ester | 405.3 |
| 339. | 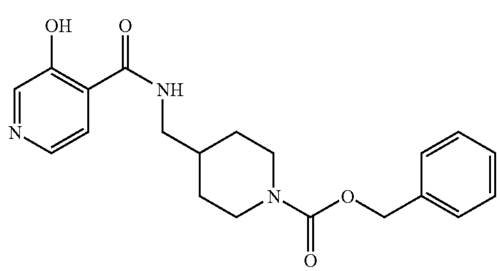 | 4-{[(3-Hydroxy-pyridine-4-carbonyl)-amino]-methyl}-piperidine-1-carboxylic acid benzyl ester | 370.4 |
| 340. | 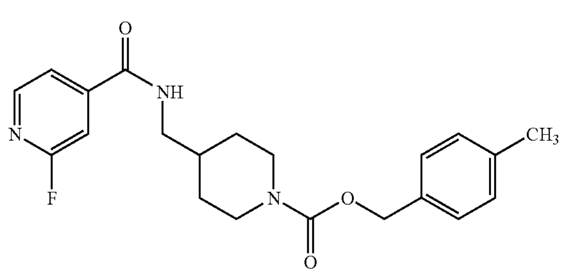 | 4-{[(2-Fluoro-pyridine-4-carbonyl)-amino]-methyl}-piperidine-1-carboxylic acid 4-methyl-benzyl ester | 386.4 |

-continued

| EX. | Structure | Name | MS (M⁺ + 1) |
|---|---|---|---|
| 341. | 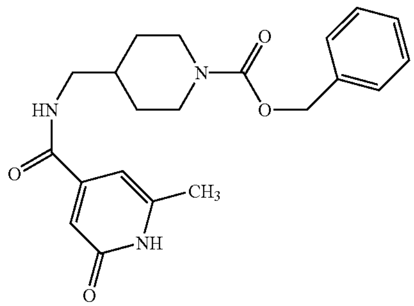 | 4-{[(6-Methyl-2-oxo-1,2-dihydro-pyridine-4-carbonyl)-amino]-methyl}-piperidine-1-carboxylic acid benzyl ester | 384.4 |
| 342. | 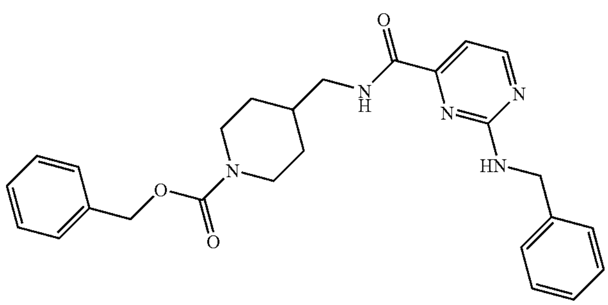 | 4-{[(2-Benzylamino-pyrimidine-4-carbonyl)-amino]-methyl}-piperidine-1-carboxylic acid benzyl ester | 460.4 |
| 343. | 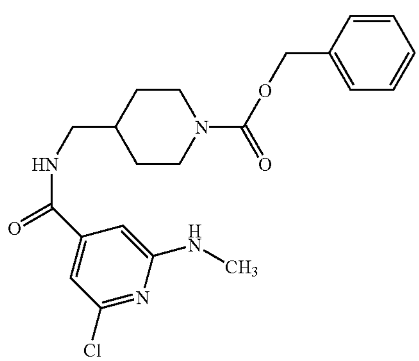 | 4-{[(2-Chloro-6-methylamino-pyridine-4-carbonyl)-amino]-methyl}-piperidine-1-carboxylic acid benzyl ester | 417.4 |
| 344. | 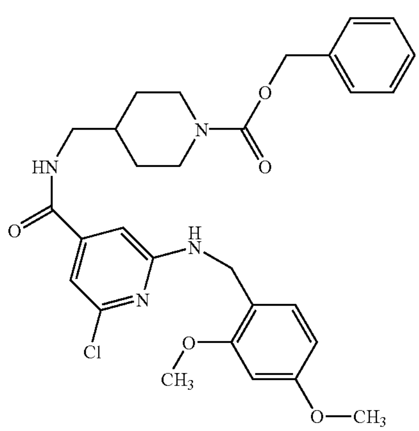 | 4-({[2-Chloro-6-(2,4-dimethoxy-benzylamino)-pyridine-4-carbonyl]-amino}-methyl)-piperidine-1-carboxylic acid benzyl ester | 553.5 |

-continued

| EX. | Structure | Name | MS (M⁺ + 1) |
|---|---|---|---|
| 345. | 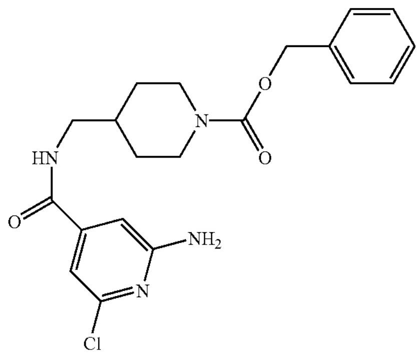 | 4-{[(2-Amino-6-chloro-pyridine-4-carbonyl)-amino]-methyl}-piperidine-1-carboxylic acid benzyl ester | 403.4 |
| 346. | 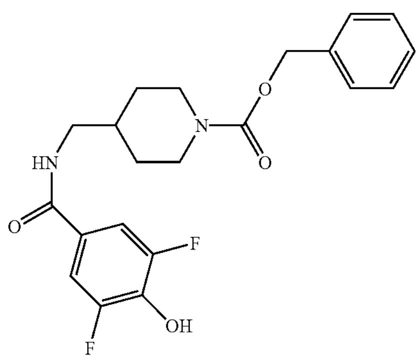 | 4-[(3,5-Difluoro-4-hydroxy-benzoylamino)-methyl]-piperidine-1-carboxylic acid benzyl ester | 405.4 |
| 347. | 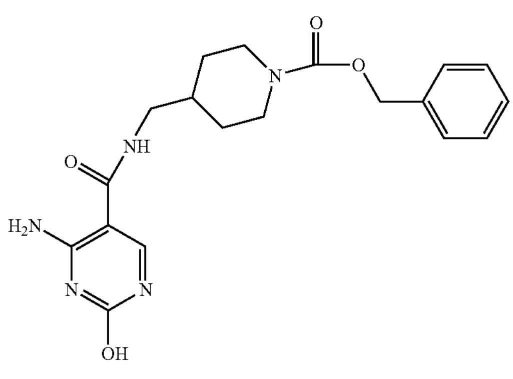 | 4-{[(4-Amino-2-hydroxy-pyrimidine-5-carbonyl)-amino]-methyl}-piperidine-1-carboxylic acid benzyl ester | 386.4 |
| 348. | 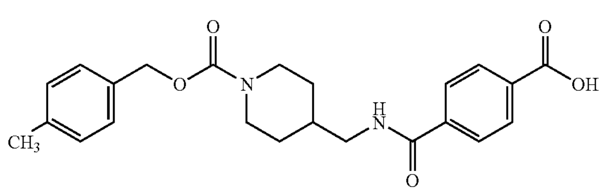 | 4-[(4-Carboxy-benzoylamino)-methyl]-piperidine-1-carboxylic acid 4-methyl-benzyl ester | 411.4 |

| EX. | Structure | Name | MS (M⁺ + 1) |
|---|---|---|---|
| 349. | 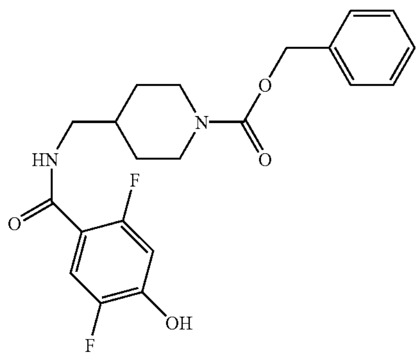 | 4-[2,5-Difluoro-4-hydroxy-benzoylamino)-methyl]-piperidine-1-carboxylic acid benzyl ester | 405.4 |
| 350. | 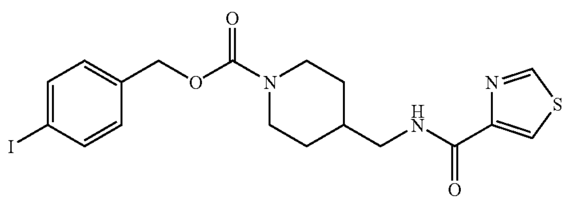 | 4-{[(Thiazole-4-carbonyl)-amino]-methyl}-piperidine-1-calboxylic acid 4-iodo-benzyl ester | 486.3 |
| 351. | 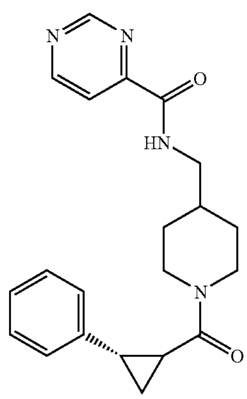 | Pyrimidine-4-carboxylic acid [1-(2-phenyl-cyclopropanecarbonyl)-piperidin-4-ylmethyl]-amide | 365.4 |
| 352. | 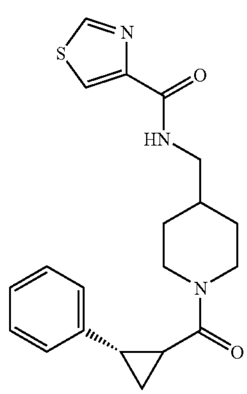 | Thiazole-4-carboxylic acid [1-(2-phenyl-cyclopropanecarbonyl)-piperidin-4-ylmethyl]-amide | 370.4 |

-continued

| EX. | Structure | Name | MS (M⁺ + 1) |
|---|---|---|---|
| 353. | 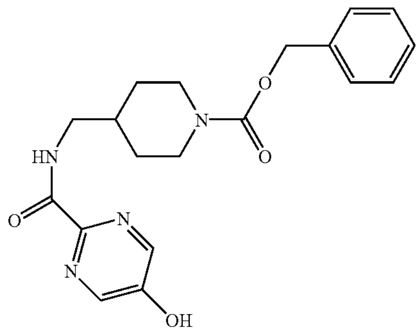 | 4-{[(5-Hydroxy-pyrimidine-2-carbonyl)-amino]-methyl}-piperidine-1-carboxylic acid benzyl ester | 371.4 |
| 354. | 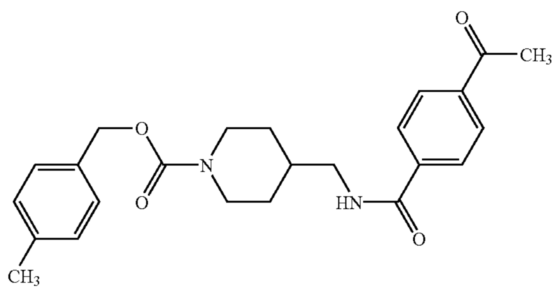 | 4-[(4-Acetyl-benzoylamino)-methyl]-piperidine-1-carboxylic acid 4-methyl-benzyl ester | 409.3 |
| 355. | 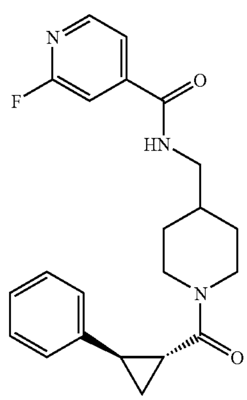 | 2-Fluoro-N-[1-(2-phenyl-cyclopropanecarbonyl)-piperidin-4-ylmethyl]-isonicotinamide | 382.4 |
| 356. | 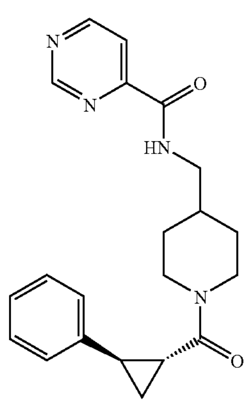 | Pyrimidine-4-carboxylic acid [1-(2-phenyl-cyclopropanecarbonyl)-piperidin-4-ylmethyl]-amide | 365.4 |

-continued

| EX. | Structure | Name | MS (M⁺ + 1) |
|---|---|---|---|
| 357. | 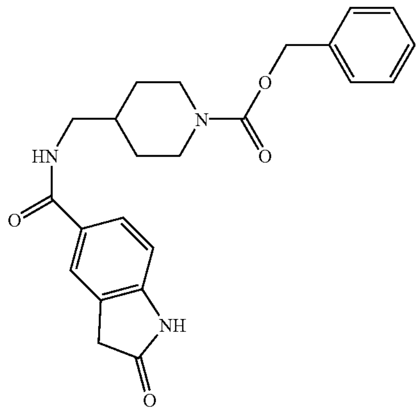 | 4-{[(2-Oxo-2,3-dihydro-1H-indole-5-carbonyl)-amino]-methyl}-piperidine-1-carboxylic acid benzyl ester | 408.3 |
| 358. | 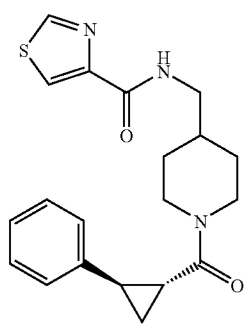 | Thiazole-4-carboxylic acid [1-(2-phenyl-cyclopropanecarbonyl)-piperidin-4-ylmethyl]-amide | 370.3 |
| 359. | 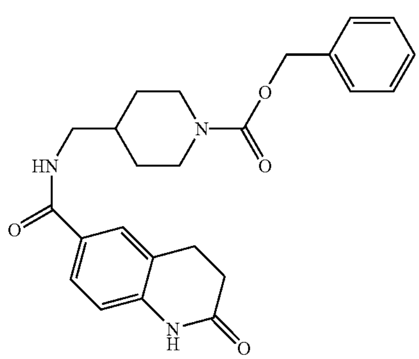 | 4-{[(2-Oxo-1,2,3,4-tetrahydro-quinoline-6-carbonyl)-amino]-methyl}-piperidine-1-carboxylic acid benzyl ester | 422.4 |
| 360. | 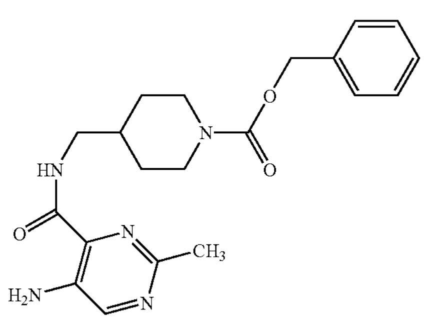 | 4-{[(5-Amino-2-methyl-pyrimidine-4-carbonyl)-amino]-methyl}-piperidine-1-carboxylic acid benzyl ester | 384.4 |

-continued

| EX. | Structure | Name | MS (M⁺ + 1) |
|---|---|---|---|
| 361. | 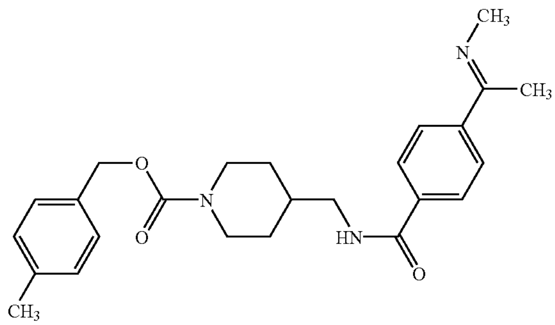 | 4-{[4-(1-Hydroxyimino-ethyl)-benzoylamino]-methyl}-piperidine-1-carboxylic acid 4-methyl-benzyl ester | 424.3 |
| 362. | 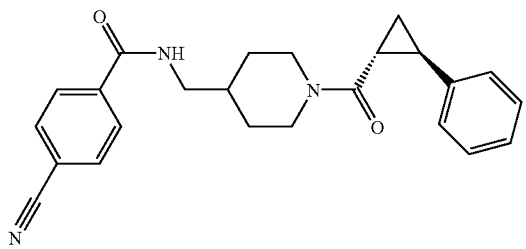 | 4-Cyano-N-[1-(2-phenyl-cyclopropanecarbonyl)-piperidin-4-ylmethyl]-benzamide | 388.3 |
| 363. | 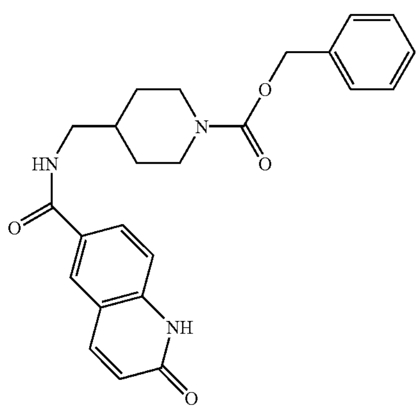 | 4-{[(2-Oxo-1,2-dihydro-quinoline-6-carbonyl)-amino]-methyl}-piperidine-1-carboxylic acid benzyl ester | 420.3 |
| 364. | 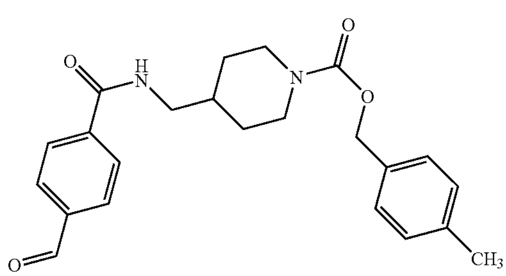 | 4-[(4-Formyl-benzoylamino)-methyl]-piperidine-1-carboxylic acid 4-methyl-benzyl ester | 395.3 |
| 365. | 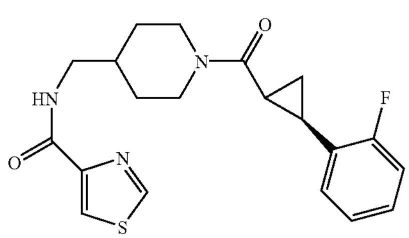 | Thiazole-4-carboxylic acid {1-[2-(2-fluoro-phenyl)-cyclopropanecarbonyl]-piperidin-4-ylmethyl}-amide | 388.2 |

-continued

| EX. | Structure | Name | MS (M+ + 1) |
|---|---|---|---|
| 366. | 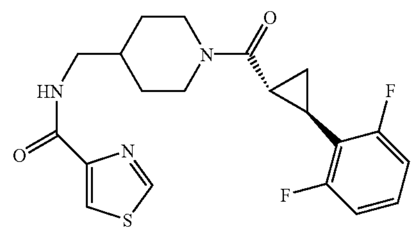 | Thiazole-4-carboxylic acid {1-[2-(2,6-difluoro-phenyl)-cyclopropanecarbonyl]-piperidin-4-ylmethyl}-amide | 406.2 |
| 367. | 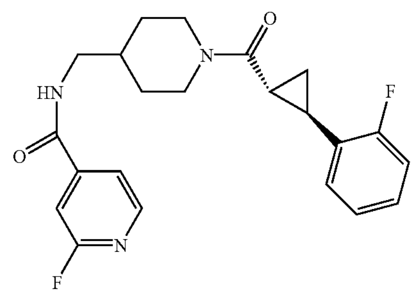 | 2-Fluoro-N-{1-[2-(2-fluoro-phenyl)-cyclopropanecarbonyl]-piperidin-4-ylmethyl}-isonicotinamide | 400.3 |
| 368. | 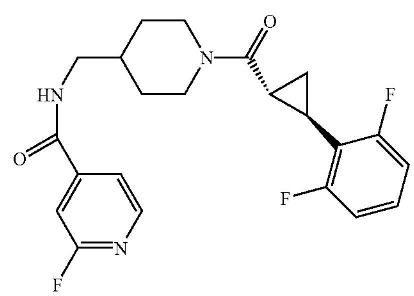 | N-{1-[2-(2,6-Difluoro-phenyl)-cyclopropanecarbonyl]-piperidin-4-ylmethyl}-2-fluoro-isonicotinamide | 418.3 |
| 369. | 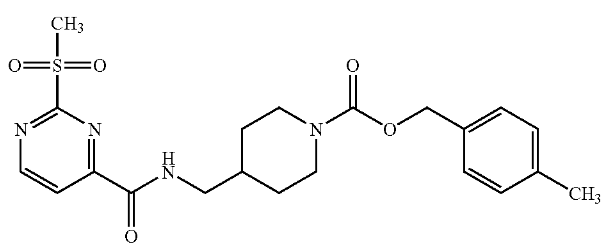 | 4-{[(2-Methanesulfonyl-pyrimidine-4-carbonyl)-amino]-methyl}-piperidine-1-carboxylic acid 4-methyl-benzyl ester | 448.2 |
| 370. | 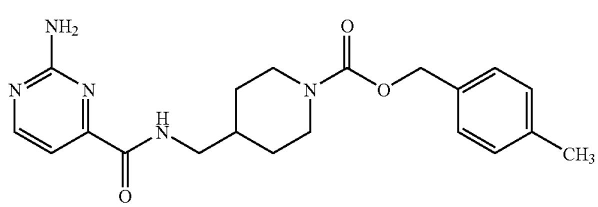 | 4-{[(2-Amino-pyrimidine-4-carbonyl)-amino]-methyl}-piperidine-1-carboxylic acid 4-methyl-benzyl ester | 384.3 |
| 371. | 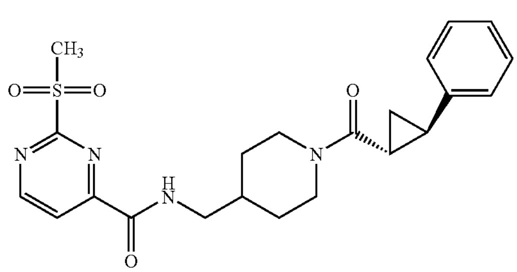 | 2-Methanesulfonyl-pyrimidine-4-carboxylic acid [1-(2-phenyl-cyclopropanecarbonyl)-piperidin-4-ylmethyl]-amide | 443.3 |

-continued

| EX. | Structure | Name | MS (M⁺ + 1) |
|---|---|---|---|
| 372. | 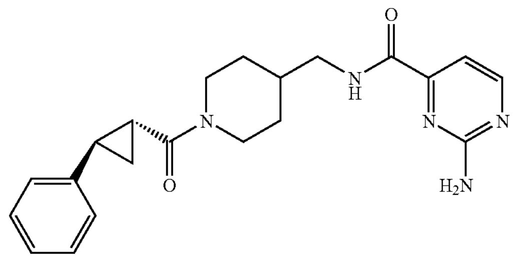 | 2-Amino-pyrimidine-4-carboxylic acid [1-(2-phenyl-cyclopropanecarbonyl)-piperidin-4-ylmethyl]-amide | 380.2 |
| 373. | 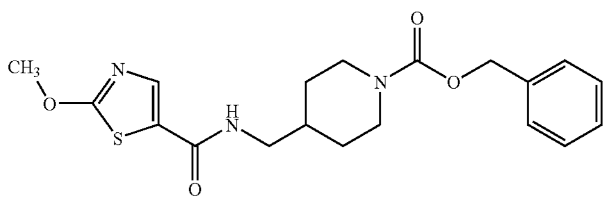 | 4-{[(2-Ethoxy-thiazole-5-carbonyl)-amino]-methyl}-piperidine-1-carboxylic acid benzyl ester | 404.2 |
| 374. | 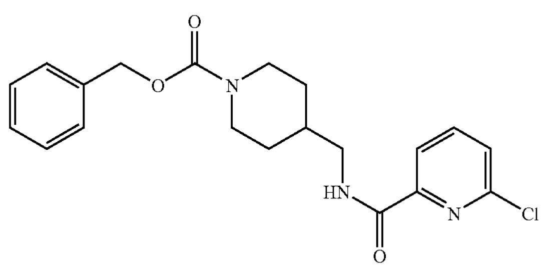 | 4-{[(6-Chloro-pyridine-2-carbonyl)-amino]-methyl}-piperidine-1-carboxylic acid benzyl ester | 388.2 |
| 375. | 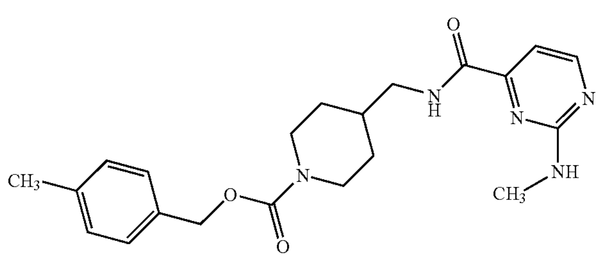 | 4-{[(2-Methylamino-pyrimidine-4-carbonyl)-amino]-methyl}-piperidine-1-carboxylic acid 4-methyl-benzyl ester | 398.3 |
| 376. | 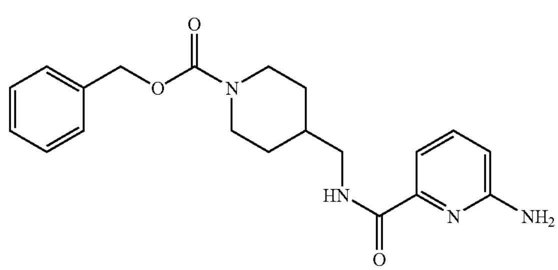 | 4-{[(6-Amino-pyridine-2-carbonyl)-amino]-methyl}-piperidine-1-carboxylic acid benzyl ester | 369.2 |

-continued

| EX. | Structure | Name | MS (M⁺ + 1) |
|---|---|---|---|
| 377. | 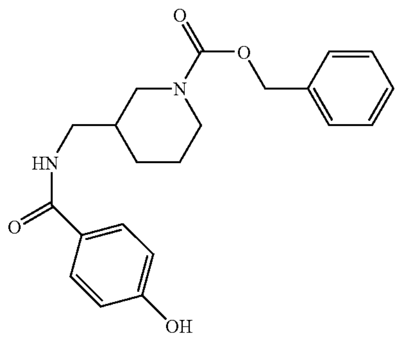 | 3-[(4-Hydroxy-benzoylamino)-methyl]-piperidine-1-carboxylic acid benzyl ester | 369.2 |
| 378. | 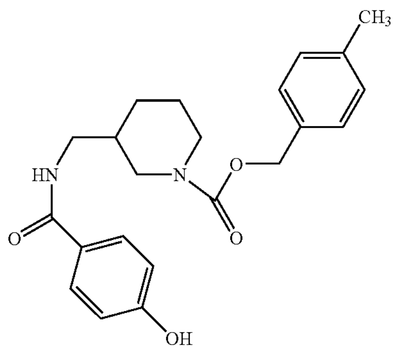 | 3-[(4-Hydroxy-benzoylamino)-methyl]-piperidine-1-carboxylic acid 4-methyl-benzyl ester | 383.3 |
| 379. | 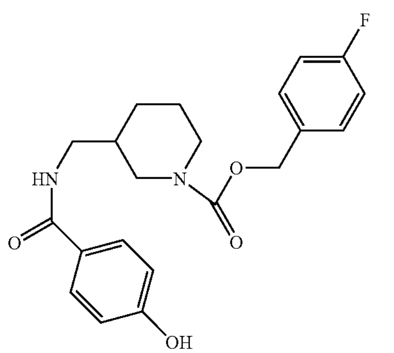 | 3-[(4-Hydroxy-benzoylamino)-methyl]-piperidine-1-carboxylic acid 4-fluoro-benzyl ester | 387.2 |
| 380. | 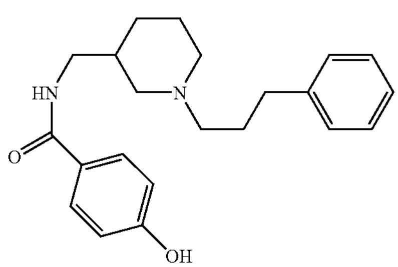 | 4-Hydroxy-N-[1-(3-phenyl-propyl)-piperidin-3-ylmethyl]-benzamide | 353.3 |
| 381. | 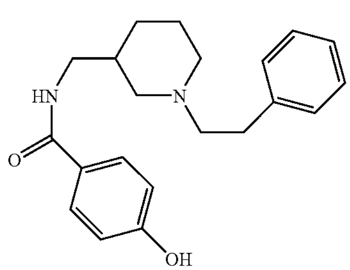 | 4-Hydroxy-N-(1-phenethyl-piperidin-3-ylmethyl)-benzamide | 339.3 |

-continued

| EX. | Structure | Name | MS (M⁺ + 1) |
|---|---|---|---|
| 382. | 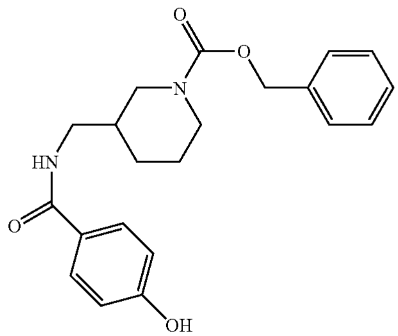 | 3-[(4-Hydroxy-benzoylamino)-methyl]-piperidine-1-carboxylic acid benzyl ester | 369.3 |
| 383. | 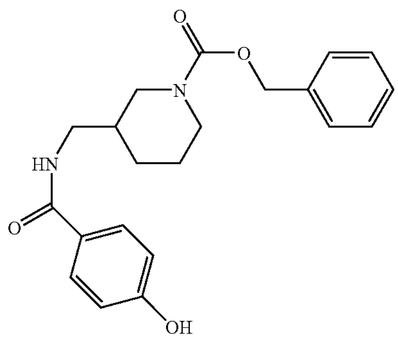 | 3-[(4-Hydroxy-benzoylamino)-methyl]-piperidine-1-carboxylic acid benzyl ester | 369.3 |
| 384. | 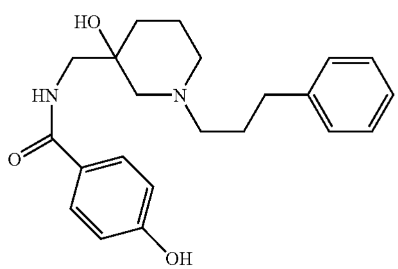 | 4-Hydroxy-N-[3-hydroxy-1-(3-phenyl-propyl)-piperidin-3-ylmethyl]-benzamide | 369.3 |
| 385. | 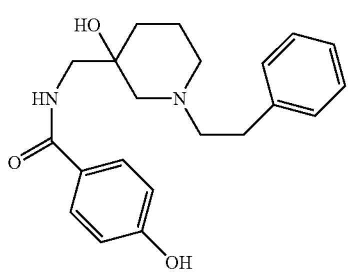 | 4-Hydroxy-N-(3-hydroxy-1-phenethyl-piperidin-3-ylmethyl)-benzamide | 355.2 |
| 386. | 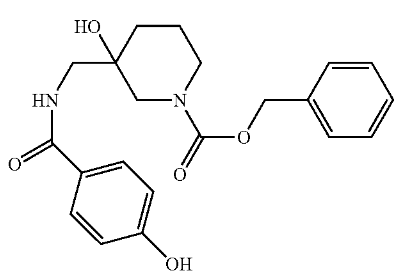 | 3-Hydroxy-3-[(4-hydroxy-benzoylamino)-methyl]-piperidine-1-carboxylic acid benzyl ester | 385.2 |

-continued

| EX. | Structure | Name | MS (M⁺ + 1) |
|---|---|---|---|
| 387. | 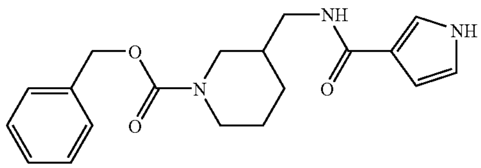 | 3-{[(1H-Pyrrole-3-carbonyl)-amino]-methyl}-piperidine-1-carboxylic acid benzyl ester | 342.7 |
| 388. | 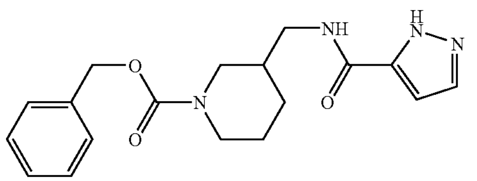 | 3-{[(2H-Pyrazole-3-carbonyl)-amino]-methyl}-piperidine-1-carboxylic acid benzyl ester | 343.2 |
| 389. | 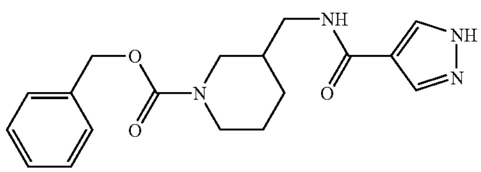 | 3-{[(1H-Pyrazole-4-carbonyl)-amino]-methyl}-piperidine-1-carboxylic acid benzyl ester | 343.2 |
| 390. | 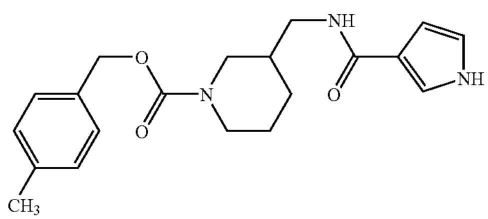 | 3-{-(1H-Pyrrole-3-carbonyl)-amino]-methyl}-piperidine-1-carboxylic acid 4-methyl-benzyl ester | 356.2 |
| 391. | 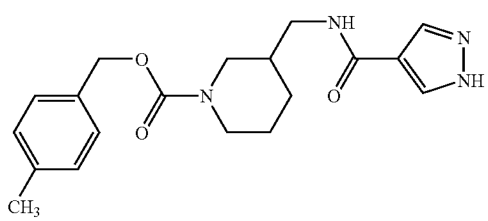 | 3-{[(1H-Pyrazole-4-carbonyl)-amino]-methyl}-piperidine-1-carboxylic acid 4-methyl-benzyl ester | 357.2 |
| 392. | 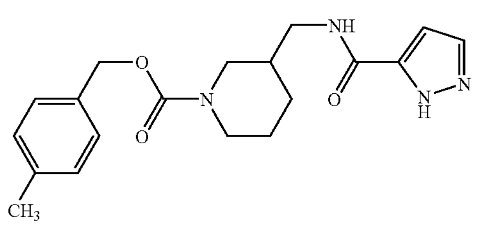 | 3-{[(2H-Pyrazole-3-carbonyl)-amino]-methyl}-piperidine-1-carboxylic acid 4-methyl-benzyl ester | 357.2 |
| 393. | 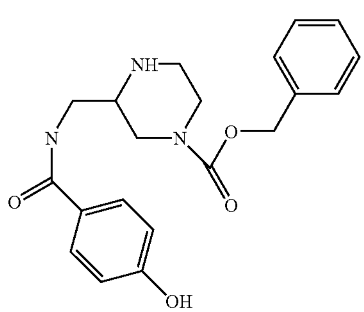 | 3-[(4-Hydroxy-benzoylamino)-methyl]-piperazine-1-carboxylic acid benzyl ester | 370.2 |

-continued
| EX. | Structure | Name | MS (M⁺ + 1) |
|---|---|---|---|
| 394. | 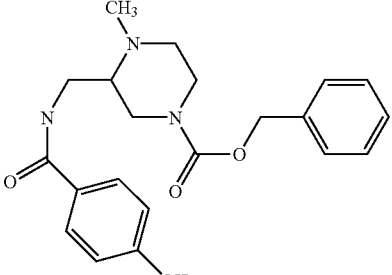 | 3-[(4-Hydroxy-benzoylamino)-methyl]-4-methyl-piperazine-1-carboxylic acid benzyl ester | 384.3 |
| 395. | 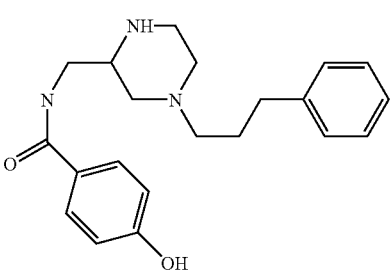 | 4-Hydroxy-N-[4-(3-phenyl-propyl)-piperazin-2-ylmethyl]-benzamide | 354.2 |
| 396. | 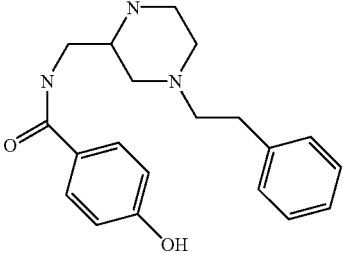 | 4-Hydroxy-N-(4-phenethyl-piperazin-2-ylmethyl)-benzamide | 340.3 |
| 397. | 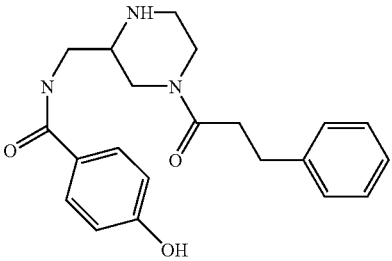 | 4-Hydroxy-N-[4-(3-phenyl-propionyl)-piperazin-2-ylmethyl]-benzamide | 368.3 |
| 398. | 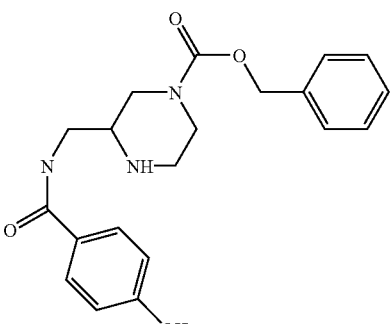 | 3-[(4-Hydroxy-benzoylamino)-methyl]-piperazine-1-carboxylic acid benzyl ester | 370.2 |

| EX. | Structure | Name | MS (M⁺ + 1) |
|---|---|---|---|
| 399. | 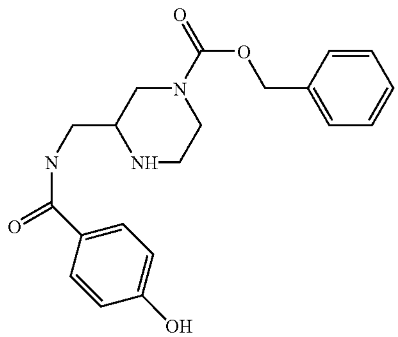 | 3-[(4-Hydroxy-benzoylamino)-methyl]-piperazine-1-carboxylic acid benzyl ester | 370.2 |
| 400. | 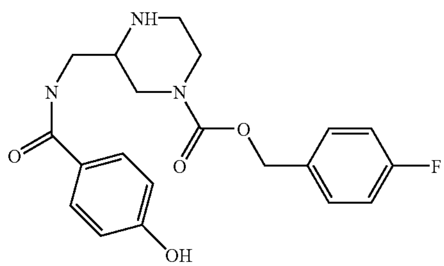 | 3-[(4-Hydroxy-benzoylamino)-methyl]-piperazine-1-carboxylic acid 4-fluoro-benzyl ester | 388.2 |
| 401. | 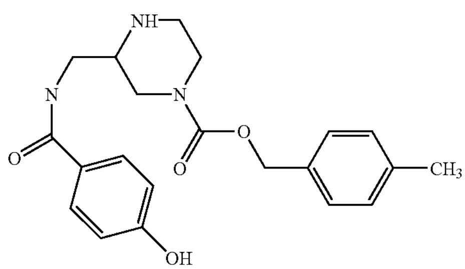 | 3-[(4-Hydroxy-benzoylamino)-methyl]-piperazine-1-carboxylic acid 4-methyl-benzyl ester | 384.2 |
| 402. | 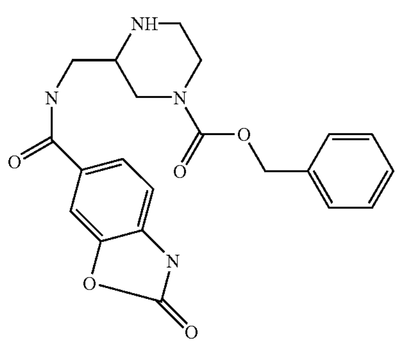 | 3-{[(2-Oxo-2,3-dihydro-benzooxazole-6-carbonyl)-amino]-methyl}-piperazine-1-carboxylic acid benzyl ester | 411.2 |
| 403. | 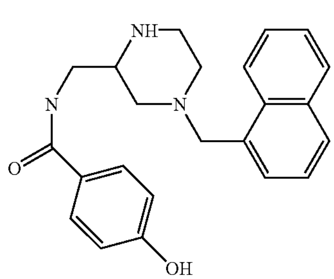 | 4-Hydroxy-N-(4-naphthalen-1-ylmethyl-piperazin-2-ylmethyl)-benzamide | 368.4 |

-continued

| EX. | Structure | Name | MS (M⁺ + 1) |
|---|---|---|---|
| 404. | 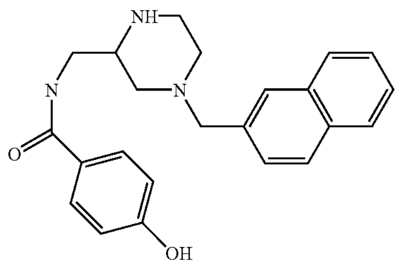 | 4-Hydroxy-N-(4-naphthalen-2-ylmethyl-piperazin-2-ylmethyl)-benzamide | 354.2 |
| 405. | 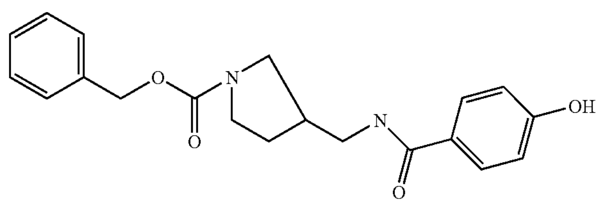 | 3-[(4-Hydroxy-benzoylamino)-methyl]-pyrrolidine-1-carboxylic acid benzyl ester | 376.3 |
| 406. | 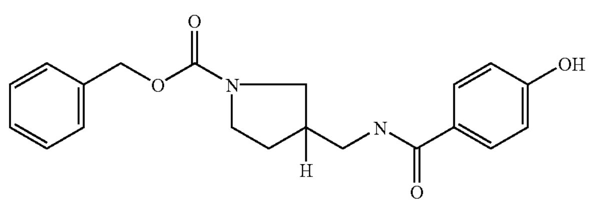 | 3-[(4-Hydroxy-benzoylamino)-methyl]-pyrrolidine-1-carboxylic acid benzyl ester | 376.3 |
| 407. | 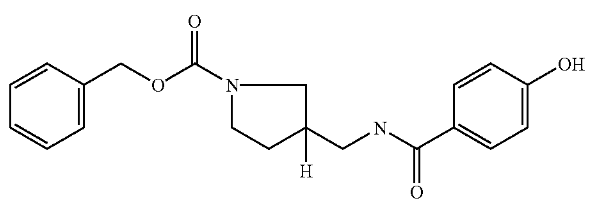 | 3-[(4-Hydroxy-benzoylamino)-methyl]-pyrrolidine-1-carboxylic acid benzyl ester | 355.3 |
| 408. | 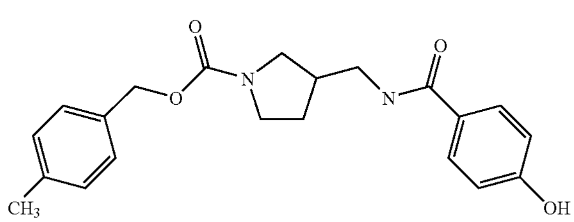 | 3-[(4-Hydroxy-benzoylamino)-methyl]-pyrrolidine-1-carboxylic acid 4-methyl-benzyl ester | 369.3 |
| 409. | 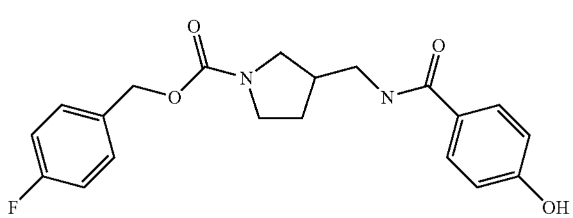 | 3-[(4-Hydroxy-benzoylamino)-methyl]-pyrrolidine-1-carboxylic acid 4-fluoro-benzyl ester | 373.3 |
| 410. | 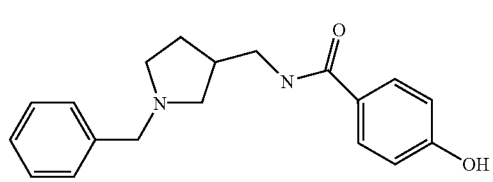 | N-(1-Benzyl-pyrrolidin-3-ylmethyl)-4-hydroxy-benzamide | 311.4 |

-continued

| EX. | Structure | Name | MS (M⁺ + 1) |
|---|---|---|---|
| 411. | 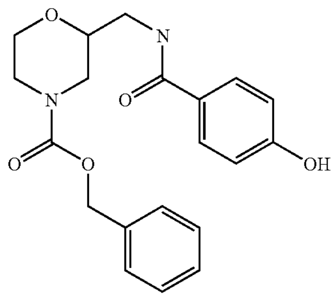 | 2-[(4-Hydroxy-benzoylamino)-methyl]-morpholine-4-carboxylic acid benzyl ester | 371.2 |
| 412. | 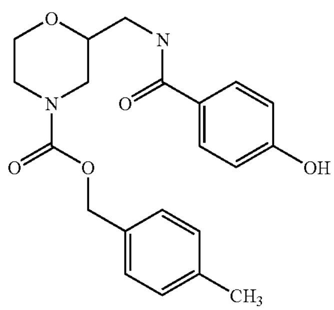 | 2-[(4-Hydroxy-benzoylamino)-methyl]-morpholine-4-carboxylic acid 4-methyl-benzyl ester | 385.7 |
| 413. | 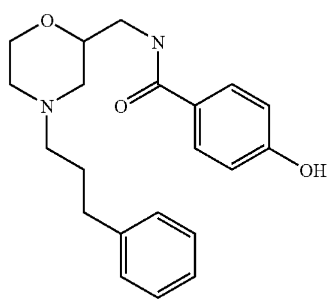 | 4-Hydroxy-N-[-(3-phenyl-propyl)-morpholin-2-ylmethyl]-benzamide | 355.2 |
| 414. | 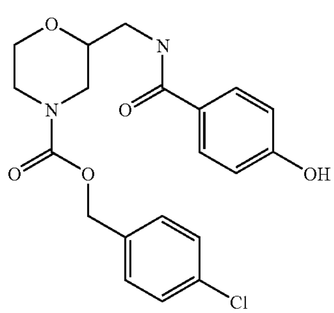 | 2-[(4-Hydroxy-benzoylamino)-methyl]-morpholine-4-carboxylic acid 4-chloro-benzyl ester | 405.1 |
| 415. | 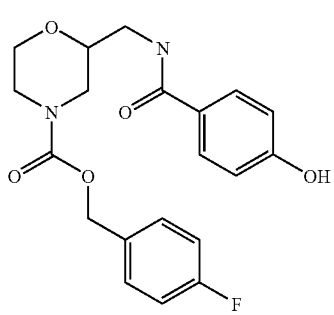 | 2-[(4-Hydroxy-benzoylamino)-methyl]-morpholine-4-carboxylic acid 4-fluoro-benzyl ester | 389.1 |

-continued

| EX. | Structure | Name | MS (M⁺ + 1) |
|---|---|---|---|
| 416. | 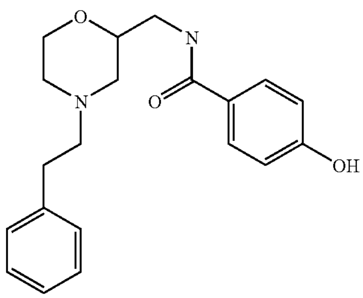 | 4-Hydroxy-N-(4-phenethyl-morpholin-2-ylmethyl)-benzamide | 341.1 |
| 417. | 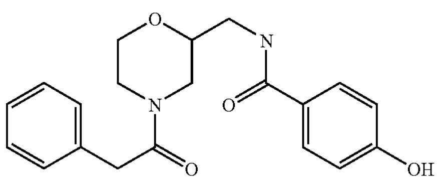 | 4-Hydroxy-N-(4-phenylacetyl-morpholin-2-ylmethyl)-benzamide | 355.2 |
| 418. | 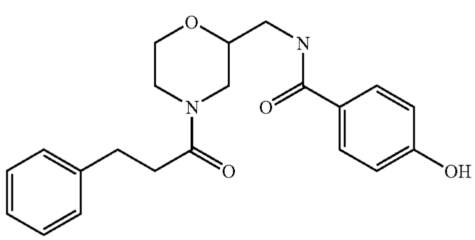 | 4-Hydroxy-N-[4-(3-phenyl-propionyl)-morpholin-2-ylmethyl]-benzamide | 369.2 |
| 419. | 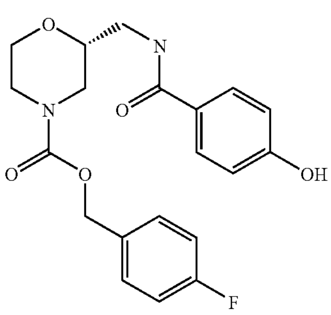 | 2-[(4-Hydroxy-benzoylamino)-methyl]-morpholine-4-carboxylic acid 4-fluoro-benzyl ester | 389.3 |
| 420. | 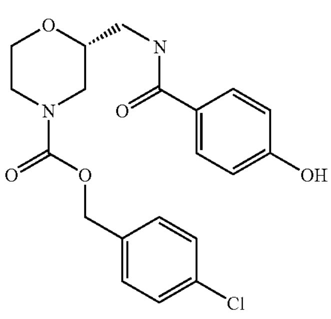 | 2-[(4-Hydroxy-benzoylamino)-methyl]-morpholine-4-carboxylic acid 4-chloro-benzyl ester | 405.1 |

| EX. | Structure | Name | MS (M⁺ + 1) |
|---|---|---|---|
| 421. | 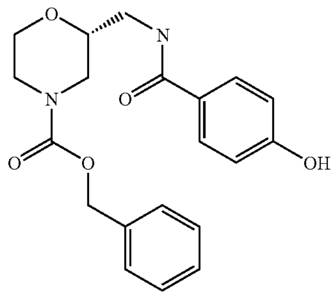 | 2-[(4-Hydroxy-benzoylamino)-methyl]-morpholine-4-carboxylic acid benzyl ester | 371.1 |
| 422. | 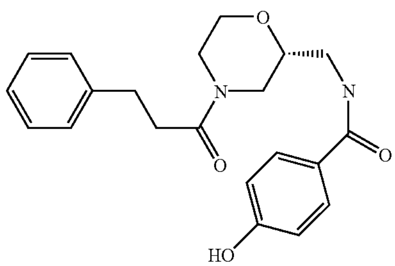 | 4-Hydroxy-N-[4-(3-phenyl-propionyl)-morpholin-2-ylmethyl]-benzamide | 369.2 |
| 423. | 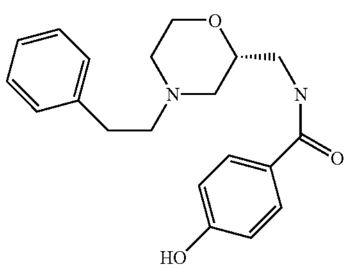 | 4-Hydroxy-N-(4-phenethyl-morpholin-ylmethyl)-benzamide | 341.2 |
| 424. | 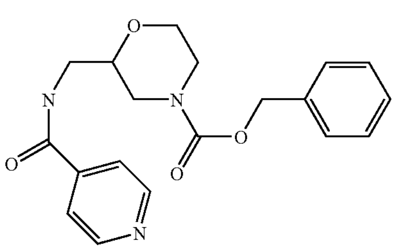 | 2-{[(Pyridine-4-carbonyl)-amino]-methyl}-morpholine-4-carboxylic acid benzyl ester | 56.2 |
| 425. | 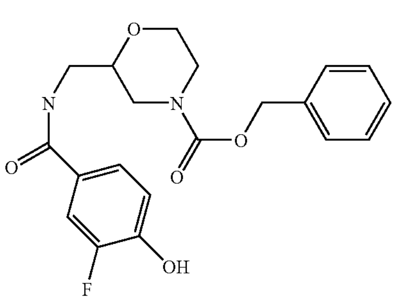 | 2-[(3-Fluoro-4-hydroxy-benzoylamino)-methyl]-morpholine-4-carboxylic acid benzyl ester | 389.1 |

-continued

| EX. | Structure | Name | MS (M⁺ + 1) |
|---|---|---|---|
| 426. | 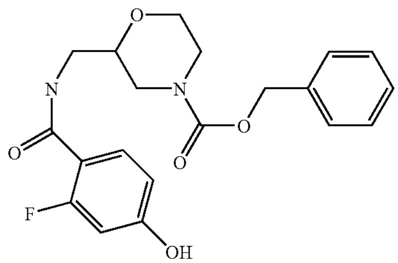 | 2-[(2-Fluoro-4-hydroxy-benzoylamino)-methyl]-morpholine-4-carboxylic acid benzyl ester | 389.1 |
| 427. | 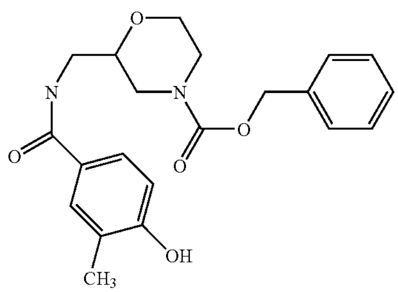 | 2-[(4-Hydroxy-3-methyl-benzoylamino)-methyl]-morpholine-4-carboxylic acid benzyl ester | 385.2 |
| 428. | 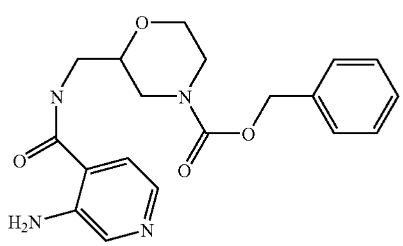 | 2-{[(3-Amino-pyridine-4-carbonyl)-amino]-methyl}-morpholine-4-carboxylic acid benzyl ester | 371.1 |
| 429. | 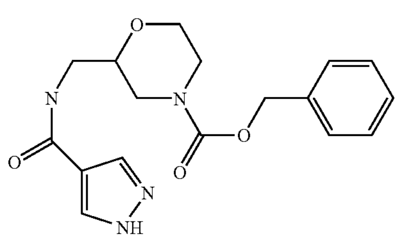 | 2-{[(1H-Pyrazole-4-carbonyl)-amino]-methyl}-morpholine-4-carboxylic acid benzyl ester | 345.2 |
| 430. | 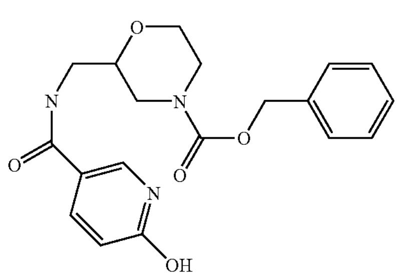 | 2-{[(6-Hydroxy-pyridine-3-carbonyl)-amino]-methyl}-morpholine-4-carboxylic acid benzyl ester | 372.2 |

| EX. | Structure | Name | MS (M⁺ + 1) |
|---|---|---|---|
| 431. | 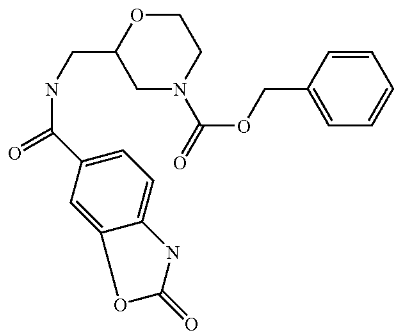 | 2-{[(2-Oxo-2,3-dihydro-benzooxazole-6-carbonyl)-amino]-methyl}-morpholine-4-carboxylic acid benzyl ester | 412.1 |
| 432. | 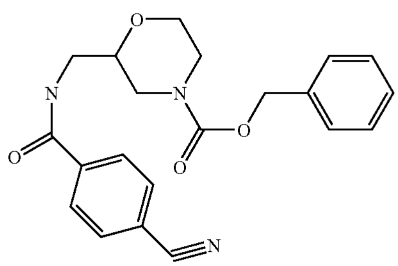 | 2-[(4-Cyano-benzoylamino)-methyl]-morpholine-4-carboxylic acid benzyl ester | 380.2 |
| 433. | 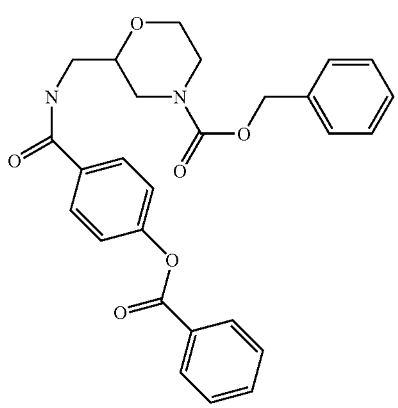 | 2-[(4-Benzoyloxy-benzoylamino)-methyl]-morpholine-4-carboxylic acid benzyl ester | 475.2 |
| 434. | 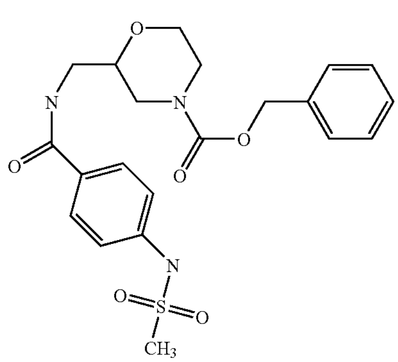 | 2-[(4-Methanesulfonylamino-benzoylamino)-methyl]-morpholine-4-carboxylic acid benzyl ester | 448.1 |

-continued
| EX. | Structure | Name | MS (M+ + 1) |
|---|---|---|---|
| 435. | 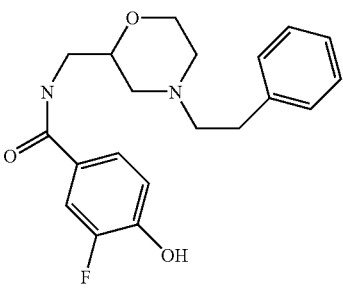 | 3-Fluoro-4-hydroxy-N-(4-phenethyl-morpholin-2-ylmethyl)-benzamide | 359.2 |
| 436. | 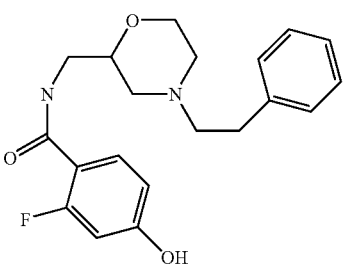 | 2-Fluoro-4-hydroxy-N-(4-phenethyl-morpholin-2-ylmethyl)-benzamide | 359.1 |
| 437. | 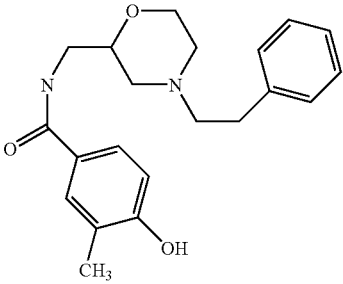 | 4-Hydroxy-3-methyl-N-(4-phenethyl-morpholin-2-ylmethyl)-benzamide | 355.2 |
| 438. | 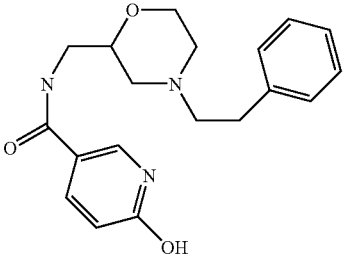 | 6-Hydroxy-N-(4-phenethyl-morpholin-2-ylmethyl)-nicotinamide | 342.2 |
| 439. | 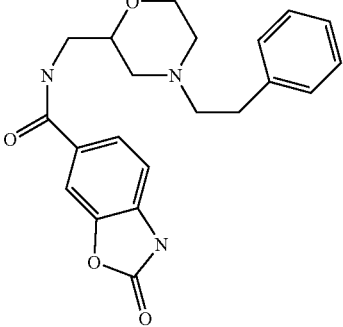 | 2-Oxo-2,3-dihydro-benzooxazole-6-carboxylic acid (4-phenethyl-morpholin-2-ylmethyl)-amide | 382.1 |

| EX. | Structure | Name | MS (M+ + 1) |
|---|---|---|---|
| 440. | 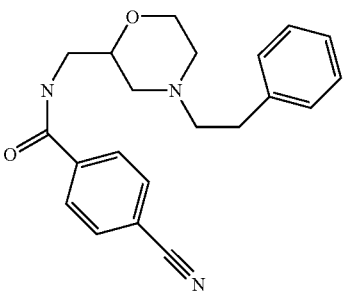 | 4-Cyano-N-(4-phenethyl-morpholin-2-ylmethyl)-benzamide | 350.2 |
| 441. | 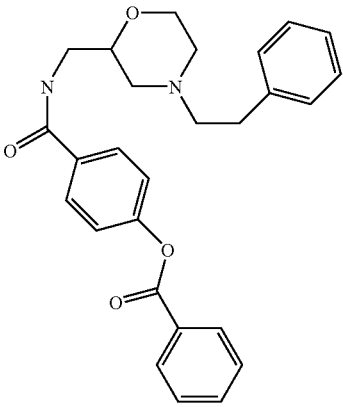 | Benzoic acid 4-[(4-phenethyl-morpholin-2-ylmethyl)-carbamoyl]-phenyl ester | 445.2 |
| 442. | 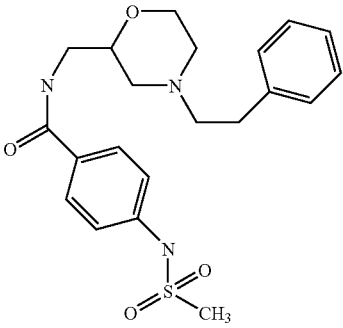 | 4-Methanesulfonylamino-N-(4-phenethyl-morpholin-2-ylmethyl)-benzamide | 418.1 |
| 443. | 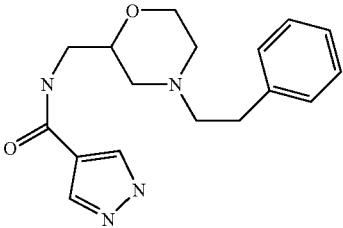 | 1H-Pyrazole-4-carboxylic acid (4-phenethyl-morpholin-2-ylmethyl)-amide | 341.2 |
| 444. | 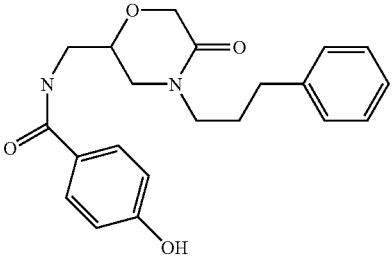 | 4-Hydroxy-N-[5-oxo-4-(3-phenyl-propyl)-morpholin-2-ylmethyl]-benzamide | 369.7 |

| EX. | Name | MS (M⁺ + 1) |
|---|---|---|
| 445. | 4-Hydroxy-N-(5-oxo-4-phenethyl-morpholin-2-ylmethyl)-benzamide | 355.6 |
| 446. | N-{4-[2-(4-Fluoro-phenyl)-ethyl]-morpholin-2-ylmethyl}-4-hydroxy-benzamide | 359.3 |
| 447. | 2-{[(2-Oxo-2,3-dihydro-benzooxazole-6-carbonyl)-amino]-methyl}-morpholine-4-carboxylic acid benzyl ester | 412.3 |
| 448. | 2-[(4-Methanesulfonylamino-benzoylamino)-methyl]-morpholine-4-carboxylic acid benzyl ester | 448.3 |
| 449. | 2-[(3-Fluoro-4-hydroxy-benzoylamino)-methyl]-morpholine-4-carboxylic acid benzyl ester | 389.3 |

| EX. | Structure | Name | MS (M⁺ + 1) |
|---|---|---|---|
| 450. | 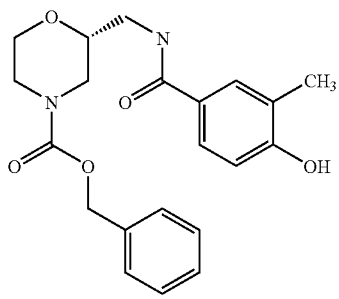 | 2-[(4-Hydroxy-3-methyl-benzoylamino)-methyl]-morpholine-4-carboxylic acid benzyl ester | 385.3 |
| 451. | 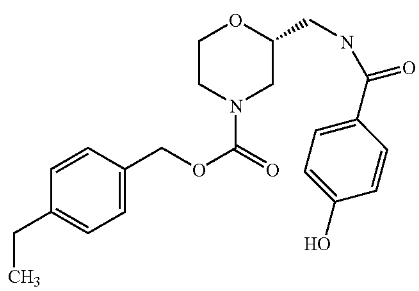 | 2-[(4-Hydroxy-benzoylamino)-methyl]-morpholine-4-carboxylic acid 4-ethyl-benzyl ester | 399.4 |
| 452. | 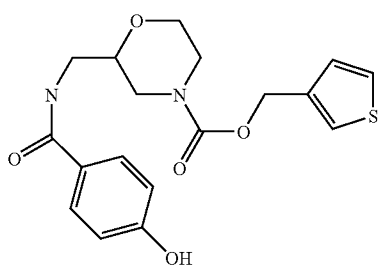 | 2-[(4-Hydroxy-benzoylamino)-methyl]-morpholine-4-carboxylic acid thiophen-3-ylmethyl ester | 377.2 |
| 453. | 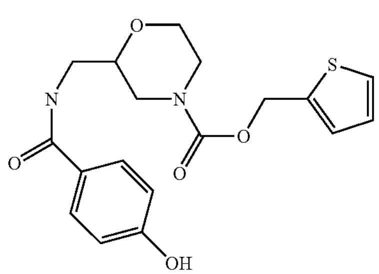 | 2-[(4-Hydroxy-benzoylamino)-methyl]-morpholine-4-carboxylic acid thiophen-2-ylmethyl ester | 377.2 |
| 454. | 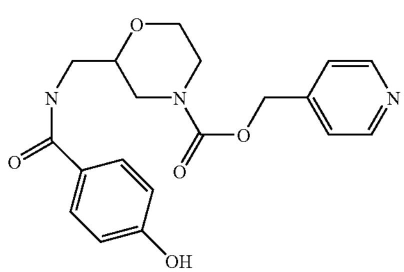 | 2-[(4-Hydroxy-benzoylamino)-methyl]-morpholine-4-carboxylic acid pyridin-4-ylmethyl ester | 372.2 |

-continued

| EX. | Structure | Name | MS (M⁺ + 1) |
|---|---|---|---|
| 455. | 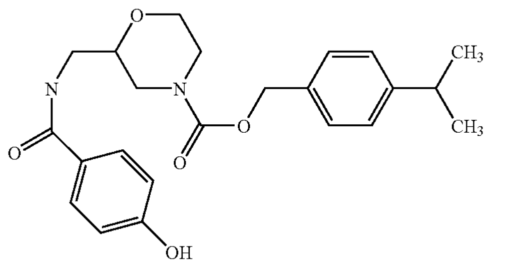 | 2-[(4-Hydroxy-benzoylamino)-methyl]-morpholine-4-carboxylic acid 4-isopropyl-benzyl ester | 413.3 |
| 456. | 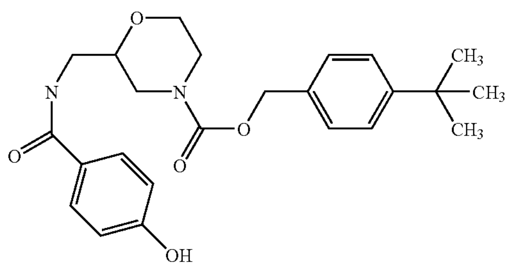 | 2-[(4-Hydroxy-benzoylamino)-methyl]-morpholine-4-carboxylic acid 4-tert-butyl-benzyl ester | 427.3 |
| 457. | 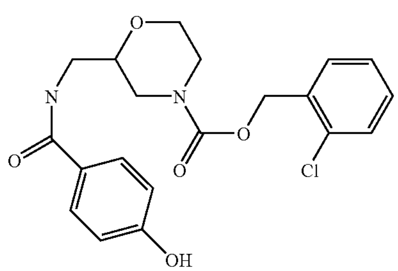 | 2-[(4-Hydroxy-benzoylamino)-methyl]-morpholine-4-carboxylic acid 2-chloro-benzyl ester | 405.2 |
| 458. | 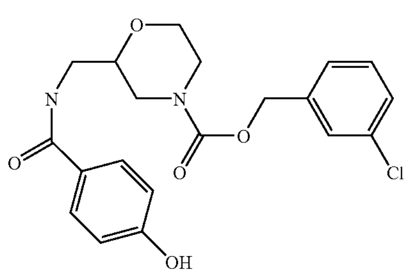 | 2-[(4-Hydroxy-benzoylamino)-methyl]-morpholine-4-carboxylic acid 3-chloro-benzyl ester | 405.2 |
| 459. | 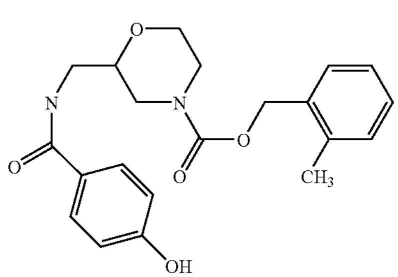 | 2-[(4-Hydroxy-benzoylamino)-methyl]-morpholine-4-carboxylic acid 2-methyl-benzyl ester | 385.3 |

-continued

| EX. | Structure | Name | MS (M⁺ + 1) |
|---|---|---|---|
| 460. | 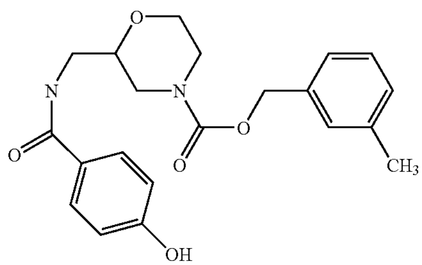 | 2-[(4-Hydroxy-benzoylamino)-methyl]-morpholine-4-carboxylic acid 3-methyl-benzyl ester | 385.3 |
| 461. | 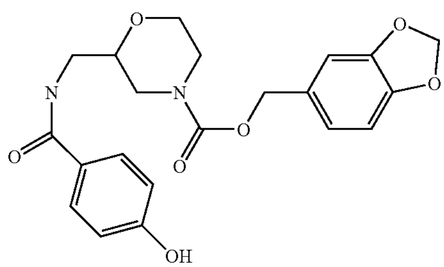 | 2-[(4-Hydroxy-benzoylamino)-methyl]-morpholine-4-carboxylic acid benzo[1,3]dioxol-5-ylmethyl ester | 415.3 |
| 462. | 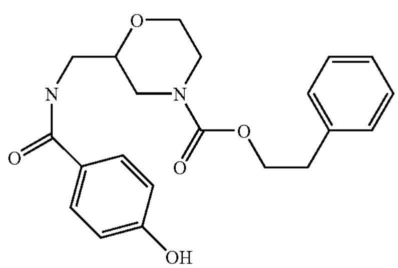 | 2-[(4-Hydroxy-benzoylamino)-methyl]-morpholine-4-carboxylic acid phenethyl ester | 385.3 |
| 463. | 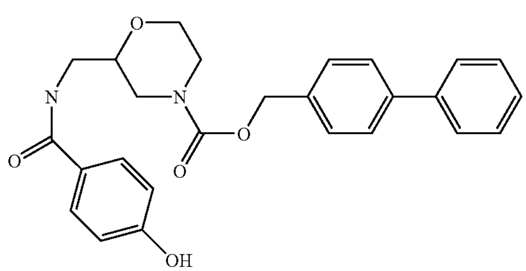 | 2-[(4-Hydroxy-benzoylamino)-methyl]-morpholine-4-carboxylic acid biphenyl-4-ylmethyl ester | 447.3 |
| 464. | 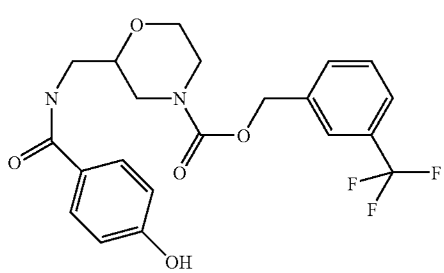 | 2-[(4-Hydroxy-benzoylamino)-methyl]-morpholine-4-carboxylic acid 3-trifluoromethyl-benzyl ester | 439.3 |

-continued

| EX. | Structure | Name | MS (M⁺ + 1) |
|---|---|---|---|
| 465. | 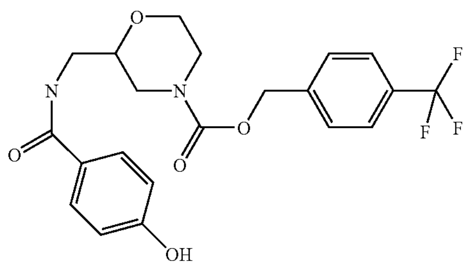 | 2-[(4-Hydroxy-benzoylamino)-methyl]-morpholine-4-carboxylic acid 4-trifluoromethyl-benzyl ester | 439.3 |
| 466. | 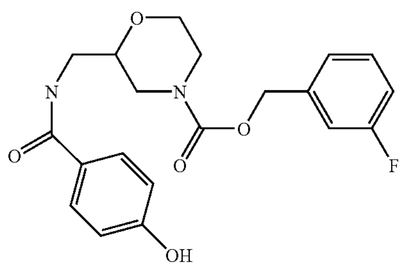 | 2-[(4-Hydroxy-benzoylamino)-methyl]-morpholine-4-carboxylic acid 3-fluoro-benzyl ester | 389.3 |
| 467. | 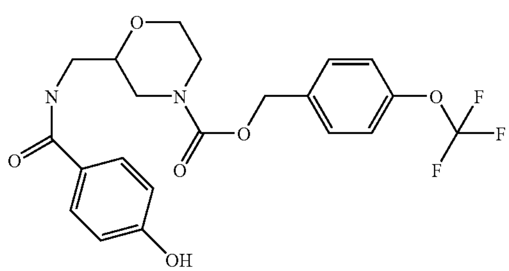 | 2-[(4-Hydroxy-benzoylamino)-methyl]-morpholine-4-carboxylic acid 4-trifluoromethoxy-benzyl ester | 455.3 |
| 468. | 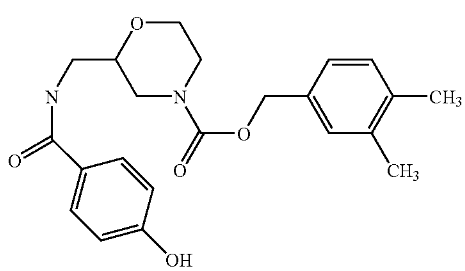 | 2-[(4-Hydroxy-benzoylamino)-methyl]-morpholine-4-carboxylic acid 3,4-dimethyl-benzyl ester | 399.3 |
| 469. | 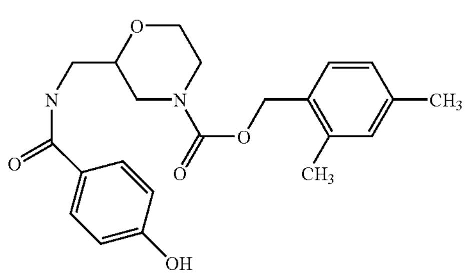 | 2-[(4-Hydroxy-benzoylamino)-methyl]-morpholine-4-carboxylic acid 2,4-dimethyl-benzyl ester | 399.3 |

-continued

| EX. | Structure | Name | MS (M⁺ + 1) |
|---|---|---|---|
| 470. | 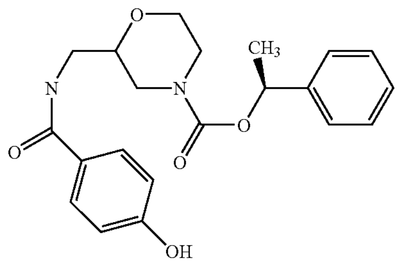 | 2-[(4-Hydroxy-benzoylamino)-methyl]-morpholine-4-carboxylic acid 1-phenyl-ethyl ester | 385.3 |
| 471. | 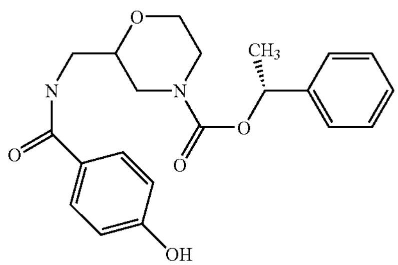 | 2-[(4-Hydroxy-benzoylamino)-methyl]-morpholine-4-carboxylic acid 1-phenyl-ethyl ester | 385.3 |
| 472. | 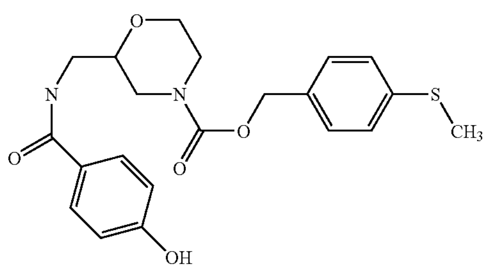 | 2-[(4-Hydroxy-benzoylamino)-methyl]-morpholine-4-carboxylic acid 4-methylsulfanyl-benzyl ester | 417.3 |
| 473. | 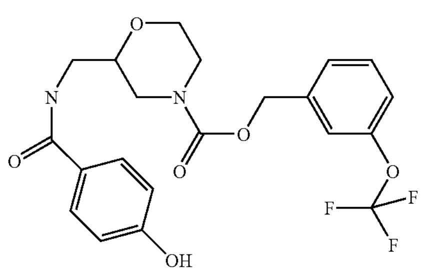 | 2-[(4-Hydroxy-benzoylamino)-methyl]-morpholine-4-carboxylic acid 3-trifluoromethoxy-benzyl ester | 455.3 |
| 474. | 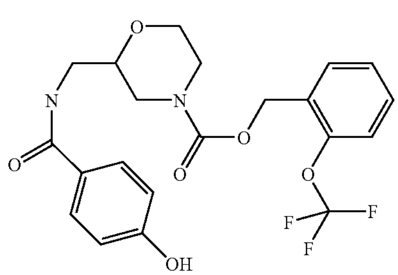 | 2-[(4-Hydroxy-benzoylamino)-methyl]-morpholine-4-carboxylic acid 2-trifluoromethoxy-benzyl ester | 455.3 |

| EX. | Structure | Name | MS (M⁺ + 1) |
|---|---|---|---|
| 475. | 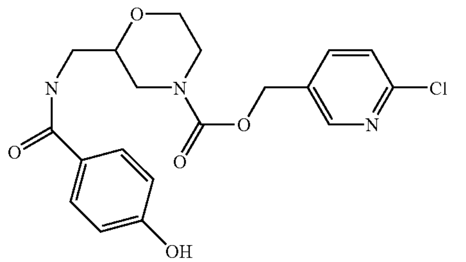 | 2-[(4-Hydroxy-benzoylamino)-methyl]-morpholine-4-carboxylic acid 6-chloro-pyridin-3-ylmethyl ester | 406.2 |
| 476. | 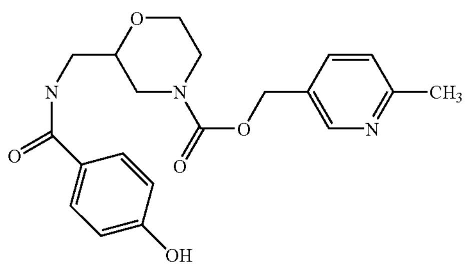 | 2-[(4-Hydroxy-benzoylamino)-methyl]-morpholine-4-carboxylic acid 6-methyl-pyridin-3-ylmethyl ester | 386.3 |
| 477. | 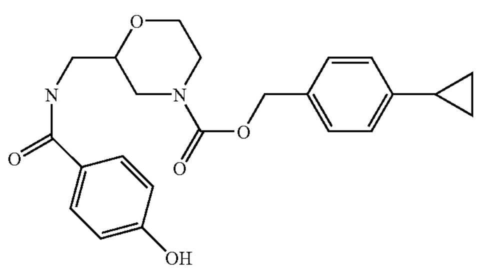 | 2-[(4-Hydroxy-benzoylamino)-methyl]-morpholine-4-carboxylic acid 4-cyclopropyl-benzyl ester | 411.3 |
| 478. | 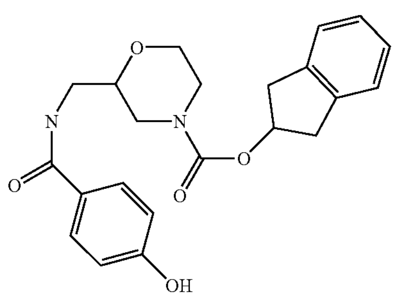 | 2-[(4-Hydroxy-benzoylamino)-methyl]-morpholine-4-carboxylic acid indan-2-yl ester | 397.3 |
| 479. | 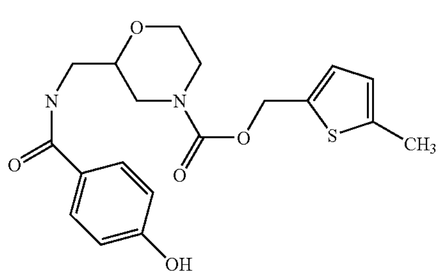 | 2-[(4-Hydroxy-benzoylamino)-methyl]-morpholine-4-carboxylic acid 5-methyl-thiophen-2-ylmethyl ester | 391.3 |

-continued

| EX. | Structure | Name | MS (M+ + 1) |
|---|---|---|---|
| 480. | 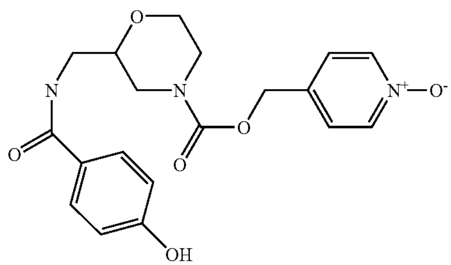 | 2-[(4-Hydroxy-benzoylamino)-methyl]-morpholine-4-carboxylic acid 1-oxy-pyridin-4-ylmethyl ester | 388.2 |
| 481. | 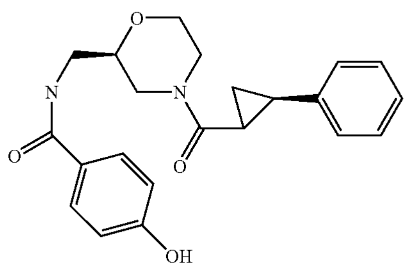 | 4-Hydroxy-N-[4-(2-phenyl-cyclopropanecarbonyl)-morpholin-2-ylmethyl]-benzamide | 381.3 |
| 482. | 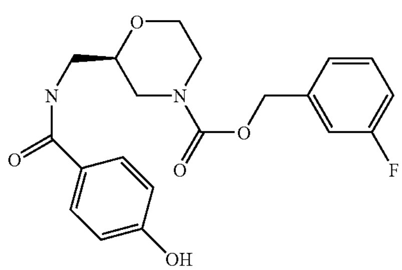 | 2-[(4-Hydroxy-benzoylamino)-methyl]-morpholine-4-carboxylic acid 3-fluoro-benzyl ester | 389.4 |
| 483. | 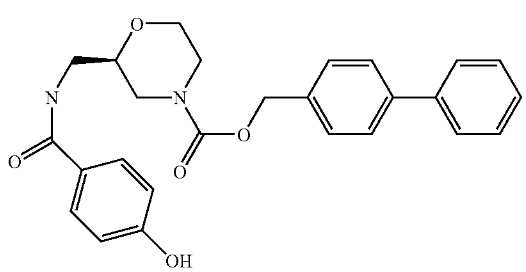 | 2-[(4-Hydroxy-benzoylamino)-methyl]-morpholine-4-carboxylic acid biphenyl-4-ylmethyl ester | 447.4 |
| 484. | 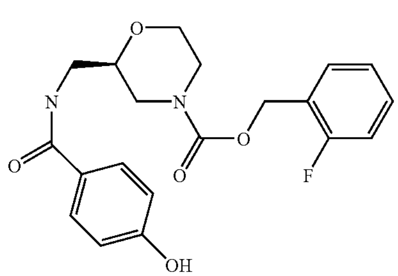 | 2-[(4-Hydroxy-benzoylamino)-methyl]-morpholine-4-carboxylic acid 2-fluoro-benzyl ester | 389.4 |

-continued

| EX. | Structure | Name | MS (M+ + 1) |
|---|---|---|---|
| 485. | 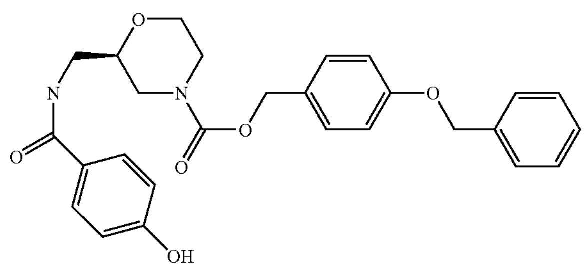 | 2-[(4-Hydroxy-benzoylamino)-methyl]-morpholine-4-carboxylic acid 4-benzyloxy-benzyl ester | 477.25 |
| 486. | 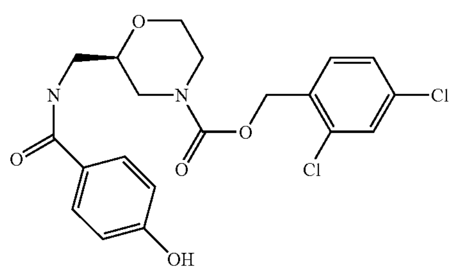 | 2-[(4-Hydroxy-benzoylamino)-methyl]-morpholine-4-carboxylic acid 2,4-dichloro-benzyl ester | 439.3 |
| 487. | 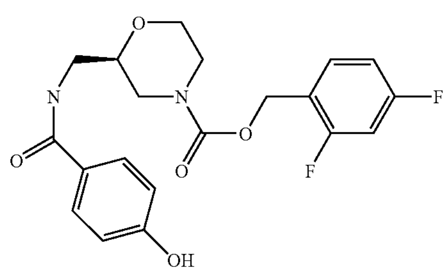 | 2-[(4-Hydroxy-benzoylamino)-methyl]-morpholine-4-carboxylic acid 2,4-difluoro-benzyl ester | 407.4 |
| 488. | 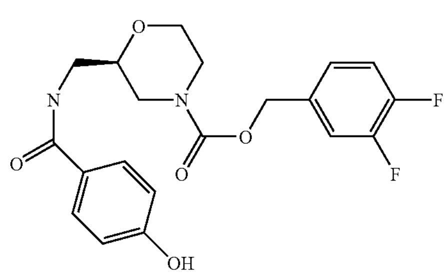 | 2-[(4-Hydroxy-benzoylamino)-methyl]-morpholine-4-carboxylic acid 3,4-difluoro-benzyl ester | 407.4 |
| 489. | 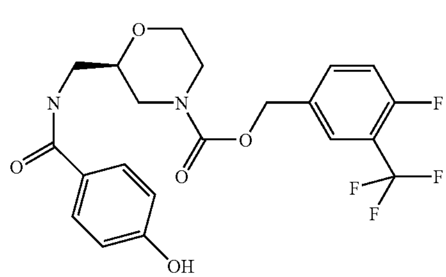 | 2-[(4-Hydroxy-benzoylamino)-methyl]-morpholine-4-carboxylic acid 4-fluoro-3-trifluoromethyl-benzyl ester | 457.4 |

-continued

| EX. | Structure | Name | MS (M+ + 1) |
|---|---|---|---|
| 490. | 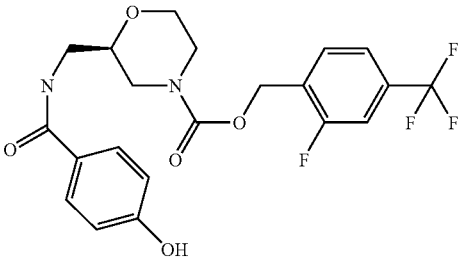 | 2-[(4-Hydroxy-benzoylamino)-methyl]-morpholine-4-carboxylic acid 2-fluoro-4-trifluoromethyl-benzyl ester | 457.4 |
| 491. | 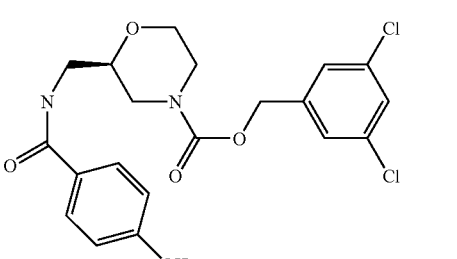 | 2-[(4-Hydroxy-benzoylamino)-methyl]-morpholine-4-carboxylic acid 3,5-dichloro-benzyl ester | 439.3 |
| 492. | 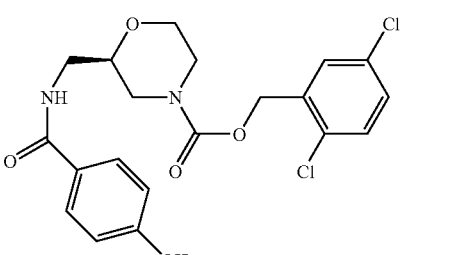 | 2-[(4-Hydroxy-benzoylamino)-methyl]-morpholine-4-carboxylic acid 2,5-dichloro-benzyl ester | 439.3 |
| 493. | 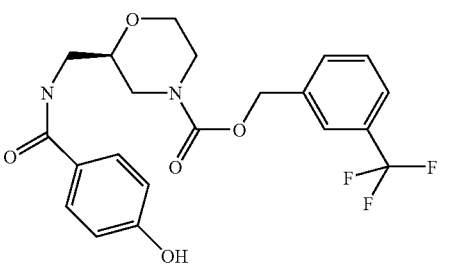 | 2-[(4-Hydroxy-benzoylamino)-methyl]-morpholine-4-carboxylic acid 3-trifluoromethyl-benzyl ester | 439.4 |
| 494. | 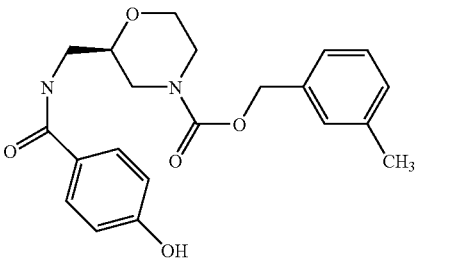 | 2-[(4-Hydroxy-benzoylamino)-methyl]-morpholine-4-carboxylic acid 3-methyl-benzyl ester | 385.4 |

-continued

| EX. | Structure | Name | MS (M⁺ + 1) |
|---|---|---|---|
| 495. | 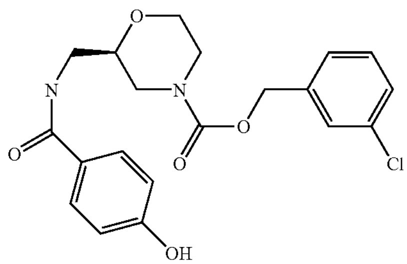 | 2-[(4-Hydroxy-benzoylamino)-methyl]-morpholine-4-carboxylic acid 3-chloro-benzyl ester | 405.3 |
| 496. | 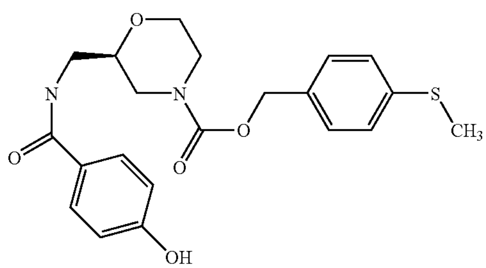 | 2-[(4-Hydroxy-benzoylamino)-methyl]-morpholine-4-carboxylic acid 4-methylsulfanyl-benzyl ester | 417.3 |
| 497. | 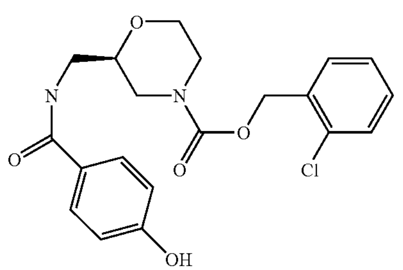 | 2-[(4-Hydroxy-benzoylamino)-methyl]-morpholine-4-carboxylic acid 2-chloro-benzyl ester | 405.3 |
| 498. | 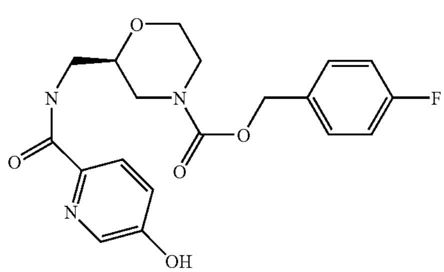 | 2-{[(5-Hydroxy-pyridine-2-carbonyl)-amino]-methyl}-morpholine-4-carboxylic acid 4-fluoro-benzyl ester | 390.3 |
| 499. | 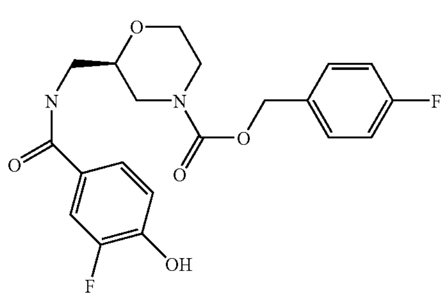 | 2-[(3-Fluoro-4-hydroxy-benzoylamino)-methyl]-morpholine-4-carboxylic acid 4-fluoro-benzyl ester | 407.3 |

-continued

| EX. | Structure | Name | MS (M⁺ + 1) |
|---|---|---|---|
| 500. | 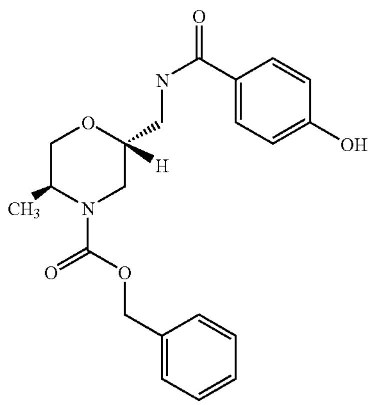 | 2-[(4-Hydroxy-benzoylamino)-methyl]-5-methyl-morpholine-4-carboxylic acid benzyl ester | 385.4 |
| 501. | 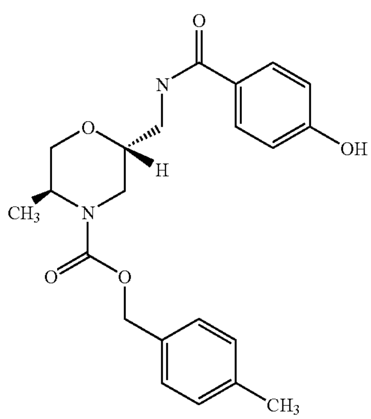 | 2-[(4-Hydroxy-benzoylamino)-methyl]-5-methyl-morpholine-4-carboxylic acid 4-methyl-benzyl ester | 399.3 |
| 502. | 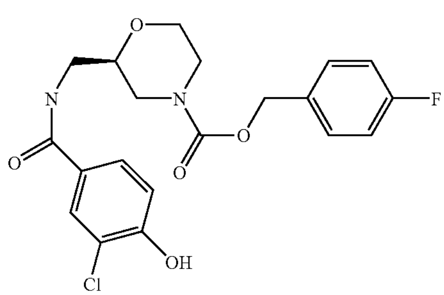 | 2-[(3-Chloro-4-hydroxy-benzoylamino)-methyl]-morpholine-4-carboxylic acid 4-fluoro-benzyl ester | 423.3 |
| 503. | 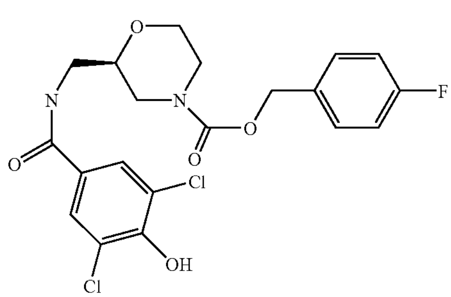 | 2-[(3,5-Dichloro-4-hydroxy-benzoylamino)-methyl]-morpholine-4-carboxylic acid 4-fluoro-benzyl ester | 457.2 |

-continued

| EX. | Structure | Name | MS (M⁺ + 1) |
|---|---|---|---|
| 504. | 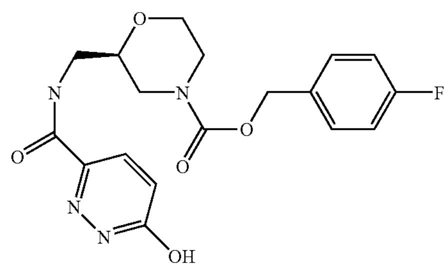 | 2-{[(6-Hydroxy-pyridazine-3-carbonyl)-amino]-methyl}-morpholine-4-carboxylic acid 4-fluoro-benzyl ester | 391.4 |
| 505. | 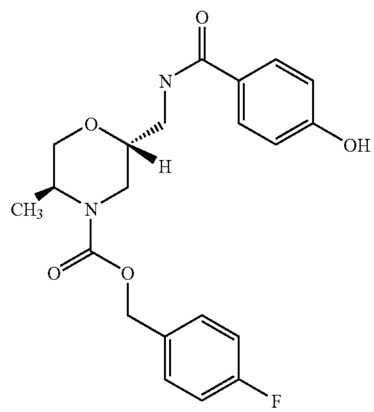 | 2-[(4-Hydroxy-benzoylamino)-methyl]-5-methyl-morpholine-4-carboxylic acid 4-fluoro-benzyl ester | 403.4 |
| 506. | 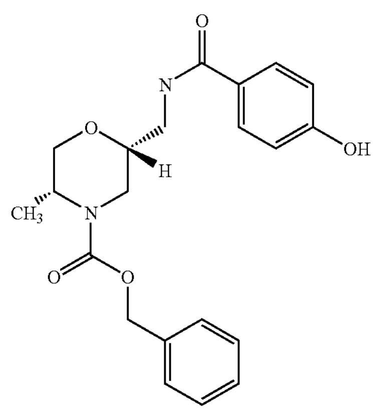 | 2-[(4-Hydroxy-benzoylamino)-methyl]-5-methyl-morpholine-4-carboxylic acid benzyl ester | 385.3 |
| 507. | 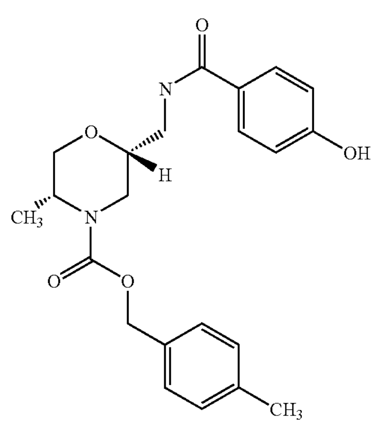 | 2-[(4-Hydroxy-benzoylamino)-methyl]-5-methyl-morpholine-4-carboxylic acid 4-methyl-benzyl ester | 399.4 |

-continued

| EX. | Structure | Name | MS (M⁺ + 1) |
|---|---|---|---|
| 508. | 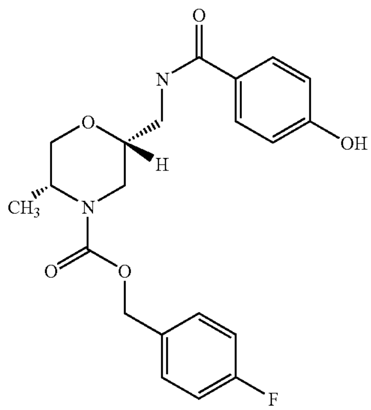 | 2-(4-Hydroxy-benzoylamino)-methyl]-5-methyl-morpholine-4-carboxylic acid 4-fluoro-benzyl ester | 403.3 |
| 509. | 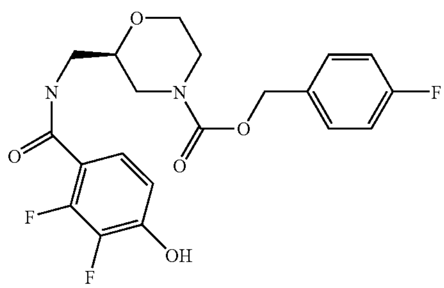 | 2-[2,3-Difluoro-4-hydroxy-benzoylamino)-methyl]-morpholine-4-carboxylic acid 4-fluoro-benzyl ester | 425.2 |
| 510. | 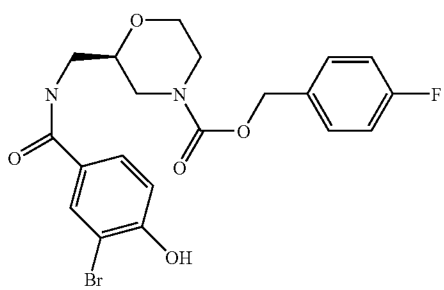 | 2-[(3-Bromo-4-hydroxy-benzoylamino)-methyl]-morpholine-4-carboxylic acid 4-fluoro-benzyl ester | 467.2 |
| 511. | 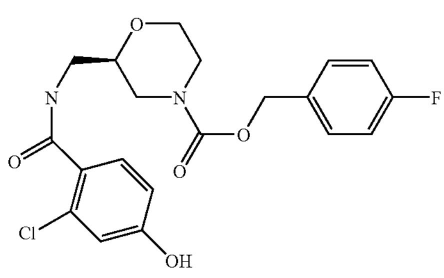 | 2-[(2-Chloro-4-hydroxy-benzoylamino)-methyl]-morpholine-4-carboxylic acid 4-fluoro-benzyl ester | 423.2 |
| 512. | 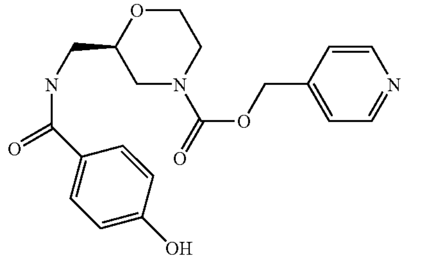 | 2-[(4-Hydroxy-benzoylamino)-methyl]-morpholine-4-carboxylic acid pyridin-4-ylmethyl ester | 372.3 |

-continued

| EX. | Structure | Name | MS (M⁺ + 1) |
|---|---|---|---|
| 513. | 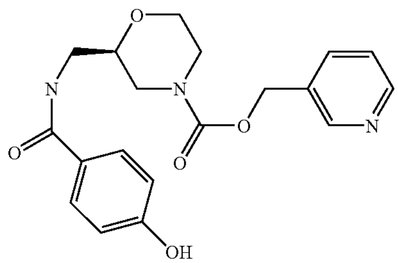 | 2-[(4-Hydroxy-benzoylamino)-methyl]-morpholine-4-carboxylic acid pyridin-3-ylmethyl ester | 372.3 |
| 514. | 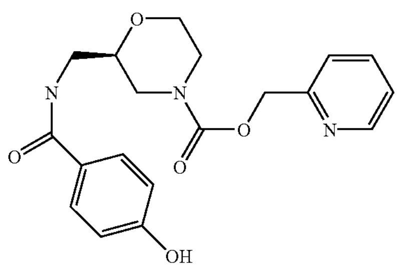 | 2-[(4-Hydroxy-benzoylamino)-methyl]-morpholine-4-carboxylic acid pyridin-2-ylmethyl ester | 372.3 |
| 515. | 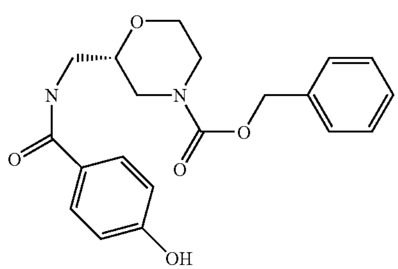 | 2-[(4-Hydroxy-benzoylamino)-methyl]-morpholine-4-carboxylic acid benzyl ester | 371.3 |
| 516. | 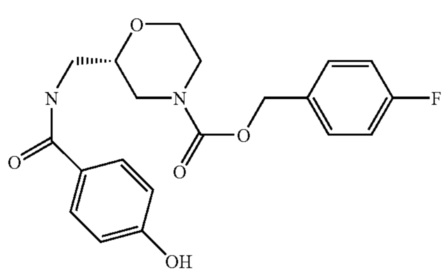 | 2-[(4-Hydroxy-benzoylamino)-methyl]-morpholine-4-carboxylic acid 4-fluoro-benzyl ester | 389.3 |
| 517. | 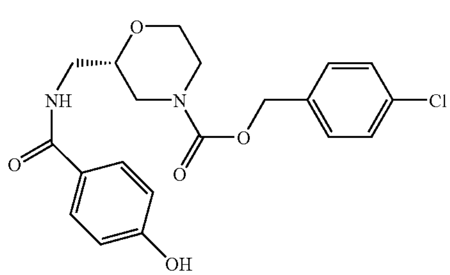 | 2-[(4-Hydroxy-benzoylamino)-methyl]-morpholine-4-carboxylic acid 4-chloro-benzyl ester | 405.3 |

-continued

| EX. | Structure | Name | MS (M+ + 1) |
|---|---|---|---|
| 518. | 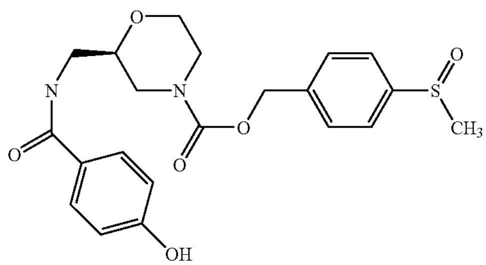 | 2-[(4-Hydroxy-benzoylamino)-methyl]-morpholine-4-carboxylic acid 4-methanesulfinyl-benzyl ester | 433.3 |
| 519. | 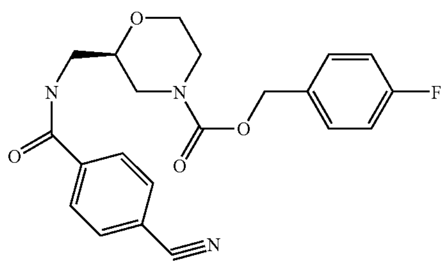 | 2-[(4-Cyano-benzoylamino)-methyl]-morpholine-4-carboxylic acid 4-fluoro-benzyl ester | 398.4 |
| 520. | 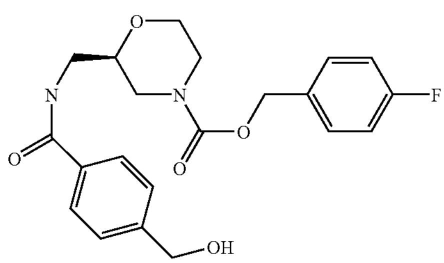 | 2-[(4-Hydroxymethyl-benzoylamino)-methyl]-morpholine-4-carboxylic acid 4-fluoro-benzyl ester | 403.4 |
| 521. | 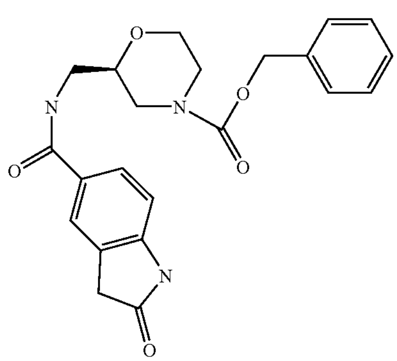 | 2-{[(2-Oxo-2,3-dihydro-1H-indole-5-carbonyl)-amino]-methyl}-morpholine-4-carboxylic acid benzyl ester | 410.3 |
| 522. | 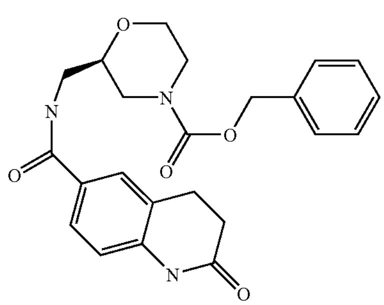 | 2-{[(2-Oxo-1,2,3,4-tetrahydro-quinoline-6-carbonyl)-amino]-methyl}-morpholine-4-carboxylic acid benzyl ester | 424.4 |

| EX. | Structure | Name | MS (M+ + 1) |
|---|---|---|---|
| 523. | 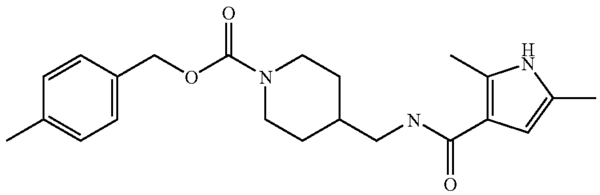 | 4-Methylbenzyl 4-({[(2,5-dimethyl-1H-pyrrol-3-yl)carbonyl]amino}methyl)piperidine 1-carboxylate | 370.2 |
| 524. | 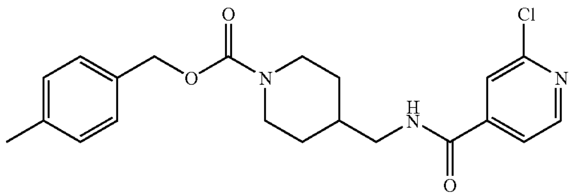 | 4-Methylbenzyl 4-{[(2-chloroisonicotinoyl)amino]methyl}piperidine-1-carboxylate | 402.1 |
| 525. | 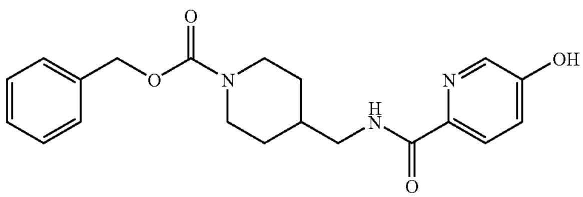 | Benzyl 4-({[(5-hydroxypyridin-2-yl)carbonyl]amino}methyl)piperidine-1-carboxylate | 370.3 |
| 526. | 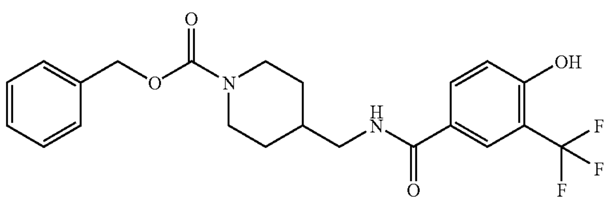 | Benzyl 4-({[4-hydroxy-3-(trifluoromethyl)benzoyl]amino}methyl)piperidine-1-carboxylate | 437.4 |
| 527. | 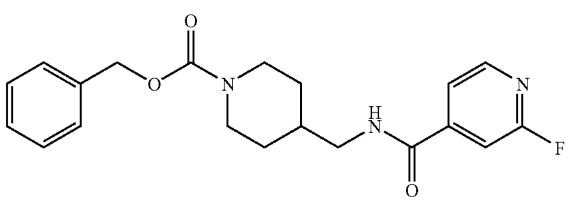 | Benzyl 4-{[(2-fluoroisonicotinoyl)amino]methyl}piperidine-1-carboxylate | 372.4 |
| 528. | 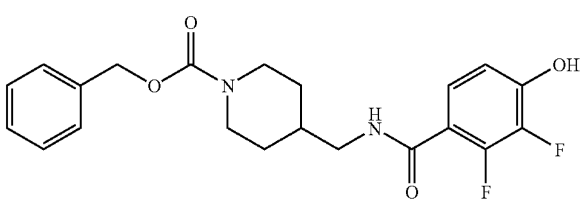 | Benzyl 4-{[(2,3-difluoro-4-hydroxybenzoyl)amino]methyl}piperidine-1-carboxylate | 405.3 |
| 529. | 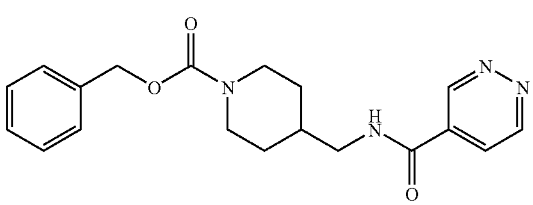 | Benzyl 4-{[(pyridazin-4-ylcarbonyl)amino]methyl}piperidine-1-carboxylate | 355.3 |

-continued

| EX. | Structure | Name | MS (M⁺ + 1) |
|---|---|---|---|
| 530. | 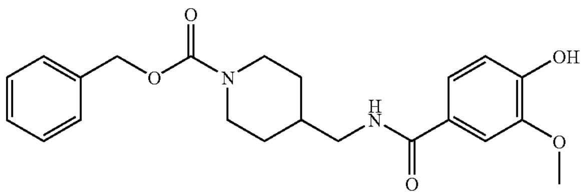 | Benzyl 4-{[(4-hydroxy-3-methoxybenzoyl)amino]methyl}piperidine-1-carboxylate | 399.4 |
| 531. | 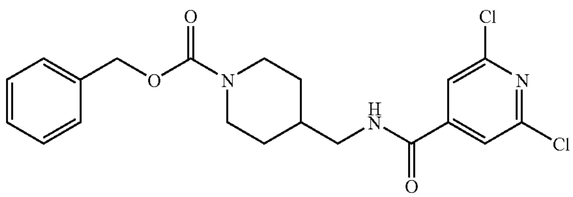 | Benzyl 4-{[(2,6-dichloroisonicotinoyl)amino]methyl}piperidine-1-carboxylate | 423.3 |
| 532. | 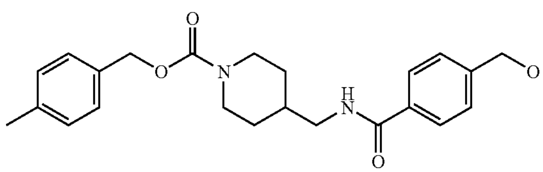 | 4-Methylbenzyl 4-({[4-(hydroxymethyl)benzoyl]amino}methyl)piperidine-1-carboxylate | 397.4 |
| 533. | 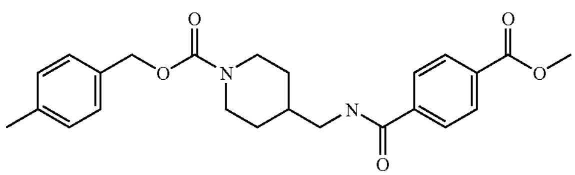 | 4-Methylbenzyl 4-({[4-(methoxycarbonyl)benzoyl]amino}methyl)piperidine-1-carboxylate | 425.5 |
| 534. | 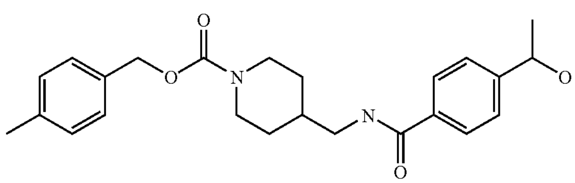 | 4-Methylbenzyl 4-({[4-(1-hydroxyethyl)benzoyl]amino}methyl)piperidine-1-carboxylate | 411.4 |
| 535. | 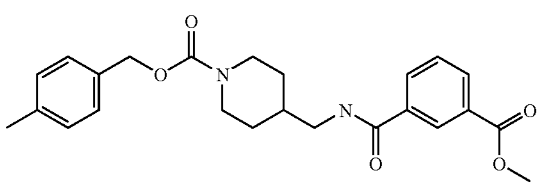 | 4-Methylbenzyl 4-({[3-(methoxycarbonyl)benzoyl]amino}methyl)piperidine-1-carboxylate | 425.4 |
| 536. | 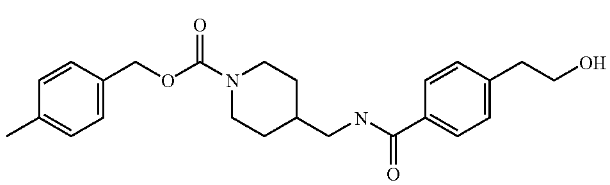 | 4-Methylbenzyl 4-({[4-(2-hydroxyethyl)benzoyl]amino}methyl)piperidine-1-carboxylate | 411.3 |
| 537. | 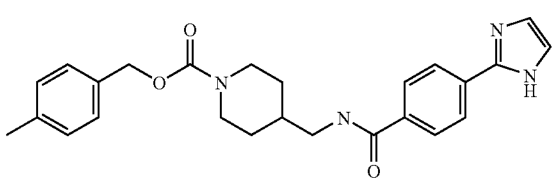 | 4-Methylbenzyl 4-({[4-(1H-imidazol-2-yl)benzoyl]amino}methyl)piperidine-1-carboxylate | 433.3 |

-continued

| EX. | Structure | Name | MS (M⁺ + 1) |
|---|---|---|---|
| 538. | 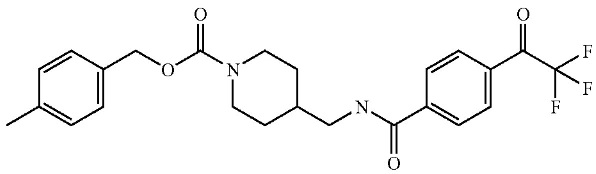 | 4-Methylbenzyl 4-({[4-(trifluoroacetyl)benzoyl]amino}methyl)piperidine-1-carboxylate | 481.2 |
| 539. | 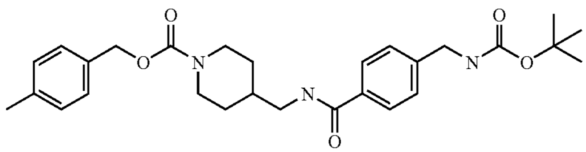 | 4-Methylbenzyl 4-{[(4-{[(tert-butoxycarbonyl)amino]methyl}benzoyl)amino]methyl}piperidine-1-carboxylate | 496.4 |
| 540. | 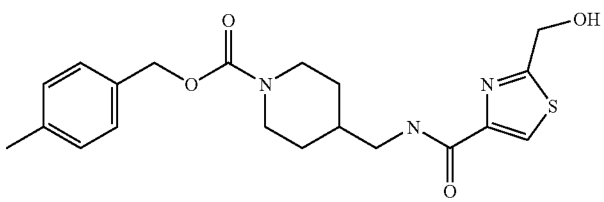 | 4-Methylbenzyl 4-[({[2-(hydroxymethyl)-1,3-thiazol-4-yl]carbonyl}amino)methyl]piperidine-1-carboxylate | 404.2 |
| 541. | 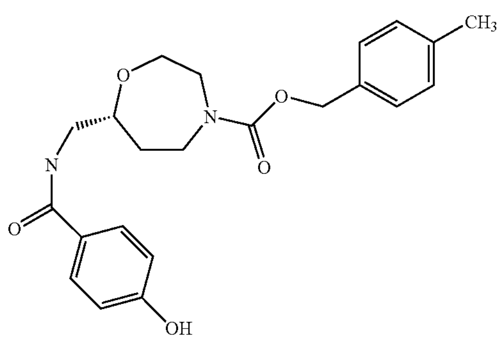 | 7-[(4-Hydroxy-benzoylamino)-methyl]-[1,4]oxazepane-4-carboxylic acid 4-methyl-benzyl ester | 399.4 |
| 542. | 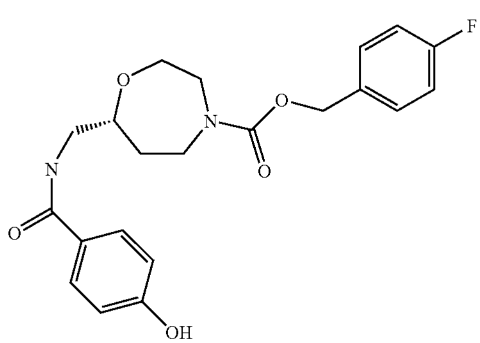 | 7-[(4-Hydroxy-benzoylamino)-methyl]-[1,4]oxazepane-4-carboxylic acid 4-fluoro-benzyl ester | 403.4 |

-continued

| EX. | Structure | Name | MS (M⁺ + 1) |
|---|---|---|---|
| 543. | 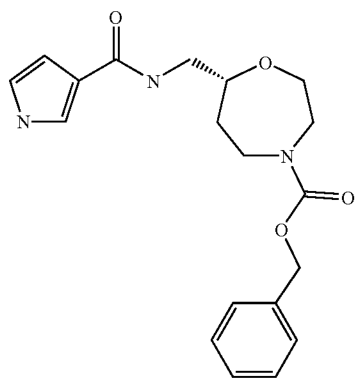 | 7-{[(1H-Pyrrole-3-carbonyl)-amino]-methyl}-[1,4]oxazepane-4-carboxylic acid benzyl ester | 358.3 |
| 544. | 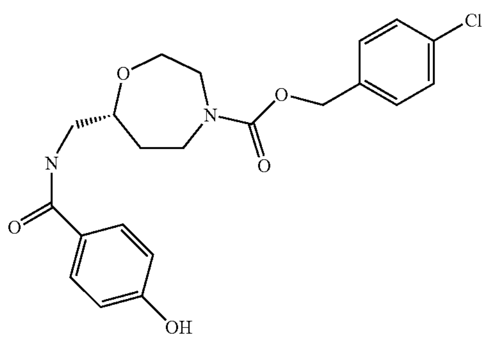 | 7-[(4-Hydroxy-benzoylamino)-methyl]-[1,4]oxazepane-4-carboxylic acid 4-chloro-benzyl ester | 419.4 |
| 545. | 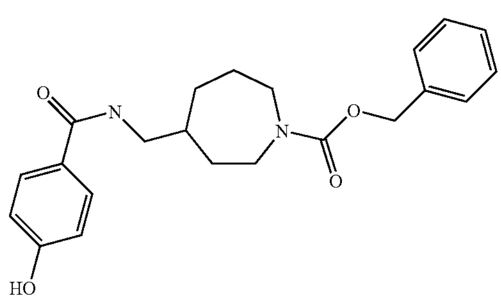 | 4-[(4-Hydroxy-benzoylamino)-methyl]-azepane-1-carboxylic acid benzyl ester | 383.4 |
| 546. | 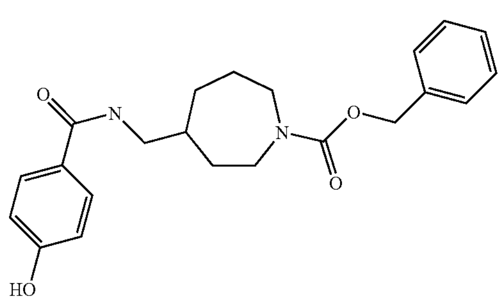 | 4-[(4-Hydroxy-benzoylamino)-methyl]-azepane-1-carboxylic acid benzyl ester | 383.4 |

-continued

| EX. | Structure | Name | MS (M⁺ + 1) |
|---|---|---|---|
| 547. | 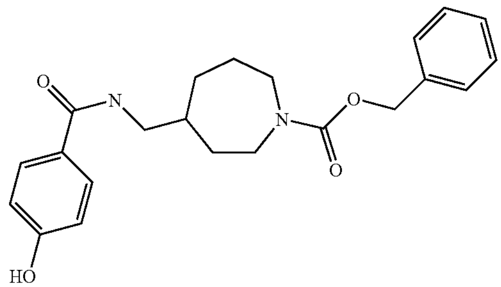 | 4-[(4-Hydroxy-benzoylamino)-methyl]-azepane-1-carboxylic acid benzyl ester | 383.4 |
| 548. | 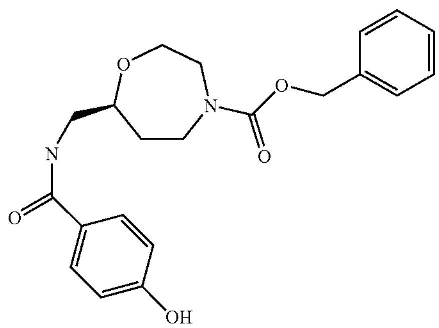 | 7-[(4-Hydroxy-benzoylamino)-methyl]-[1,4]oxazepane-4-carboxylic acid benzyl ester | 385.4 |
| 549. | 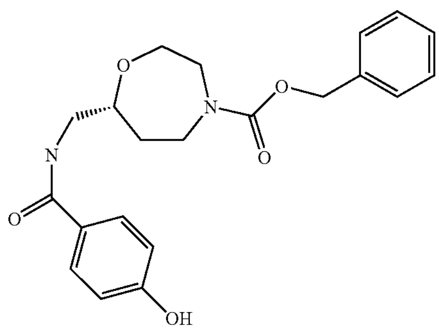 | 7-[(4-Hydroxy-benzoylamino)-methyl]-[1,4]oxazepane-4-carboxylic acid benzyl ester | 385.4 |

What is claimed is:

1. A compound having the Formula (I):

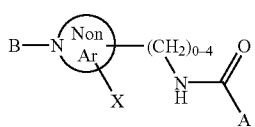

or a pharmaceutically acceptable salt thereof, wherein

NonAr is a nonaromatic 6 membered ring containing 1 nitrogen ring atom, wherein the remaining ring atoms are carbon;

A is a phenyl optionally substituted with 1–5 substituents, each substituent independently is $C_{1-4}$alkyl, $C_{3-7}$cycloalkyl, —$CF_3$, halogen, —OH, —CN, imidazolyl, —$C_{0-4}$alkyl-N($C_{0-5}$alkyl)($C_{0-5}$alkyl), —O—$C_{1-4}$alkyl, —C(O)—$C_{0-4}$alkyl, —C(O)—O—$C_{0-4}$alkyl, —O—C(O)—$C_{0-4}$alkyl, —O—C(O)—$C_{0-4}$alkylphenyl, —$C_{0-4}$alkyl—N($C_{0-5}$alkyl)-C(O)—$C_{0-4}$alkyl, —$C_{0-4}$alkyl-N($C_{0-5}$alkyl)-C(O)—O—$C_{0-4}$alkyl, —$C_{0-4}$alkyl-N($C_{0-5}$alkyl)-C(O)—O—$C_{1-4}$alkyl, or —$NHSO_2$—$C_{1-4}$alkyl, —O—$C_{1-4}$alkylphenyl, or hydroxyiminoethyl; any alkyl optionally substituted with 1–6 —OH or halogen; or A is pyrrolyl, imidazolyl, pyrazolyl, triazolyl, thiophenyl, thiazolyl, thiadiazolyl, oxazolyl, or isoxazolyl, each optionally substituted with 1–3 substituents, each substituent independently is —$C_{1-4}$alkyl, —$C_{3-7}$cycloalkyl, —$CF_3$, halogen, —OH, —CN, —$C_{1-4}$alkoxyl, phenyl, —$C_{0-4}$alkyl-N($C_{0-5}$alkyl)($C_{0-5}$alkyl), —$C_{1-4}$ hydroxyalkyl; or A is pyridyl, pyradazinyl, pyrimidinyl, or pyrazinyl, each optionally substituted with 1–5 substituents; each substituent independently is —$C_{1-4}$alkyl, —$C_{3-7}$cycloalkyl, —$CF_3$, halogen, —OH, —CN, phenyl, pyrrolidinyl, azepanyl, —$C_{1-4}$hydroxyalkyl, —$C_{1-4}$alkoxy, $(CH_3)_2N$—$(CH_2)_2$—NH—, —$SO_2$—$C_{1-4}$alkyl, —$C_{0-4}$alkyl-N($C_{0-5}$alkyl)($C_{0-5}$alkyl), —$C_{0-4}$alkyl-N($C_{3-6}$cycloalkyl)($C_{0-5}$alkyl), —$C_{0-4}$alkyl-N($C_{0-5}$alkyl)($C_{1-4}$alkyloxy$C_{1-4}$alkyl), —N($C_{0-5}$alkyl)-$C_{0-4}$alkyl-phenyl ($C_{1-4}$alkoxyl)$_{0-3}$, —N($C_{0-5}$alkyl)—$C_{0-4}$ alkylthiaphenyl, dimethoxyphenyl-$CH_2$—NH—; any phenyl optionally substituted with 1–5 —OH, halogen, or C$_{1-4}$alkyl; any alkyl optionally substituted with 1–5 —OH or halogen; or the substituent taken with a neighboring bond is =O; or A is pyrrolophenyl, pyrazolophenyl, triazolophenyl, pyridinoimidazolyl, naphthyridinyl, tetrahydrocyclopentopyrazolyl, quinolinyl, pyrimidinopyrazololyl, benzothiazolyl, benzoimidazolyl, benzoxazolonyl, oxodihydrobenzoxazolyl, indolinonyl, oxadihydroquinolinyl, oxatetrahydroquinolinyl, or purinyl, each optionally substituted with 1–5 substituents, each substituent independently is —C$_{1-4}$alkyl, —C$_{3-7}$cycloalkyl, —CF$_3$, halogen, —OH, or —CN;

B is aryl(CH$_2$)$_{0-3}$—O—(CH$_2$)$_{0-2}$—C(O)—, heteroaryl (CH$_2$)$_{1-3}$—O—(CH$_2$)$_{0-2}$—C(O)—, indanyl(CH$_2$)$_{0-3}$—O—(CH$_2$)$_{0-2}$—C(O)—, aryl-cyclopropyl-C(O)—(CH$_2$)$_{0-2}$—, heteroaryl(CH$_2$)$_{1-3}$—C(O)—, aryl (CH$_2$)$_{1-3}$—, heteroaryl(CH$_2$)$_{1-3}$—, aryl(CH$_2$)$_{1-3}$—NH—C(O)—, aryl(CH$_2$)$_{1-3}$—NH—C(NCN)—, aryl (CH$_2$)$_{1-3}$—SO$_2$—, aryl(CH$_2$)$_{0-3}$—S—(CH$_2$)$_{0-2}$—C(O)—, or heteroaryl(CH$_2$)$_{1-3}$—SO$_2$— wherein any of the aryl or heteroaryl is optionally substituted by 1–5 substituents, each substituent independently is C$_{1-4}$alkyl, C$_{3-6}$cycloalkyl, C$_{1-4}$alkoxy, trifluoromethyl, phenyl, —O—C$_{1-4}$alkylphenyl, —S(O)—C$_{1-4}$alkyl, bromo, fluoro, chloro, or 2 substituents together form methylene dioxy; any (CH$_2$) optionally is substituted with C$_{1-2}$alkyl; or B is

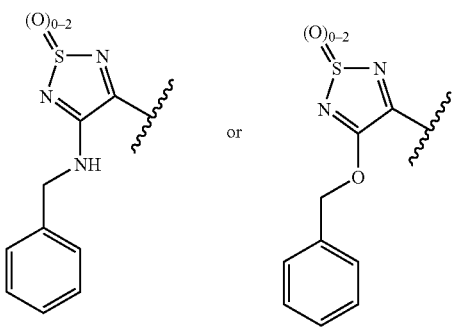

wherein the phenyl is optionally substituted by 1–3 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, —N(C$_{0-5}$alkyl)(C$_{0-5}$alkyl), phenyl, or =O.

2. The compound according to claim 1, or a pharmaceutically acceptable salt thereof, wherein A is a phenyl optionally substituted with 1–5 substituents, each substituent independently is C$_{1-4}$alkyl, C$_{3-7}$cycloalkyl, —CF$_3$, halogen, —OH, —CN, imidazolyl, —C$_{0-4}$alkyl-N(C$_{0-5}$alkyl)(C$_{0-5}$alkyl), —O—C$_{1-4}$alkyl, —C(O)—C$_{0-4}$alkyl, —C(O)—O—C$_{0-4}$alkyl, —O—C(O)—C$_{0-4}$alkyl, —O—C(O)—C$_{0-4}$alkylphenyl, —C$_{0-4}$alkyl-N(C$_{0-5}$alkyl)-C(O)—O—C$_{0-4}$alkyl, —C$_{0-4}$alkyl-N (C$_{0-5}$alkyl)-C(O)—O—C$_{0-4}$alkyl, —C$_{0-4}$alkyl-N(C$_{0-5}$ alkyl)-C(O)—O—C$_{1-4}$alkyl, or —NHSO$_2$—C$_{1-4}$ alkyl, —O—C$_{1-4}$alkylphenyl, or hydroxyiminoethyl; any alkyl optionally substituted with 1–6 —OH or halogen.

3. The compound according to claim 1, or a pharmaceutically acceptable salt thereof, wherein A is pyrrolyl, imidazolyl, pyrazolyl, triazolyl, thiophenyl, thiazolyl, thiadiazolyl, oxazolyl, or isoxazolyl, each optionally substituted with 1–3 substituents, each substituent independently is —C$_{1-4}$alkyl, —C$_{3-7}$cycloalkyl, —CF$_3$, halogen, —OH, —CN, phenyl, —C$_{1-4}$ hydroxyalkyl.

4. The compound according to claim 1, or a pharmaceutically acceptable salt thereof, wherein A is pyridyl, pyradazinyl, pyrimidinyl, or pyrazinyl, each optionally substituted with 1–3 substituents, each substituent independently is —C$_{1-4}$alkyl, —C$_{3-7}$cycloalkyl, —CF$_3$, halogen, —OH, —CN, phenyl, —C$_{1-4}$ hydroxyalkyl, —C$_{1-4}$alkoxy, (CH$_3$)$_2$N—(CH$_2$)$_2$—NH—, —C$_{0-4}$alkyl-N(C$_{0-4}$alkyl)(C$_{0-4}$alkyl), dimethoxyphenyl-CH$_2$—NH—, or the substituent taken with a neighboring bond is =O.

5. The compound according to claim 1, or a pharmaceutically acceptable salt thereof, wherein A is pyrrolophenyl, pyrazolophenyl, triazolophenyl, pyridinoimidazolyl, naphthyridinyl, tetrahydrocyclopentopyrazolyl, quinolinyl, pyrimidinopyrazololyl, benzothiazolyl, benzoimidazolyl, or purinyl, each optionally substituted with 1–3 substituents, each substituent independently is —C$_{1-4}$alkyl, —C$_{3-7}$cycloalkyl, —CF$_3$, halogen, —OH, or —CN.

6. The compound according to claim 1, wherein said compound is

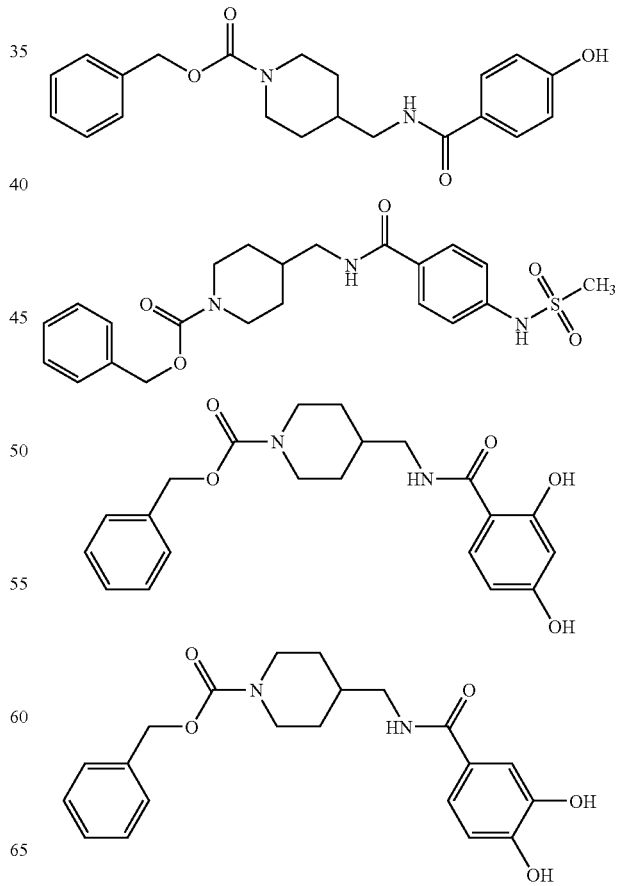

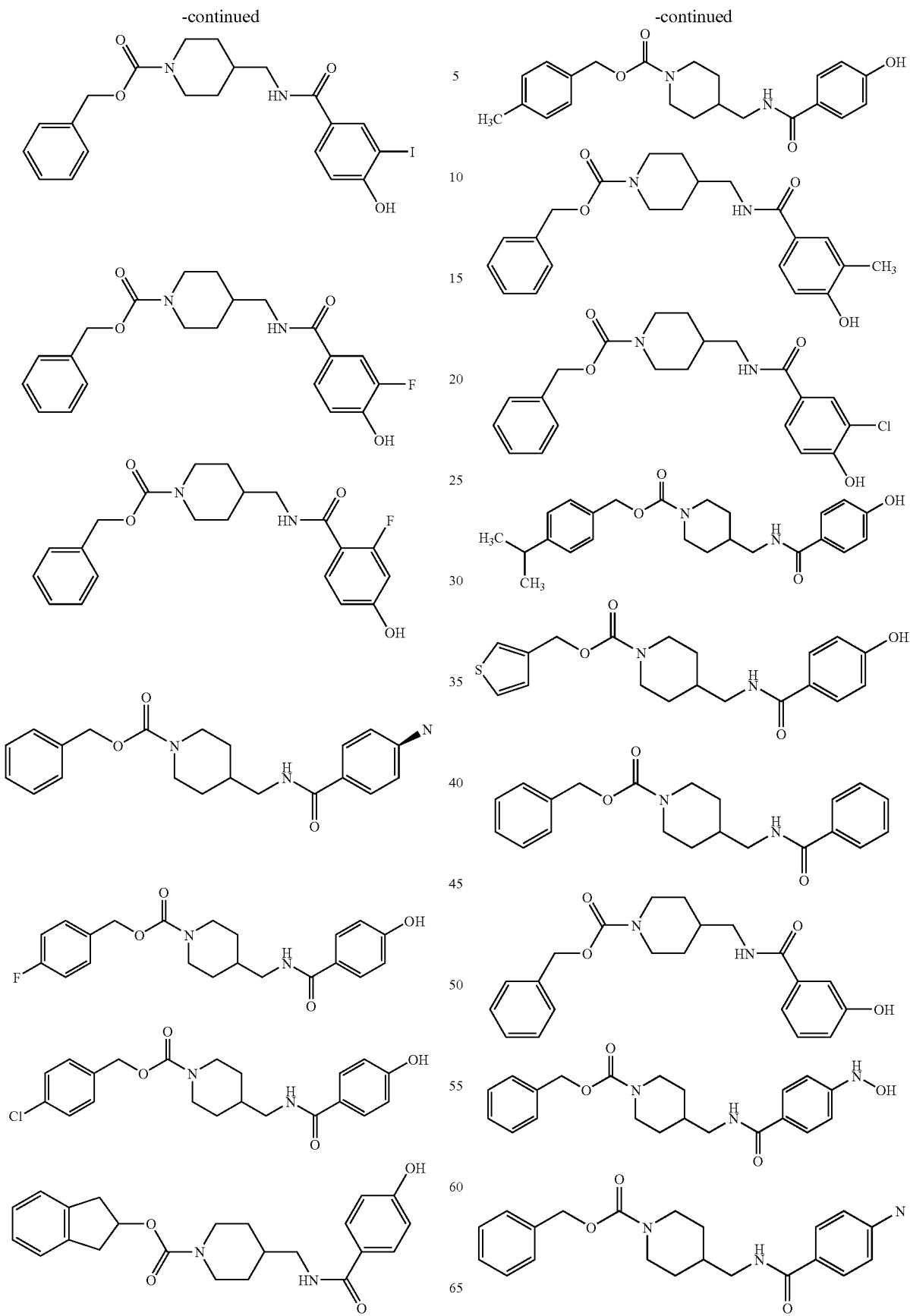

-continued
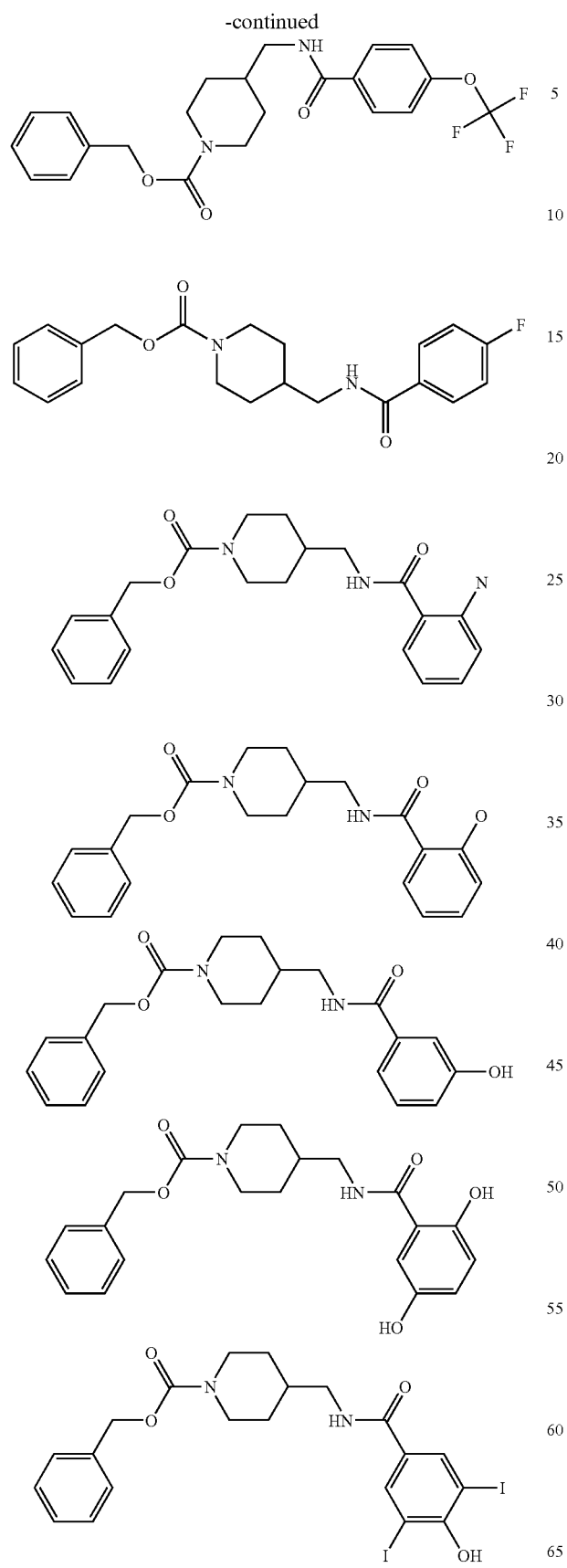
-continued
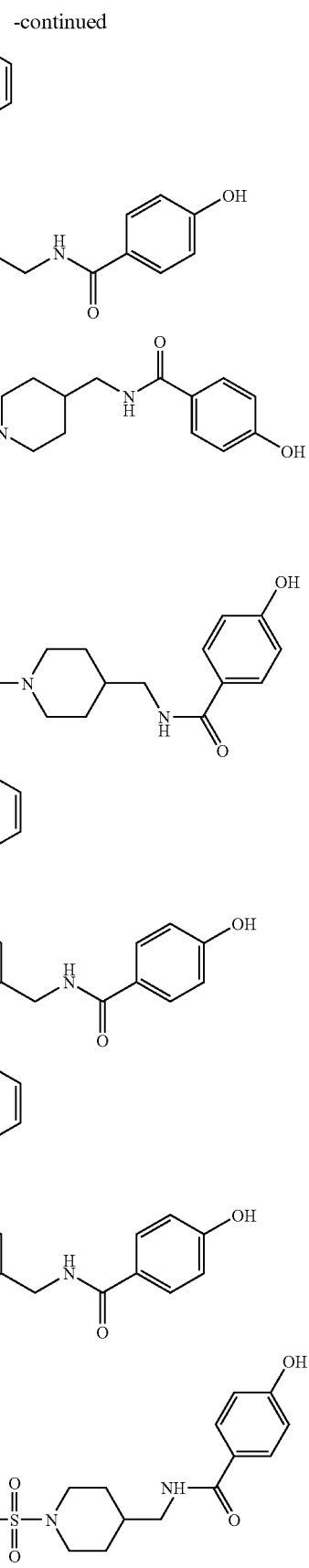

-continued
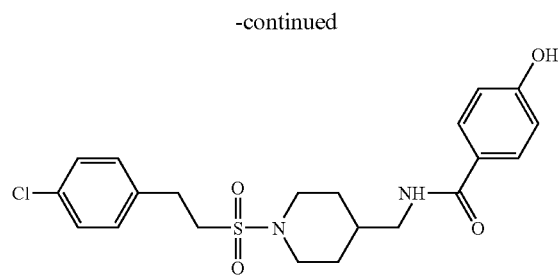
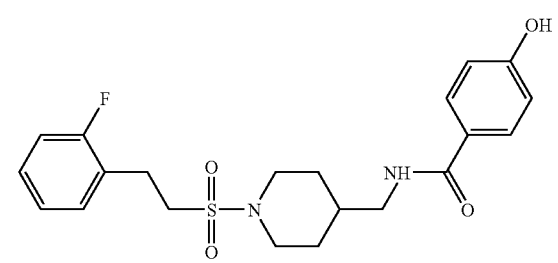
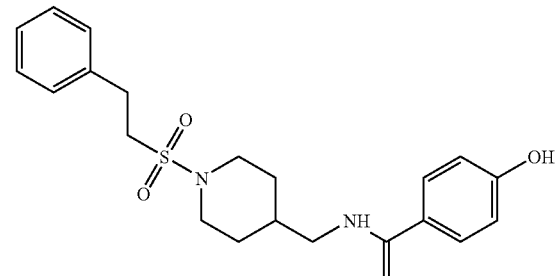
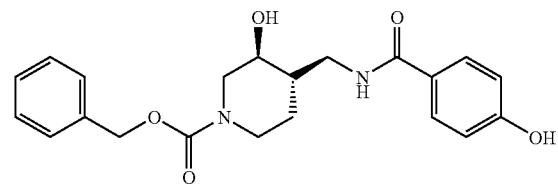
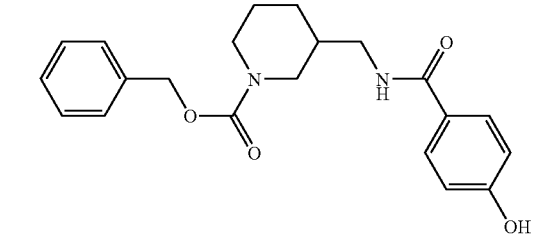
or a pharmaceutically acceptable salt thereof.
7. The compound according to claim 1, wherein said compound is
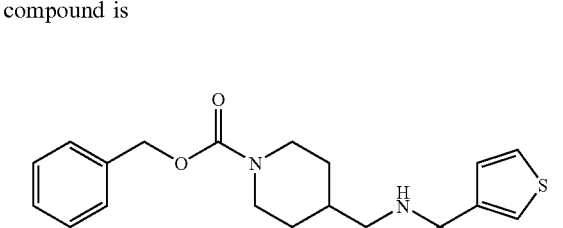
-continued
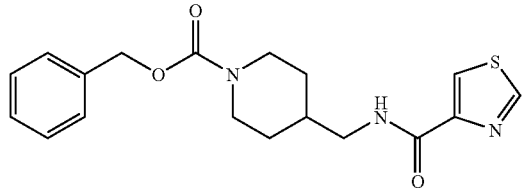
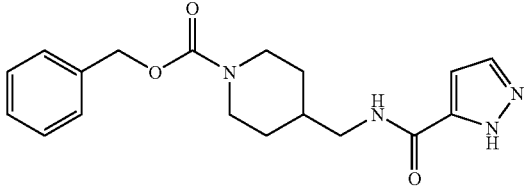
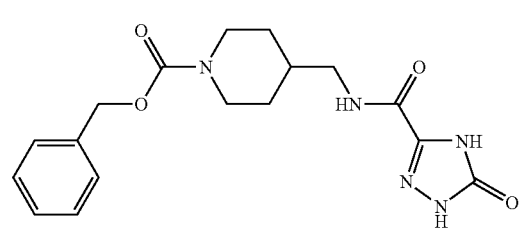
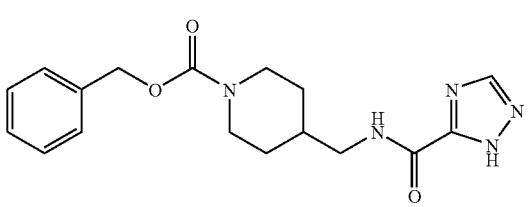
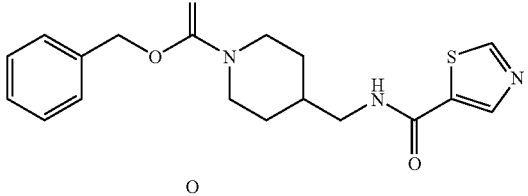
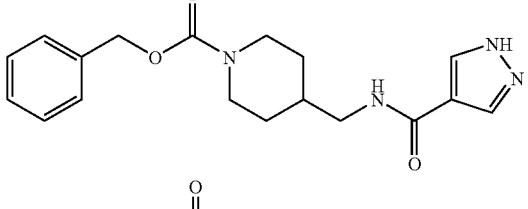
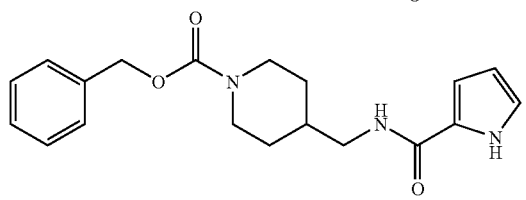
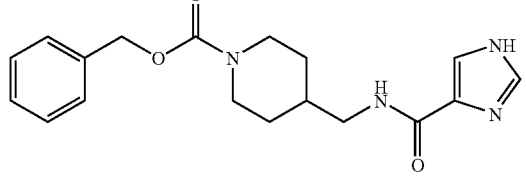

-continued
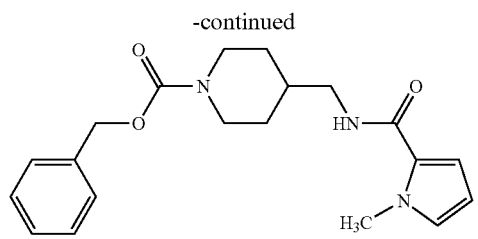
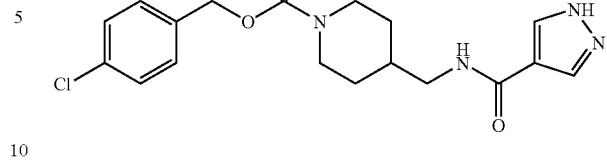
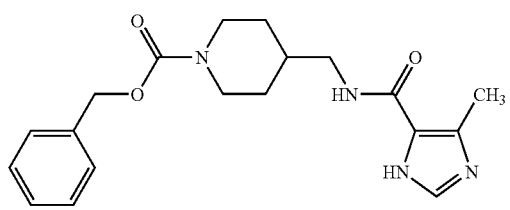
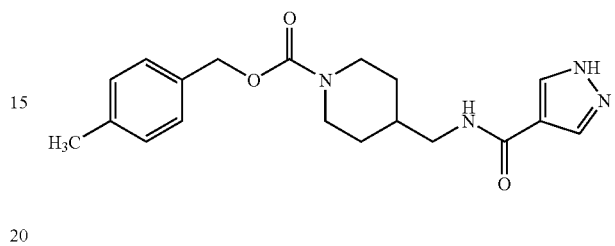
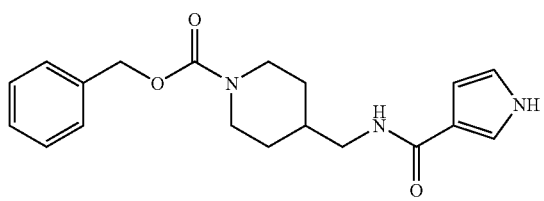
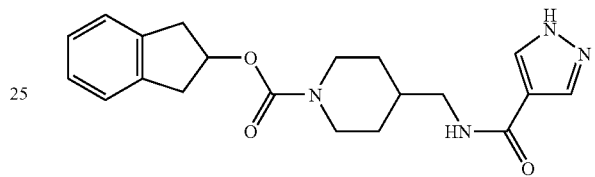
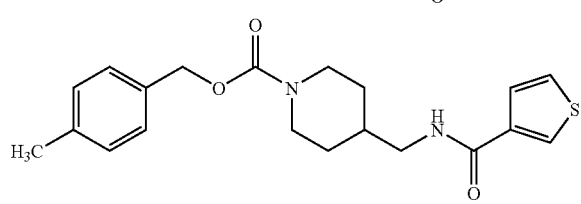
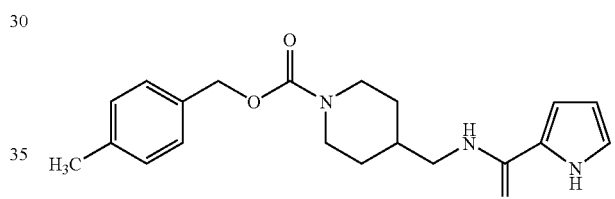
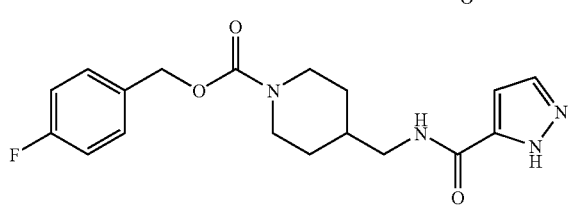
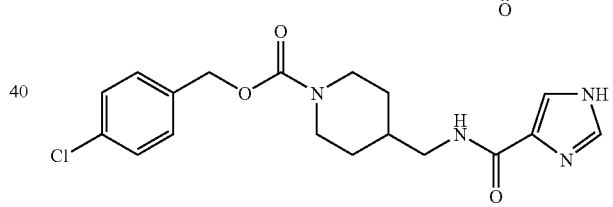
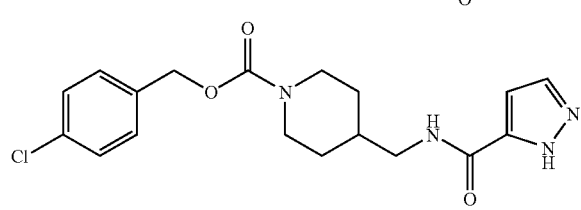
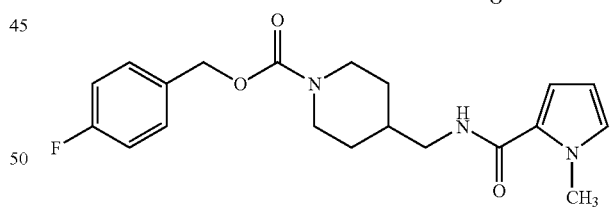
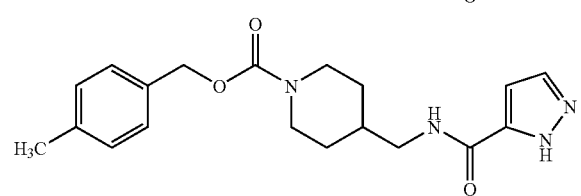
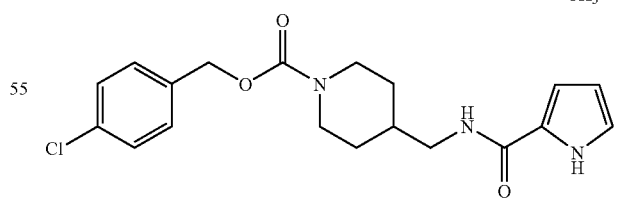
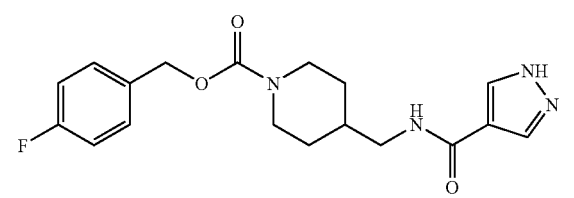
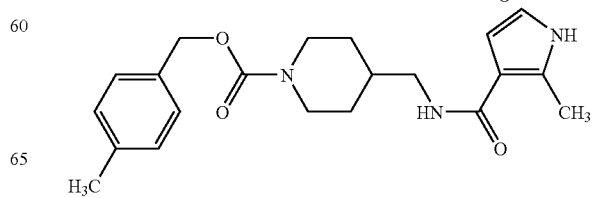

-continued
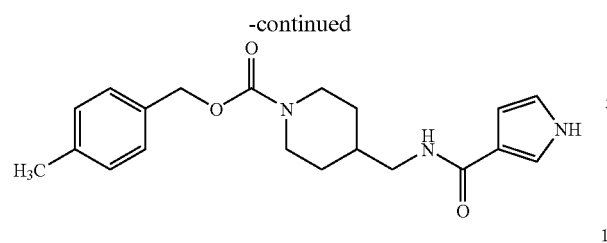
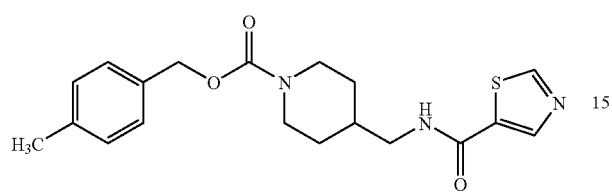
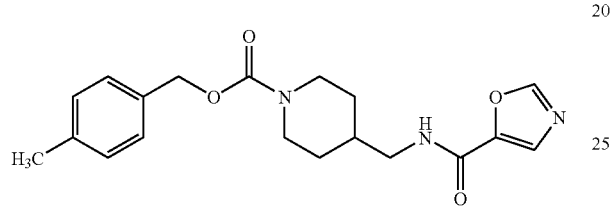
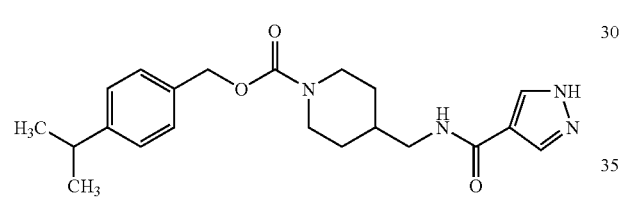
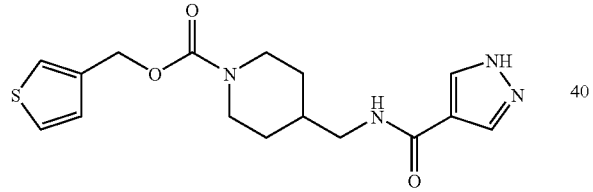
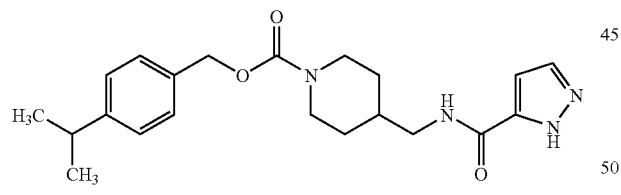
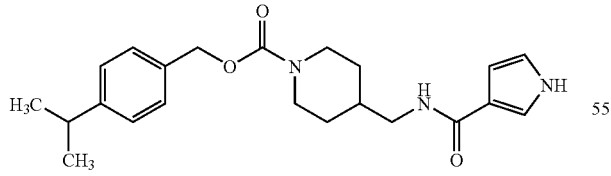
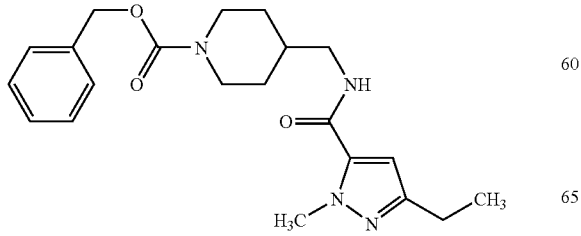
-continued
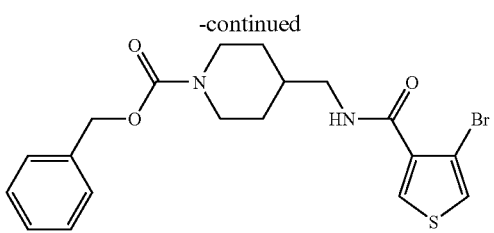
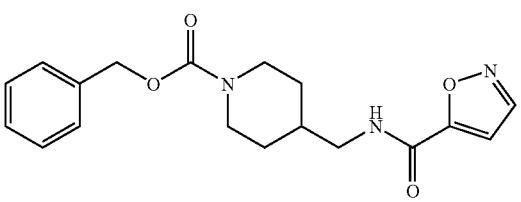
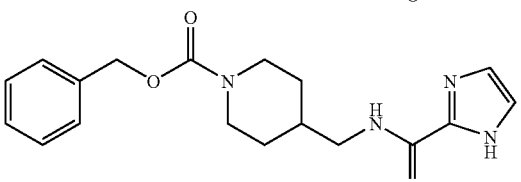
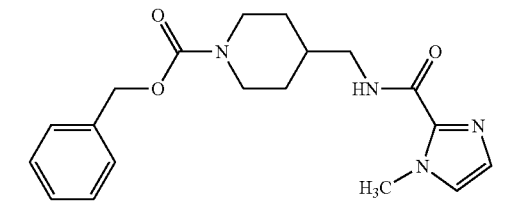
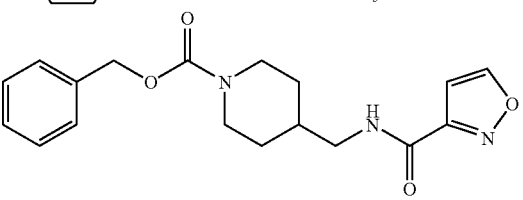
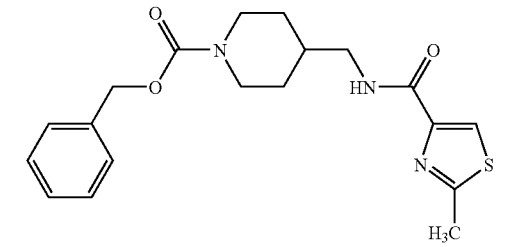
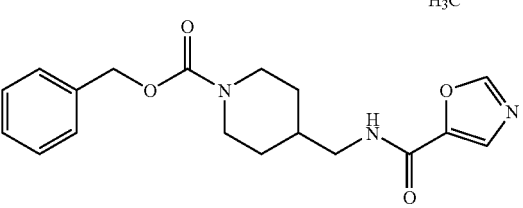
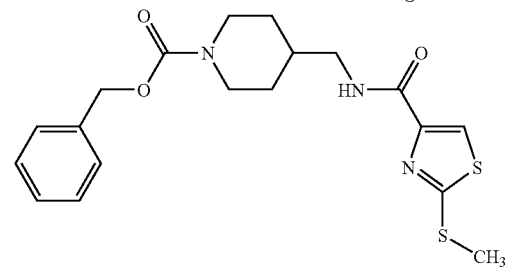

351
-continued
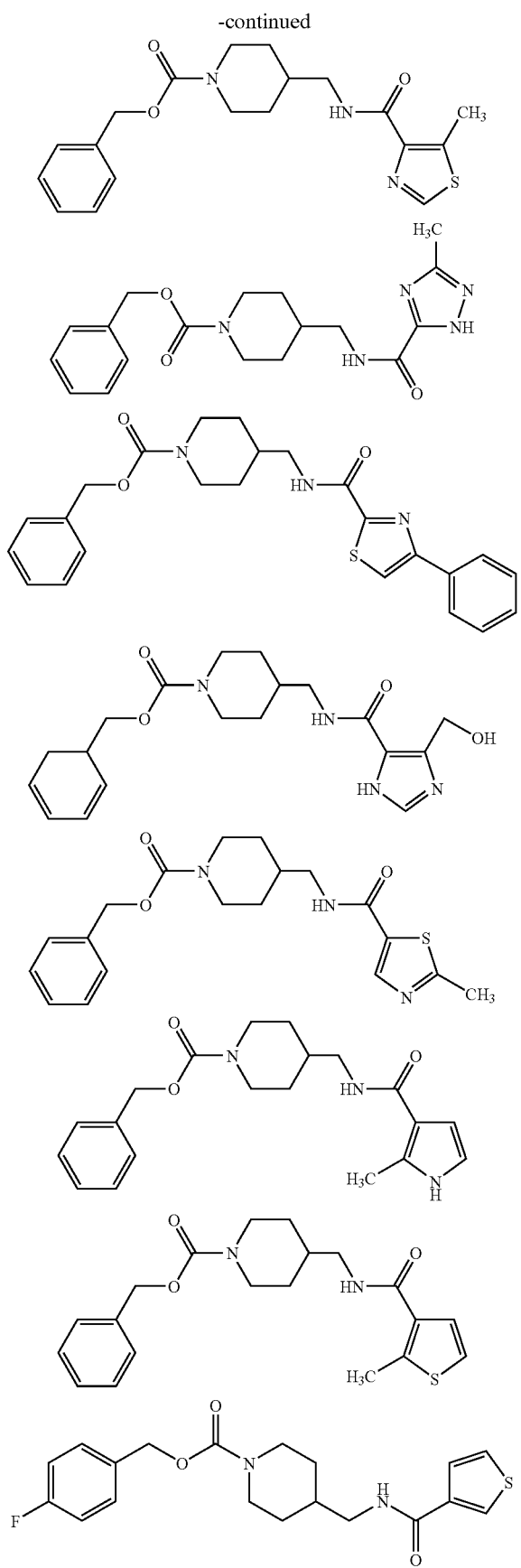
352
-continued
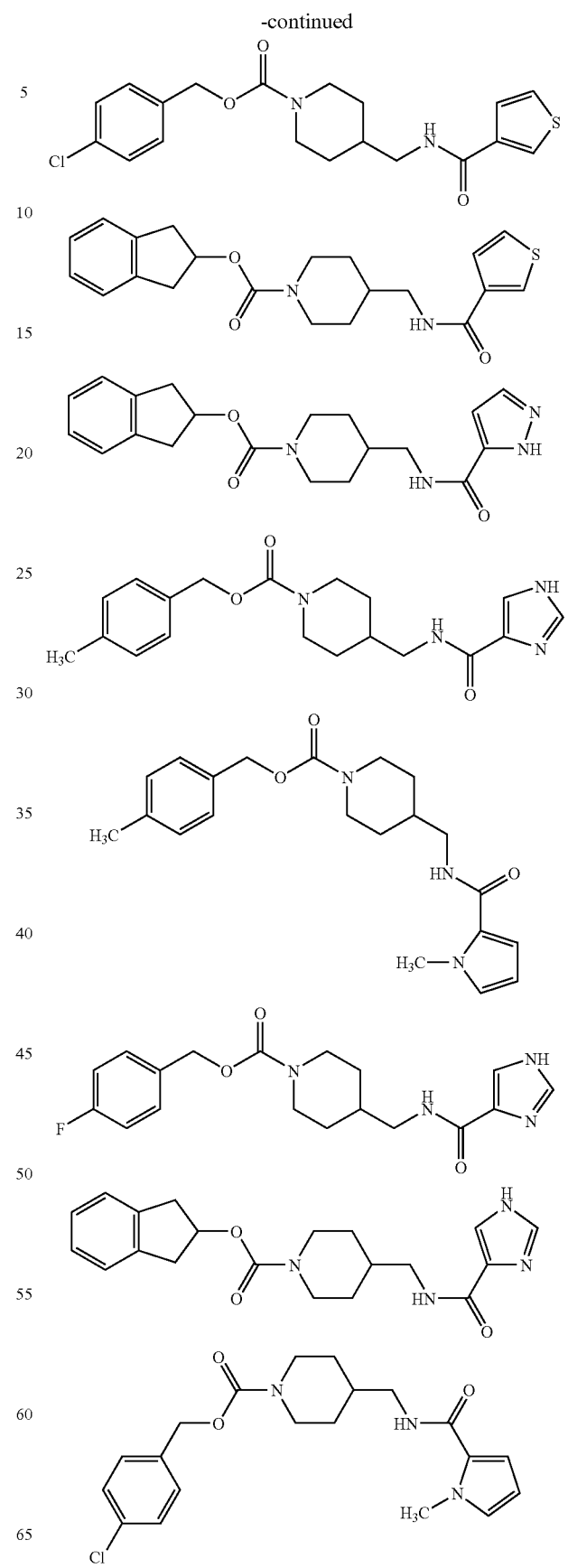

353
-continued
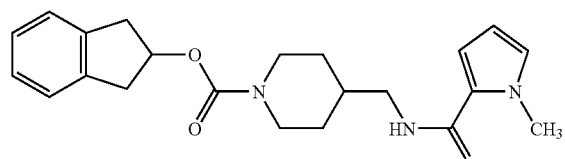
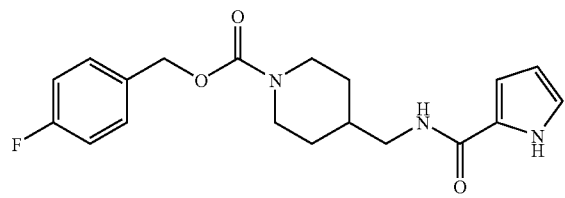
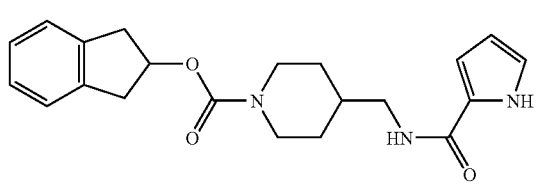
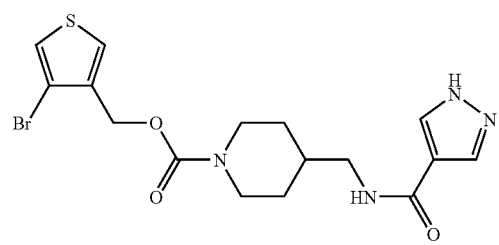
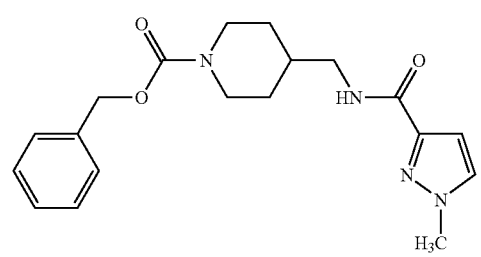
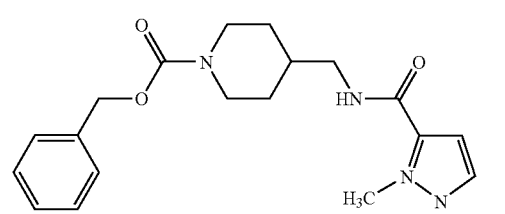
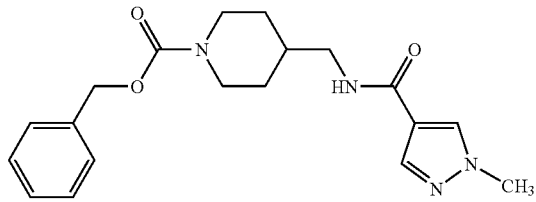
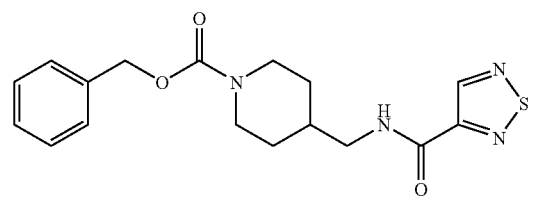
354
-continued
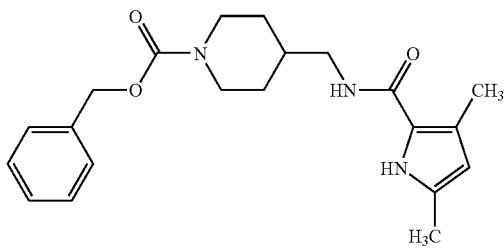
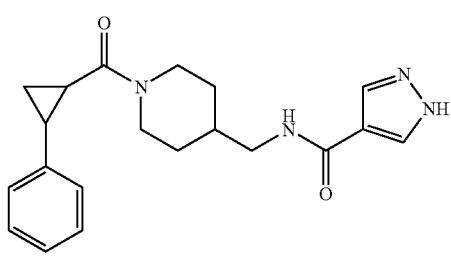
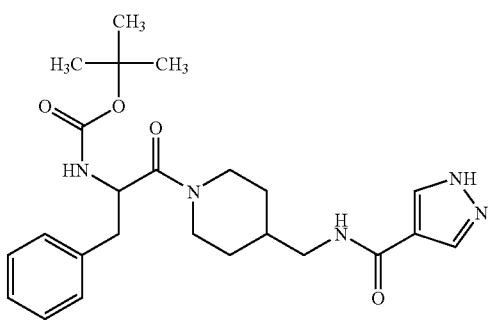
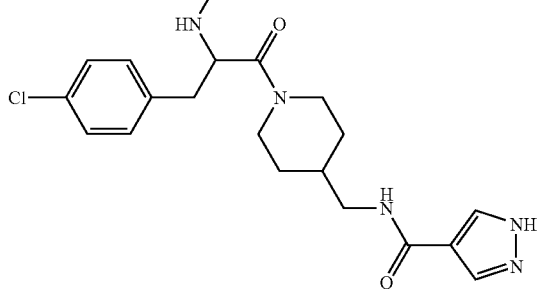
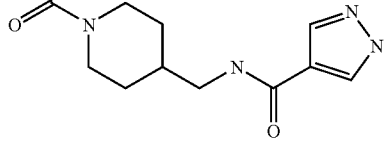

-continued
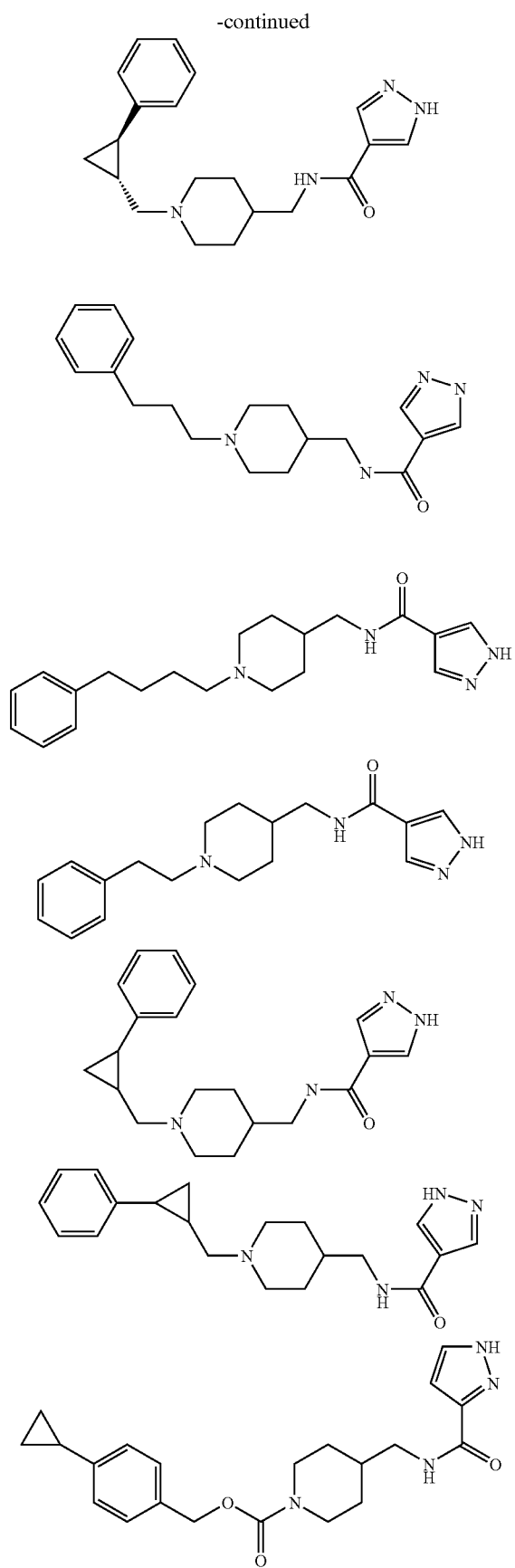
-continued
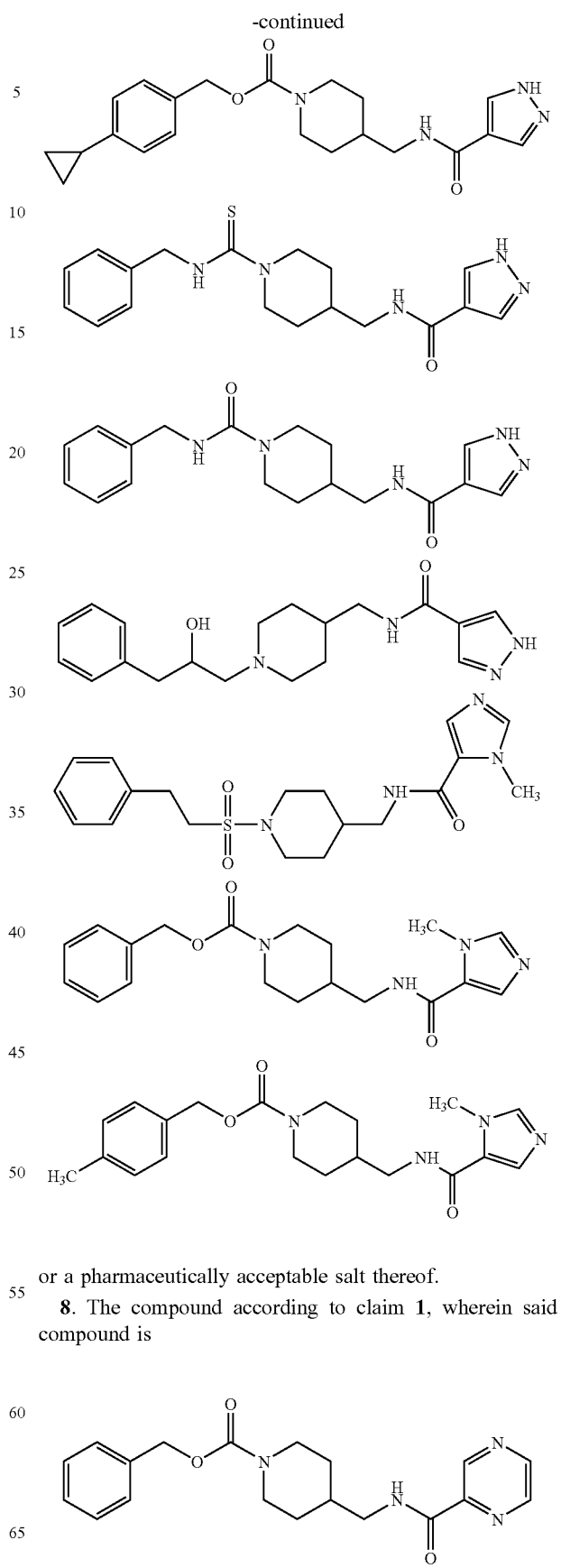
or a pharmaceutically acceptable salt thereof.
8. The compound according to claim 1, wherein said compound is
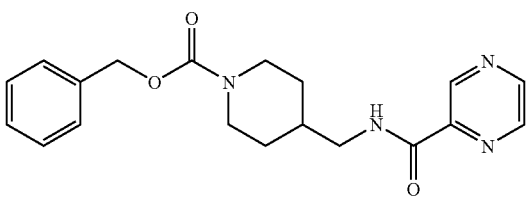

-continued
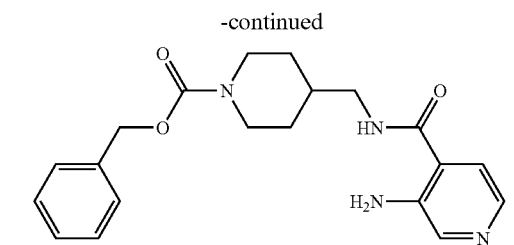
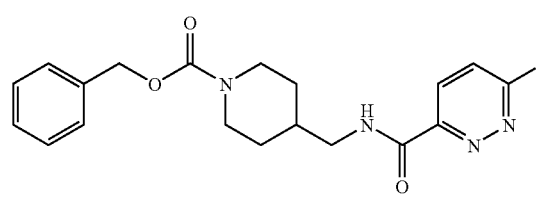
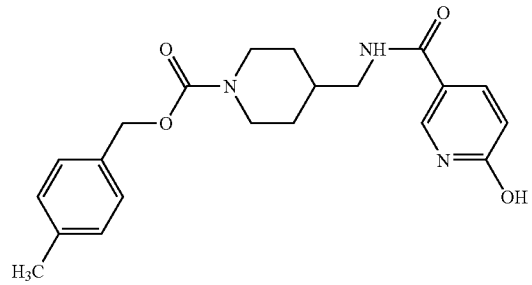
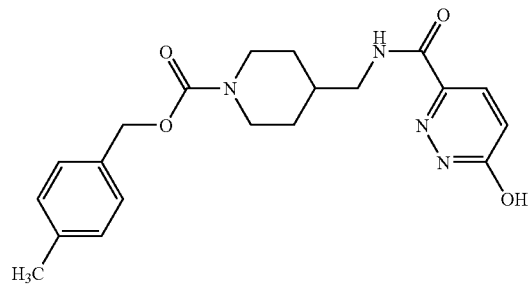
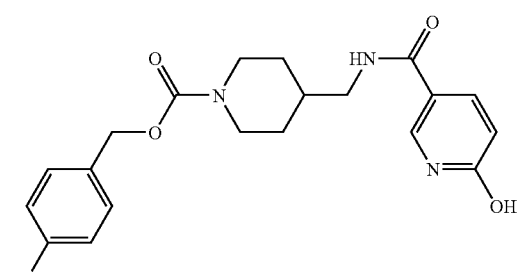
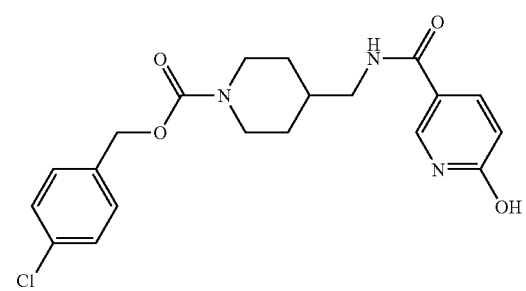
-continued
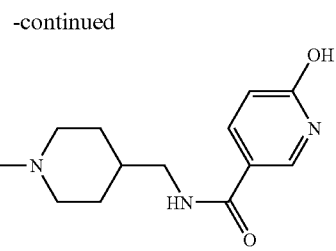
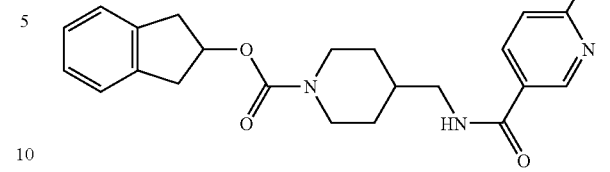
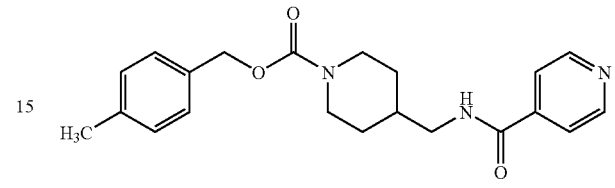
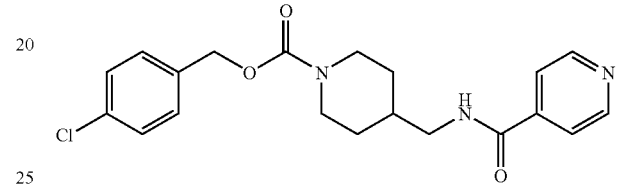
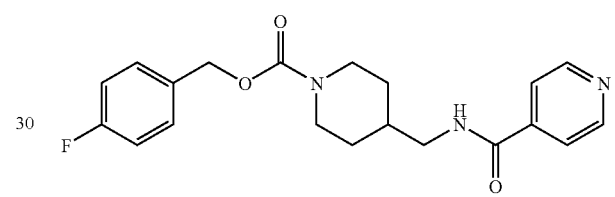
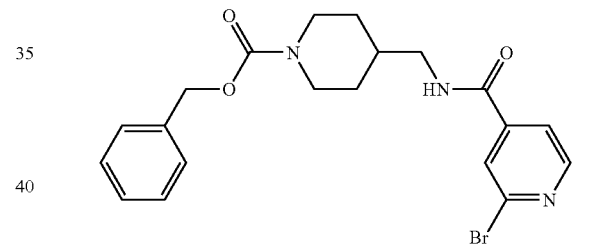
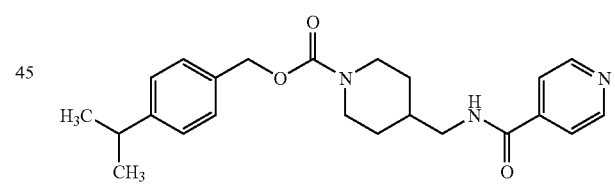
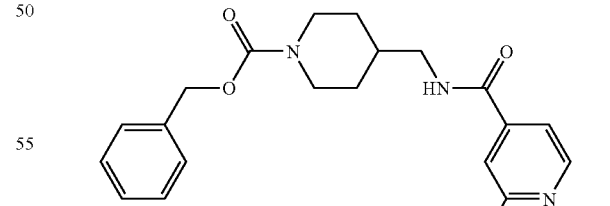
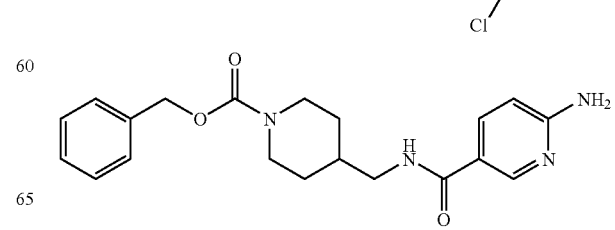

359
-continued
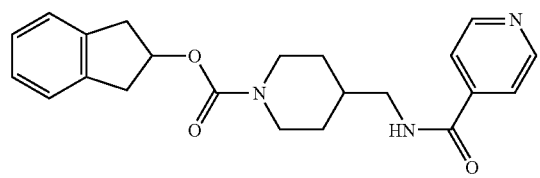
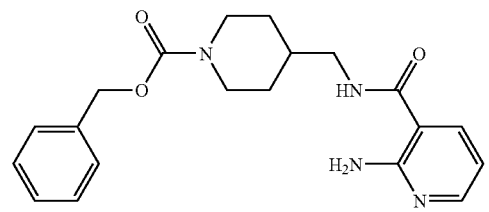
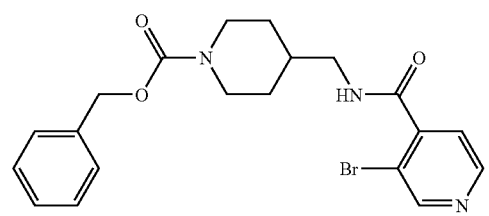
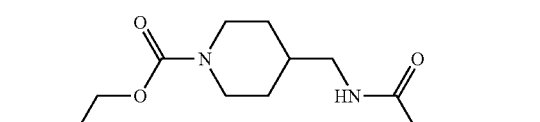
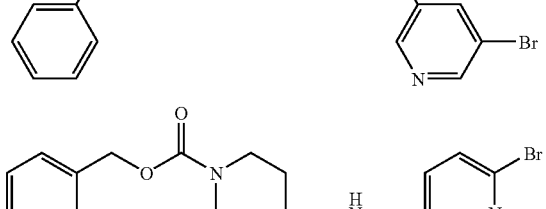
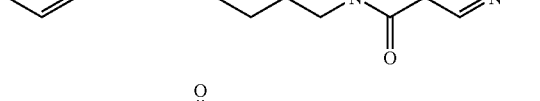
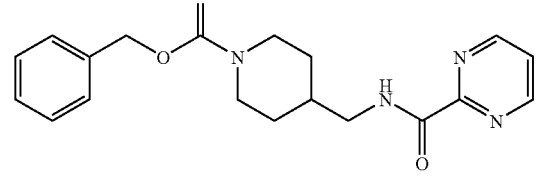
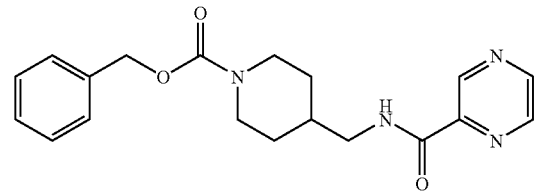
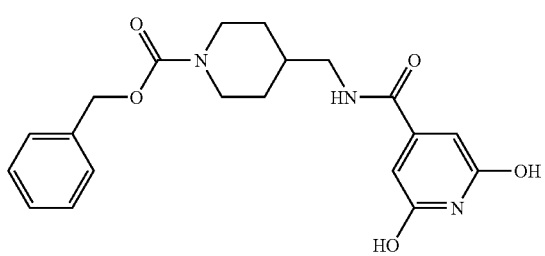
360
-continued
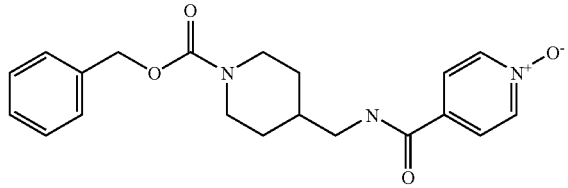
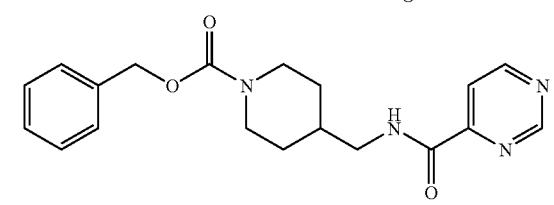
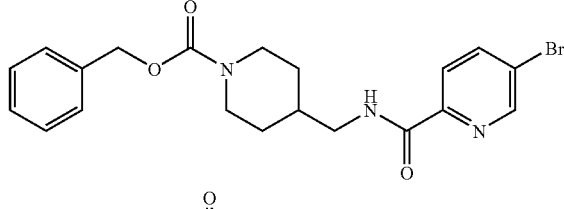
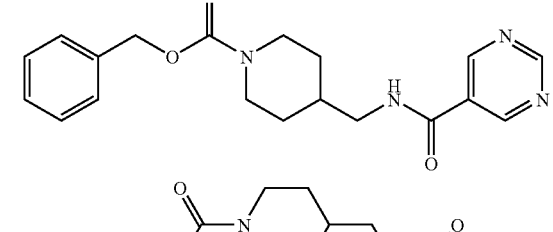
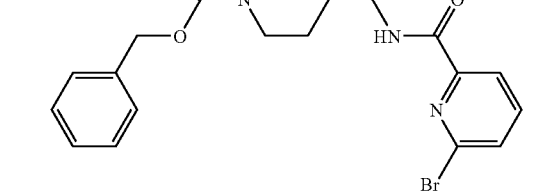
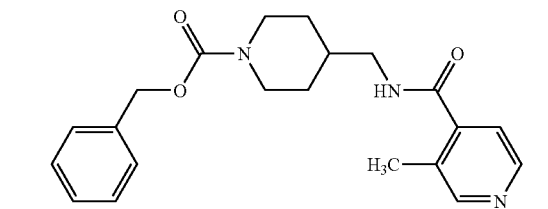
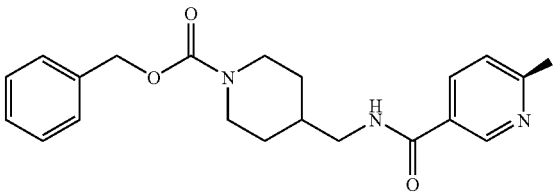
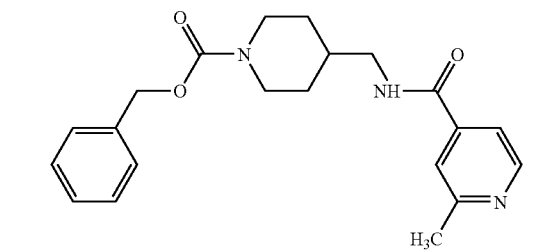

361
-continued
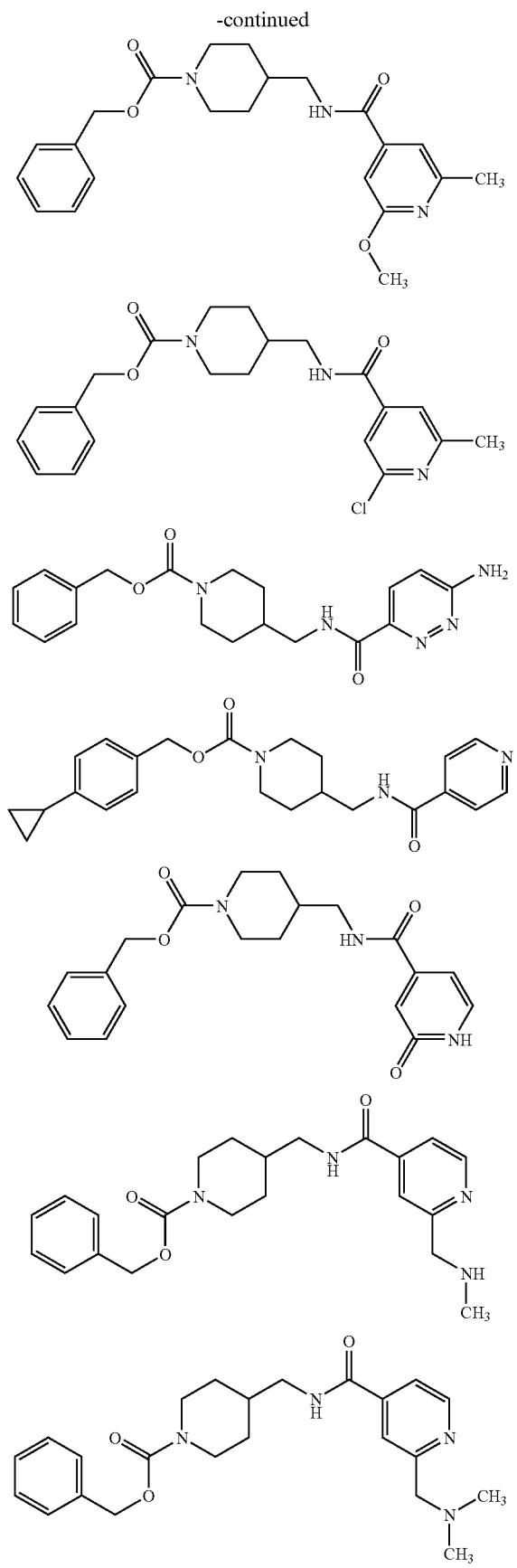
362
-continued
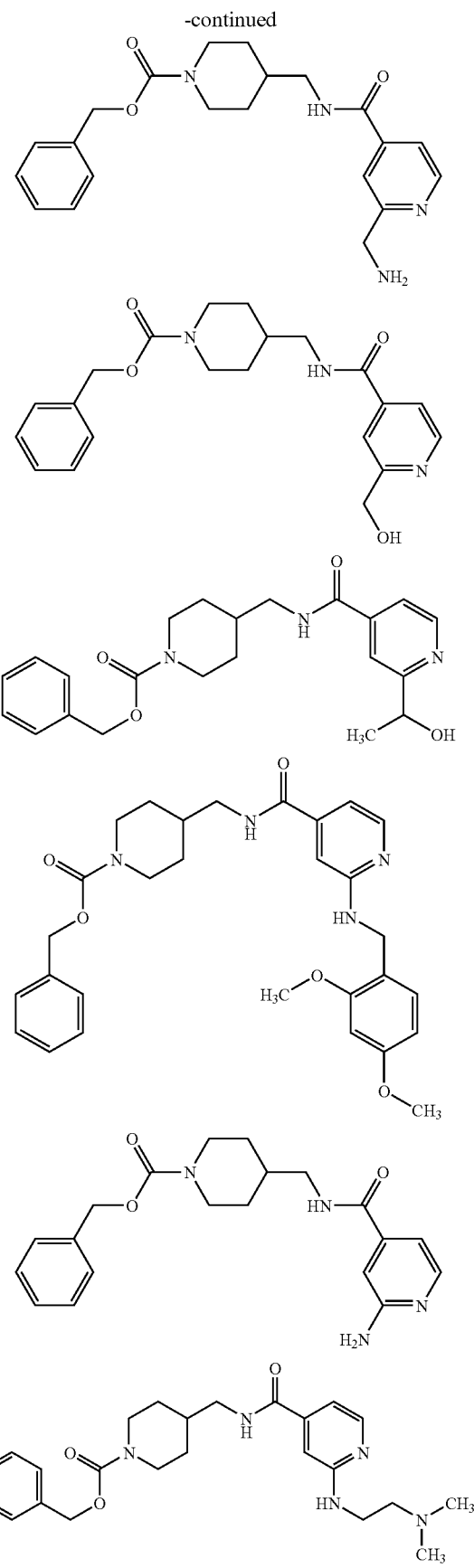

-continued
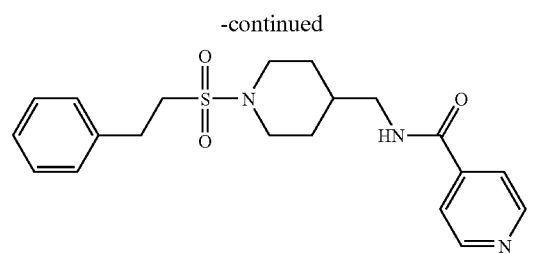
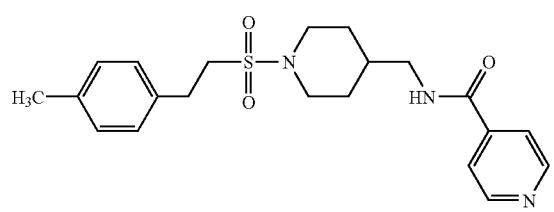
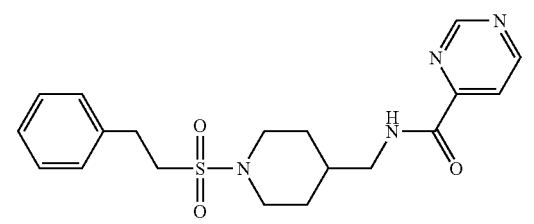
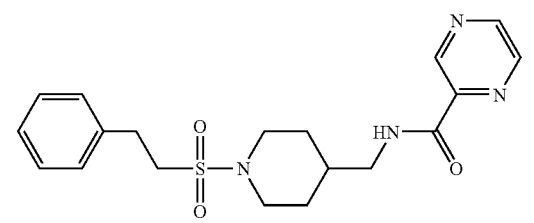
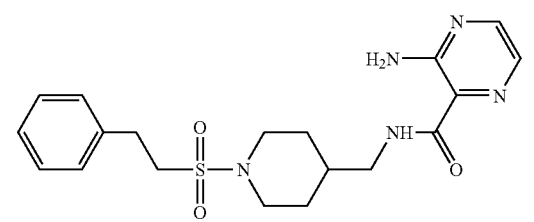
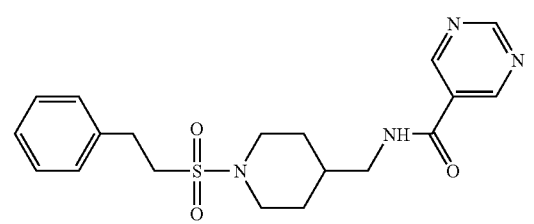
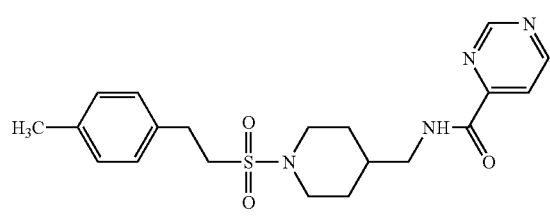
-continued
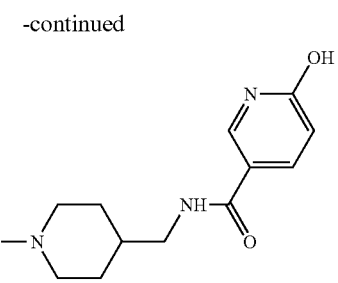
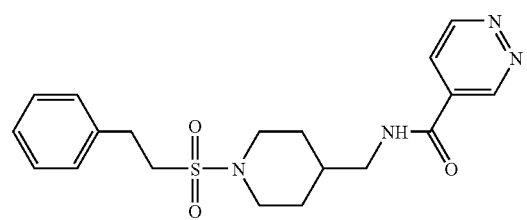
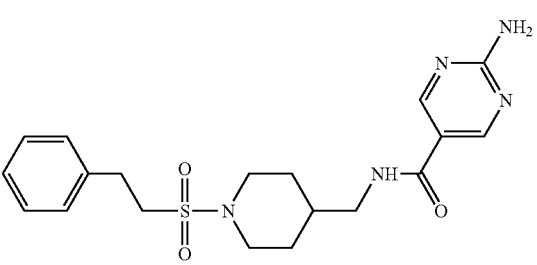
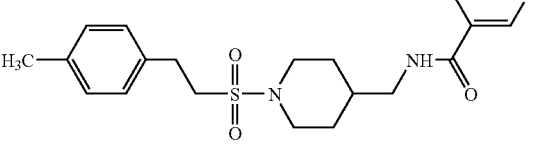
or a pharmaceutically acceptable salt thereof.
9. The compound according to claim 1, wherein said compound is
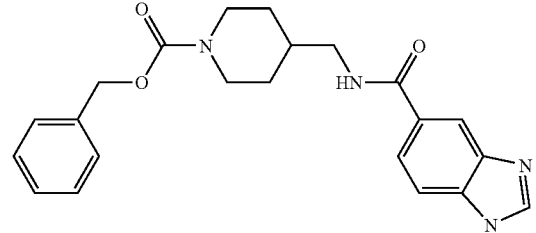
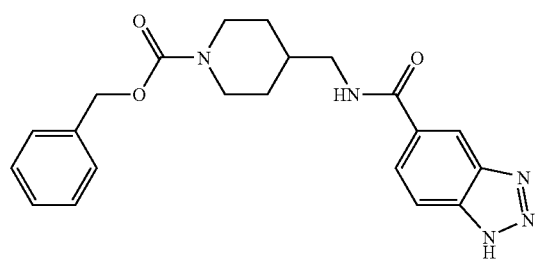

-continued
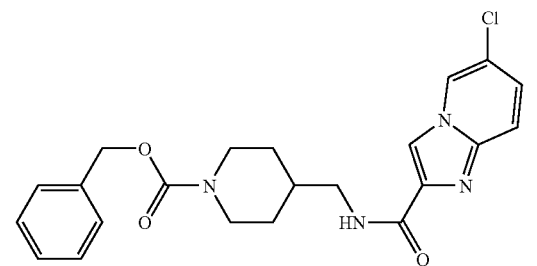
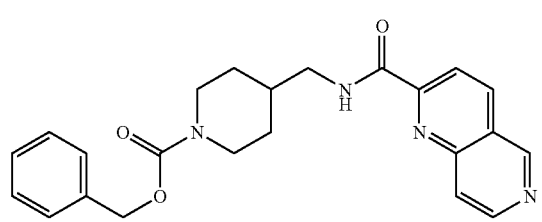
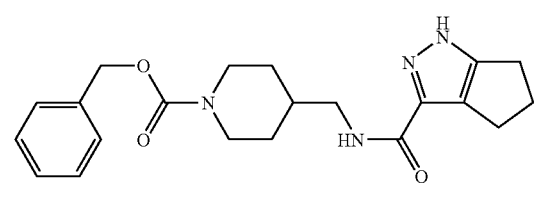
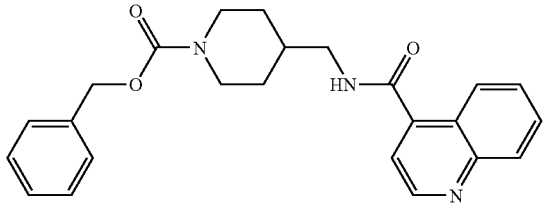
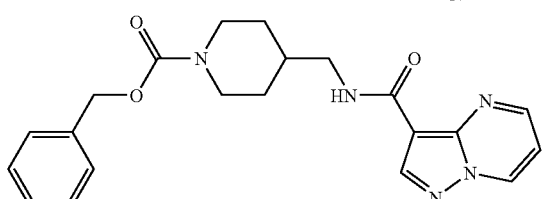
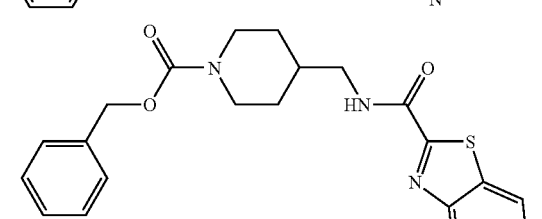
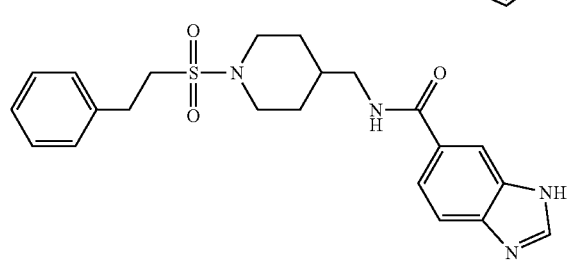
-continued
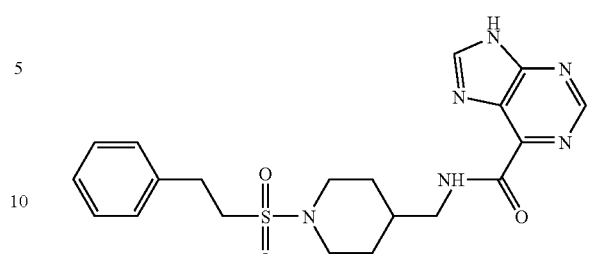
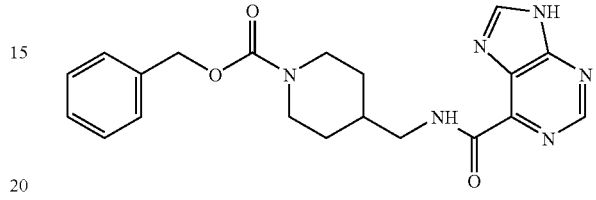
or a pharmaceutically acceptable salt thereof.
10. The compound according to claim 1, wherein said compound is
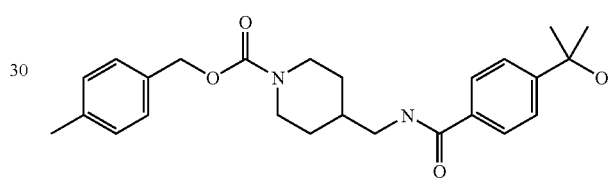
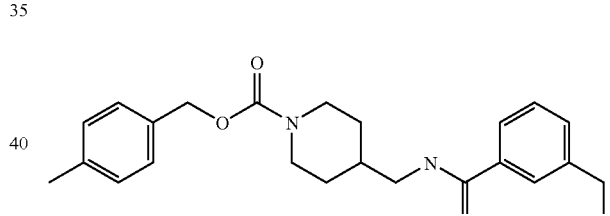
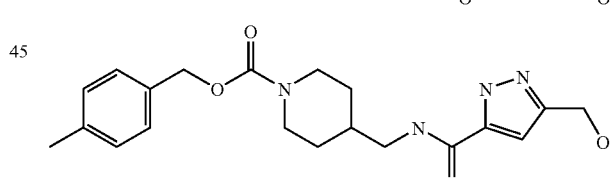
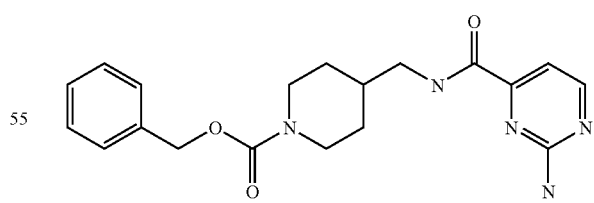
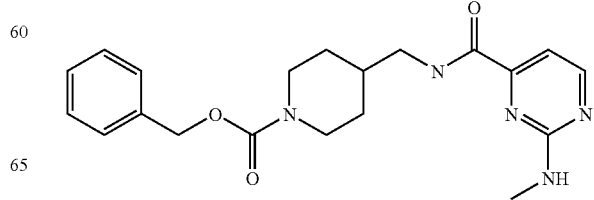

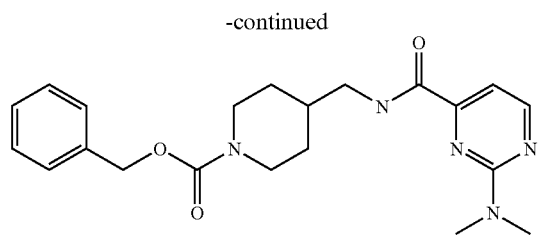
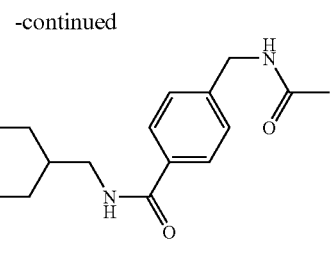
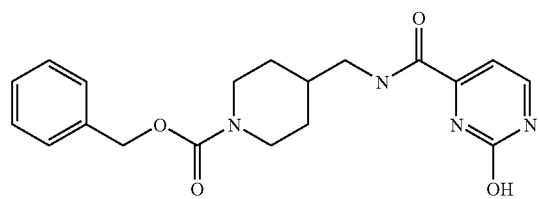
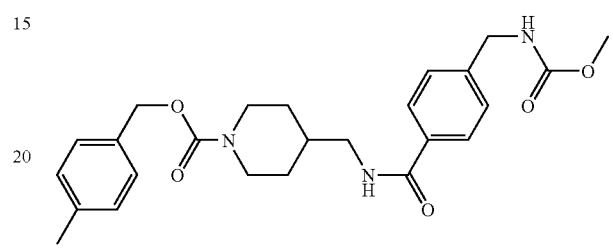
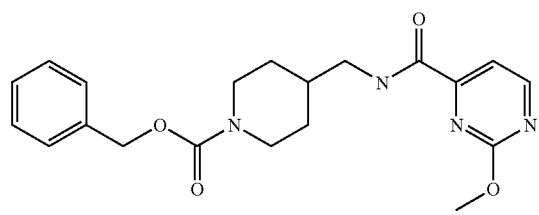
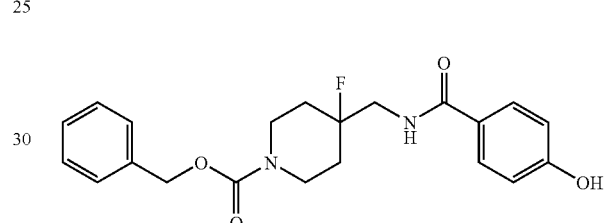
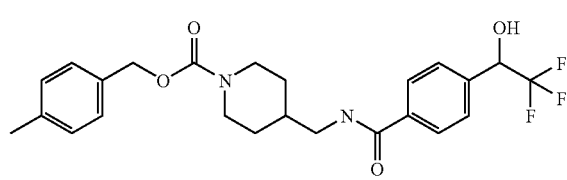
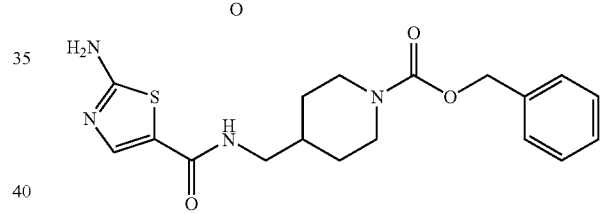
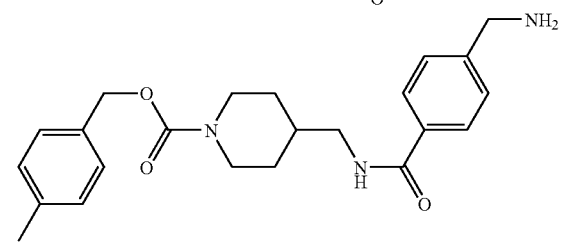
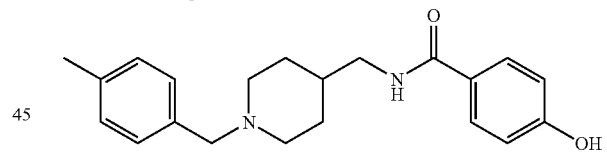
or a pharmaceutically acceptable salt thereof.
11. The compound according to claim 1, wherein said compound is
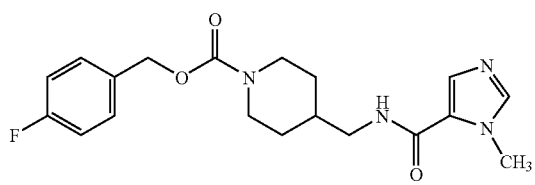
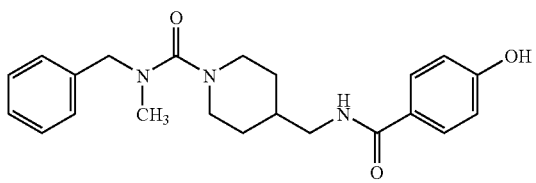

| 369 | 370 |
|---|---|
| 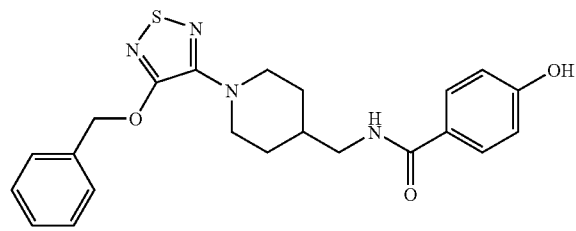 | 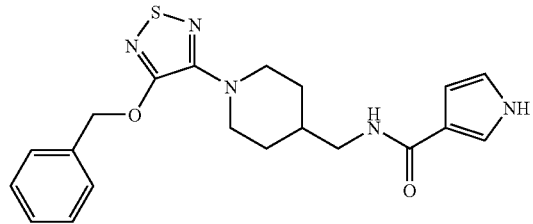 |
| 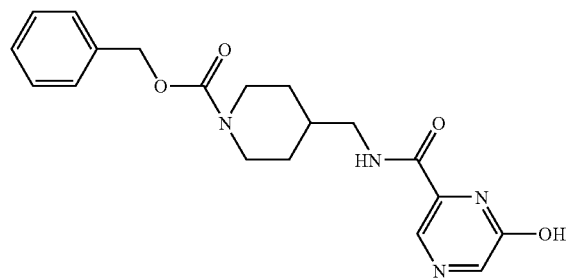 | 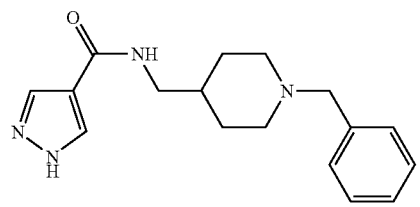 |
| 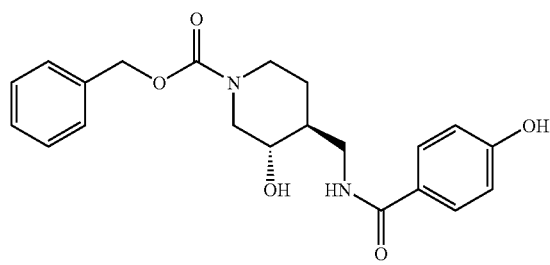 | 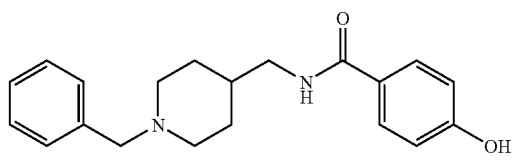 |
| 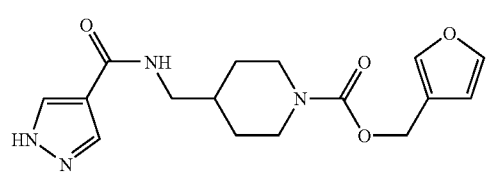 | 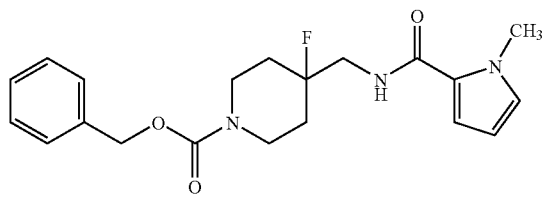 |
| 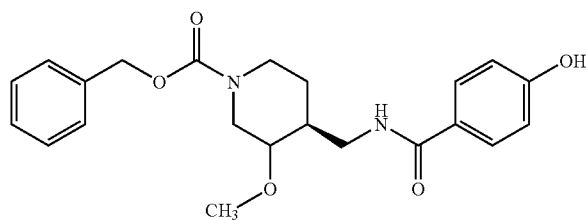 | 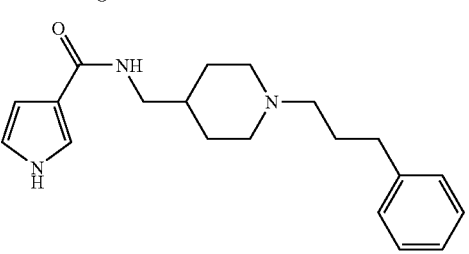 |
| 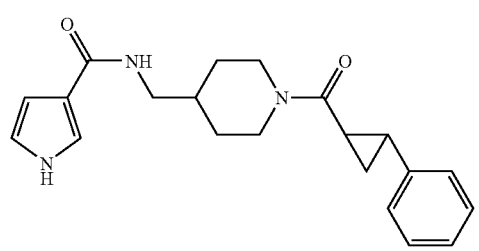 | 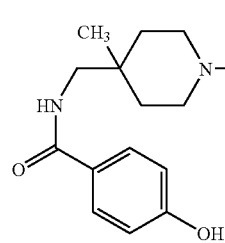 |

371
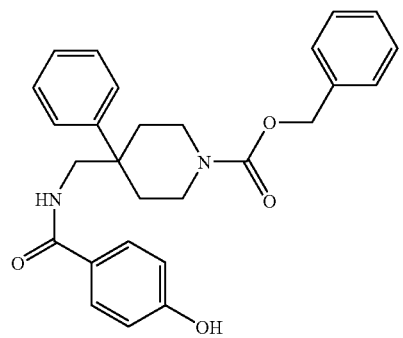
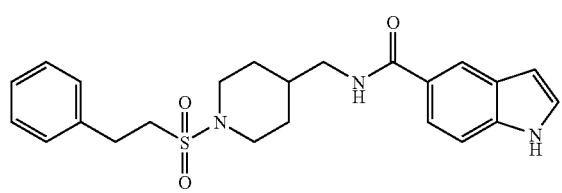
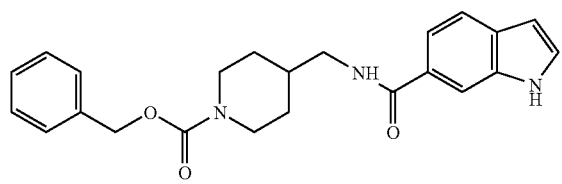
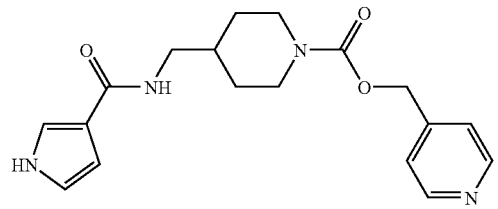
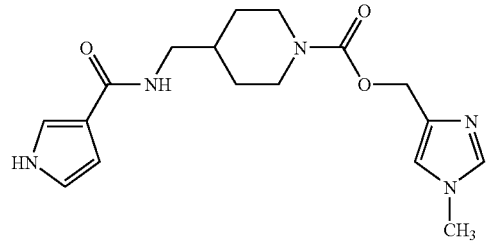
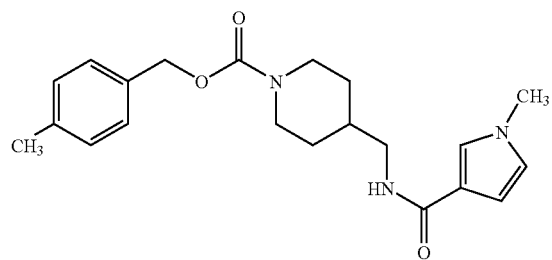
372
-continued
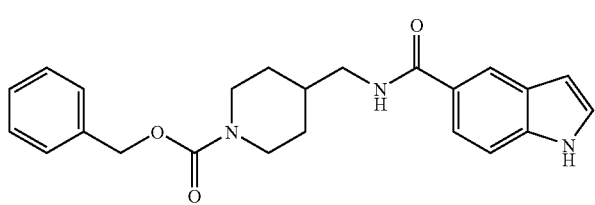
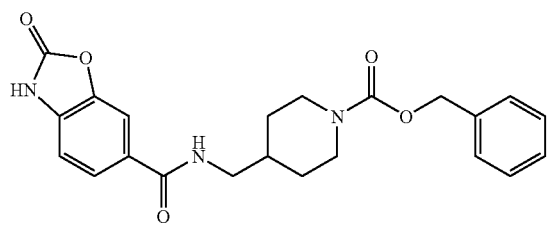
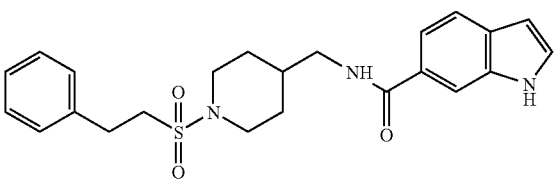
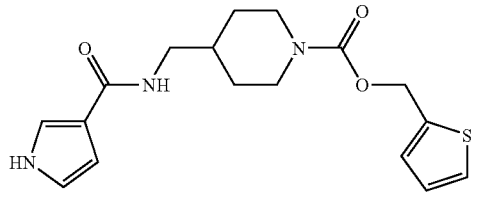
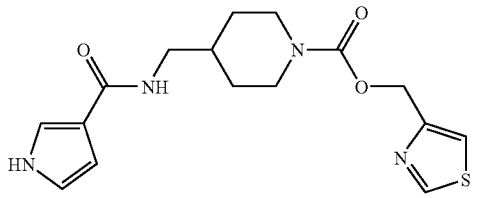
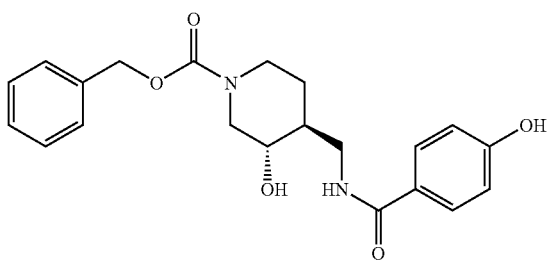

373    374
-continued
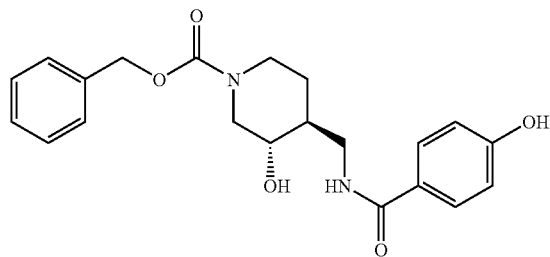
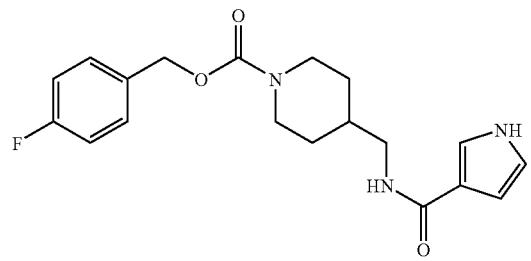
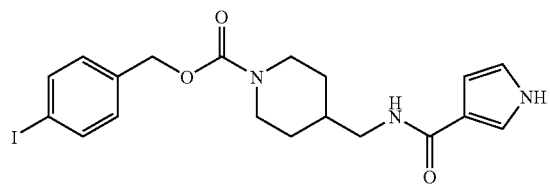
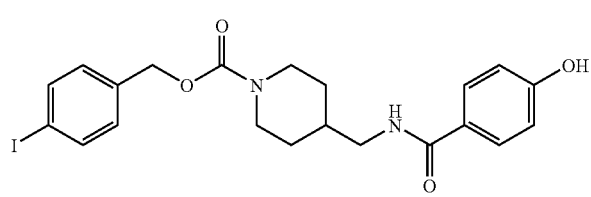
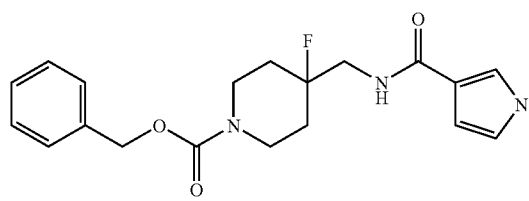
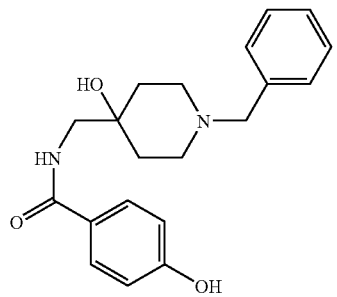
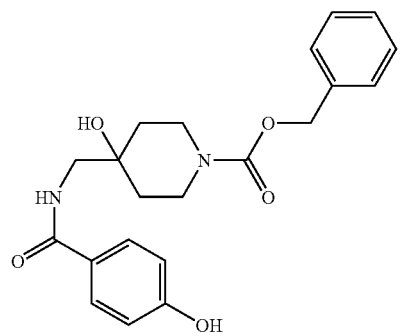
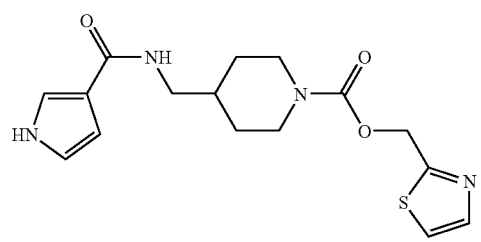
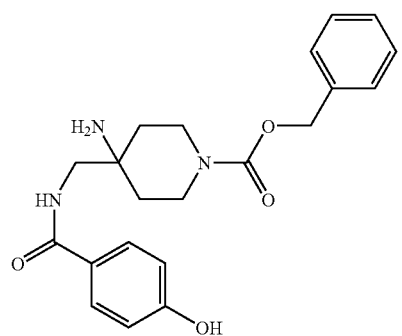
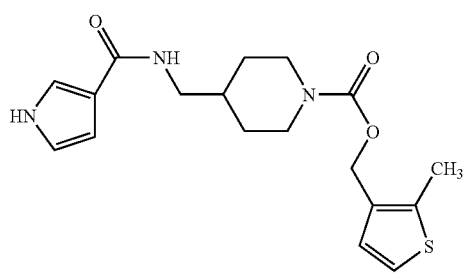

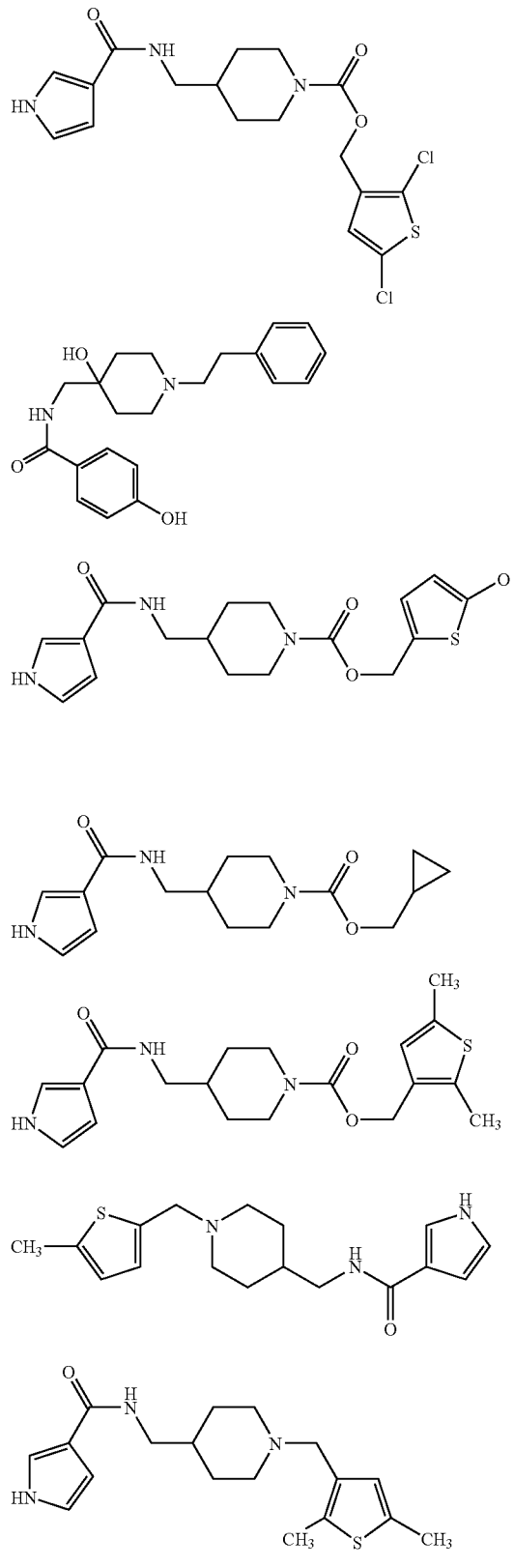
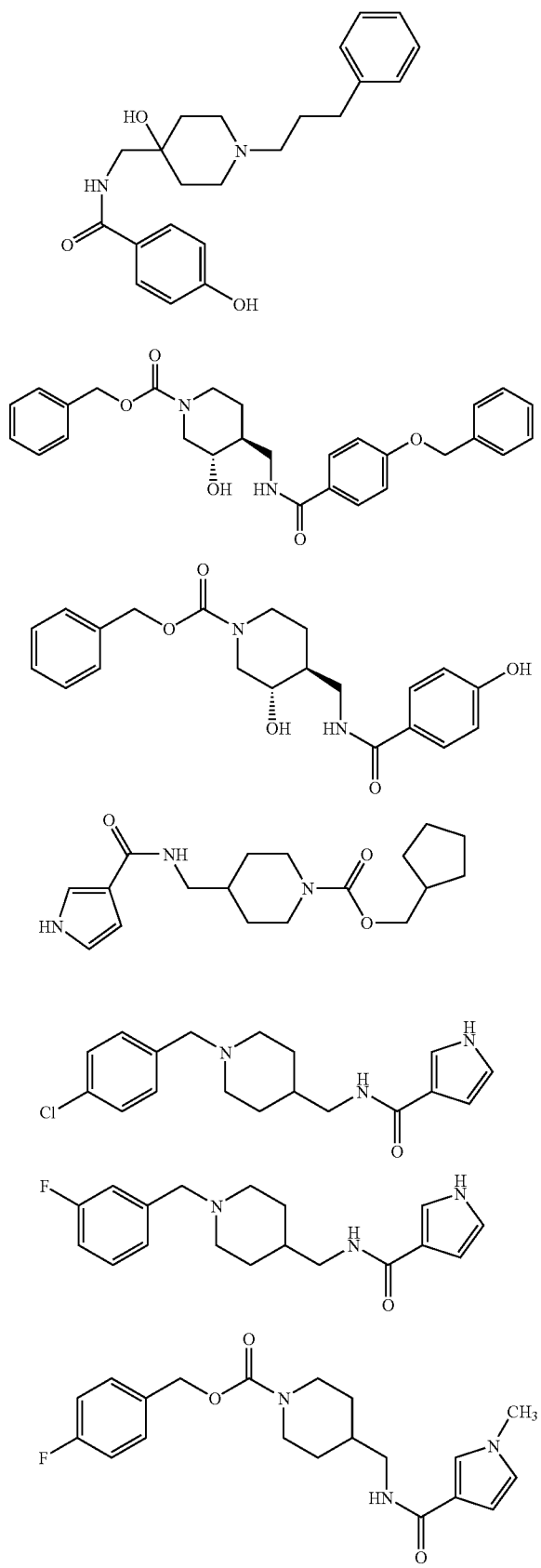

377 378
-continued
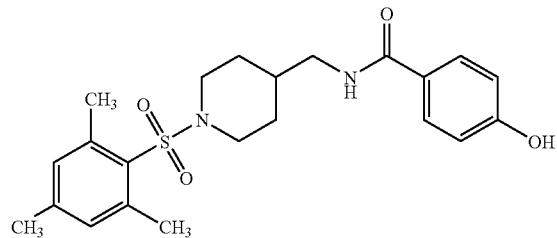 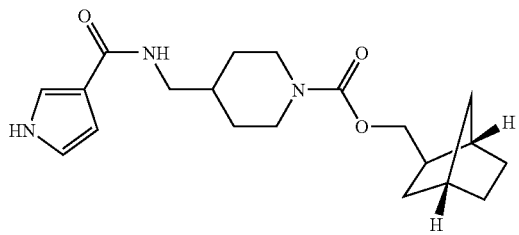
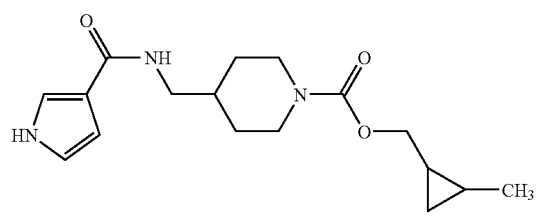 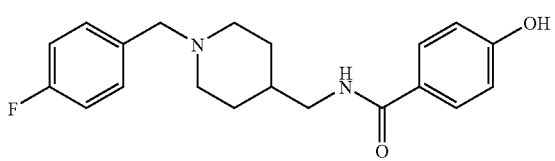
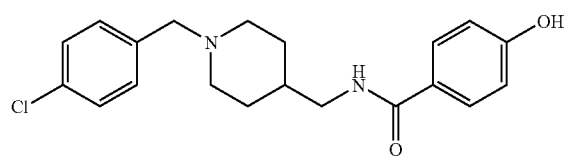 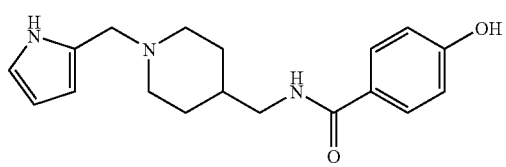
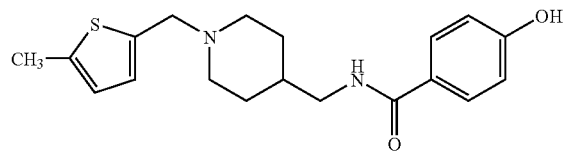 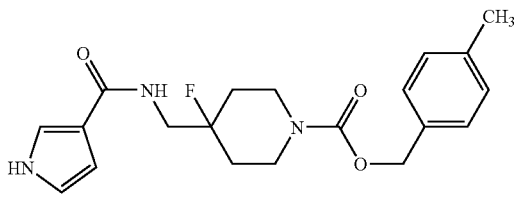
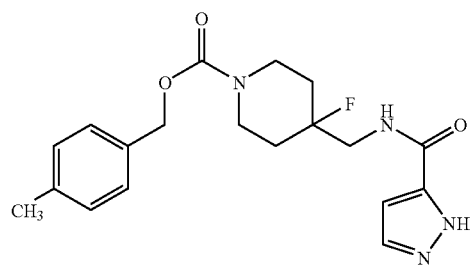 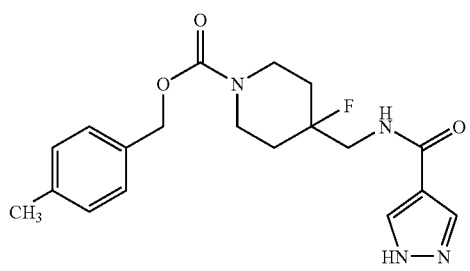
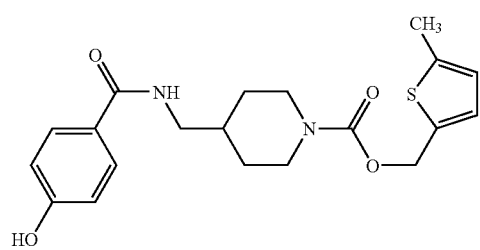 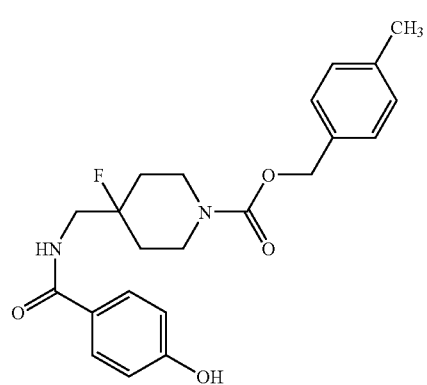

-continued
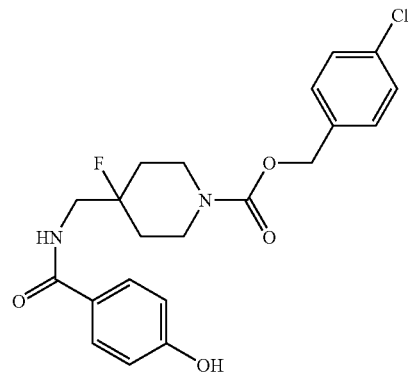 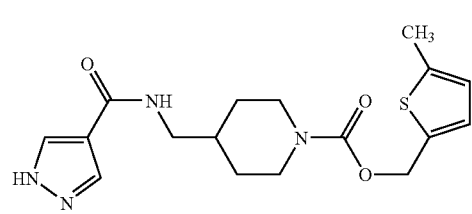
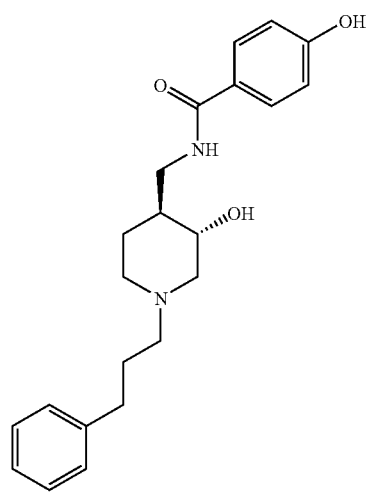 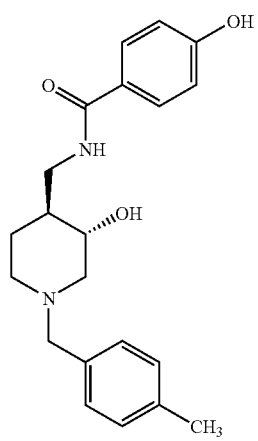 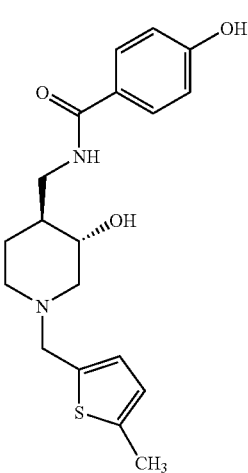
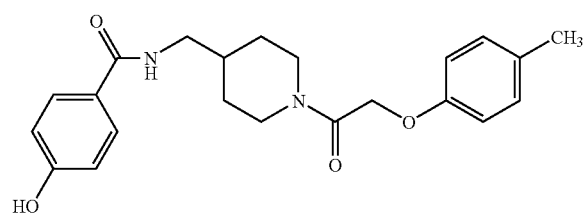 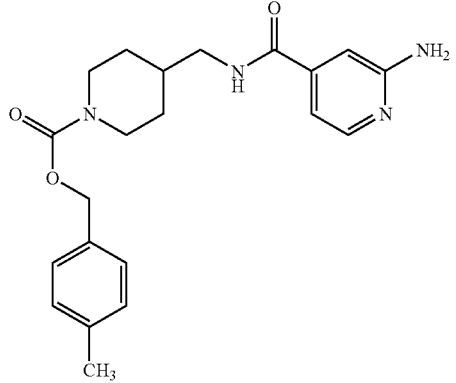
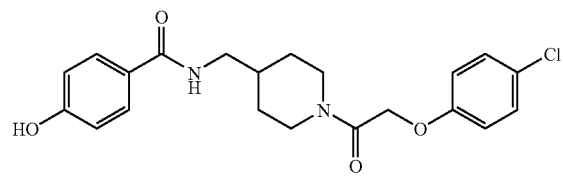 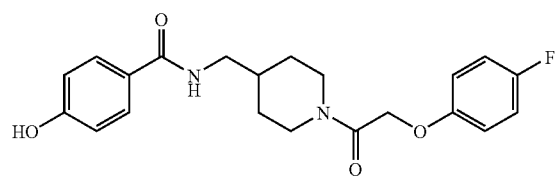
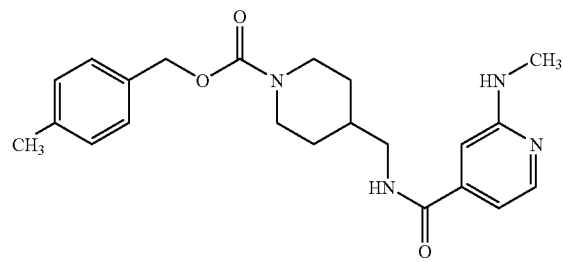 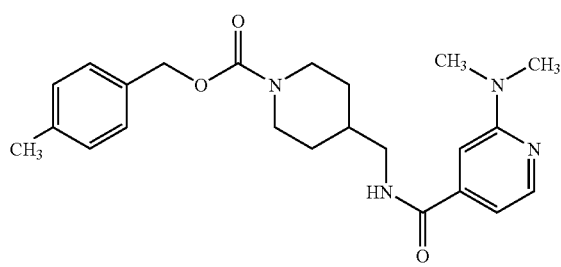

-continued
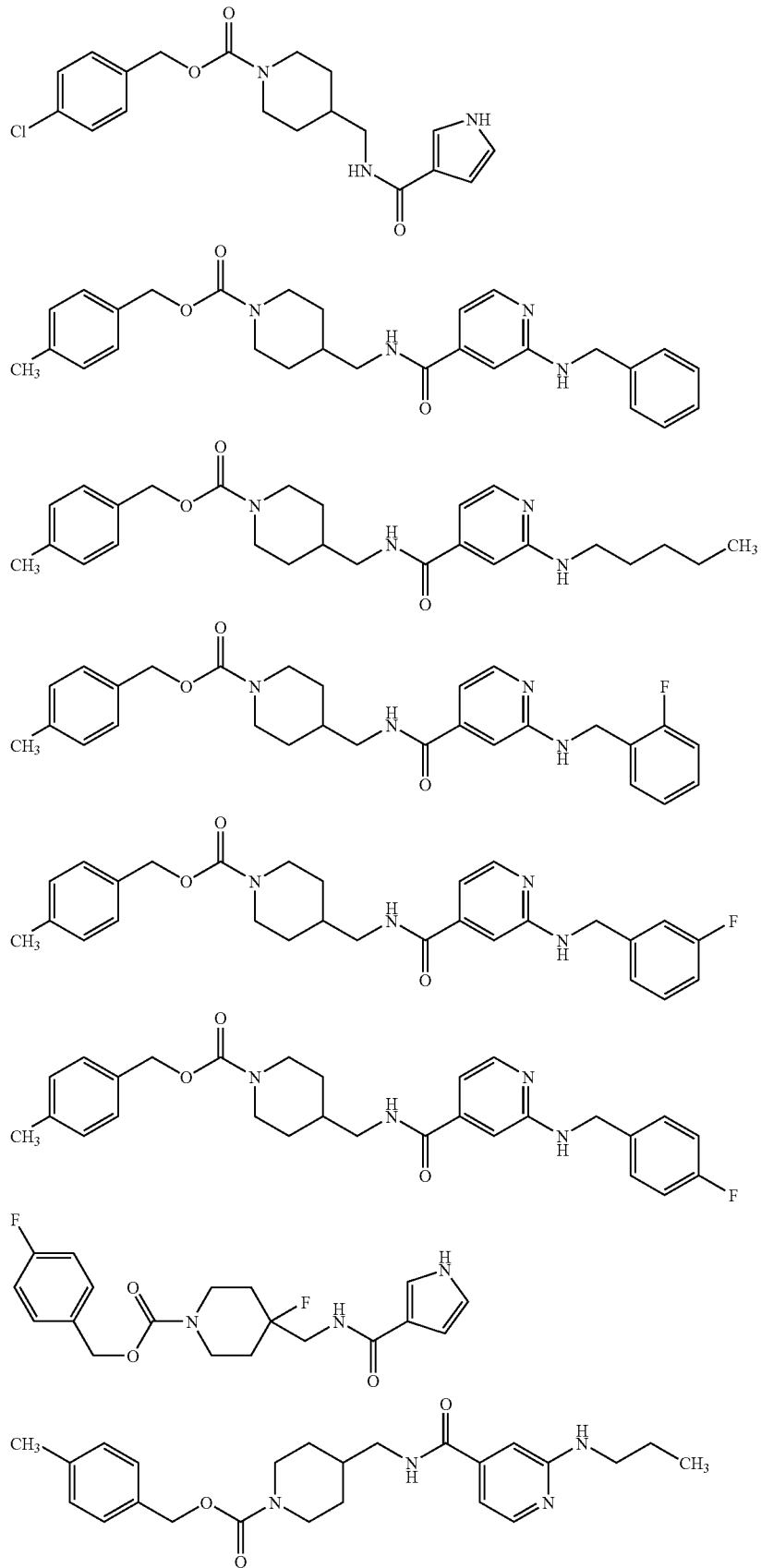

-continued
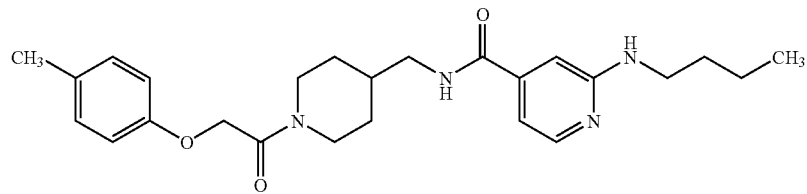
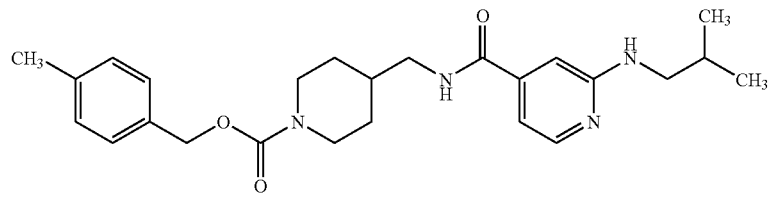
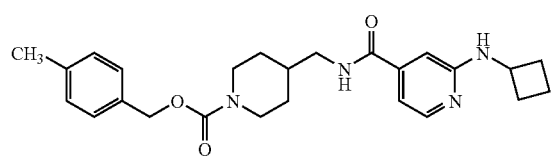
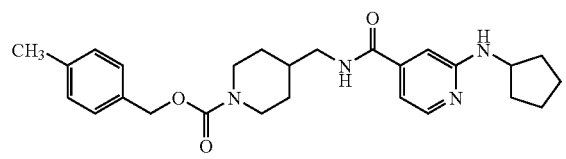
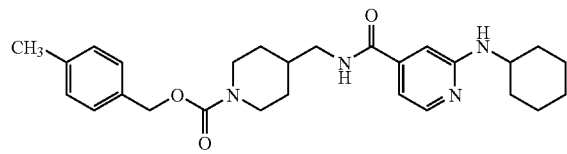
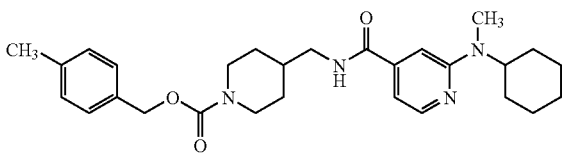
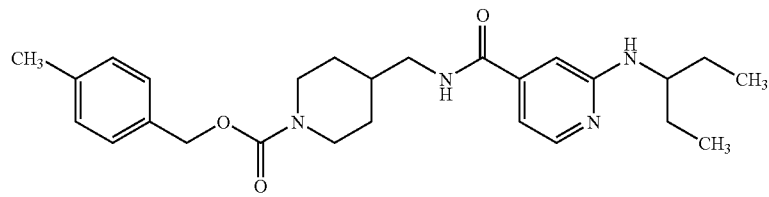
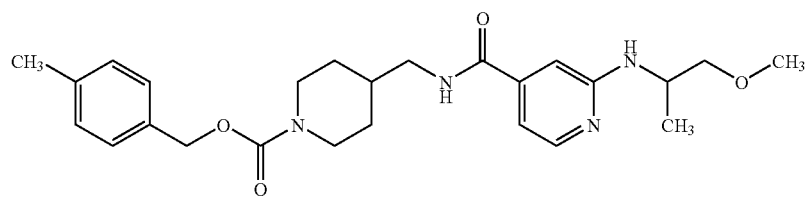
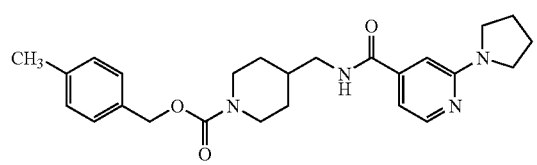
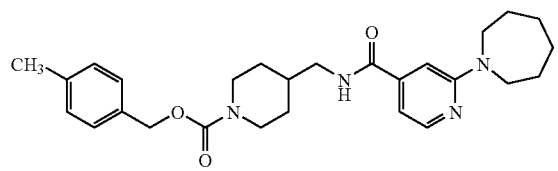
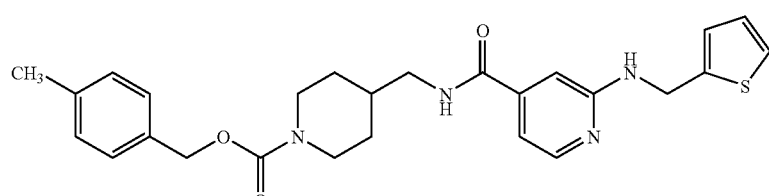
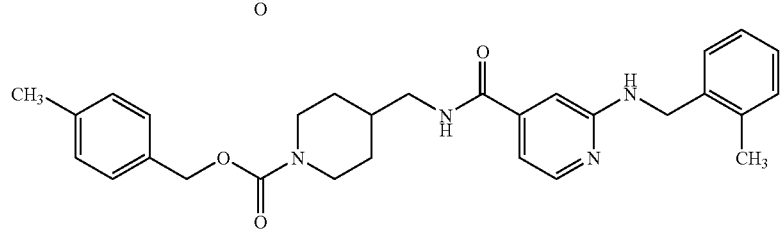

-continued
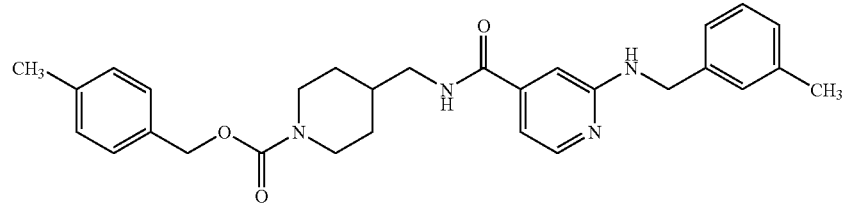
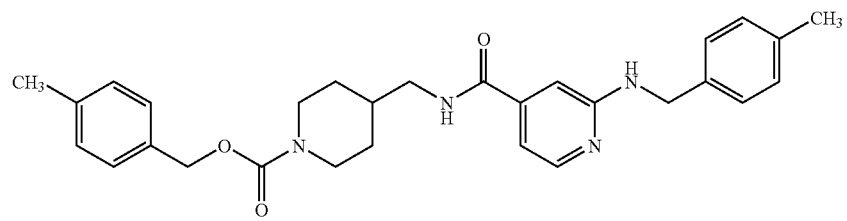
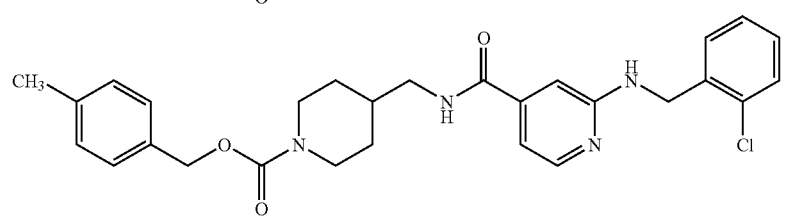
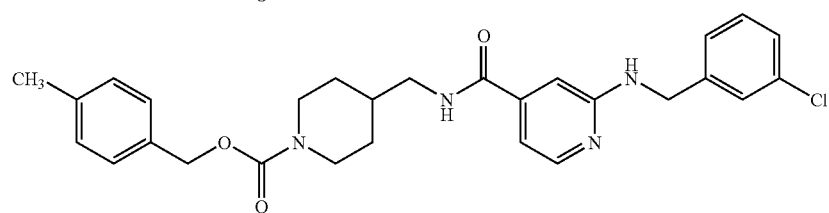
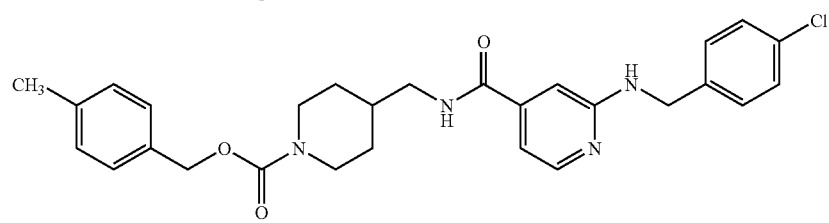
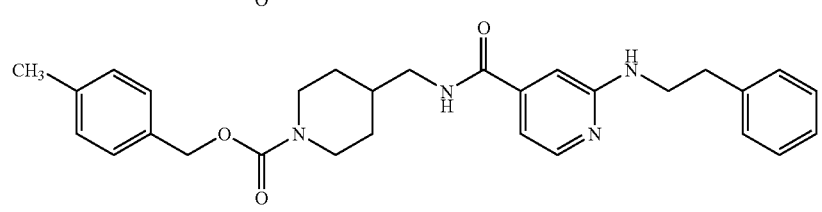
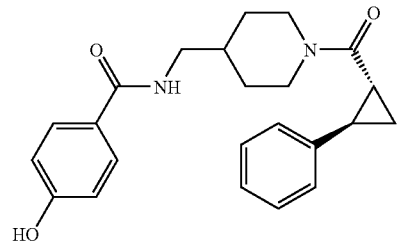
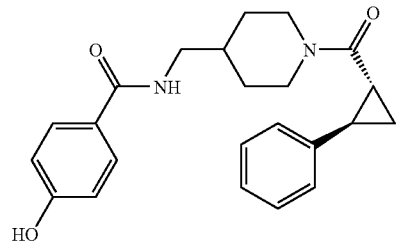
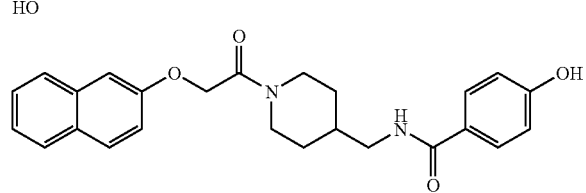
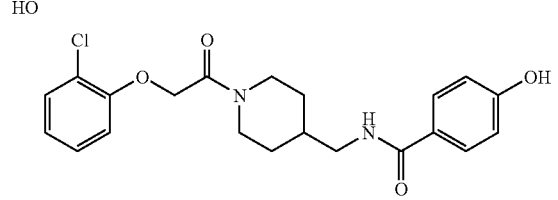

-continued
| 387 | 388 |
|---|---|
| 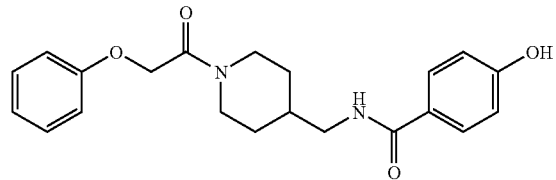 | 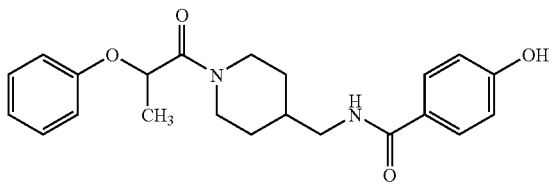 |
| 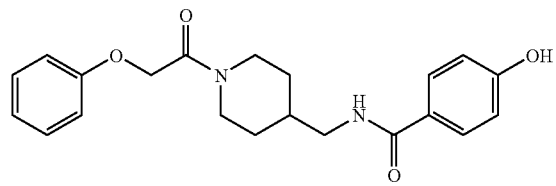 | 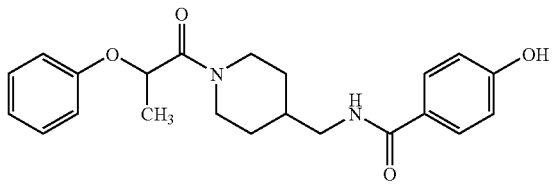 |
| 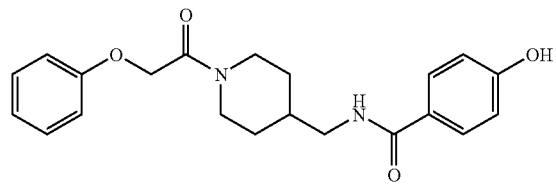 | 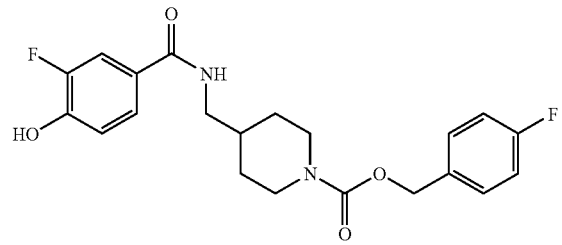 |
| 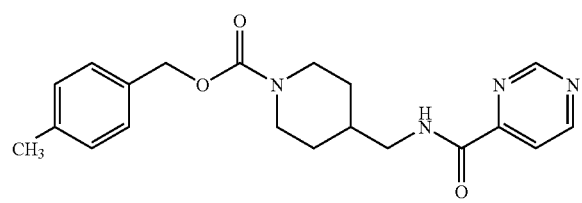 | 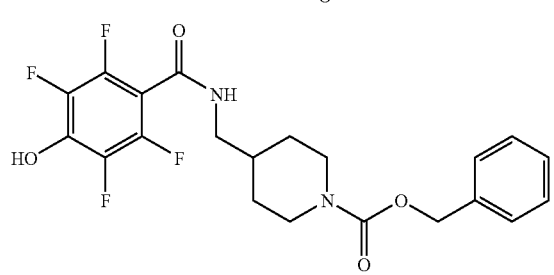 |
| 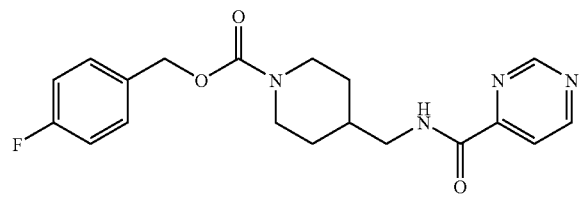 | 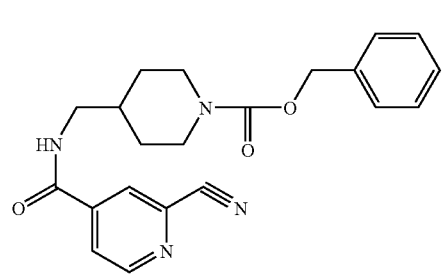 |
| 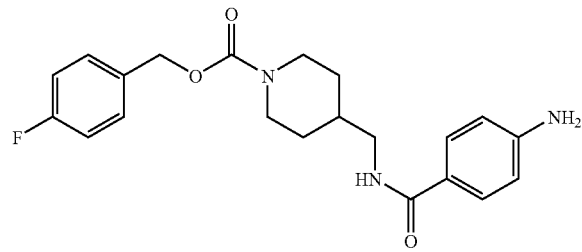 | 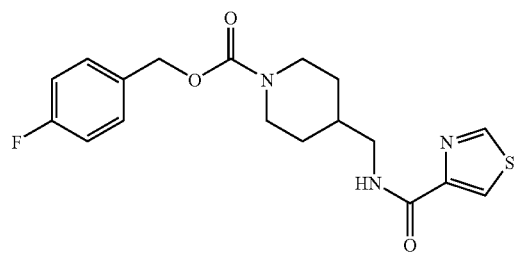 |
| 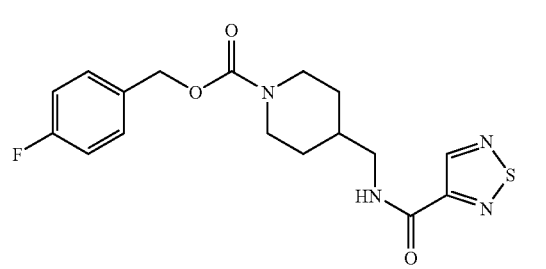 | 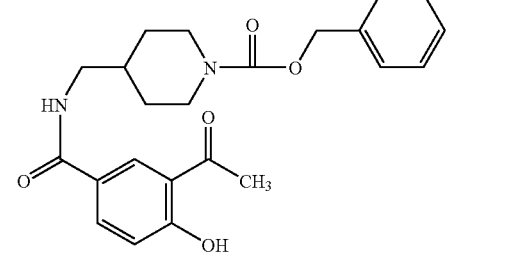 |

389 390
-continued
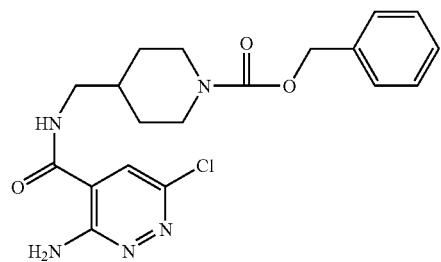
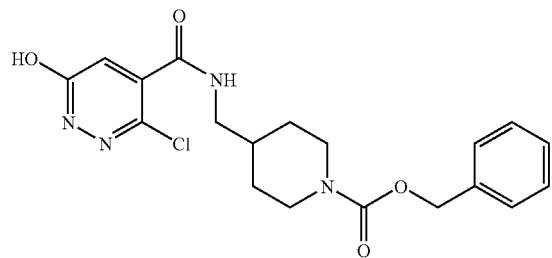
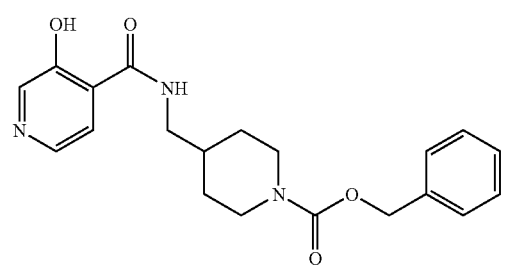
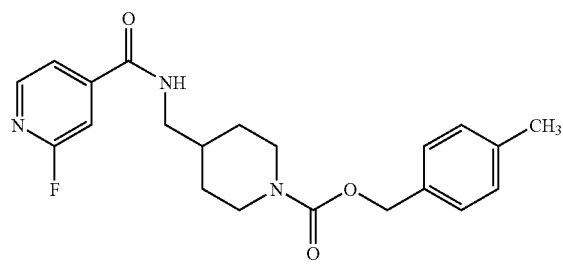
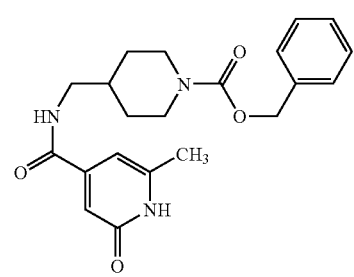
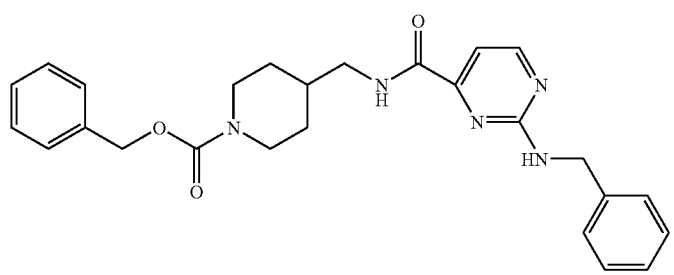
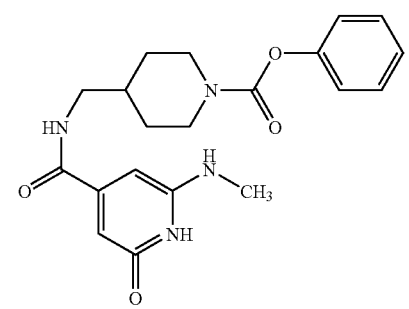
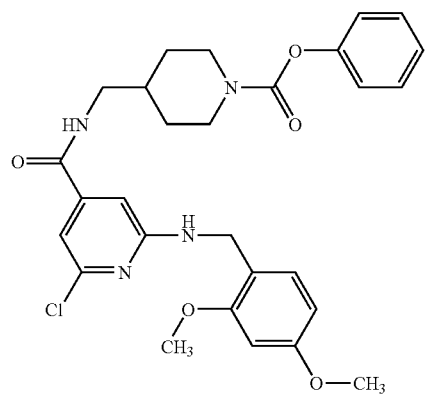
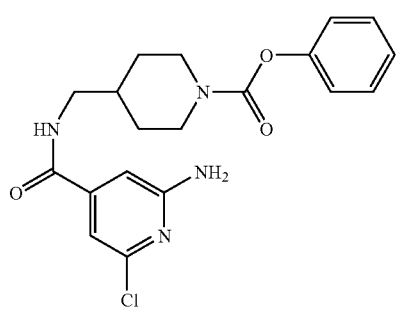

391
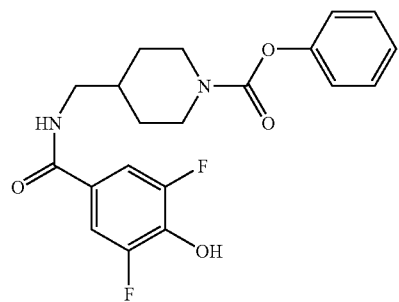
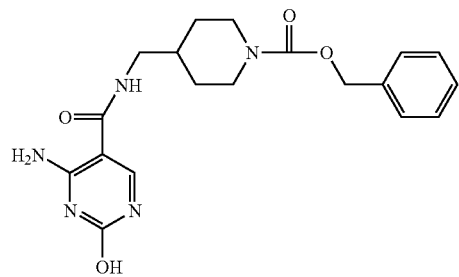
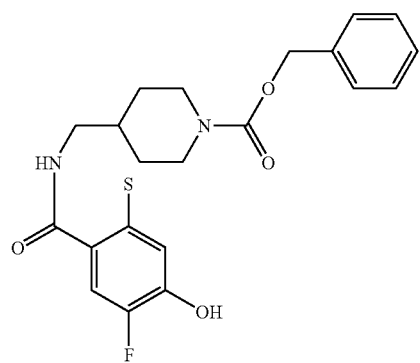
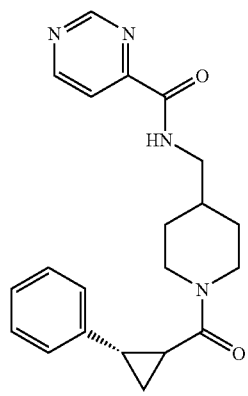
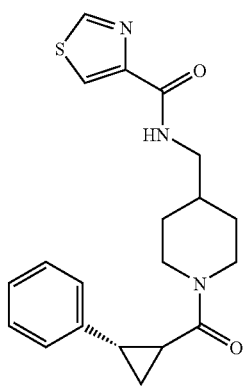
392
-continued
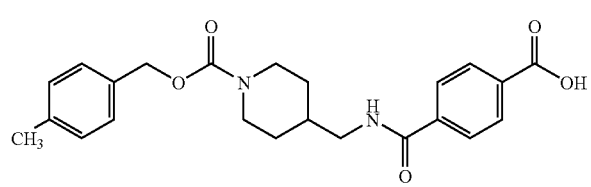
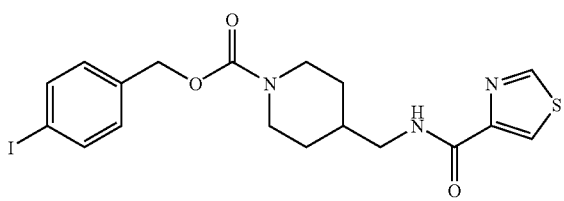
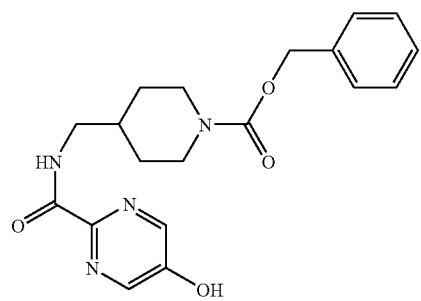

393
394
-continued
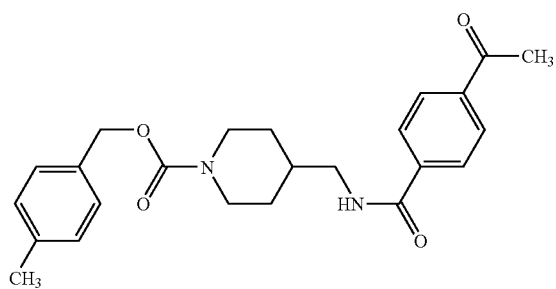
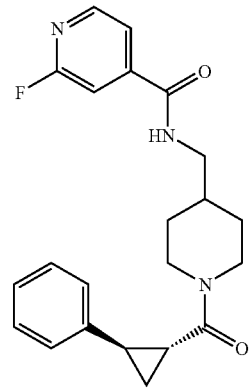
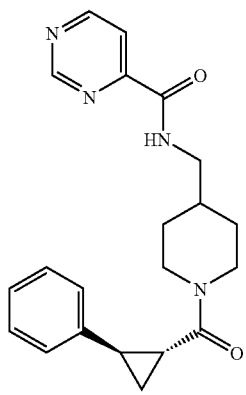
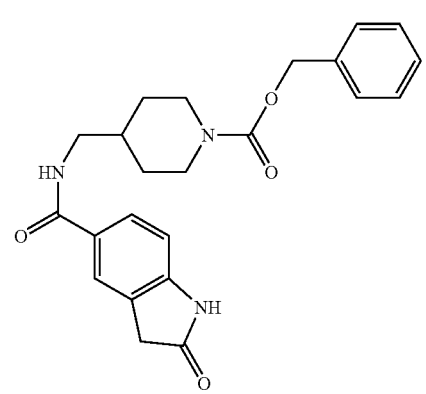
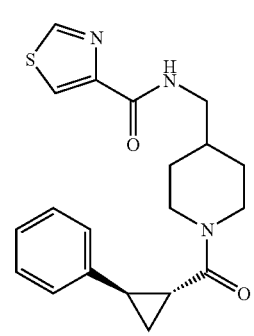
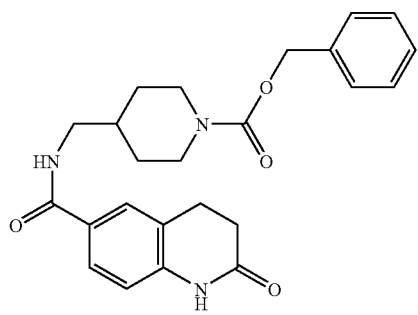
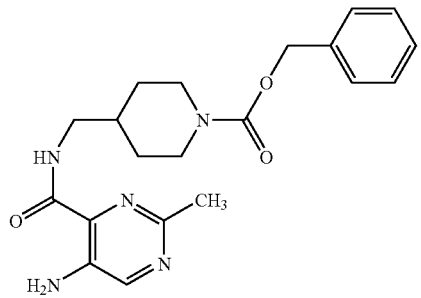
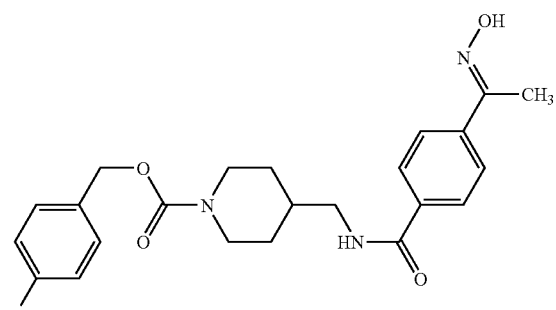
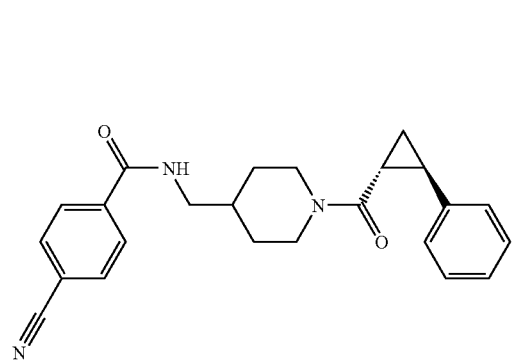

-continued
395
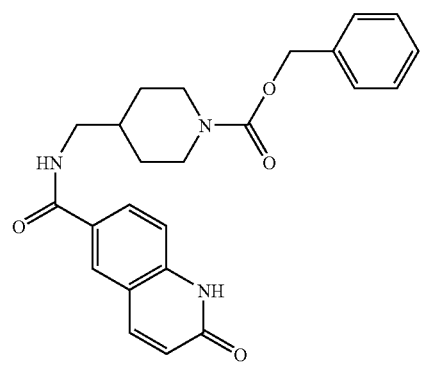
396
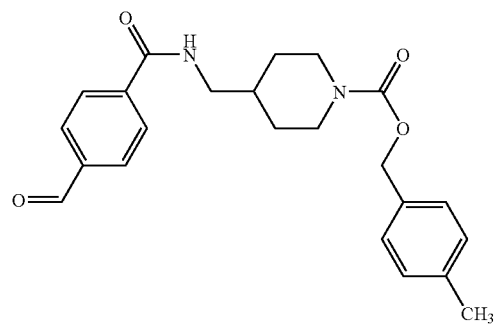
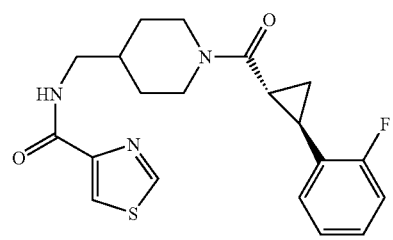
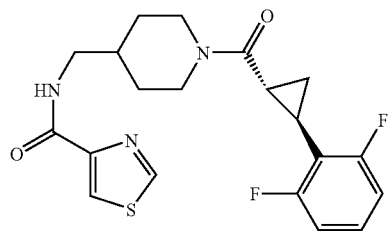
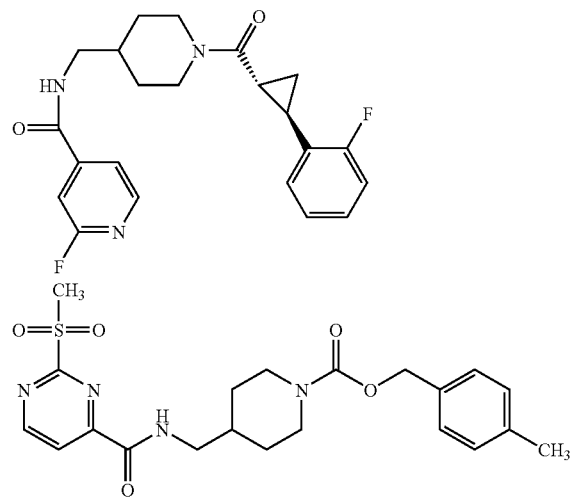
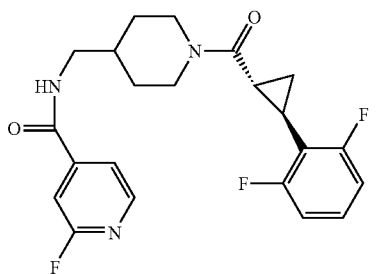
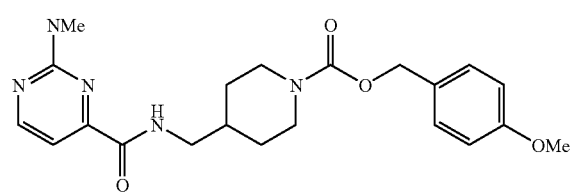
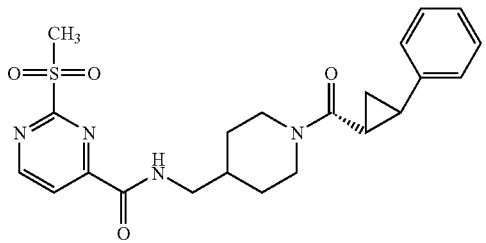
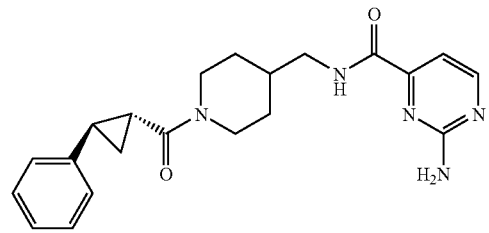

-continued
397
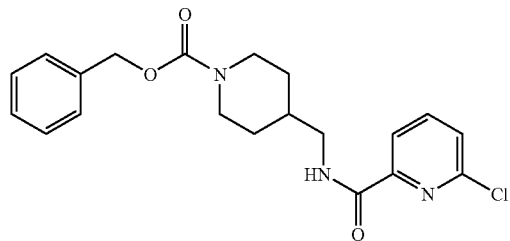
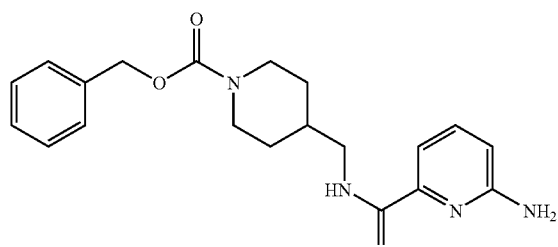
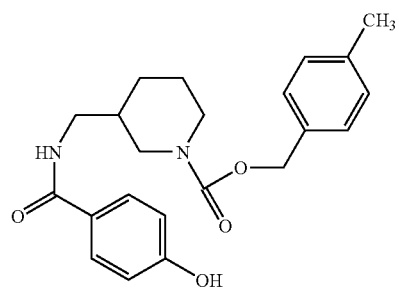
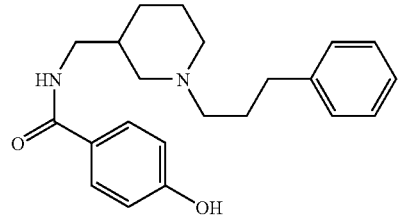
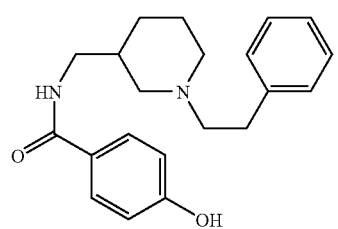
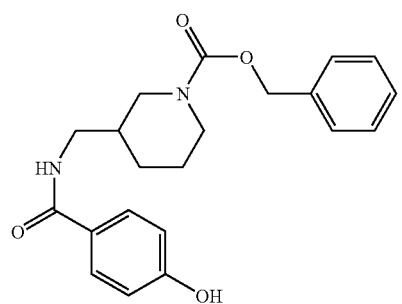
398
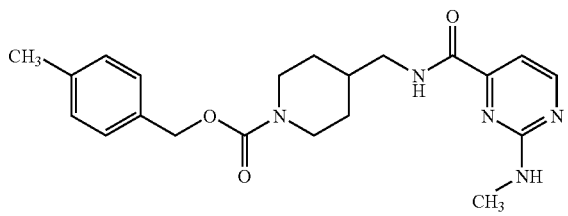
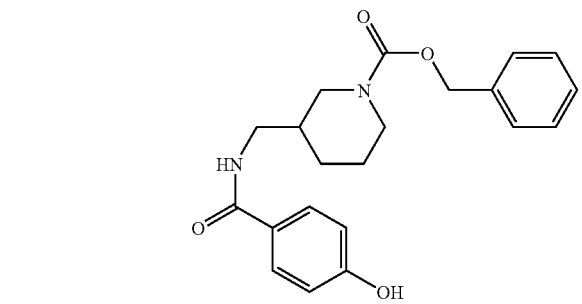
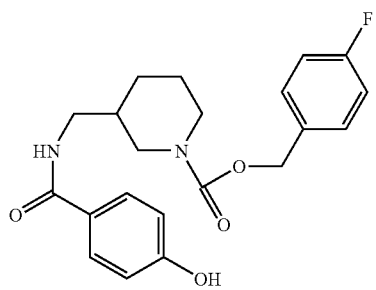
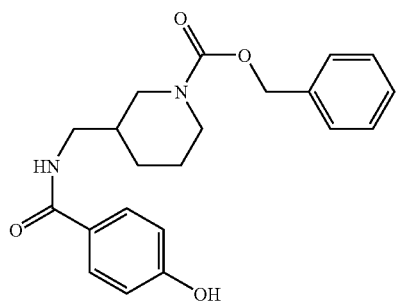
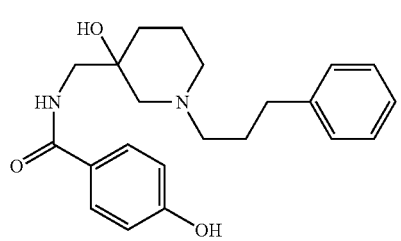

399
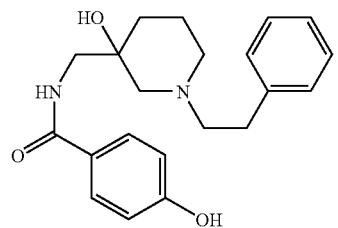
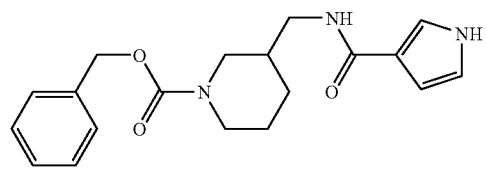
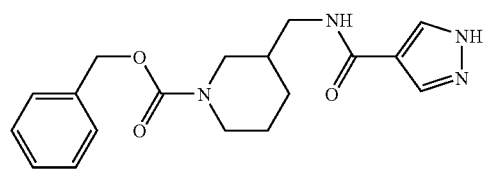
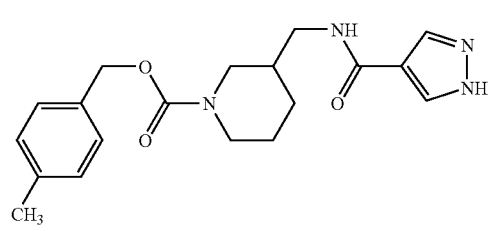
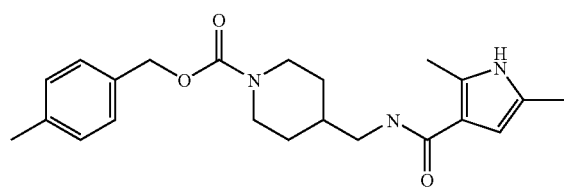
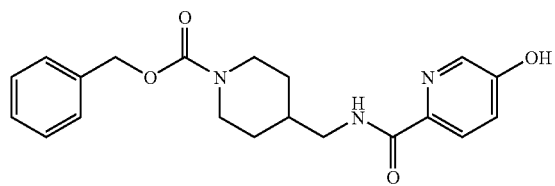
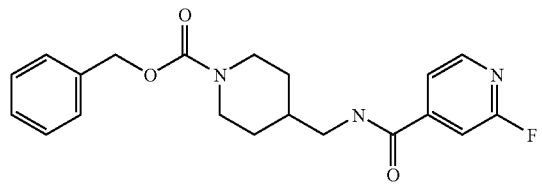
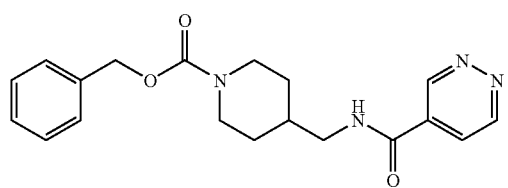
400
-continued
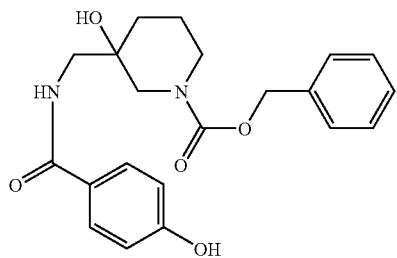
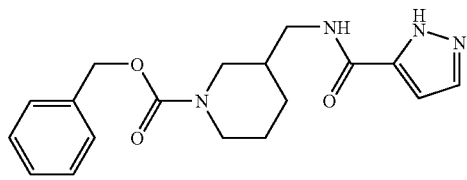
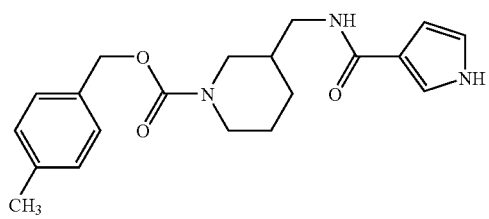
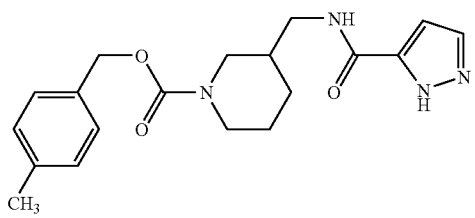
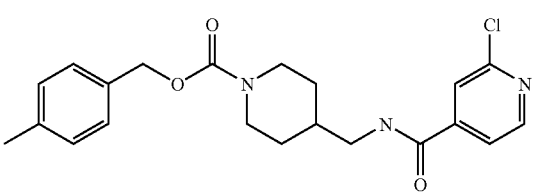
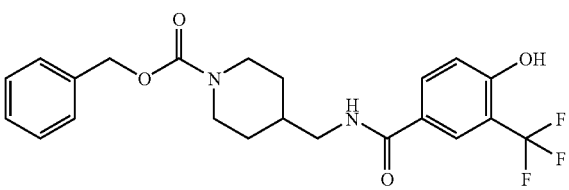
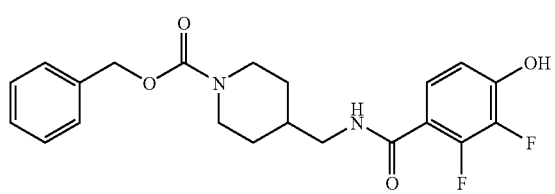
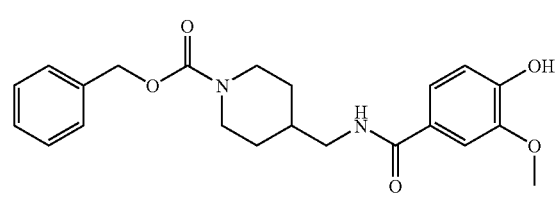

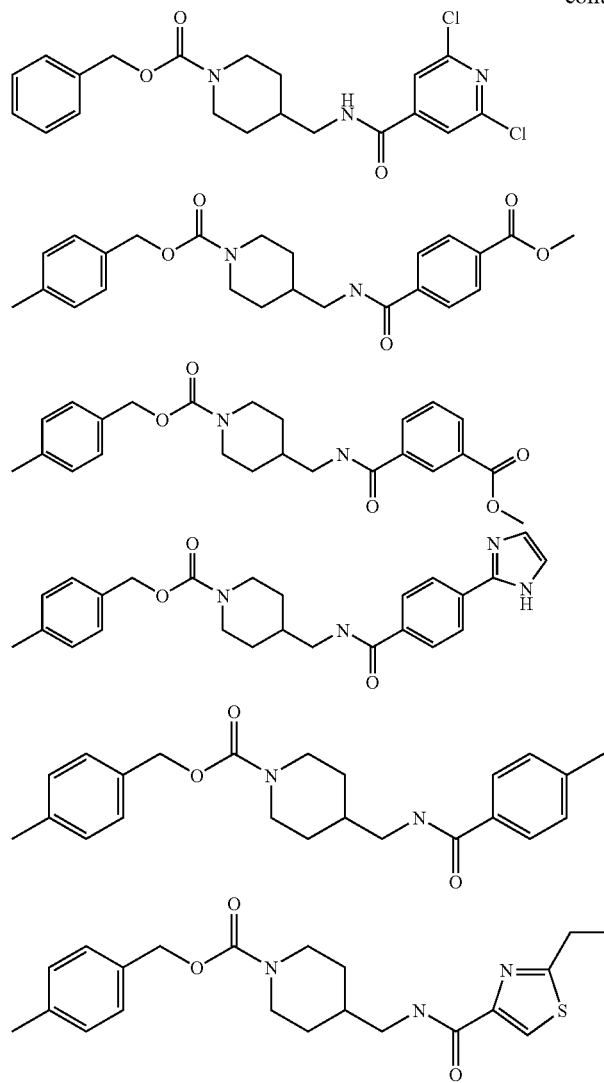

or a pharmaceutically acceptable salt thereof.

12. A pharmaceutical composition comprising an inert carrier and an effective amount of a compound according to claim 1.

13. The pharmaceutical composition according to claim 12 for the treatment of pain.

14. The pharmaceutical composition according to claim 12 for the treatment of migraine, depression, anxiety, schizophrenia, Parkinson's disease, or stroke.

15. A method of treating pain comprising a step of administering to one in need of such treatment a therapeutically effective amount of a compound according to claim 1.

16. A method of treating migraine, depression, anxiety, schizophrenia, Parkinson's disease, or stroke comprising a step of administering to one in need of such treatment a therapeutically effective amount of a compound according to claim 1.

\* \* \* \* \*